US012778931B2

(12) United States Patent
Depue et al.

(10) Patent No.: US 12,778,931 B2
(45) Date of Patent: Nov. 3, 2026

(54) VIRAL INHIBITORS, THE SYNTHESIS THEREOF, AND INTERMEDIATES THERETO

(71) Applicant: Takeda Pharmaceutical Company Limited, Osaka (JP)

(72) Inventors: Jeffrey Scott Depue, Windham, NH (US); Suresh Kumar Tipparaju, Arlington, MA (US); Helge Alfred Reisch, Sarasota, FL (US); Datong Tang, Weston, MA (US); Kishore Ramachandran, Westford, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 19/396,502

(22) Filed: Nov. 21, 2025

(65) Prior Publication Data

US 2026/0076945 A1 Mar. 19, 2026

Related U.S. Application Data

(60) Continuation of application No. 19/373,143, filed on Oct. 29, 2025, which is a continuation of application No. 19/261,756, filed on Jul. 7, 2025, now Pat. No. 12,527,771, which is a division of application No. 18/777,489, filed on Jul. 18, 2024, now Pat. No. 12,377,078, which is a continuation of application No. 18/379,047, filed on Oct. 11, 2023.

(60) Provisional application No. 63/415,438, filed on Oct. 12, 2022.

(51) Int. Cl.

| | |
|---|---|
| ***A61K 31/4184*** | (2006.01) |
| ***A61K 9/00*** | (2006.01) |
| ***A61K 31/7056*** | (2006.01) |
| ***C07H 19/052*** | (2006.01) |

(52) U.S. Cl.

CPC ........ *A61K 31/4184* (2013.01); *A61K 9/0053* (2013.01); *A61K 31/7056* (2013.01); *C07H 19/052* (2013.01)

(58) Field of Classification Search

CPC .......................... A61K 31/7056; C07H 19/052

See application file for complete search history.

(56) References Cited

U.S. PATENT DOCUMENTS

| | | | |
|---|---|---|---|
| 6,077,832 | A | 6/2000 | Chamberlain et al. |
| 6,482,939 | B1 | 11/2002 | Hodgson et al. |
| 6,617,315 | B1 | 9/2003 | Chamberlain et al. |
| 8,541,391 | B2 | 9/2013 | Amparo et al. |
| 8,546,344 | B2 | 10/2013 | Coquerel et al. |
| 11,130,777 | B2 | 9/2021 | Coquerel et al. |

FOREIGN PATENT DOCUMENTS

| | | | |
|---|---|---|---|
| WO | 1998/035977 | A1 | 8/1998 |
| WO | 1999/051618 | A1 | 10/1999 |
| WO | 2001/077083 | A1 | 10/2001 |

OTHER PUBLICATIONS

Shekunov et al., Pharmaceutical Research, 2007, 24(2), p. 203-227. (Year: 2007).*

Kumar et al., Journal of Pharmaceutical Innovation, 2022, 17, p. 333-352, Published online: Jan. 11, 2021. (Year: 2021).*

Berge, S.M. et al., "Pharmaceutical Salts," J. Pharm. Sci., 66(1):1-19.

Chung et al., "Optimal Seeding in Batch Crystallization"0, Canadian Journal of Chemical Engineering, 1999, vol. 77, No. 3, pp. 590-596.

Fichtner et al., "Particle size distribution and evvolution in tablet structure during and after compaction," International Journal of Pharmaceutics, 2005, 292, p. 211-225.

Gudmundsson Kristjan S. et al, "dicyclohexyl carbodiimide or 1-cyclohexyl-3-(2-morpholinoethyl)carbodiimide metho-p-toluenesulphonate", Journal of Medicinal Chemistry,vol. {0} 43, No. {0} 12, May 17, 2000 (May 17, 2000), p. 2464-2472.

Kurzer et al., "Advances in the Chemistry of Carbodimides", Chemical Reviews, 1967, vol. 67, No. 2, pp. 107-152.

Lin et al., Chiral Drugs: Chemistry and Biological Action, 2011, John Wiley & Sons, Inc, 1st Edition, pp. 137-194.

PCT/US2023/034933 International Search Report and Written Opinion, mailed Feb. 13, 2024, 22 pages.

Verma A., "Synlett Spotlight 389, Diisopropylarbodiimide", Synlett, 2012, vol. 23, pp. 1099-1100.

Behl, C.R., et al., "Effects of Physicochemical Properties and Other Factors on Systemic Nasal Drug Delivery", Advanced Drug Delivery Reviews, 1998, vol. 29, pp. 89-116.

FDA Approved Drug Products with Therapeutic Equivalence Evaluations 46th Ed. ("Orange Book") p. 3-308.

NCT00223925, https://clinicaltrials.gov/study/NCT00223925?term=NCT00223925&viewType=Card&rank=1, retrieved May 22, 2026.

NCT01611974, https://clinicaltrials.gov/study/NCT01611974?term=NCT01611974&viewType=Card&rank=1, retrieved May 22, 2026.

NCT02931539, https://clinicaltrials.gov/study/NCT02931539?term=NCT02931539&viewType=Card&rank=1, retrieved May 22, 2026.

Papadakis, G. et al., "Synthesis of New Imidazopyridine Nucleoside Derivatives Designed as Maribavir Analogues," Molecules, Oct. 3, 2020, vol. 25, Article 4531, 13 pages.

Pilaniya, K. et al, "Recent Trends in the Impurity Profile of Pharmaceuticals", Journal of Advanced Pharmaceutical Technology & Research, Jul.-Sep. 2010, Vo.I 1, No. 3, pp. 302-310.

Shekunov, B.Y., "Particle Size Analysis Pharmaceutics: Principles, Methods and Applications," Pharmaceuitcal Research, Feb. 2007, vol. 24, No. 2, pp. 203-227.

Sun, K. et al., "Maribavir: Mechanism of Action, Clinical, and Translational Science", Clinical and Translational Science, 2024, vol. 17, No. 1, pp. 1-10.

NCT02927067, https://clinicaltrials.gov/study/NCT02927067?term=NCT02927067&viewType=Card&rank=1, retrieved May 22, 2026.

* cited by examiner

*Primary Examiner* — Jonathan S Lau

(74) *Attorney, Agent, or Firm* — Honigman LLP; Andrew S. Chipouras; Jonathan P. O'Brien

(57) ABSTRACT

The present disclosure discloses compositions comprising maribavir, methods of providing the same, and compositions providing intermediates useful in providing maribavir.

12 Claims, 4 Drawing Sheets

VIRAL INHIBITORS, THE SYNTHESIS THEREOF, AND INTERMEDIATES THERETO

CROSS-REFERENCE TO RELATED APPLICATIONS

The present application is a continuation of U.S. application Ser. No. 19/373,143 filed on Oct. 29, 2025, which is a continuation of U.S. application Ser. No. 19/261,756 filed on Jul. 7, 2025, which is a divisional of U.S. patent application Ser. No. 18/777,489 filed on Jul. 18, 2024, which is a continuation of U.S. patent application Ser. No. 18/379,047, filed Oct. 11, 2023, which claims the benefit of U.S. Provisional Patent Application No. 63/415,438, filed Oct. 12, 2022, the entire disclosures of which are incorporated by reference herein in their entirety.

TECHNICAL FIELD OF INVENTION

The present invention relates to compounds useful as antivirals, pharmaceutical compositions thereof, and methods of making said compounds and compositions.

BACKGROUND

Cytomegalovirus (CMV) is a member of the herpes virus family. Human cytomegalovirus (HCMV) infection is common, with serologic evidence of prior infection in 40% to 100% of various adult populations. However, serious HCMV disease occurs almost exclusively in individuals with compromised or immature immune systems. Cytomegalovirus remains a significant problem for patients undergoing various types of transplants that are associated with the use of potent immunosuppressive chemotherapy, including hematopoietic stem cell transplants (HSCTs) and solid organ transplants (SOTs).

SUMMARY

Maribavir is a benzimidazole riboside, and is an orally available antiviral medication against CMV. Maribavir is also known under its trade name LIVTENCITY™. Maribavir ((2S,3S,4R,5S)-2-(5,6-dichloro-2-(isopropylamino)-1H-benzo[d]imidazol-1-yl)-5-(hydroxymethyl)tetrahydrofuran-3,4-diol), a compound having the chemical structure:

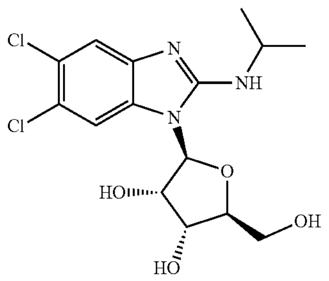 [SMILES: CC(C)Nc1nc2cc(Cl)c(Cl)cc2n1[C@H]1O[C@@H](CO)[C@H](O)[C@@H]1O]

is a potent and orally bioavailable antiviral for the treatment of CMV infection and disease in transplant recipients. Transplant recipients are at significant risk of CMV infection.

The synthesis of maribavir is described in Examples 1, 2, and 5 of U.S. Pat. No. 6,077,832 (the '832 patent). This synthesis, depicted in Scheme 1 below, consists of three chemical transformation steps with a combined yield of about 27%.

Scheme 1

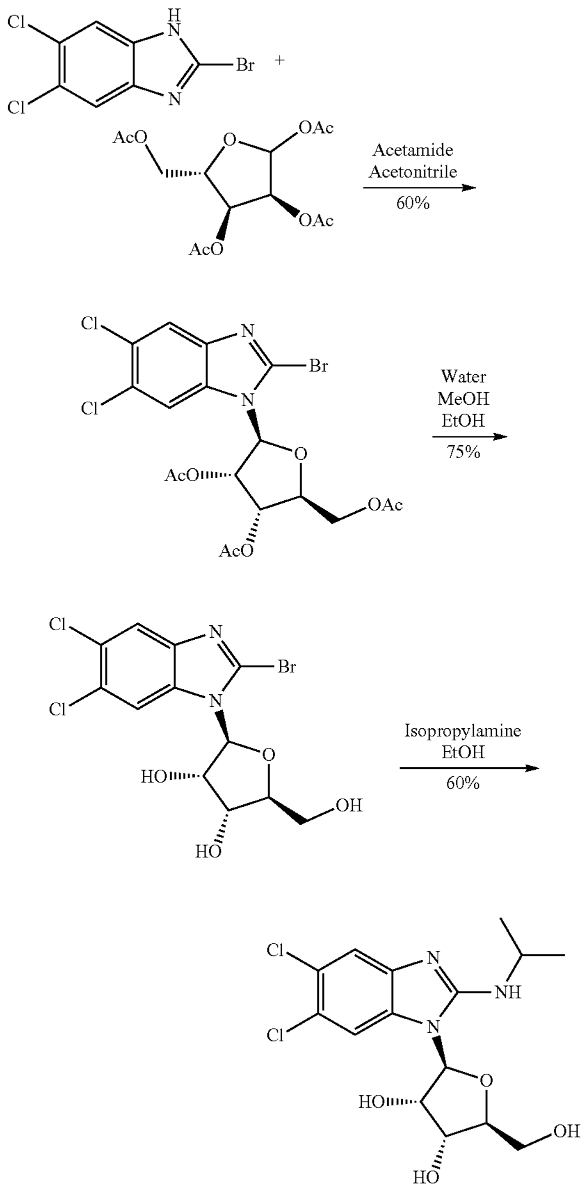

Maribavir

The synthesis depicted in Scheme 1 first couples 2-bromo-5,6-dichlorobenzimidazole with 1,2,3,5-tetra-O-acetyl-L-ribofuranose. Next, the acetyl groups are removed on the ribofuranose moiety followed by installation of the isopropylamine to provide maribavir. Notably, the first step also produced the alpha anomer in about 6% yield (see the '832 patent at Example 1).

The synthesis of maribavir is also described in WO 2001/077083 (the '083 publication) at Examples 1-4 and 7. This synthesis, depicted in Scheme 2 below, consists of five chemical transformations with a combined yield of between about 18-20%.

Scheme 2

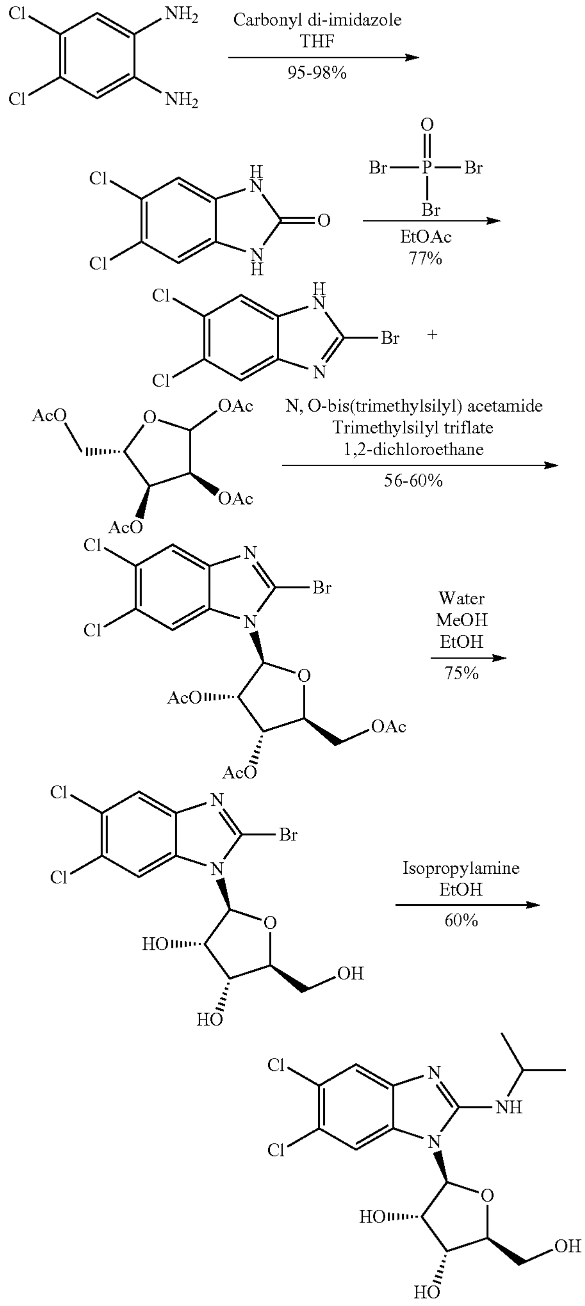

The synthesis in Scheme 2 follows a similar route as that provided in Scheme 1 as disclosed within the '832 patent, but replaces some reagents in the first step. Additionally, the '083 publication also discloses a two-step process for providing 2-bromo-5,6-dichlorobenzimidazole.

U.S. Pat. No. 6,617,315 (the '315 patent) discloses an alternative route: synthesis of 2-(alkylamino)-1H-benzimidazoles using 1-cyclohexyl-3-(2-morpholinoethyl)carbodiimde metho-p-toluenesulfonate as a desulfurizing agent; coupling 2-(alkylamino)-1H-benzimidazoles with 1,2,3,5-tri-O-acetyl-ribofuranose; and deprotection of 2-(alkylamino)-1-(2,3,5-tri-O-acetyl-beta-L-ribofuranosyl-1H-benzimidazoles. See General Procedures I, II, and III at columns 27-28 of the '315 patent. Specifically, the '315 patent discloses the synthesis of the acetyl-protected intermediate in Scheme 3 at Examples 24 and 25:

Scheme 3

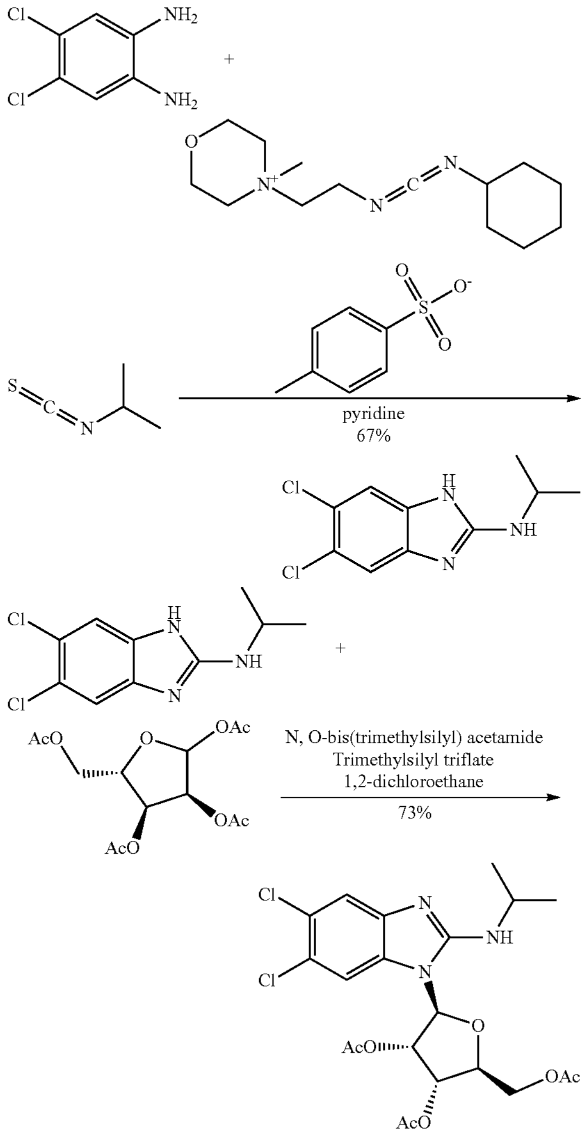

These two-steps have a combined yield of about 49%. Notably, the '315 patent does not exemplify deacetylation of 5,6-dichloro-2-(isopropylamino)-1-(2,3,5-tri-O-acetyl-betal-L-ribofuranosyl)-1H-benzimidazole to afford maribavir. While the synthesis disclosed in the '315 patent appears to be a marked improvement over the syntheses described in the '832 patent and the '083 publication, the yield of maribavir is still expected to be below 49% (e.g., 37% when assuming 75% yield for deacetylation as exemplified in the '832 patent and the '083 publication).

Accordingly, in some embodiments, the present invention encompasses the recognition that the synthesis of maribavir can be modified to increase the overall yield. In some embodiments, maribavir, or a pharmaceutically acceptable salt thereof, is prepared according to Scheme 4 or Scheme 5, set forth below:

Scheme 4
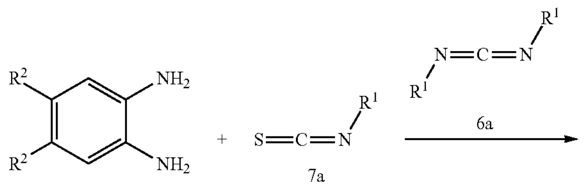
5a 7a
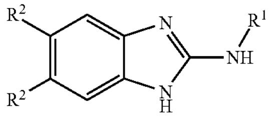
2a
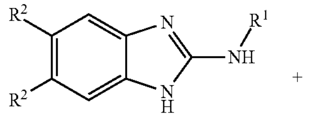
2a
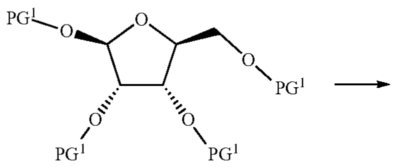
8a
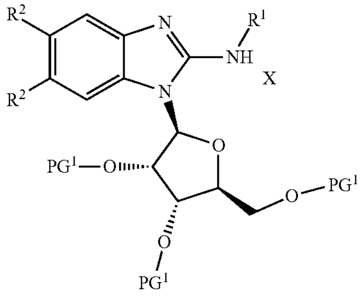
3a
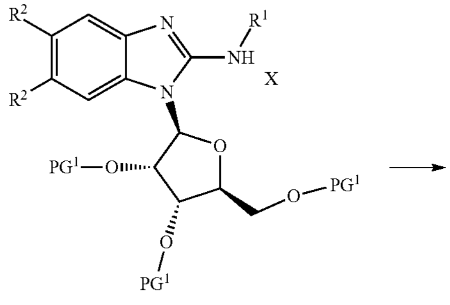
3a
-continued
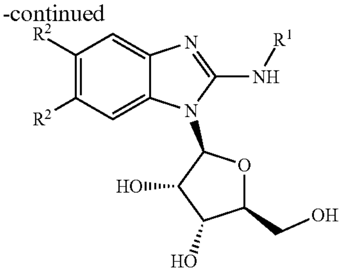
1
Scheme 5
Step 1
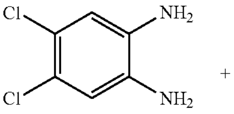
5
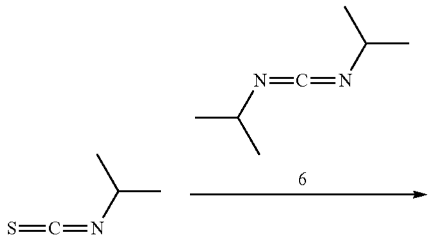
7
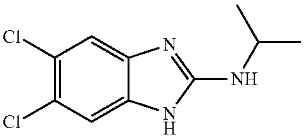
2
Step 2
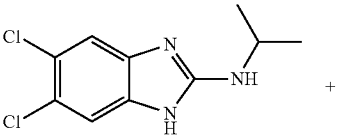
2
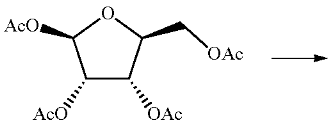
8
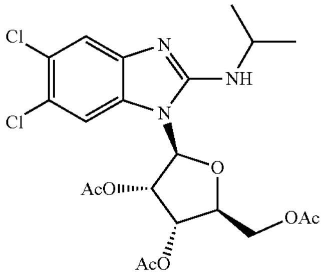
3

-continued

Step 3

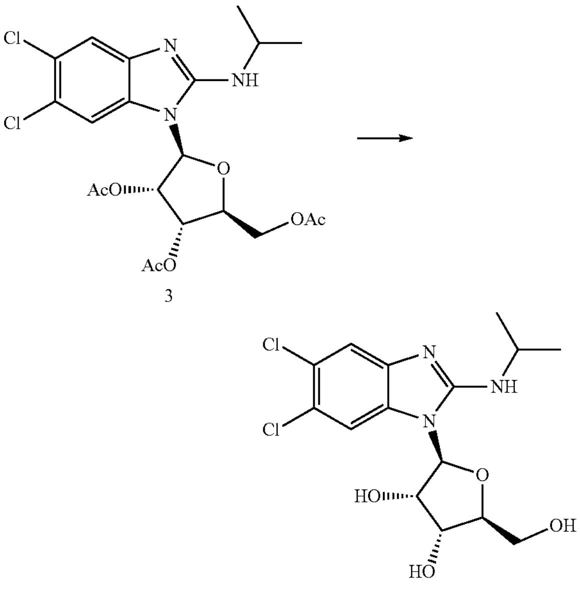

3

Maribavir

In some embodiments, the present disclosure provides an improved synthesis of maribavir in Scheme 5 with overall yields of at least 45%. It will be appreciated that the physical and/or chemical properties of certain intermediate compounds (e.g., compounds 2-3 or 5-8), solvents and/or reagents, as well as reaction conditions may contribute to the overall yield of maribavir and/or help control impurities, particularly when scaling-up the synthesis.

Additionally or alternatively, the present disclosure also provides the recognition that maribavir of acceptable quality is important to be properly milled and formulated into a tablet. For example, in some embodiments, a particular polymorphic form of maribavir (e.g., Form VI as disclosed in U.S. Pat. No. 6,482,939) is desired, free of other crystal forms, solvates, or hydrates. In some embodiments, the present disclosure provides methods of preparing maribavir in a particular polymorphic form (e.g., Form VI as disclosed in U.S. Pat. No. 6,482,939), free of other crystal forms, solvates, or hydrates. Additionally or alternatively, in some embodiments, the particular size distribution of maribavir is important for tablet manufacture. In some embodiments, the present disclosure provides methods of preparing maribavir with particular particle size distributions that are amenable for milling and formulating into a tablet. Additionally or alternatively, in some embodiments, the particular size distribution of maribavir is important for manufacturing an oral solid formulation. In some embodiments, the present disclosure provides methods of preparing maribavir with particular particle size distributions that are amenable for formulating into an oral solid formulation. Additionally or alternatively, in some embodiments, the particular size distribution of maribavir may affect bioavailability of maribavir. In some embodiments, the present disclosure provides a solid oral formulation comprising maribavir polymorphic Form VI having particular particle size distributions (e.g., d(50) is between about 50 and about 400 μm). In some embodiments, the present disclosure provides methods of crystallization of maribavir polymorphic Form VI having particular particle size distributions (e.g., d(50) is between about 50 and about 400 μm).

Additionally or alternatively, the present disclosure provides the recognition that minimizing certain impurities is important when manufacturing a drug product. For example, impurity profiles should be consistent to maintain consistency of efficacy and minimize potential adverse effects. In some embodiments, where synthesis of a drug product consists of multiple steps, it will be appreciated that impurities formed in an early step may be carried through subsequent steps to form additional impurities. Therefore, reducing impurities at each step in the synthesis of maribavir (e.g., Steps 1, 2, or 3) is important to maintain consistency in the manufactured drug product.

Accordingly, in some embodiments, the present disclosure provides compositions comprising maribavir, or a pharmaceutically acceptable salt thereof, and methods of preparing the same. In some embodiments, provided compositions comprise maribavir and one or more compounds selected from:

2

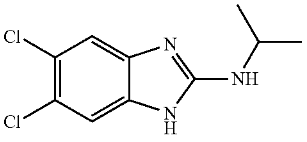

3

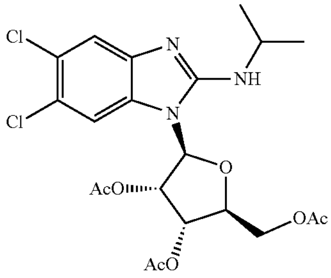

or

4

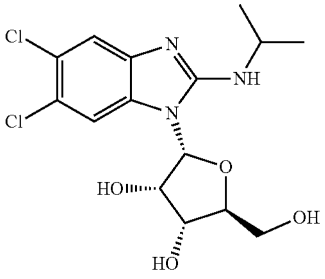

or pharmaceutically acceptable salts thereof.

In some embodiments, provided compositions are prepared according to methods disclosed herein (e.g., Steps 1-3). In some embodiments, provided composition comprise at least 90%, 95%, 99%, 99.5%, or 99.9% by weight of maribavir. In some embodiments, provided composition comprise maribavir substantially free of impurities. As used herein, the term "substantially free of impurities" means that the composition or compound contains no significant amount of extraneous matter. Such extraneous matter may include starting materials, residual solvents, or other impurities that may result from the preparation of, and/or isolation of maribavir. In some embodiments, provided compositions comprise maribavir, or a pharmaceutically acceptable salt thereof, and compound 2, 3, and/or 4 in an amount of less than 0.10% (w/w HPLC), relative to maribavir. In some embodiments, provided compositions comprise maribavir, or a pharmaceutically acceptable salt thereof, and compound 2, 3, and/or 4 in an amount of less than 0.10% (w/w HPLC), relative to maribavir. In some embodiments, provided compositions comprise maribavir, or a pharmaceutically acceptable salt thereof, and compound 2, 3, and/or 4 in an amount of less than 0.10% (a/a HPLC), relative to maribavir. In some embodiments, provided compositions comprise maribavir, or a pharmaceutically acceptable salt thereof, and compound 2, 3, and/or 4 in an amount not detectable by HPLC. In some embodiments, provided compositions comprise maribavir as Form VI, as described in U.S. Pat. No. 6,482,939. In some embodiments, provided compositions comprise at least 90%, 95%, 99%, 99.5%, or 99.9% by weight of Form VI maribavir. In some embodiments, provided compositions comprise maribavir substantially free of other polymorphic forms, e.g., as described in U.S. Pat. Nos. 6,482,939, 8,546,344, or U.S. Pat. No. 11,130,777. U.S. Pat. No. 8,546,344, or U.S. Pat. No. 11,130,777. In some embodiments, provided compositions comprise maribavir having a particular size distribution as defined and described herein. Impurities (e.g., intermediates, enantiomeric impurities) would potentially impact drug substance and drug product quality and may represent a risk to the drug product safety. There is a possible impact to patient safety if certain impurities are present in quantities above qualified limits. There are unknown risks to drug product safety for unknown impurities.

DETAILED DESCRIPTION

Definitions

Figure 1:
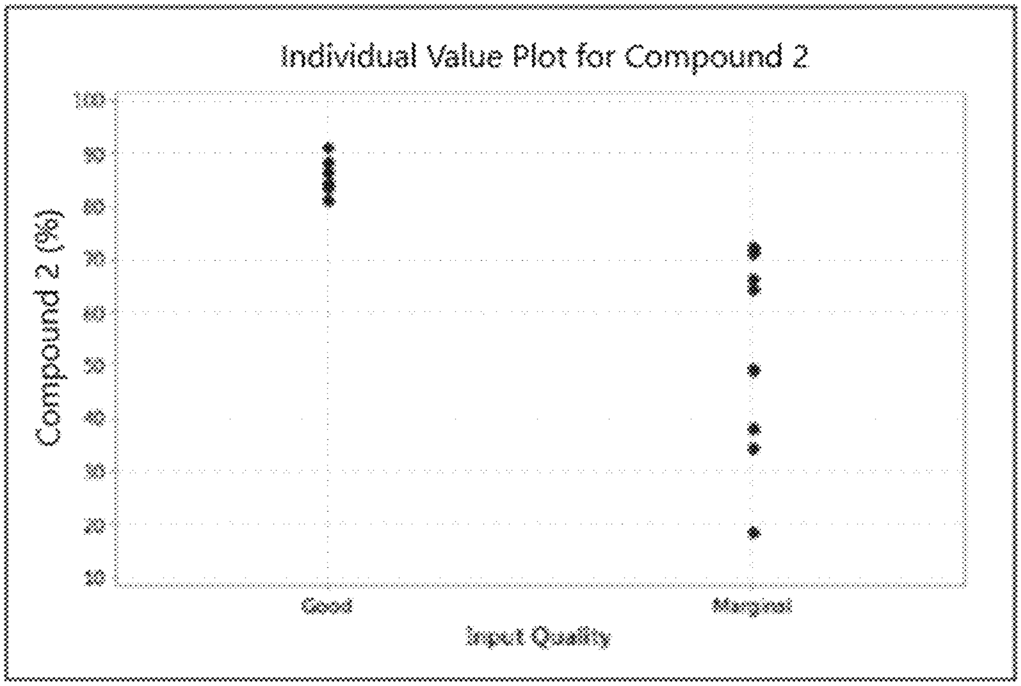
FIG. 1 displays a plot of Compound 2 purity as a function of input quality, after filtration of the recrystallized Compound 2 (i.e., before the wash steps).

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 p electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As described herein, compounds may contain "optionally substituted" moieties. In general, the term "substituted", whether preceded by the term "optionally" or not, means that one or more hydrogens of the designated moiety of compounds are replaced with a suitable substituent. "Substituted" applies to one or more hydrogens that are either explicit or implicit from the structure (e.g., 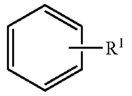

refers to at least

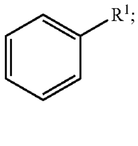 ; and 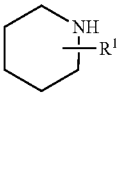

refers to at least

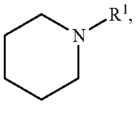 , 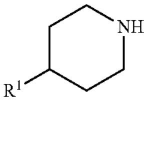

-continued

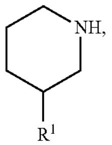 , or 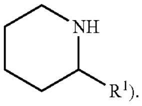 ).

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$ $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR^\circ$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5- to 6 membered heteroaryl ring), or a 5- to 6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, $-(haloR^\bullet)$, $—(CH_2)_{0-2}OH$, $—(CH_2)_{0-2}OR^\bullet$, $—(CH_2)_{0-2}CH(OR^\bullet)_2$; $—O(haloR^\bullet)$, —CN, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, —($C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group of a compound of Formula I, and subgenera thereof, include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^{\bullet}$, -(halo$R^{\bullet}$), $-OH$, $-OR^{\bullet}$, —O(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, $-R^{\bullet}$, -(halo$R^{\bullet}$), $-OH$, $-OR^{\bullet}$, —O(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within (i.e., ±) 10%, 9%, 8%, 7%, 6%, 5%, 4%, 3%, 2%, 1%, or less of the referred value. For example, a dose that comprises "about 200 mg" of maribavir encompasses any amount of maribavir within a range of 180 mg to 220 mg.

As used herein, the term "administering" or "administration" typically refers to administration of a composition to a subject to achieve delivery of an active agent to a site of interest (e.g., a target site which may, in some embodiments, be a site of disease or damage, and/or a site of responsive processes, cells, tissues, etc.) As will be understood by those skilled in the art, reading the present disclosure, in some embodiments, one or more particular routes of administration may be feasible and/or useful in the practice of the present disclosure. In some embodiments, administration may be oral. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing.

The terms "treat" or "treating," as used herein, refers to partially or completely alleviating, inhibiting, ameliorating and/or relieving a disorder or condition, or one or more symptoms of the disorder or condition. As used herein, the terms "treatment," "treat," and "treating" refer to partially or completely alleviating, inhibiting, ameliorating and/or relieving a disorder or condition, or one or more symptoms of the disorder or condition, as described herein. In some embodiments, treatment may be administered after one or more symptoms have developed. In some embodiments, the term "treating" includes halting the progression of a disease or disorder. Treatment may also be continued after symptoms have resolved, for example to prevent or delay their recurrence. Thus, in some embodiments, the term "treating" includes preventing relapse or recurrence of a disease or disorder.

It will be understood that unit ratios of L/kg, kg/kg, etc. are expressions that, for each reagent/component/etc. described, are relative to the mass (in kilograms) of the limiting reagent (e.g., in each of Steps 1, 2, or 3 as defined and described herein).

Provided compounds may be synthesized according to the schemes described herein. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.).

It will be appreciated that any intermediate depicted in Schemes 4 or 5 may be isolated and/or purified prior to each subsequent step. Alternatively, any intermediate depicted in Schemes 4 or 5 may be utilized in subsequent steps without isolation and/or purification. Such telescoping of steps is contemplated in the present disclosure.

In some embodiments, compounds described herein may be purified by any means known in the art. In some embodiments, purification of a compound described herein comprises filtration, chromatography, distillation, crystallization, or a combination thereof. In some embodiments, chromatography comprises high performance liquid chromatography (HPLC). In some embodiments, chromatography comprises normal phase, reverse phase, or ion-exchange elution over a cartridge comprising suitable sorbent media. Purification via chromatography methods typically utilizes one or more solvents, which are known to the skilled artisan or determined by routine experimentation.

Step 1

In some embodiments, the present disclosure provides an improved synthesis of compound 2a:

2a

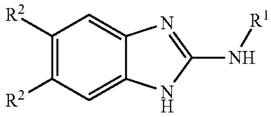

or a salt thereof, wherein $R^1$ and $R^2$ are as defined and described herein.

In some embodiments, the present disclosure provides an improved synthesis of compound 2:

2

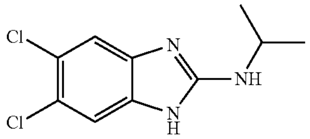

or a salt thereof.

As shown in Schemes 4 and 5, Step 1 is the first of three steps for preparing maribavir as disclosed herein. Any byproducts formed within Step 1 may be present in a provided composition, may further react to form additional byproducts, and/or may lower the overall yield or quality of maribavir. In some embodiments, the present disclosure provides methods of preparing compound 2, or a salt thereof, with reduced and/or low levels of impurities. Without wishing to be bound by a particular theory, a lower volume of reaction solvent (e.g., 1,4-dioxane) can allow for a more efficient conversion to compound 2, resulting in reduced and/or low levels of impurities. Additionally or alternatively, without wishing to be bound by a particular theory, provided crystallization step(s) can result in compound 2 with reduced and/or low levels of impurities.

In some embodiments, the present disclosure provides compositions comprising compound 2, or a salt thereof, and one or more of the following compounds:

9

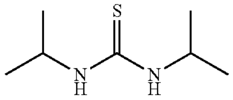

10

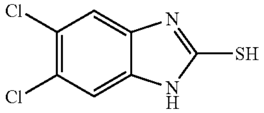

11

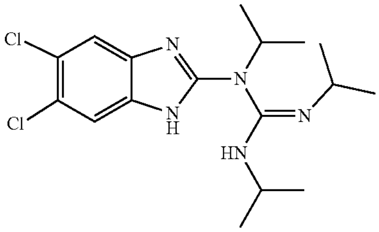

12

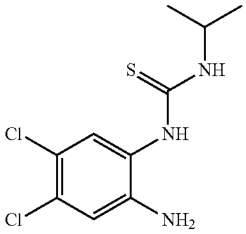

or salts thereof.

In some embodiments, provided compositions comprise compound 2, or a salt thereof, and compound 9, 10, 11, and/or 12, or salts thereof, in an amount of less than 1.00%, 0.5%, 0.1%, 0.05%, or 0.02% (w/w HPLC), relative to maribavir. In some embodiments, provided compositions comprise compound 2, or a salt thereof, and compound 9, 10, 11, and/or 12, or salts thereof, in an amount of less than 1.00%, 0.5%, 0.1%, 0.05%, or 0.02% (a/a HPLC), relative to maribavir.

In some embodiments, provided compositions comprise compound 2, or a salt thereof, and compound 9, or a salt thereof. In some embodiments, provided compositions comprise compound 2, or a salt thereof, and compound 9, or a salt thereof, in an amount of less than 1.00%, 0.5%, 0.1%, 0.05%, or 0.02% (w/w HPLC), relative to maribavir. In some embodiments, provided compositions comprise compound 2, or a salt thereof, and compound 9, or a salt thereof, in an amount of less than 1.00%, 0.5%, 0.1%, 0.05%, or 0.02% (a/a HPLC), relative to maribavir. In some embodiments, provided compositions comprise compound 2, or a salt thereof, wherein compound 9, or a salt thereof, is not detectable (e.g., by HPLC or $^1$H NMR).

In some embodiments, provided compositions comprise compound 2, or a salt thereof, and compound 10, or a salt thereof. In some embodiments, provided compositions comprise compound 2, or a salt thereof, and compound 10, or a salt thereof, in an amount of less than 1.00%, 0.5%, 0.1%, 0.05%, or 0.02% (w/w HPLC), relative to maribavir. In some embodiments, provided compositions comprise compound 2, or a salt thereof, and compound 10, or a salt thereof, in an amount of less than 1.00%, 0.5%, 0.1%, 0.05%, or 0.02% (a/a HPLC), relative to maribavir. In some embodiments, provided compositions comprise compound 2, or a salt thereof, wherein compound 10, or a salt thereof, is not detectable (e.g., by HPLC or $^1$H NMR).

In some embodiments, provided compositions comprise compound 2, or a salt thereof, and compound 11, or a salt thereof. In some embodiments, provided compositions comprise compound 2, or a salt thereof, and compound 11, or a salt thereof, in an amount of less than 1.00%, 0.5%, 0.1%, 0.05%, or 0.02% (w/w HPLC), relative to maribavir. In some embodiments, provided compositions comprise compound 2, or a salt thereof, and compound 11, or a salt thereof, in an amount of less than 1.00%, 0.5%, 0.1%, 0.05%, or 0.02% (a/a HPLC), relative to maribavir. In some embodiments, provided compositions comprise compound 2, or a salt thereof, wherein compound 11, or a salt thereof, is not detectable (e.g., by HPLC or $^1$H NMR).

In some embodiments, provided compositions comprise compound 2, or a salt thereof, and compound 12, or a salt thereof. In some embodiments, provided compositions comprise compound 2, or a salt thereof, and compound 12, or a salt thereof, in an amount of less than 1.00%, 0.5%, 0.1%, 0.05%, or 0.02% (w/w HPLC), relative to maribavir. In some embodiments, provided compositions comprise compound 2, or a salt thereof, and compound 12, or a salt thereof, in an amount of less than 1.00%, 0.5%, 0.1%, 0.05%, or 0.02% (a/a HPLC), relative to maribavir. In some embodiments, provided compositions comprise compound 2, or a salt thereof, wherein compound 12, or a salt thereof, is not detectable (e.g., by HPLC or $^1$H NMR).

In some embodiments, such compositions comprising compound 2, or salt thereof are prepared as described herein. In some embodiments, the present disclosure also provides the recognition that certain reagents (and amounts thereof) and/or reaction conditions may provide improved quality compound 2, or a salt thereof (e.g., with higher purity and/or minimal byproducts), and/or improve the yield of compound 2, or a salt thereof. In some embodiments, such improvements in yield or quality of compound 2, or a salt thereof, may also improve the yield or quality of maribavir. Without wishing to be bound to a particular theory, the present disclosure provides the recognition that incorporation of a crystallization and/or recrystallization into Step 1 may improve the yield, purity, and/or reduce the formation of byproducts (e.g., compounds 9, 10, 11, and 12).

In some embodiments, compound 2a, or a salt thereof, is prepared as shown in Step 1 of Scheme 4. In some embodiments, at Step 1, compound 2a, or a salt thereof, is prepared by a method comprising:

(a) reacting compound 5a:

5a

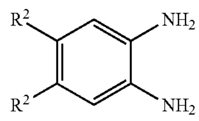

or a salt thereof, wherein each $R^2$ is independently halogen;

with compounds 6a and 7a:

6a

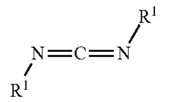

7a

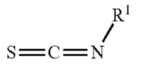

or salts thereof, wherein each $R^1$ is independently an optionally substituted group selected from $C_{1-6}$ aliphatic, 3- to 7-membered saturated or partially unsaturated carbocyclyl, 3- to 7-membered saturated or partially unsaturated heterocyclyl having 1-3 heteroatoms independently selected from nitrogen, oxygen, or sulfur, phenyl, or 5- to 6-membered heteroaryl having 1-3 heteroatoms independently selected from nitrogen, oxygen, or sulfur;

under suitable reaction conditions to provide compound 2a, or a salt thereof.

As generally defined above, each $R^2$ is independently halogen. In some embodiments, each $R^2$ is independently fluoro or chloro. In some embodiments, each $R^2$ is fluoro. In some embodiments, each $R^2$ is chloro.

As generally defined above, each $R^1$ is independently an optionally substituted group selected from $C_{1-6}$ aliphatic, 3- to 7-membered saturated or partially unsaturated carbocyclyl, 3- to 7-membered saturated or partially unsaturated heterocyclyl having 1-3 heteroatoms independently selected from nitrogen, oxygen, or sulfur, phenyl, or 5- to 6-membered heteroaryl having 1-3 heteroatoms independently selected from nitrogen, oxygen, or sulfur. In some embodiments, each $R^1$ is independently an optionally substituted group selected from $C_{1-6}$ aliphatic or 3- to 7-membered saturated or partially unsaturated carbocyclyl. In some embodiments, $R^1$ is an optionally substituted $C_{1-6}$ aliphatic. In some embodiments, $R^1$ is an optionally substituted $C_{1-3}$ aliphatic. In some embodiments, $R^1$ is an optionally substituted methyl, ethyl, n-propyl, isopropyl, n-butyl, s-butyl, or t-butyl. In some embodiments, $R^1$ is methyl, ethyl, n-propyl, isopropyl, n-butyl, s-butyl, or t-butyl. In some embodiments, $R^1$ is isopropyl. In some embodiments, $R^1$ is an optionally substituted group 3- to 7-membered saturated or partially unsaturated carbocyclyl. In some embodiments, $R^1$ is an optionally substituted cyclopropyl, cyclobutyl, cyclopentyl, or cyclohexyl. In some embodiments, $R^1$ is cyclopropyl, cyclobutyl, cyclopentyl, or cyclohexyl.

In some embodiments, compound 2, or a salt thereof, is prepared as shown in Step 1 of Scheme 5. In some embodiments, at Step 1, compound 2, or a salt thereof, is prepared by a method comprising:

(a) reacting compound 5:

5

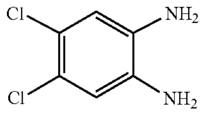

or a salt thereof, with compounds 6 and 7:

6

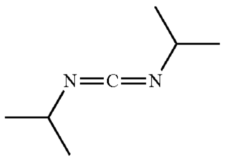

7

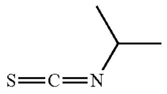

or salts thereof, under suitable reaction conditions to provide compound 2, or a salt thereof.

In some embodiments, Step 1 further provides one or more of the following compounds:

9

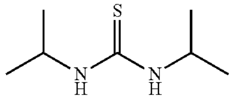

10

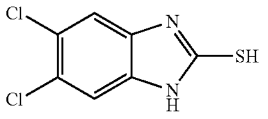

11

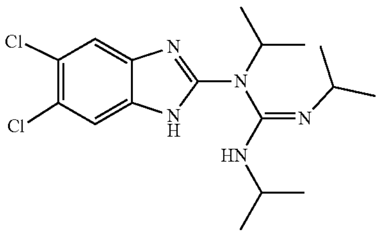

-continued

12

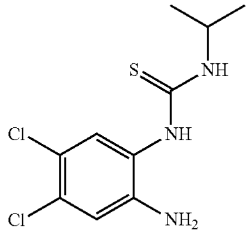

or salts thereof.

In some embodiments, Step 1 provides a composition comprising less than 1.00%, 0.5%, 0.1%, 0.05%, or 0.02% w/w of compound 9, relative to compound 2 (e.g., as measured by HPLC or $^1$H NMR). In some embodiments, Step 1 provides a composition comprising about 1.1%, about 0.9%, about 0.8%, about 0.7%, about 0.6%, about 0.5%, about 0.4%, about 0.3%, about 0.2%, about 0.1%, about 0.05%, or about 0.02% w/w of compound 9, relative to compound 2 (e.g., as measured by HPLC or $^1$H NMR). In some embodiments, Step 1 provides a composition comprising less than 1.00%, 0.5%, 0.1%, 0.05%, or 0.02% a/a of compound 9, relative to compound 2 (e.g., as measured by HPLC or $^1$H NMR). In some embodiments, Step 1 provides a composition comprising about 1.1%, about 0.9%, about 0.8%, about 0.7%, about 0.6%, about 0.5%, about 0.4%, about 0.3%, about 0.2%, about 0.1%, about 0.05%, or about 0.02% a/a of compound 9, relative to compound 2 (e.g., as measured by HPLC or $^1$H NMR). In some embodiments, Step 1 provides a composition wherein compound 9, or a salt thereof, is not detectable (e.g., by HPLC or $^1$H NMR).

In some embodiments, Step 1 provides a composition comprising less than 1.00%, 0.5%, 0.1%, 0.05%, or 0.02% (w/w HPLC) of compound 10, relative to compound 2. In some embodiments, Step 1 provides a composition comprising about 0.63%, about 0.5%, about 0.4%, about 0.3%, about 0.2%, about 0.11%, about 0.1%, about 0.08%, or about 0.05% (w/w HPLC) of compound 10, relative to compound 2. In some embodiments, Step 1 provides a composition comprising less than 1.00%, 0.5%, 0.1%, 0.05%, or 0.02% (a/a HPLC) of compound 10, relative to compound 2. In some embodiments, Step 1 provides a composition comprising about 0.63%, about 0.5%, about 0.4%, about 0.3%, about 0.2%, about 0.11%, about 0.1%, about 0.08%, or about 0.05% (a/a HPLC) of compound 10, relative to compound 2. In some embodiments, Step 1 provides a composition wherein compound 10, or a salt thereof, is not detectable (e.g., by HPLC or $^1$H NMR).

In some embodiments, Step 1 provides a composition comprising less than 1.00%, 0.5%, 0.1%, 0.05%, or 0.02% (w/w HPLC) of compound 11, relative to compound 2. In some embodiments, Step 1 provides a composition comprising about 1.00%, about 0.5%, about 0.1%, about 0.05%, or about 0.02% (w/w HPLC) of compound 11, relative to compound 2. In some embodiments, Step 1 provides a composition comprising less than 1.00%, 0.5%, 0.1%, 0.05%, or 0.02% (a/a HPLC) of compound 11, relative to compound 2. In some embodiments, Step 1 provides a composition comprising about 1.00%, about 0.5%, about 0.1%, about 0.05%, or about 0.02% (a/a HPLC) of compound 11, relative to compound 2. In some embodiments, Step 1 provides a composition wherein compound 11, or a salt thereof, is not detectable (e.g., by HPLC or $^1$H NMR).

In some embodiments, Step 1 provides a composition comprising less than 1.00%, 0.5%, 0.1%, 0.05%, or 0.02% (w/w HPLC) of compound 12, relative to compound 2. In some embodiments, Step 1 provides a composition comprising about 1.00%, about 0.5%, about 0.1%, about 0.05%, or about 0.02% (w/w HPLC) of compound 12, relative to compound 2. In some embodiments, Step 1 provides a composition comprising less than 1.00%, 0.5%, 0.1%, 0.05%, or 0.02% (a/a HPLC) of compound 12, relative to compound 2. In some embodiments, Step 1 provides a composition comprising about 1.00%, about 0.5%, about 0.1%, about 0.05%, or about 0.02% (a/a HPLC) of compound 12, relative to compound 2. In some embodiments, Step 1 provides a composition wherein compound 12, or a salt thereof, is not detectable (e.g., by HPLC or $^1$H NMR).

In some embodiments, Step 1 provides a composition as provided in any one of Tables 4-1 to 4-6 in Example 4.

In some embodiments, compound 6, or a salt thereof, is present in an amount between about 0.50 to 1.50 equivalents relative to compound 5, or a salt thereof. In some embodiments, compound 6, or a salt thereof, is present in an amount between about 0.70 to 1.30 equivalents relative to compound 5, or a salt thereof. In some embodiments, compound 6, or a salt thereof, is present in an amount between about 0.70 to 1.10 equivalents relative to compound 5, or a salt thereof. In some embodiments, compound 6, or a salt thereof, is present in an amount between about 0.70 to 0.90 equivalents relative to compound 5, or a salt thereof. In some embodiments, compound 6, or a salt thereof, is present in an amount between about 0.90 to 1.30 equivalents relative to compound 5, or a salt thereof. In some embodiments, compound 6, or a salt thereof, is present in an amount between about 1.10 to 1.30 equivalents relative to compound 5, or a salt thereof. In some embodiments, compound 6, or a salt thereof, is present in an amount between about 0.80 to 1.20 equivalents relative to compound 5, or a salt thereof. In some embodiments, compound 6, or a salt thereof, is present in an amount between about 0.95 to 1.10 equivalents relative to compound 5, or a salt thereof. In some embodiments, compound 6, or a salt thereof, is present in an amount between about 1.00 to 1.10 equivalents relative to compound 5, or a salt thereof. In some embodiments, compound 6, or a salt thereof, is present in an amount between about 0.95 to 1.05 equivalents relative to compound 5, or a salt thereof. In some embodiments, compound 6, or a salt thereof, is present at an amount of about 0.90 to about 1.09 equivalents relative to compound 5, or a salt thereof. In some embodiments, compound 6, or a salt thereof, is present at an amount of about 1.00 equivalents relative to compound 5, or a salt thereof. In some embodiments, compound 6, or a salt thereof, is present at an amount of about 0.99, 1.00, 1.01, 1.02, 1.03, 1.04, 1.05, 1.06, 1.07, 1.08, or 1.09 equivalents relative to compound 5, or a salt thereof. In some embodiments, compound 6, or a salt thereof, is present at an amount of about 1.02 equivalents relative to compound 5, or a salt thereof. In some embodiments, compound 6, or a salt thereof, is present at an amount of about 1.04 equivalents relative to compound 5, or a salt thereof. In some embodiments, compound 6, or a salt thereof, is present at an amount of about 1.06 equivalents relative to compound 5, or a salt thereof.

In some embodiments, compound 7, or a salt thereof, is present in an amount between about 0.50 to 1.50 equivalents relative to compound 5, or a salt thereof. In some embodiments, compound 7, or a salt thereof, is present in an amount between about 0.70 to 1.30 equivalents relative to compound 5, or a salt thereof. In some embodiments, compound 7, or a salt thereof, is present in an amount between about 0.70 to 1.10 equivalents relative to compound 5, or a salt thereof. In some embodiments, compound 7, or a salt thereof, is present in an amount between about 0.70 to 0.90 equivalents relative to compound 5, or a salt thereof. In some embodiments, compound 7, or a salt thereof, is present in an amount between about 0.90 to 1.30 equivalents relative to compound 5, or a salt thereof. In some embodiments, compound 7, or a salt thereof, is present in an amount between about 0.95 to 1.15 equivalents relative to compound 5, or a salt thereof. In some embodiments, compound 7, or a salt thereof, is present in an amount between about 0.90 to 1.20 equivalents relative to compound 5, or a salt thereof. In some embodiments, compound 7, or a salt thereof, is present in an amount between about 1.00 to 1.15 equivalents relative to compound 5, or a salt thereof. In some embodiments, compound 7, or a salt thereof, is present at an amount of about 1.03 to about 1.13 equivalents relative to compound 5, or a salt thereof. In some embodiments, compound 7, or a salt thereof, is present in an amount between about 1.05 to 1.10 equivalents relative to compound 5, or a salt thereof. In some embodiments, compound 7, or a salt thereof, is present at an amount of about 1.05, 1.06, 1.07, 1.08, 1.09, 1.10, 1.11, or 1.12 equivalents relative to compound 5, or a salt thereof. In some embodiments, compound 7, or a salt thereof, is present at an amount of about 1.06 equivalents relative to compound 5, or a salt thereof. In some embodiments, compound 7, or a salt thereof, is present at an amount of about 1.08 equivalents relative to compound 5, or a salt thereof. In some embodiments, compound 7, or a salt thereof, is present at an amount of about 1.10 equivalents relative to compound 5, or a salt thereof.

In some embodiments, reaction conditions comprise a solvent. In some embodiments, the solvent is or comprises acetone, acetonitrile, 1,2-dimethoxyethane, 1,4-dioxane, N,N-dimethylformamide, N,N-dimethylacetamide, N-methylpyrrolidinone, dimethylsulfoxide, ethyl acetate, isopropyl acetate, pyridine, sulfolane, tetrahydrofuran, 2-methyltetrahydrofuran, toluene, benzene, α,α,α-trifluorotoluene, chlorobenzene, xylene, tert-butyl methyl ether, or cyclopentyl methyl ether. In some embodiments, the solvent is or comprises acetone. In some embodiments, the solvent is or comprises acetonitrile. In some embodiments, the solvent is or comprises 1,2-dimethoxyethane. In some embodiments, the solvent is or comprises N,N-dimethylformamide. In some embodiments, the solvent is or comprises N,N-dimethylacetamide. In some embodiments, the solvent is or comprises N-methylpyrrolidinone. In some embodiments, the solvent is or comprises dimethylsulfoxide. In some embodiments, the solvent is or comprises ethyl acetate. In some embodiments, the solvent is or comprises isopropyl acetate. In some embodiments, the solvent is or comprises pyridine. In some embodiments, the solvent is or comprises sulfolane. In some embodiments, the solvent is or comprises tetrahydrofuran. In some embodiments, the solvent is or comprises 2-methyltetrahydrofuran. In some embodiments, the solvent is or comprises toluene. In some embodiments, the solvent is or comprises benzene. In some embodiments, the solvent is or comprises α,α,α-trifluorotoluene. In some embodiments, the solvent is or comprises chlorobenzene. In some embodiments, the solvent is or comprises xylene. In some embodiments, the solvent is or comprises tert-butyl methyl ether. In some embodiments, the solvent is or comprises cyclopentyl methyl ether. In some embodiments, the solvent is or comprises 1,4-dioxane.

In some embodiments, the solvent is present in an amount between about 1.0 L/kg and about 20.0 L/kg. In some embodiments, the solvent is present in an amount between about 5.0 L/kg and about 20.0 L/kg. In some embodiments, the solvent is present in an amount between about 5.0 L/kg and about 15.0 L/kg. In some embodiments, the solvent is present in an amount between about 5.0 L/kg and about 12.0 L/kg. In some embodiments, the solvent is present in an amount between about 5.0 L/kg and about 10.0 L/kg. In some embodiments, the solvent is present in an amount between about 5.0 L/kg and about 8.0 L/kg. In some embodiments, the solvent is present in an amount between about 5.0 L/kg and about 6.0 L/kg. In some embodiments, the solvent is present in an amount between about 1.0 L/kg and about 5.0 L/kg. In some embodiments, the solvent is present in an amount between about 2.0 L/kg and about 5.0 L/kg. In some embodiments, the solvent is present in an amount between about 3.0 L/kg and about 5.0 L/kg. In some embodiments, the solvent is present in an amount between about 4.0 L/kg and about 5.0 L/kg. In some embodiments, the solvent is present in an amount between about 2.0 L/kg and about 8.0 L/kg. In some embodiments, the solvent is present in an amount between about 3.0 L/kg and about 7.0 L/kg. In some embodiments, the solvent is present in an amount between about 4.0 L/kg and about 6.0 L/kg. In some embodiments, the solvent is present in an amount of about 1.0 L/kg, 2.0 L/kg, 3.0 L/kg, 4.0 L/kg, 5.0 L/kg, 6.0 L/kg, 7 L/kg, 8 L/kg, 9 L/kg, or 10 L/kg. In some embodiments, the solvent is present in an amount of about 5.0 L/kg. In some embodiments, the solvent is present in an amount of about 4.0 L/kg. In some embodiments, the solvent is present in an amount of about 6.0 L/kg.

In some embodiments, reaction conditions comprise heating to a temperature $T_7$. In embodiments, the temperature $T_7$ is between about 50° C. and about 150° C. In embodiments, the temperature $T_7$ is between about 50° C. and about 130° C. In embodiments, the temperature $T_7$ is between about 50° C. and about 110° C. In embodiments, the temperature $T_7$ is between about 50° C. and about 100° C. In embodiments, the temperature $T_7$ is between about 60° C. and about 150° C. In embodiments, the temperature $T_7$ is between about 80° C. and about 150° C. In embodiments, the temperature $T_7$ is between about 100° C. and about 150° C. In some embodiments, the temperature $T_7$ is about 50° C., 55° C., 60° C., 65° C., 70° C., 75° C., 80° C., 85° C., 90° C., 95° C., 105° C., 110° C., 115° C., 120° C., 125° C., 130° C., 135° C., 140° C., 145° C., or 150° C. In some embodiments, the temperature $T_7$ is about 90° C. In some embodiments, the temperature $T_7$ is about 95° C. In some embodiments, the temperature $T_7$ is about 100° C. In some embodiments, the temperature $T_7$ is about 105° C. In some embodiments, the temperature $T_7$ is about 110° C. In some embodiments, the temperature $T_7$ is about 115° C. In some embodiments, the temperature $T_7$ is about 120° C.

In some embodiments, reaction conditions comprise maintaining the reaction at temperature $T_7$ for a period of time. In some embodiments, the period of time is at least 12 hrs. In some embodiments, the period of time is at least 24 hrs. In some embodiments, the period of time is at least 48 hrs. In some embodiments, the period of time is between about 2 hrs and about 20 hrs. In some embodiments, the period of time is between about 3 hrs and about 20 hrs. In some embodiments, the period of time is between about 4 hrs and about 20 hrs. In some embodiments, the period of time is between about 5 hrs and about 20 hrs. In some embodiments, the period of time is between about 7.5 hrs and about 20 hrs. In some embodiments, the period of time is between about 10 hrs and about 20 hrs. In some embodiments, the period of time is between about 11 hrs and about 20 hrs. In some embodiments, the period of time is between about 12 hrs and about 20 hrs. In some embodiments, the period of time is between about 13 hrs and about 20 hrs. In some embodiments, the period of time is between about 14 hrs and about 20 hrs. In some embodiments, the period of time is between about 14 hrs and about 19 hrs. In some embodiments, the period of time is between about 14 hrs and about 18 hrs. In some embodiments, the period of time is between about 14 hrs and about 17 hrs. In some embodiments, the period of time is between about 14 hrs and about 16 hrs. In some embodiments, the period of time is between about 14 hrs and about 15 hrs.

In some embodiments, e.g., after the reaction is performed, Step 1 further comprises (b) cooling the reaction mixture.

In some embodiments, after heating to a temperature $T_7$, the reaction conditions further comprise cooling to a temperature $T_8$. In some embodiments, the temperature $T_8$ is between about 50° C. and about 110° C. In some embodiments, the temperature $T_8$ is between about 50° C. and about 100° C. In some embodiments, the temperature $T_8$ is between about 50° C. and about 90° C. In some embodiments, the temperature $T_8$ is between about 50° C. and about 85° C. In some embodiments, the temperature $T_8$ is between about 50° C. and about 80° C. In some embodiments, the temperature $T_8$ is between about 65° C. and about 110° C. In some embodiments, the temperature $T_8$ is between about 75° C. and about 110° C. In some embodiments, the temperature $T_8$ is between about 60° C. and about 100° C. In some embodiments, the temperature $T_8$ is between about 70° C. and about 90° C. In some embodiments, the temperature $T_8$ is between about 75° C. and about 85° C. In some embodiments, the temperature $T_8$ is between about 75° C. and about 80° C. In some embodiments, the temperature $T_8$ is between about 80° C. and about 85° C. In some embodiments, the temperature $T_8$ is about 50° C., 55° C., 60° C., 65° C., 70° C., 75° C., 80° C., 85° C., 90° C., 95° C., 105° C., or 110° C. In some embodiments, the temperature $T_8$ is about 80° C. In some embodiments, the temperature $T_8$ is about 75° C. In some embodiments, the temperature $T_8$ is about 85° C.

In some embodiments, a reaction mixture is cooled to temperature $T_8$ at a rate of between about 2° C./hr and about 20° C./hr. In some embodiments, a reaction mixture is cooled to temperature $T_8$ at a rate of between about 2° C./hr and about 17.5° C./hr. In some embodiments, a reaction mixture is cooled to temperature $T_8$ at a rate of between about 2° C./hr and about 15° C./hr. In some embodiments, a reaction mixture is cooled to temperature $T_8$ at a rate of between about 2° C./hr and about 12.5° C./hr. In some embodiments, a reaction mixture is cooled to temperature $T_8$ at a rate of between about 2° C./hr and about 10° C./hr. In some embodiments, a reaction mixture is cooled to temperature $T_8$ at a rate of between about 2° C./hr and about 7.5° C./hr. In some embodiments, a reaction mixture is cooled to temperature $T_8$ at a rate of between about 5° C./hr and about 20° C./hr. In some embodiments, a reaction mixture is cooled to temperature $T_8$ at a rate of between about 7.5° C./hr and about 20° C./hr. In some embodiments, a reaction mixture is cooled to temperature $T_8$ at a rate of between about 10° C./hr and about 20° C./hr. In some embodiments, a reaction mixture is cooled to temperature $T_8$ at a rate of between about 4° C./hr and about 17.5° C./hr. In some embodiments, a reaction mixture is cooled to temperature $T_8$ at a rate of between about 4° C./hr and about 15° C./hr. In some embodiments, a reaction mixture is cooled to temperature $T_8$ at a rate of between about 4° C./hr and about 12.5° C./hr. In some embodiments, a reaction mixture is cooled to temperature $T_8$ at a rate of between about 5° C./hr and about 10° C./hr. In some embodiments, a reaction mixture is cooled to temperature $T_8$ at a rate of between about 6° C./hr and about 8° C./hr. In some embodiments, a reaction mixture is cooled to $T_8$ at a rate of about 2.0° C./hr, 3.0° C./hr, 4.0° C./hr, 5.0° C./hr, 6.0° C./hr, 7.0° C./hr, 8.0° C./hr, 9.0° C./hr, or 10.0° C./hr. In some embodiments, a reaction mixture is cooled to temperature $T_8$ at a rate of about 6.5° C./hr. In some embodiments, a reaction mixture is cooled to temperature $T_8$ at a rate of about 6.5° C./hr. In some embodiments, a reaction mixture is cooled to temperature $T_8$ at a rate of about 7.0° C./hr.

In some embodiments, a reaction (e.g., presence of compound 5 or compound 2) is monitored for completion by HPLC. In some embodiments, a reaction is monitored for presence of compound 5 or compound 2 (e.g., a/a by HPLC).

In some embodiments, a reaction is determined to be complete when less than 25% a/a of compound 5, or a salt thereof, is detected (e.g., by HPLC). In some embodiments, a reaction is determined to be complete when less than 10% a/a of compound 5, or a salt thereof, is detected (e.g., by HPLC). In some embodiments, a reaction is determined to be complete when less than 5% a/a of compound 5, or a salt thereof, is detected (e.g., by HPLC). In some embodiments, a reaction is determined to be complete when less than 4% a/a of compound 5, or a salt thereof, is detected (e.g., by HPLC). In some embodiments, a reaction is determined to be complete when less than 3% a/a of compound 5, or a salt thereof, is detected (e.g., by HPLC). In some embodiments, a reaction is determined to be complete when less than 2% a/a of compound 5, or a salt thereof, is detected (e.g., by HPLC). In some embodiments, a reaction is determined to be complete when less than 1% a/a of compound 5, or a salt thereof, is detected (e.g., by HPLC).

In some embodiments, Step 1 further comprises a step of (c) crystallization of compound 2, or a salt thereof (e.g., from the reaction mixture). In some embodiments, the present disclosure provides the recognition that a crystallization may provide a higher yield and/or purity of compound 2, or a salt thereof, and/or provide compound 2, or a salt thereof, e.g., with low levels or undetectable levels of byproducts (e.g., compounds 9, 10, 11, or 12, or salts thereof), in particular when the reaction is scaled-up. Without wishing to be bound to a particular theory, it is thought that compound 2, or a salt thereof, crystalizes out at a different temperature than a byproduct (e.g., compounds 9, 10, 11, or 12, or salts thereof). Accordingly, without wishing to be bound to a particular theory, it is thought that performing the crystallization at particular temperatures and/or controlling the cooling rate of the reaction may provide a higher yield and/or purity of compound 2, or a salt thereof, and/or provide compound 2, or a salt thereof, e.g., with reduced or undetectable levels of byproducts (e.g., compounds 9, 10, 11, or 12, or salts thereof).

In some embodiments, crystallization of compound 2, or a salt thereof, comprises providing a primary mixture, wherein the primary mixture comprises compound 2, or a salt thereof, and a primary solvent. In some embodiments, the primary mixture is provided at temperature $T_8$.

In some embodiments, the primary solvent is or comprises acetone, acetonitrile, dichloromethane, 1,2-dichloroethane, 1,2-dimethoxyethane, 1,4-dioxane, N,N-dimethylformamide, N,N-dimethylacetamide, N-methylpyrrolidinone, dimethylsulfoxide, ethyl acetate, isopropyl acetate, pyridine, sulfolane, tetrahydrofuran, 2-methyltetrahydrofuran, toluene, benzene, α,α,α-trifluorotoluene, chlorobenzene, xylene, tert-butyl methyl ether, or cyclopentyl methyl ether. In some embodiments, the primary solvent is or comprises acetone. In some embodiments, the primary solvent is or comprises acetonitrile. In some embodiments, the primary solvent is or comprises dichloromethane. In some embodiments, the primary solvent is or comprises 1,2-dichloroethane. In some embodiments, the primary solvent is or comprises 1,2-dimethoxyethane. In some embodiments, the primary solvent is or comprises N,N-dimethylformamide. In some embodiments, the primary solvent is or comprises N,N-dimethylacetamide. In some embodiments, the primary solvent is or comprises N-methylpyrrolidinone. In some embodiments, the primary solvent is or comprises dimethylsulfoxide. In some embodiments, the primary solvent is or comprises ethyl acetate. In some embodiments, the primary solvent is or comprises isopropyl acetate. In some embodiments, the solvent is or comprises pyridine. In some embodiments, the primary solvent is or comprises sulfolane. In some embodiments, the solvent is or comprises tetrahydrofuran. In some embodiments, the primary solvent is or comprises 2-methyltetrahydrofuran. In some embodiments, the primary solvent is or comprises toluene. In some embodiments, the primary solvent is benzene. In some embodiments, the primary solvent is or comprises α,α,α-trifluorotoluene. In some embodiments, the primary solvent is or comprises chlorobenzene. In some embodiments, the primary solvent is or comprises xylene. In some embodiments, the primary solvent is or comprises tert-butyl methyl ether. In some embodiments, the primary solvent is or comprises cyclopentyl methyl ether. In some embodiments, the primary solvent is or comprises 1,4-dioxane.

In some embodiments, the primary solvent is present at an amount of about 1.0 L/kg to 10.0 L/kg of solute. In some embodiments, the primary solvent is present at an amount of about 1.0 L/kg to 8.0 L/kg of solute. In some embodiments, the primary solvent is present at an amount of about 1.0 L/kg to 6.0 L/kg of solute. In some embodiments, the primary solvent is present at an amount of about 1.0 L/kg to 4.0 L/kg of solute. In some embodiments, the primary solvent is present at an amount of about 2.0 L/kg to 10.0 L/kg of solute. In some embodiments, the primary solvent is present at an amount of about 4.0 L/kg to 10 L/kg of solute. In some embodiments, the primary solvent is present at an amount of about 6.0 L/kg to 10 L/kg of solute. In some embodiments, the primary solvent is present at an amount of about 2.0 L/kg to 8.0 L/kg of solute. In some embodiments, the primary solvent is present at an amount of about 4.0 L/kg to 6.0 L/kg of solute. In some embodiments, the primary solvent is present at an amount of about 1.0 L/kg, 2.0 L/kg, 3.0 L/kg, 4.0 L/kg, 5.0 L/kg, 6.0 L/kg, 7.0 L/kg, 8.0 L/kg, 9.0 L/kg, or 10.0 L/kg. In some embodiments, the primary solvent is present at an amount of about 3.0 L/kg, 4.0 L/kg, 5.0 L/kg, 6.0, or 7.0 L/kg. In some embodiments, the primary solvent is present at an amount of about 3.0 L/kg of solute. In some embodiments, the primary solvent is present at an amount of about 4.0 L/kg of solute. In some embodiments, the primary solvent is present at an amount of about 4.9 L/kg of solute. In some embodiments, the primary solvent is present at an amount of about 5.0 L/kg of solute. In some embodiments, the primary solvent is present at an amount of about 6.0 L/kg of solute.

In some embodiments, crystallization of compound 2, or a salt thereof, comprises adding a seed crystal to the primary mixture. In some embodiments, the seed crystal is added in an amount between about 0.01 wt % and about 5.0 wt % of compound 5, or a salt thereof. In some embodiments, the seed crystal is added in an amount between about 0.1 wt % and about 5.0 wt % of compound 5, or a salt thereof. In some embodiments, the seed crystal is added in an amount between about 0.1 wt % and about 4.0 wt % of compound 5, or a salt thereof. In some embodiments, the seed crystal is added in an amount between about 0.1 wt % and about 3.0 wt % of compound 5, or a salt thereof. In some embodiments, the seed crystal is added in an amount between about 0.1 wt % and about 2.0 wt % of compound 5, or a salt thereof. In some embodiments, the seed crystal is added in an amount between about 0.1 wt % and about 1.5 wt % of compound 5, or a salt thereof. In some embodiments, the seed crystal is added in an amount between about 0.10 wt % and about 1.00 wt % of compound 5, or a salt thereof. In some embodiments, the seed crystal is added in an amount between about 0.1 wt % and about 0.75 wt % of compound 5, or a salt thereof. In some embodiments, the seed crystal is added in an amount between about 0.1 wt % and about 0.50 wt % of compound 5, or a salt thereof. In some embodiments, the seed crystal is added in an amount between about 0.1 wt % and about 0.40 wt % of compound 5, or a salt thereof. In some embodiments, the seed crystal is added in an amount between about 0.1 wt % and about 0.30 wt % of compound 5, or a salt thereof. In some embodiments, the seed crystal is added in an amount between about 0.1 wt % and about 0.25 wt % of compound 5, or a salt thereof. In some embodiments, the seed crystal is added in an amount between about 0.20 wt % and about 1.00 wt % of compound 5, or a salt thereof. In some embodiments, the seed crystal is added in an amount between about 0.25 wt % and about 1.00 wt % of compound 5, or a salt thereof. In some embodiments, the seed crystal is added in an amount between about 0.50 wt % and about 1.00 wt % of compound 5, or a salt thereof. In some embodiments, the seed crystal is added in an amount of about 0.10 wt %, 0.15 wt %, 0.20 wt %, 0.25 wt %, 0.30 wt %, 0.35 wt %, 0.40 wt %, 0.45 wt %, or 0.50 wt % of compound 5, or a salt thereof.

In some embodiments, the seed crystal is added in an amount of about 0.05 wt % of compound 5, or a salt thereof. In some embodiments, the seed crystal is added in an amount of about 0.10 wt % of compound 5, or a salt thereof. In some embodiments, the seed crystal is added in an amount of about 0.15 wt % of compound 5, or a salt thereof. In some embodiments, the seed crystal is added in an amount of about 0.20 wt % of compound 5, or a salt thereof. In some embodiments, the seed crystal is added in an amount of about 0.25 wt % of compound 5, or a salt thereof. In some embodiments, the seed crystal is added in an amount of about 0.30 wt % of compound 5, or a salt thereof. In some embodiments, the seed crystal is added in an amount of about 0.35 wt % of compound 5, or a salt thereof. In some embodiments, the seed crystal is added in an amount of about 0.45 wt % of compound 5, or a salt thereof. In some embodiments, the seed crystal is compound 2, or a salt thereof.

In some embodiments, crystallization of compound 2, or a salt thereof, comprises cooling the primary mixture to a temperature $T_9$. In some embodiments, temperature $T_9$ is between about 0° C. and about 50° C. In some embodiments, temperature $T_9$ is between about 0° C. and about 45° C. In some embodiments, temperature $T_9$ is between about 0° C. and about 40° C. In some embodiments, temperature $T_9$ is between about 0° C. and about 35° C. In some embodiments, temperature $T_9$ is between about 0° C. and about 30° C. In some embodiments, temperature $T_9$ is between about 0° C. and about 25° C. In some embodiments, temperature $T_9$ is between about 10° C. and about 50° C. In some embodiments, temperature $T_9$ is between about 15° C. and about 50° C. In some embodiments, temperature $T_9$ is between about 20° C. and about 50° C. In some embodiments, temperature $T_9$ is between about 25° C. and about 50° C. In some embodiments, temperature $T_9$ is between about 15° C. and about 40° C. In some embodiments, temperature $T_9$ is between about 20° C. and about 35° C. In some embodiments, temperature $T_9$ is between about 18° C. and about 32° C. In some embodiments, temperature $T_9$ is between about 20° C. and about 35° C. In some embodiments, temperature $T_9$ is between about 25° C. and about 30° C. In some embodiments, temperature $T_9$ is between about 26° C. and about 28° C. In some embodiments, the temperature $T_9$ is about 22° C., 23° C., 24° C., 25° C., 26° C., 27° C., 28° C., 29° C., 30° C., 31° C., or 32° C. In some embodiments, the temperature $T_9$ is about 24° C. In some embodiments, the temperature $T_9$ is about 25° C. In some embodiments, the temperature $T_9$ is about 26° C. In some embodiments, the temperature $T_9$ is about 27° C. In some embodiments, the temperature $T_9$ is about 29° C. In some embodiments, the temperature $T_9$ is about 30° C. In some embodiments, the temperature $T_9$ is about 31° C.

In some embodiments, the primary mixture is cooled at a rate of between about 2.0° C./hr and about 20° C./hr. In some embodiments, the primary mixture is cooled to temperature $T_9$ at a rate of between about 4.0° C./hr and about 20° C./hr. In some embodiments, the reaction mixture is cooled to temperature $T_9$ at a rate of between about 6° C./hr and about 20° C./hr. In some embodiments, the reaction mixture is cooled to temperature $T_9$ at a rate of between about 8° C./hr and about 20° C./hr. In some embodiments, the reaction mixture is cooled to temperature $T_9$ at a rate of between about 2.0° C./hr and about 15° C./hr. In some embodiments, the reaction mixture is cooled to temperature $T_9$ at a rate of between about 2.0° C./hr and about 10° C./hr. In some embodiments, the reaction mixture is cooled to temperature $T_9$ at a rate of between about 2.0° C./hr and about 8.0° C./hr. In some embodiments, the reaction mixture is cooled to temperature $T_9$ at a rate of between about 4.0° C./hr and about 12.0° C./hr. In some embodiments, the reaction mixture is cooled to temperature $T_9$ at a rate of between about 5.0° C./hr and about 12.0° C./hr. In some embodiments, the reaction mixture is cooled to temperature $T_9$ at a rate of between about 5.0° C./hr and about 10.0° C./hr. In some embodiments, the reaction mixture is cooled to temperature $T_9$ at a rate of between about 5.0° C./hr and about 8.0° C./hr. In some embodiments, the reaction mixture is cooled to temperature $T_9$ at a rate of between about 6.0° C./hr and about 7.0° C./hr. In some embodiments, the reaction mixture is cooled to temperature $T_9$ at a rate of about 2.0° C./hr, 3.0° C./hr, 4.0° C./hr, 5.0° C./hr, 6.0° C./hr, 7.0° C./hr, 8.0° C./hr, 9.0° C./hr, or 10.0° C./hr. In some embodiments, the reaction mixture is cooled to temperature $T_9$ at a rate of about 5.5° C./hr. In some embodiments, the reaction mixture is cooled to temperature $T_9$ at a rate of about 6.0° C./hr. In some embodiments, the primary mixture is cooled to temperature $T_9$ at a rate of about 6.5° C./hr. In some embodiments, the reaction mixture is cooled to temperature $T_9$ at a rate of about 7.0° C./hr. In some embodiments, the reaction mixture is cooled to temperature $T_9$ at a rate of about 7.5° C./hr.

In some embodiments, Step 1 further comprises a step of (d) recrystallization of compound 2, or a salt thereof (e.g., from the reaction mixture or the primary mixture). In some embodiments, the present disclosure provides the recognition that a recrystallization may provide a higher yield and/or purity of compound 2, or a salt thereof, and/or provide compound 2, or a salt thereof, e.g., with reduced or undetectable levels of byproducts (e.g., compounds 9, 10, 11, and/or 12, or salts thereof), in particular when the reaction is scaled-up. In some embodiments, recrystallization conditions provided herein may provide a higher yield and/or purity of compound 2, or a salt thereof, and/or provide compound 2, or a salt thereof, e.g., with reduced or undetectable levels of byproducts (e.g., compounds 9, 10, 11, and/or 12, or salts thereof).

In some embodiments, recrystallization of compound 2, or a salt thereof, comprises (i) providing a primary mixture, wherein the primary mixture comprises compound 2, or a salt thereof, and a primary solvent, wherein the primary solvent is as described above and herein.

In some embodiments, the primary mixture is provided at the temperature $T_9$, wherein temperature $T_9$ is as described above and herein.

In some embodiments, the primary solvent is as described above and herein.

In some embodiments, recrystallization of compound 2, or a salt thereof, further comprises (ii) adding a secondary solvent to the primary mixture to form a secondary mixture. In some embodiments, the secondary solvent is or comprises chloroform, hexane, pentane, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the secondary solvent is or comprises chloroform. In some embodiments, the secondary solvent is or comprises hexane. In some embodiments, the secondary solvent is or comprises pentane. In some embodiments, the secondary solvent is or comprises diethyl ether. In some embodiments, the secondary solvent is or comprises ethyl acetate. In some embodiments, the secondary solvent is or comprises isopropyl acetate. In some embodiments, the secondary solvent is or comprises tert-butyl methyl ether. In some embodiments, the secondary solvent is or comprises cyclopentyl methyl ether. In some embodiments, the secondary solvent is or comprises toluene. In some embodiments, the secondary solvent is or comprises benzene. In some embodiments, the secondary solvent is or comprises α,α,α-trifluorotoluene. In some embodiments, the secondary solvent is or comprises chlorobenzene. In some embodiments, the secondary solvent is or comprises xylene. In some embodiments, the secondary solvent is or comprises dichloromethane.

In some embodiments, the secondary solvent is present at an amount between about 1 L/kg and about 20 L/kg of solute. In some embodiments, the secondary solvent is present at an amount between about 2 L/kg and about 20 L/kg of solute. In some embodiments, the secondary solvent is present at an amount between about 6 L/kg and about 20 L/kg of solute. In some embodiments, the secondary solvent is present at an amount between about 10 L/kg and about 20 L/kg of solute. In some embodiments, the secondary solvent is present at an amount between about 2 L/kg and about 18 L/kg of solute. In some embodiments, the secondary solvent is present at an amount between about 2 L/kg and about 14 L/kg of solute. In some embodiments, the secondary solvent is present at an amount between about 2 L/kg and about 10 L/kg of solute. In some embodiments, the secondary solvent is present at an amount between about 4 L/kg and about 18 L/kg of solute. In some embodiments, the secondary solvent is present at an amount between about 6 L/kg and about 14 L/kg of solute. In some embodiments, the secondary solvent is present at an amount between about 8 L/kg and about 12 L/kg of solute. In some embodiments, the secondary solvent is present at an amount between about 9 L/kg and about 11 L/kg of solute. In some embodiments, the secondary solvent is present at an amount of about 5 L/kg, 6 L/kg, 7 L/kg, 8 L/kg, 9 L/kg, 10 L/kg, 11 L/kg, 12 L/kg, 13 L/kg, 14 L/kg, or 15 L/kg, of solute. In some embodiments, the secondary solvent is present at an amount of about 8 L/kg of solute. In some embodiments, the secondary solvent is present at an amount of about 9 L/kg of solute. In some embodiments, the secondary solvent is present at an amount of about 10 L/kg of solute. In some embodiments, the secondary solvent is present at an amount of about 11 L/kg of solute. In some embodiments, the secondary solvent is present at an amount of about 12 L/kg of solute.

In some embodiments, recrystallization of compound 2, or a salt thereof, further comprises (iii) holding and optionally agitating the secondary mixture at temperature $T_9$ for a period of time. In some embodiments, the secondary mixture is agitated at temperature $T_9$ for the period of time. In some embodiments, the period of time is at least 1 hr. In some embodiments, the period of time is at least 3 hrs. In some embodiments, the period of time is at least 6 hrs. In some embodiments, the period of time is between about 1 hr and about 8 hrs. In some embodiments, the period of time is between about 2 hrs and about 6 hrs. In some embodiments, the period of time is between about 2 hrs and about 5 hrs. In some embodiments, the period of time is between about 2 hrs and about 4 hrs. In some embodiments, the period of time is about 1 hr, 2 hrs, 3, hrs, 4 hrs, or 5 hrs. In some embodiments, the period of time is about 1 hrs. In some embodiments, the period of time is about 2 hrs. In some embodiments, the period of time is about 3 hrs. In some embodiments, the period of time is about 4 hrs. In some embodiments, the period of time is about 5 hrs.

In some embodiments, Step 1 further comprises a step of (e) filtering (e.g., the reaction mixture, primary mixture, or secondary mixture) to provide a filtered mixture.

In some embodiments, the secondary mixture is filtered at a temperature $T_{10}$. In some embodiments, temperature $T_{10}$ is between about 0° C. and about 60° C. In some embodiments, temperature $T_{10}$ is between about 0° C. and about 50° C. In some embodiments, temperature $T_{10}$ is between about 0° C. and about 40° C. In some embodiments, temperature $T_{10}$ is between about 0° C. and about 30° C. In some embodiments, temperature $T_{10}$ is between about 10° C. and about 60° C. In some embodiments, temperature $T_{10}$ is between about 20° C. and about 60° C. In some embodiments, temperature $T_{10}$ is between about 10° C. and about 50° C. In some embodiments, temperature $T_{10}$ is between about 15° C. and about 45° C. In some embodiments, temperature $T_{10}$ is between about 20° C. and about 40° C. In some embodiments, temperature $T_{10}$ is between about 25° C. and about 35° C. In some embodiments, temperature $T_{10}$ is between about 24° C. and about 32° C. In some embodiments, temperature $T_{10}$ is between about 26° C. and about 28° C. In some embodiments, temperature $T_{10}$ is about 20° C., 21° C., 22° C., 23° C., 24° C., 25° C., 26° C., 27° C., 28° C., 29° C., 30° C., 31° C., or 32° C. In some embodiments, temperature $T_{10}$ is about 24° C. In some embodiments, temperature $T_{10}$ is about 26° C. In some embodiments, temperature $T_{10}$ is about 27° C. In some embodiments, temperature $T_{10}$ is about 28° C. In some embodiments, temperature $T_{10}$ is about 30° C.

In some embodiments, Step 1 further comprises a step of (f) washing (e.g. the filtered mixture or secondary mixture), to provide a final mixture.

In some embodiments, washing comprises wash solvent 1. In some embodiments, wash solvent 1 comprises adding a wash solvent 1 to, e.g., the filtered mixture. In some embodiments, the wash solvent 1 is or comprises acetone, acetonitrile, dichloromethane, 1,2-dichloroethane, 1,2-dimethoxyethane, 1,4-dioxane, N,N-dimethylformamide, N,N-dimethylacetamide, N-methylpyrrolidinone, dimethylsulfoxide, ethyl acetate, isopropyl acetate, pyridine, sulfolane, tetrahydrofuran, 2-methyltetrahydrofuran, toluene, benzene, α,α,α-trifluorotoluene, chlorobenzene, xylene, tert-butyl methyl ether, or cyclopentyl methyl ether. In some embodiments, wash solvent 1 is or comprises acetone. In some embodiments, wash solvent 1 is or comprises acetonitrile. In some embodiments, wash solvent 1 is or comprises dichloromethane. In some embodiments, wash solvent 1 is or comprises 1,2-dichloroethane. In some embodiments, wash solvent 1 is or comprises 1,2-dimethoxyethane. In some embodiments, wash solvent 1 is or comprises N,N-dimethylformamide. In some embodiments, wash solvent 1 is or comprises N,N-dimethylacetamide. In some embodiments, wash solvent 1 is or comprises N-methylpyrrolidinone. In some embodiments, wash solvent 1 is or comprises dimethylsulfoxide. In some embodiments, wash solvent 1 is or comprises ethyl acetate. In some embodiments, wash solvent 1 is or comprises isopropyl acetate. In some embodiments, wash solvent 1 is or comprises pyridine. In some embodiments, wash solvent 1 is or comprises sulfolane. In some embodiments, wash solvent 1 is or comprises tetrahydrofuran. In some embodiments, wash solvent 1 is or comprises 2-methyltetrahydrofuran. In some embodiments, wash solvent 1 is or comprises toluene. In some embodiments, wash solvent 1 is or comprises benzene. In some embodiments, wash solvent 1 is or comprises α,α,α-trifluorotoluene. In some embodiments, wash solvent 1 is or comprises chlorobenzene. In some embodiments, wash solvent 1 is or comprises xylene. In some embodiments, wash solvent 1 is or comprises tert-butyl methyl ether. In some embodiments, wash solvent 1 is or comprises cyclopentyl methyl ether. In some embodiments, wash solvent 1 is or comprises 1,4-dioxane. In some embodiments, wash solvent 1 is or comprises dichloromethane. In some embodiments, wash solvent 1 comprises 1,4-dioxane and dichloromethane.

In some embodiments, wash solvent 1 is in an amount between 0.30 L/kg and 5.00 L/kg. In some embodiments, wash solvent 1 is in an amount between 1.0 L/kg and 5.00 L/kg. In some embodiments, wash solvent 1 is in an amount between 1.50 L/kg and 5.00 L/kg. In some embodiments, wash solvent 1 is in an amount between 2.50 L/kg and 5.00 L/kg. In some embodiments, wash solvent 1 is in an amount between 0.30 L/kg and 4.50 L/kg. In some embodiments, wash solvent 1 is in an amount between 0.50 L/kg and 3.00 L/kg. In some embodiments, wash solvent 1 is in an amount between 0.50 L/kg and 2.50 L/kg. In some embodiments, wash solvent 1 is in an amount between 0.50 L/kg and 2.00 L/kg. In some embodiments, wash solvent 1 is in an amount between 1.50 L/kg and 4.00 L/kg. In some embodiments, wash solvent 1 is in an amount between 2.25 L/kg and 3.00 L/kg. In some embodiments, wash solvent 1 is in an amount between 2.50 L/kg and 2.75 L/kg. In some embodiments, wash solvent 1 is in an amount of about 0.50 L/kg, 1.05 L/kg, 1.65 L/kg, 2.00 L/kg, 2.25 L/kg, 2.50 L/kg, or 2.70 L/kg. In some embodiments, wash solvent 1 is in an amount of about 0.50 L/kg. In some embodiments, wash solvent 1 is in an amount of about 1.65 L/kg. In some embodiments, wash solvent 1 is in an amount of about 2.00 L/kg. In some embodiments, wash solvent 1 is in an amount of about 2.25 L/kg. In some embodiments, wash solvent 1 is in an amount of about 2.50 L/kg. In some embodiments, wash solvent 1 is in an amount of about 2.75 L/kg.

In some embodiments, wash solvent 1 comprises 1,4-dioxane in an amount between about 0.4 L/kg and about 1.5 L/kg. In some embodiments, wash solvent 1 comprises 1,4-dioxane in an amount between about 0.4 L/kg and about 1.3 L/kg. In some embodiments, wash solvent 1 comprises 1,4-dioxane in an amount between about 0.4 L/kg and about 1.0 L/kg. In some embodiments, wash solvent 1 comprises 1,4-dioxane in an amount between about 0.6 L/kg and about 1.5 L/kg. In some embodiments, wash solvent 1 comprises 1,4-dioxane in an amount between about 0.8 L/kg and about 1.5 L/kg. In some embodiments, wash solvent 1 comprises 1,4-dioxane in an amount between about 0.6 L/kg and about 1.3 L/kg. In some embodiments, wash solvent 1 comprises 1,4-dioxane in an amount between about 0.8 L/kg and about 0.9 L/kg. In some embodiments, wash solvent 1 comprises 1,4-dioxane in an amount of about 0.60 L/kg, 0.70 L/kg, 0.80 L/kg, 0.90 L/kg, or 1.00 L/kg. In some embodiments, wash solvent 1 comprises 1,4-dioxane in an amount of about 0.60 L/kg. In some embodiments, wash solvent 1 comprises 1,4-dioxane in an amount of about 0.70 L/kg. In some embodiments, wash solvent 1 comprises 1,4-dioxane in an amount of about 0.80 L/kg. In some embodiments, wash solvent 1 comprises 1,4-dioxane in an amount of about 0.90 L/kg. In some embodiments, wash solvent 1 comprises 1,4-dioxane in an amount of about 1.00 L/kg.

In some embodiments, wash solvent 1 comprises dichloromethane in an amount between about 1.0 L/kg and about 3.2 L/kg. In some embodiments, wash solvent 1 comprises dichloromethane in an amount between about 1.0 L/kg and about 3.0 L/kg. In some embodiments, wash solvent 1 comprises dichloromethane in an amount between about 1.0 L/kg and about 2.5 L/kg. In some embodiments, wash solvent 1 comprises dichloromethane in an amount between about 1.0 L/kg and about 2.0 L/kg. In some embodiments, wash solvent 1 comprises dichloromethane in an amount between about 1.5 L/kg and about 3.0 L/kg. In some embodiments, wash solvent 1 comprises dichloromethane in an amount between about 1.25 L/kg and about 2.0 L/kg. In some embodiments, wash solvent 1 comprises dichloromethane in an amount between about 1.5 L/kg and about 1.7 L/kg. In some embodiments, wash solvent 1 comprises dichloromethane in an amount between about 1.35 L/kg, 1.45 L/kg, 1.55 L/kg, 1.65 L/kg, 1.75 L/kg, or 1.85 L/kg. In some embodiments, wash solvent 1 comprises dichloromethane in an amount between about 1.35 L/kg. In some embodiments, wash solvent 1 comprises dichloromethane in an amount between about 1.45 L/kg. In some embodiments, wash solvent 1 comprises dichloromethane in an amount between about 1.55 L/kg. In some embodiments, wash solvent 1 comprises dichloromethane in an amount between about 1.64 L/kg. In some embodiments, wash solvent 1 comprises dichloromethane in an amount between about 1.75 L/kg.

In some embodiments, wash solvent 1 comprises 1,4-dioxane in an amount between about 0.4 L/kg and about 1.5 L/kg, and dichloromethane in an amount between about 1.0 L/kg and about 3.2 L/kg. In some embodiments, wash solvent 1 comprises 1,4-dioxane in an amount between about 0.8 L/kg and about 0.9 L/kg, and dichloromethane in an amount between about 1.5 L/kg and about 1.7 L/kg. In some embodiments, wash solvent 1 comprises 1,4-dioxane in an amount of about 0.60 L/kg, 0.70 L/kg, 0.80 L/kg, 0.90 L/kg, or 1.00 L/kg, and dichloromethane in an amount of about 1.40 L/kg, 1.50 L/kg, 1.60 L/kg, 1.70 L/kg, or 1.80 L/kg. In some embodiments, wash solvent 1 comprises 1,4-dioxane in an amount of about 0.86 L/kg and dichloromethane in an amount of about 1.64 L/kg.

In some embodiments, wash solvent 1 is provided at between about 0° C. and 50° C. In some embodiments, wash solvent 1 is provided at between about 0° C. and 40° C. In some embodiments, wash solvent 1 is provided at between about 0° C. and 30° C. In some embodiments, wash solvent 1 is provided at between about 10° C. and 50° C. In some embodiments, wash solvent 1 is provided at between about 20° C. and 50° C. In some embodiments, wash solvent 1 is provided at between about 30° C. and 50° C. In some embodiments, wash solvent 1 is provided at between about 10° C. and 40° C. In some embodiments, wash solvent 1 is provided at between about 18° C. and 32° C. In some embodiments, wash solvent 1 is provided at between about 20° C. and 30° C. In some embodiments, wash solvent 1 is provided at between about 23° C. and 27° C. In some embodiments, wash solvent 1 is provided at about 20° C., 22° C., 24° C., 25° C., 26° C., 28° C., or 30° C. In some embodiments, wash solvent 1 is provided at or about 23° C. In some embodiments, wash solvent 1 is provided at or about 25° C. In some embodiments, wash solvent 1 is provided at or about 27° C. In some embodiments, Wash 1 comprises agitating, e.g., the filtered mixture. In some embodiments, Wash 1 further comprises removing wash solvent 1.

In some embodiments, washing comprises Wash 2. In some embodiments, Wash 2 comprises adding a wash solvent 2 to, e.g., the filtered mixture. In some embodiments, wash solvent 2 is or comprises chloroform, hexane, pentane, 1,4-dioxane, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, wash solvent 2 is or comprises chloroform. In some embodiments, wash solvent 2 is or comprises hexane. In some embodiments, wash solvent 2 is or comprises pentane. In some embodiments, wash solvent 2 is or comprises diethyl ether. In some embodiments, wash solvent 2 is or comprises ethyl acetate. In some embodiments, wash solvent 2 is or comprises isopropyl acetate. In some embodiments, wash solvent 2 is or comprises tert-butyl methyl ether. In some embodiments, wash solvent 2 is or comprises cyclopentyl methyl ether. In some embodiments, wash solvent 2 is or comprises toluene. In some embodiments, wash solvent 2 is or comprises benzene. In some embodiments, wash solvent 2 is or comprises α,α,α-trifluorotoluene. In some embodiments, wash solvent 2 is or comprises chlorobenzene. In some embodiments, wash solvent 2 is or comprises xylene. In some embodiments, wash solvent 2 is or comprises 1,4-dioxane.

In some embodiments, wash solvent 2 is provided in an amount between about 0.5 L/kg and 5.0 L/kg. In some embodiments, wash solvent 2 is provided in an amount between about 0.5 L/kg and 4.0 L/kg. In some embodiments, wash solvent 2 is provided in an amount between about 0.5 L/kg and 3.0 L/kg. In some embodiments, wash solvent 2 is provided in an amount between about 1.0 L/kg and 5.0 L/kg. In some embodiments, wash solvent 2 is provided in an amount between about 2.5 L/kg and 5.0 L/kg. In some embodiments, wash solvent 2 is provided in an amount between about 1.0 L/kg and 4.0 L/kg. In some embodiments, wash solvent 2 is provided in an amount between about 1.0 L/kg and 3.0 L/kg. In some embodiments, wash solvent 2 is provided in an amount between about 2.0 L/kg and 2.5 L/kg. In some embodiments, wash solvent 2 is provided in an amount between about 2.3 L/kg and 2.7 L/kg. In some embodiments, wash solvent 2 is provided in an amount of about 1.0 L/kg, 1.5 L/kg, 2.0 L/kg, 2.5 L/kg, 3.0, 3.5, 4.0, 4.5, or 5.0 L/kg. In some embodiments, wash solvent 2 is provided in an amount of about 2.0 L/kg. In some embodiments, wash solvent 2 is provided in an amount of about 2.5 L/kg. In some embodiments, wash solvent 2 is provided in an amount of about 3.0 L/kg.

In some embodiments, wash solvent 2 is provided at between about 0° C. and 50° C. In some embodiments, wash solvent 2 is provided at between about 0° C. and 40° C. In some embodiments, wash solvent 2 is provided at between about 0° C. and 30° C. In some embodiments, wash solvent 2 is provided at between about 10° C. and 50° C. In some embodiments, wash solvent 2 is provided at between about 20° C. and 50° C. In some embodiments, wash solvent 2 is provided at between about 30° C. and 50° C. In some embodiments, wash solvent 2 is provided at between about 10° C. and 40° C. In some embodiments, wash solvent 2 is provided at between about 18° C. and 32° C. In some embodiments, wash solvent 2 is provided at between about 20° C. and 30° C. In some embodiments, wash solvent 2 is provided at between about 23° C. and 27° C. In some embodiments, wash solvent 2 is provided at about 20° C., 22° C., 24° C., 25° C., 26° C., 28° C., or 30° C. In some embodiments, wash solvent 2 is provided at or about 23° C. In some embodiments, wash solvent 2 is provided at or about 25° C. In some embodiments, wash solvent 2 is provided at or about 27° C. In some embodiments, Wash 2 further comprises agitating, e.g., the filtered mixture. In some embodiments, Wash 2 further comprises removing wash solvent 2.

In some embodiments, washing comprises Wash 3 or Wash 4. In some embodiments, Wash 3 or Wash 4 is the same as Wash 2. In some embodiments, Wash 3 comprises adding a wash solvent 3 to, e.g., the filtered mixture. In some embodiments, wash solvent 3 is or comprises chloroform, hexane, pentane, 1,4-dioxane, diethyl ether, ethyl acetate, isopropyl acetate, tert-butyl methyl ether, cyclopentyl methyl ether, toluene, benzene, α,α,α-trifluorotoluene, chlorobenzene, xylene, chlorobenzene, or dichloromethane. In some embodiments, wash solvent 3 is or comprises chloroform. In some embodiments, wash solvent 3 is or comprises hexane. In some embodiments, wash solvent 3 is or comprises pentane. In some embodiments, wash solvent 3 is or comprises diethyl ether. In some embodiments, wash solvent 3 is or comprises ethyl acetate. In some embodiments, wash solvent 3 is or comprises isopropyl acetate. In some embodiments, wash solvent 3 is or comprises tert-butyl methyl ether. In some embodiments, wash solvent 3 is or comprises cyclopentyl methyl ether. In some embodiments, wash solvent 3 is or comprises toluene. In some embodiments, wash solvent 3 is or comprises benzene. In some embodiments, wash solvent 3 is or comprises α,α,α-trifluorotoluene. In some embodiments, wash solvent 3 is or comprises xylene. In some embodiments, wash solvent 3 is or comprises chlorobenzene. In some embodiments, wash solvent 3 is or comprises 1,4-dioxane.

In some embodiments, wash solvent 3 is provided in an amount between about 0.5 L/kg and 5.0 L/kg. In some embodiments, wash solvent 3 is provided in an amount between about 0.5 L/kg and 4.0 L/kg. In some embodiments, wash solvent 3 is provided in an amount between about 0.5 L/kg and 3.0 L/kg. In some embodiments, wash solvent 3 is provided in an amount between about 1.0 L/kg and 5.0 L/kg. In some embodiments, wash solvent 3 is provided in an amount between about 2.5 L/kg and 5.0 L/kg. In some embodiments, wash solvent 3 is provided in an amount between about 1.0 L/kg and 4.0 L/kg. In some embodiments, wash solvent 3 is provided in an amount between about 1.0 L/kg and 3.0 L/kg. In some embodiments, wash solvent 3 is provided in an amount between about 1.5 L/kg and 3.0 L/kg. In some embodiments, wash solvent 3 is provided in an amount between about 2.0 L/kg and 2.8 L/kg. In some embodiments, wash solvent 3 is provided in an amount between about 2.3 L/kg and 2.7 L/kg. In some embodiments, wash solvent 3 is provided in an amount of about 1.0 L/kg, 1.5 L/kg, 2.0 L/kg, 2.5 L/kg, 3.0 L/kg. In some embodiments, wash solvent 3 is provided in an amount of about 2.0 L/kg. In some embodiments, wash solvent 3 is provided in an amount of about 2.5 L/kg. In some embodiments, wash solvent 3 is provided in an amount of about 3.0 L/kg.

In some embodiments, wash solvent 3 is provided at between about 0° C. and 50° C. In some embodiments, wash solvent 3 is provided at between about 0° C. and 40° C. In some embodiments, wash solvent 3 is provided at between about 0° C. and 30° C. In some embodiments, wash solvent 3 is provided at between about 10° C. and 50° C. In some embodiments, wash solvent 3 is provided at between about 20° C. and 50° C. In some embodiments, wash solvent 3 is provided at between about 30° C. and 50° C. In some embodiments, wash solvent 3 is provided at between about 10° C. and 40° C. In some embodiments, wash solvent 3 is provided at between about 20° C. and 30° C. In some embodiments, wash solvent 3 is provided at between about 22° C. and 28° C. In some embodiments, wash solvent 3 is provided at between about 24° C. and 26° C. In some embodiments, wash solvent 3 is provided at about 20° C., 22° C., 24° C., 25° C., 26° C., 28° C., or 30° C. In some embodiments, wash solvent 3 is provided at or about 25° C. In some embodiments, Wash 3 further comprises agitating, e.g., the filtered mixture. In some embodiments, Wash 3 further comprises removing wash solvent 3.

In some embodiments, Wash 4 comprises adding a wash solvent 4 to, e.g., the filtered mixture. In some embodiments, wash solvent 4 is or comprises chloroform, hexane, pentane, 1,4-dioxane, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, wash solvent 4 is or comprises chloroform. In some embodiments, wash solvent 4 is or comprises hexane. In some embodiments, wash solvent 4 is or comprises pentane. In some embodiments, wash solvent 4 is or comprises diethyl ether. In some embodiments, wash solvent 4 is or comprises ethyl acetate. In some embodiments, wash solvent 4 is or comprises isopropyl acetate. In some embodiments, wash solvent 4 is or comprises tert-butyl methyl ether. In some embodiments, wash solvent 4 is or comprises cyclopentyl methyl ether. In some embodiments, wash solvent 4 is or comprises toluene. In some embodiments, wash solvent 4 is or comprises benzene. In some embodiments, wash solvent 4 is or comprises α,α,α-trifluorotoluene. In some embodiments, wash solvent 4 is or comprises chlorobenzene. In some embodiments, wash solvent 4 is or comprises xylene. In some embodiments, wash solvent 4 is or comprises 1,4-dioxane.

In some embodiments, wash solvent 4 is provided in an amount between about 0.5 L/kg and 5.0 L/kg. In some embodiments, wash solvent 4 is provided in an amount between about 0.5 L/kg and 4.0 L/kg. In some embodiments, wash solvent 4 is provided in an amount between about 0.5 L/kg and 3.0 L/kg. In some embodiments, wash solvent 4 is provided in an amount between about 1.0 L/kg and 5.0 L/kg. In some embodiments, wash solvent 4 is provided in an amount between about 2.5 L/kg and 5.0 L/kg. In some embodiments, wash solvent 4 is provided in an amount between about 1.0 L/kg and 4.0 L/kg. In some embodiments, wash solvent 4 is provided in an amount between about 1.0 L/kg and 3.0 L/kg. In some embodiments, wash solvent 4 is provided in an amount between about 1.5 L/kg and 3.0 L/kg. In some embodiments, wash solvent 4 is provided in an amount between about 2.0 L/kg and 2.8 L/kg. In some embodiments, wash solvent 4 is provided in an amount between about 2.3 L/kg and 2.7 L/kg. In some embodiments, wash solvent 4 is provided in an amount between about 2.4 L/kg and 2.5 L/kg. In some embodiments, wash solvent 4 is provided in an amount of about 1.0 L/kg, 1.5 L/kg, 2.0 L/kg, 2.5 L/kg, 3.0 L/kg. In some embodiments, wash solvent 4 is provided in an amount of about 2.0 L/kg. In some embodiments, wash solvent 4 is provided in an amount of about 2.5 L/kg. In some embodiments, wash solvent 4 is provided in an amount of about 3.0 L/kg.

In some embodiments, wash solvent 4 is provided at between about 0° C. and 50° C. In some embodiments, wash solvent 4 is provided at between about 0° C. and 40° C. In some embodiments, wash solvent 4 is provided at between about 0° C. and 30° C. In some embodiments, wash solvent 4 is provided at between about 10° C. and 20° C. In some embodiments, wash solvent 4 is provided at between about 20° C. and 50° C. In some embodiments, wash solvent 4 is provided at between about 30° C. and 50° C. In some embodiments, wash solvent 4 is provided at between about 10° C. and 40° C. In some embodiments, wash solvent 4 is provided at between about 18° C. and 32° C. In some embodiments, wash solvent 4 is provided at between about 20° C. and 30° C. In some embodiments, wash solvent 4 is provided at between about 23° C. and 27° C. In some embodiments, wash solvent 4 is provided at about 20° C., 22° C., 24° C., 25° C., 26° C., 28° C., or 30° C. In some embodiments, wash solvent 4 is provided at or about 25° C. In some embodiments, Wash 4 further comprises agitating, e.g., the filtered mixture. In some embodiments, Wash 4 further comprises removing wash solvent 4.

In some embodiments, washing comprises Wash 5. In some embodiments, Wash 5 comprises adding a wash solvent 5 to, e.g., the filtered mixture. In some embodiments, wash solvent 5 is or comprises chloroform, hexane, pentane, 1,4-dioxane, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, wash solvent 5 is or comprises chloroform. In some embodiments, wash solvent 5 is or comprises hexane. In some embodiments, wash solvent 5 is or comprises pentane. In some embodiments, wash solvent 5 is or comprises diethyl ether. In some embodiments, wash solvent 5 is or comprises ethyl acetate. In some embodiments, wash solvent 5 is or comprises isopropyl acetate. In some embodiments, wash solvent 5 is or comprises cyclopentyl methyl ether. In some embodiments, wash solvent 5 is or comprises toluene. In some embodiments, wash solvent 5 is or comprises benzene. In some embodiments, wash solvent 5 is or comprises α,α,α-trifluorotoluene. In some embodiments, wash solvent 5 is or comprises chlorobenzene. In some embodiments, wash solvent 5 is or comprises xylene. In some embodiments, wash solvent 5 is or comprises tert-butyl methyl ether.

In some embodiments, wash solvent 5 is provided at between 0.5 L/kg and 4.0 L/kg. In some embodiments, wash solvent 5 is provided at between 0.5 L/kg and 3.0 L/kg. In some embodiments, wash solvent 5 is provided at between 0.5 L/kg and 2.0 L/kg. In some embodiments, wash solvent 5 is provided at between 1.0 L/kg and 4.0 L/kg. In some embodiments, wash solvent 5 is provided at between 1.5 L/kg and 4.0 L/kg. In some embodiments, wash solvent 5 is provided at between 2.0 L/kg and 4.0 L/kg. In some embodiments, wash solvent 5 is provided at between 1.5 L/kg and 2.5 L/kg. In some embodiments, wash solvent 5 is provided at between 1.8 L/kg and 2.2 L/kg. In some embodiments, wash solvent 5 is provided in an amount of about 1.0 L/kg, 1.5 L/kg, 2.0 L/kg, 2.5 L/kg, 3.0, 3.5, or 4.0 L/kg. In some embodiments, wash solvent 5 is provided in an amount of about 1.5 L/kg. In some embodiments, wash solvent 5 is provided in an amount of about 2.0 L/kg. In some embodiments, wash solvent 5 is provided in an amount of about 2.5 L/kg.

In some embodiments, wash solvent 5 is provided at between about 0° C. and 50° C. In some embodiments, wash solvent 5 is provided at between about 0° C. and 40° C. In some embodiments, wash solvent 5 is provided at between about 0° C. and 30° C. In some embodiments, wash solvent 5 is provided at between about 20° C. and 50° C. In some embodiments, wash solvent 5 is provided at between about 30° C. and 50° C. In some embodiments, wash solvent 5 is provided at between about 10° C. and 40° C. In some embodiments, wash solvent 5 is provided at between about 18° C. and 32° C. In some embodiments, wash solvent 5 is provided at between about 20° C. and 30° C. In some embodiments, wash solvent 5 is provided at between about 23° C. and 37° C. In some embodiments, wash solvent 5 is provided at about 20° C., 22° C., 24° C., 25° C., 26° C., 28° C., or 30° C. In some embodiments, wash solvent 5 is provided at or about 25° C. In some embodiments, Wash 5 further comprises agitating, e.g., the filtered mixture. In some embodiments, Wash 5 further comprises removing wash solvent 5.

In some embodiments, washing further comprises Wash 6. In some embodiments, Wash 6 comprises adding a wash solvent 6 to, e.g., the filtered mixture. In some embodiments, wash solvent 6 is or comprises pentane, hexane, or heptane. In some embodiments, wash solvent 6 is or comprises n-pentane, n-hexane, or n-heptane. In some embodiments, wash solvent 6 is or comprises pentane. In some embodiments, wash solvent 6 is or comprises n-pentane. In some embodiments, wash solvent 6 is or comprises hexane. In some embodiments, wash solvent 6 is or comprises n-hexane. In some embodiments, wash solvent 6 is or comprises heptane. In some embodiments, wash solvent 6 is or comprises n-heptane.

In some embodiments, wash solvent 6 is provided at between 0.5 L/kg and 4.0 L/kg. In some embodiments, wash solvent 6 is provided at between 0.5 L/kg and 3.0 L/kg. In some embodiments, wash solvent 6 is provided at between 1.0 L/kg and 4.0 L/kg. In some embodiments, wash solvent 6 is provided at between 1.5 L/kg and 4.0 L/kg. In some embodiments, wash solvent 6 is provided at between 2.0 L/kg and 4.0 L/kg. In some embodiments, wash solvent 6 is provided at between 2.25 L/kg and 3.0 L/kg. In some embodiments, wash solvent 6 is provided at between 2.3 L/kg and 2.75 L/kg. In some embodiments, wash solvent 6 is provided in an amount of about 1.0 L/kg, 1.5 L/kg, 2.0 L/kg, 2.5 L/kg, or 3.0 L/kg. In some embodiments, wash solvent 6 is provided in an amount of about 2.0 L/kg. In some embodiments, wash solvent 6 is provided in an amount of about 2.5 L/kg. In some embodiments, wash solvent 6 is provided in an amount of about 3.0 L/kg.

In some embodiments, wash solvent 6 is provided at between about 0° C. and 50° C. In some embodiments, wash solvent 6 is provided at between about 0° C. and 40° C. In some embodiments, wash solvent 6 is provided at between about 0° C. and 30° C. In some embodiments, wash solvent 6 is provided at between about 10° C. and 20° C. In some embodiments, wash solvent 6 is provided at between about 20° C. and 50° C. In some embodiments, wash solvent 6 is provided at between about 30° C. and 50° C. In some embodiments, wash solvent 6 is provided at between about 10° C. and 40° C. In some embodiments, wash solvent 6 is provided at between about 18° C. and 32° C. In some embodiments, wash solvent 6 is provided at between about 20° C. and 30° C. In some embodiments, wash solvent 6 is provided at between about 23° C. and 27° C. In some embodiments, wash solvent 6 is provided at about 20° C., 22° C., 24° C., 25° C., 26° C., 28° C., or 30° C. In some embodiments, wash solvent 6 is provided at or about 25° C. In some embodiments, Wash 6 further comprises agitating, e.g., the filtered mixture. In some embodiments, Wash 6 further comprises removing wash solvent 6.

In some embodiments, Step 1 further comprises a step of (g) deliquoring, drying, and/or isolating compound 2, or a salt thereof.

Step 2

In some embodiments, the present disclosure provides an improved synthesis of compound 3a:

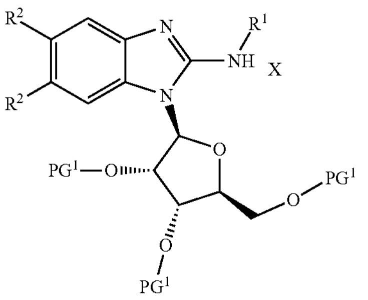

3a or a salt thereof, wherein $R^1$, $R^2$, $PG^1$, and X are as defined and described herein.

In some embodiments, the present disclosure provides an improved synthesis of compound 3:

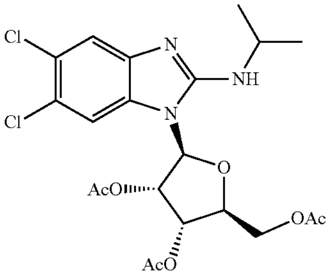

3 or a salt thereof.

As shown in Schemes 4 and 5, Step 2 is the second of three steps for preparing maribavir as disclosed herein. Any byproducts formed within Step 2 may be present in a provided composition, may further react to form additional byproducts, and/or may lower the overall yield or quality of maribavir. In some embodiments, the present disclosure provides methods of preparing compound 3, or a salt thereof, with reduced and/or low levels of impurities.

In some embodiments, the present disclosure provides compositions comprising compound 3, or a salt thereof, and one or more of the following compounds:

2

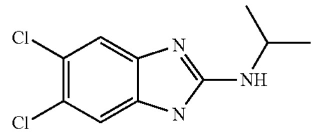

8

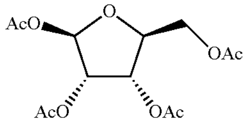

13

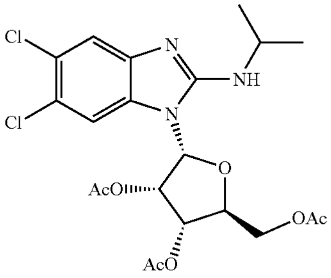

14

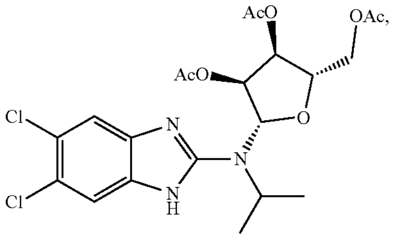

or

15

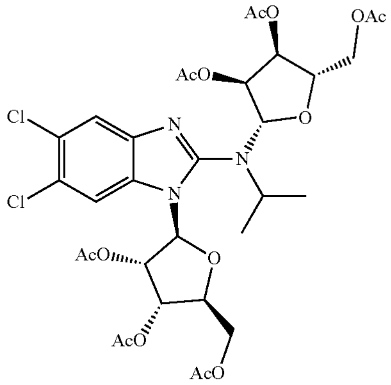

or salts thereof.

It will be appreciated that compound 14 may exist in a mixture of α and β isomers, with the β isomer being predominant. It will also be appreciated that compound 15 can be a mixture of four stereoisomers: β, β isomer; α, β isomer; β, α isomer; and α, α isomer.

In some embodiments, provided compositions comprise compound 3, or a salt thereof, and compound 2, 8, 13, 14, and/or 15, or salts thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 2, 8, 13, 14, and/or 15, or salts thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir.

In some embodiments, provided compositions comprise compound 3, or a salt thereof, and compound 13, 14, and/or 15, or salts thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 13, 14, and/or 15, or salts thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir.

In some embodiments, provided compositions comprise compound 3, or a salt thereof, and compound 2, or a salt thereof. In some embodiments, provided compositions comprise compound 3, or a salt thereof, and compound 2, or a salt thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 2, or a salt thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir. In some embodiments, provided compositions comprise compound 3, or a salt thereof, wherein compound 2, or a salt thereof, is not detectable (e.g., by HPLC or $^{1}H$ NMR).

In some embodiments, provided compositions comprise compound 3, or a salt thereof, and compound 8, or a salt thereof. In some embodiments, provided compositions comprise compound 3, or a salt thereof, and compound 8, or a salt thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 8, or a salt thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir. In some embodiments, provided compositions comprise compound 3, or a salt thereof, wherein compound 8, or a salt thereof, is not detectable (e.g., by HPLC or $^{1}H$ NMR).

In some embodiments, provided compositions comprise compound 3, or a salt thereof, and compound 13, or a salt thereof. In some embodiments, provided compositions comprise compound 3, or a salt thereof, and compound 13, or a salt thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 13, or a salt thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir. In some embodiments, provided compositions comprise compound 3, or a salt thereof, wherein compound 13, or a salt thereof, is not detectable (e.g., by HPLC or $^{1}H$ NMR).

In some embodiments, provided compositions comprise compound 3, or a salt thereof, and compound 14, or a salt thereof. In some embodiments, provided compositions comprise compound 3, or a salt thereof, and compound 14, or a salt thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 14, or a salt thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir. In some embodiments, provided compositions comprise compound 3, or a salt thereof, wherein compound 14, or a salt thereof, is not detectable (e.g., by HPLC or $^{1}H$ NMR). In some embodiments, provided compositions comprise compound 3, or a salt thereof, and compound 15, or a salt thereof. In some embodiments, provided compositions comprise compound 3, or a salt thereof, and compound 15, or a salt thereof, in an amount of less than 7%, 5%, 3%, 2%, 1%, 0.75%, 0.5%, 0.4%, 0.3%, 0.2%, 0.1%, 0.05%, or 0.02% (w/w HPLC), relative to maribavir. In some embodiments, provided compositions comprise compound 3, or a salt thereof, and compound 15, or a salt thereof, in an amount of less than 7%, 5%, 3%, 2%, 1%, 0.75%, 0.5%, 0.4%, 0.3%, 0.2%, 0.1%, 0.05%, or 0.02% (a/a HPLC), relative to maribavir. In some embodiments, provided compositions comprise compound 3, or a salt thereof, wherein compound 15, or a salt thereof, is not detectable (e.g., by HPLC or $^{1}$H NMR).

In some embodiments, such compositions comprising compound 3, or salt thereof are prepared as described herein. In some embodiments, the present disclosure also provides the recognition that certain reagents (and amounts thereof) and/or reaction conditions may provide improved quality compound 3, or a salt thereof (e.g., with higher purity and/or minimal byproducts), and/or improve the yield and/or purity of compound 3, or a salt thereof. In some embodiments, such improvements in yield or quality of compound 3, or a salt thereof, may also improve the yield or quality of maribavir. Without wishing to be bound to a particular theory, the present disclosure provides the recognition that incorporation of a crystallization (e.g., comprising salt formation) into Step 2 may improve the yield and/or reduce the formation of byproducts (e.g., compounds 2, 8, 13, 14, and/or 15, or salts thereof).

In some embodiments, compound 3a, or a salt thereof, is prepared as shown in Step 2 of Scheme 4. In some embodiments, at Step 2, compound 3a, or a salt thereof, is prepared by a method comprising:

(a) providing compound 2a:

2a

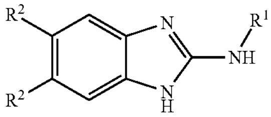

or a salt thereof, wherein each $R^1$ and $R^2$ is as defined above and described herein; and compound 8a:

8a

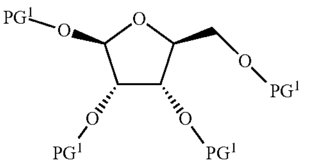

or a salt thereof, wherein each $PG^1$ is independently a suitable oxygen protecting group;

under suitable reaction conditions to afford compound 3a, or a salt thereof.

As generally defined above, each $PG^1$ is independently a suitable oxygen protecting group. Various methods and conditions for protecting and deprotecting alcohols are known in the chemical arts. For example, methods and conditions for protecting and deprotecting alcohols are well known in the art and include those described in detail in *Protecting Groups in Organic Synthesis*, T. W. Green and P. G. M. Wuts, 3rd edition, John Wiley & Sons, 1999, the entirety of which is incorporated herein by reference. In some embodiments, $PG^1$ is acetyl (Ac), benzoyl (Bz), benzyl (Bn), β-methoxyethoxymethyl ether (MEM), dimethoxytrityl (DMT), methoxymethyl ether (MOM), methoxytrityl (MMT), p-methoxybenzyl ether (PMB), p-methoxyphenyl ether (PMP), methylthiomethyl ether, pivaloyl (Piv), tetrahydropyranyl (THP), tetrahydrofuran (THF), a silyl ether (e.g., trimethylsilyl (TMS), tert-butyldimethylsilyl (TBS), tri-iso-propylsilyloxymethyl (TOM), and triisopropylsilyl (TIPS) ether), methyl ether, or ethoxyethyl ether. In some embodiments, each $PG^1$ is the same. In some embodiments, each $PG^1$ is acetyl (Ac).

In some embodiments, X represents a salt of compound 3a. Suitable salts are well known in the art, e.g., see generally, *March's Advanced Organic Chemistry: Reactions, Mechanisms, and Structure*, M. B. Smith and J. March, 5th Edition, John Wiley & Sons, 2001. In some embodiments, X is camphorsulfonic acid (CSA), benzenesulfonic acid ($PhSO_3H$), methanesulfonic acid (MsOH), toluenesulfonic acid (TsOH), 1,5-naphthalenedisulfonic acid (napsylic acid), 1,2-ethanedisulfonic acid (edisic acid), ethanesulfonic acid (esic acid), 4-chlorobenzenesulfonic acid (closic acid), 6,7-dihydroxycoumarin-4-methanesulfonic acid (cromesic acid), or trifluoromethanesulfonic acid (HOTf) salt. In some embodiments, X is a HF, HCl, HBr, or HI. In some embodiments, X is HCl. In some embodiments, X is HBr.

In some embodiments, compound 3, or a salt thereof, is prepared as shown in Step 2 of Scheme 5. In some embodiments, at Step 2, compound 3, or a salt thereof, is prepared by a method comprising:

(a) providing compound 2:

2

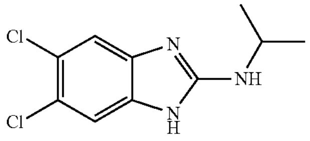

or a salt thereof, and compound 8:

8

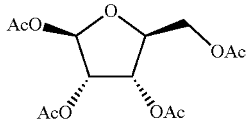

or a salt thereof, under suitable reaction conditions to afford compound 3, or a salt thereof.

In some embodiments, Step 2 further provides one or more of the following compounds:

2

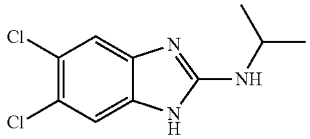

8

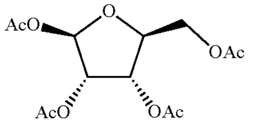

13

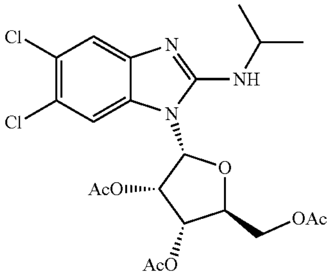

14

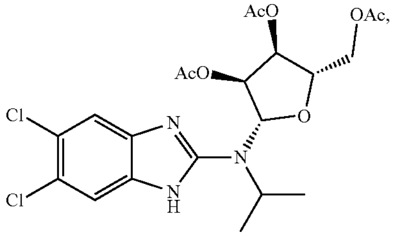

, or

15

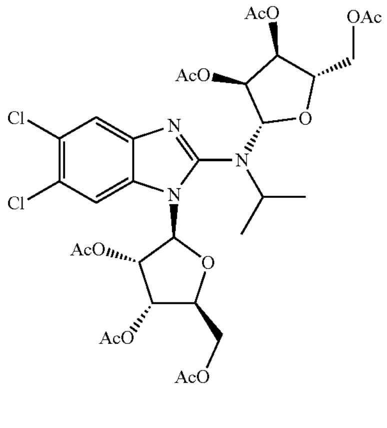

or salts thereof.

In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (w/w HPLC) of compound 2, relative to compound 3. In some embodiments, Step 2 provides a composition comprising about 0.12%, about 0.1%, about 0.09%, about 0.08%, about 0.07%, about 0.05%, or about 0.02% (w/w HPLC) of compound 2, relative to compound 3. In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (a/a HPLC) of compound 2 relative to compound 3. In some embodiments, Step 2 provides a composition comprising about 0.12%, about 0.1%, about 0.09%, about 0.08%, about 0.07%, about 0.05%, or about 0.02% (a/a HPLC) of compound 2, relative to compound 3. In some embodiments, Step 2 provides a composition wherein compound 2, or a salt thereof, is not detectable (e.g., by HPLC or $^{1}$H NMR).

In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (w/w HPLC) of compound 8, relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (w/w HPLC) of compound 8, relative to compound 3. In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (a/a HPLC) of compound 8 relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (a/a HPLC) of compound 8, relative to compound 3. In some embodiments, Step 2 provides a composition wherein compound 8, or a salt thereof, is not detectable (e.g., by HPLC or $^{1}$H NMR).

In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (w/w HPLC) of compound 13, relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (w/w HPLC) of compound 13, relative to compound 3. In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (a/a HPLC) of compound 13 relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (a/a HPLC) of compound 13, relative to compound 3. In some embodiments, Step 2 provides a composition wherein compound 13, or a salt thereof, is not detectable (e.g., by HPLC or $^{1}$H NMR).

In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (w/w HPLC) of compound 14, relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (w/w HPLC) of compound 14, relative to compound 3. In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (a/a HPLC) of compound 14 relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (a/a HPLC) of compound 14, relative to compound 3. In some embodiments, Step 2 provides a composition wherein compound 14, or a salt thereof, is not detectable (e.g., by HPLC or $^{1}$H NMR).

In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (w/w HPLC) of compound 15, relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (w/w HPLC) of compound 15, relative to compound 3. In some embodiments, Step 2 provides a composition comprising less than 7%, 5%, 3%, 2%, 1%, 0.75%, 0.5%, 0.4%, 0.3%, 0.2%, 0.1%, 0.05%, or 0.02% (a/a HPLC) of compound 15 relative to compound 3. In some embodiments, Step 2 provides a composition comprising about 1%, about 0.75%, about 0.5%, about 0.4%, about 0.3%, about 0.2%, about 0.1%, about 0.05%, or about 0.02% (a/a HPLC) of compound 15, relative to compound 3. In some embodiments, Step 2 provides a composition wherein compound 15, or a salt thereof, is not detectable (e.g., by HPLC or $^1$H NMR).

In some embodiments, Step 2 provides a composition as provided in any one of Tables 4-7 to 4-11 in Example 4.

In some embodiments, Step 2 provides compound 3 as a camphorsulfonic acid (CSA), benzenesulfonic acid ($PhSO_3H$), methanesulfonic acid (MsOH), toluenesulfonic acid (TsOH), 1,5-naphthalenedisulfonic acid (napsylic acid), 1,2-ethanedisulfonic acid (edisic acid), ethanesulfonic acid (esic acid), 4-chlorobenzenesulfonic acid (closic acid), 6,7-dihydroxycoumarin-4-methanesulfonic acid (cromesic acid), or trifluoromethanesulfonic acid (HOTf) salt. In some embodiments, Step 2 provides compound 3 as a hydrohalide salt. In some embodiments, Step 2 provides compound 3 as an HCl salt. In some embodiments, Step 2 provides compound 3 as an HBr salt.

In some embodiments, compound 2, or a salt thereof, is provided in an amount between about 0.50 and about 1.50 equivalents relative to compound 8, or a salt thereof. In some embodiments, compound 2, or a salt thereof, is provided in an amount between about 0.75 and about 1.25 equivalents relative to compound 8, or a salt thereof. In some embodiments, compound 2, or a salt thereof, is provided in an amount between about 0.90 and about 1.51 equivalents relative to compound 8, or a salt thereof. In some embodiments, compound 2, or a salt thereof, is provided in an amount between about 0.99 and about 1.01 equivalents relative to compound 8, or a salt thereof. In some embodiments, compound 2, or a salt thereof, is provided in an amount of about 0.90, 0.95, 1.0, 1.05, or 1.10 equivalent relative to compound 8, or a salt thereof. In some embodiments, compound 2, or a salt thereof, is provided in an amount of about 0.90 equivalent relative to compound 8, or a salt thereof. In some embodiments, compound 2, or a salt thereof, is provided in an amount of about 0.95 equivalent relative to compound 8, or a salt thereof. In some embodiments, compound 2, or a salt thereof, is provided in an amount of about 1.0 equivalent relative to compound 8, or a salt thereof. In some embodiments, compound 2, or a salt thereof, is provided in an amount of about 1.05 equivalent relative to compound 8, or a salt thereof. In some embodiments, compound 2, or a salt thereof, is provided in an amount of about 1.10 equivalent relative to compound 8, or a salt thereof.

In some embodiments, compound 8, or a salt thereof, is provided in an amount between about 0.50 and about 2.0 equivalents relative to compound 2, or a salt thereof. In some embodiments, compound 8, or a salt thereof, is provided in an amount between about 1.00 and about 1.50 equivalents relative to compound 2, or a salt thereof. In some embodiments, compound 8, or a salt thereof, is provided in an amount between about 1.10 and about 1.40 equivalents relative to compound 2, or a salt thereof. In some embodiments, compound 8, or a salt thereof, is provided in an amount between about 1.1, 1.2, 1.3, 1.4 or 1.5 equivalents relative to compound 2, or a salt thereof. In some embodiments, compound 8, or a salt thereof, is provided in an amount between about 1.0 equivalents relative to compound 2, or a salt thereof. In some embodiments, compound 8, or a salt thereof, is provided in an amount between about 1.1 equivalents relative to compound 2, or a salt thereof. In some embodiments, compound 8, or a salt thereof, is provided in an amount between about 1.2 equivalents relative to compound 2, or a salt thereof. In some embodiments, compound 8, or a salt thereof, is provided in an amount between about 1.3 equivalents relative to compound 2, or a salt thereof. In some embodiments, compound 8, or a salt thereof, is provided in an amount between about 1.4 equivalents relative to compound 2, or a salt thereof.

In some embodiments, reaction conditions comprise a solvent. In some embodiments, the solvent is or comprises acetone, acetonitrile, dichloromethane, 1,2-dichloroethane, 1,2-dimethoxyethane, 1,4-dioxane, ethyl acetate, isopropyl acetate, tetrahydrofuran, 2-methyltetrahydrofuran, toluene, benzene, α,α,α-trifluorotoluene, chlorobenzene, xylene, tert-butyl methyl ether, or cyclopentyl methyl ether. In some embodiments, the solvent is or comprises acetone. In some embodiments, the solvent is or comprises acetonitrile. In some embodiments, the solvent is or comprises dichloromethane. In some embodiments, the solvent is or comprises 1,2-dichloroethane. In some embodiments, the solvent is or comprises 1,2-dimethoxyethane. In some embodiments, the solvent is or comprises isopropyl acetate. In some embodiments, the solvent is or comprises tetrahydrofuran. In some embodiments, the solvent is or comprises 2-methyltetrahydrofuran. In some embodiments, the solvent is or comprises toluene. In some embodiments, the solvent is or comprises benzene. In some embodiments, the solvent is or comprises α,α,α-trifluorotoluene. In some embodiments, the solvent is or comprises chlorobenzene. In some embodiments, the solvent is or comprises xylene. In some embodiments, the solvent is or comprises tert-butyl methyl ether. In some embodiments, the solvent is or comprises cyclopentyl methyl ether. In some embodiments, the solvent is or comprises 1,4-dioxane. In some embodiments, the solvent is ethyl acetate.

In some embodiments, the solvent is present in an amount between about 2.8 kg/kg and about 16.0 kg/kg. In some embodiments, the solvent is present in an amount between about 2.8 kg/kg and about 14.0 kg/kg. In some embodiments, the solvent is present in an amount between about 2.8 kg/kg and about 10.0 kg/kg. In some embodiments, the solvent is present in an amount between about 2.8 kg/kg and about 8.0 kg/kg. In some embodiments, the solvent is present in an amount between about 3.6 kg/kg and about 10.0 kg/kg. In some embodiments, the solvent is present in an amount between about 4.4 kg/kg and about 10.0 kg/kg. In some embodiments, the solvent is present in an amount between about 5.2 kg/kg and about 10.0 kg/kg. In some embodiments, the solvent is present in an amount between about 5.2 kg/kg and about 8.0 kg/kg. In some embodiments, the solvent is present in an amount between about 5.5 kg/kg and about 7.5 kg/kg. In some embodiments, the solvent is present in an amount between about 6.0 kg/kg and about 7.4 kg/kg. In some embodiments, the solvent is present in an amount between about 6.5 kg/kg and about 7.3 kg/kg. In some embodiments, the solvent is present in an amount between about 6.0 kg/kg and about 7.5 kg/kg. In some embodiments, the solvent is present in an amount of about 6.5 kg/kg, 6.6 kg/kg, 6.7 kg/kg, 6.8 kg/kg, 6.89 kg/kg, 7.0 kg/kg, 7.1 kg/kg, or 7.2 kg/kg. In some embodiments, the solvent is present in an amount of about 6.7 kg/kg. In some embodiments, the solvent is present in an amount of about 6.8 kg/kg. In some embodiments, the solvent is present in an amount of about 6.89 kg/kg. In some embodiments, the solvent is present in an amount of about 7.0 kg/kg. In some embodiments, the solvent is present in an amount of about 7.1 kg/kg.

In some embodiments, the reaction conditions comprise a desiccant. In some embodiments, the desiccant is or comprises N,O-bis(trimethylsilyl)-acetamide, N,O-bis(trimethylsilyl)trifluoroacetamide, N-(trimethylsilyl)acetamide, molecular sieves. In some embodiments, the desiccant is or comprises N,O-bis(trimethylsilyl)-acetamide. In some embodiments, the desiccant is or comprises N,O-bis(trimethylsilyl)trifluoroacetamide. In some embodiments, the desiccant is or comprises N-(trimethylsilyl)acetamide. In some embodiments, the desiccant is or comprises molecular sieves.

In some embodiments, the desiccant is present in an amount between about 0.25 and about 1.50 equivalents. In some embodiments, the desiccant is present in an amount between about 0.55 and about 1.25 equivalents. In some embodiments, the desiccant is present in an amount between about 0.25 and about 1.00 equivalents. In some embodiments, the desiccant is present in an amount between about 0.25 and about 0.75 equivalents. In some embodiments, the desiccant is present in an amount between about 0.50 and about 1.00 equivalents. In some embodiments, the desiccant is present in an amount between about 0.45 and about 0.75 equivalents. In some embodiments, the desiccant is present in an amount between about 0.50 and about 0.65 equivalents. In some embodiments, the desiccant is present in an amount between about 0.55 and about 0.63 equivalents. In some embodiments, the desiccant is present in an amount of about 0.56, 0.57, 0.58, 0.59, 0.60, 0.61, 0.62, 0.63, 0.64 or 0.65 equivalents. In some embodiments, the desiccant is present in an amount of about 0.56 equivalents. In some embodiments, the desiccant is present in an amount of about 0.58 equivalents. In some embodiments, the desiccant is present in an amount of about 0.59 equivalents. In some embodiments, the desiccant is present in an amount of about 0.593 equivalents. In some embodiments, the desiccant is present in an amount of about 0.60 equivalents. In some embodiments, the desiccant is present in an amount of about 0.62 equivalents. In some embodiments, desiccant is present in an amount of about 0.65 equivalents.

In some embodiments, reaction conditions comprise agitation for a period of time. In some embodiments, the reaction is agitated for about 25 minutes to about 5 days. In some embodiments, the reaction is agitated for about 25 minutes to about 1 day. In some embodiments, the reaction is agitated for about 25 minutes to about 12 hrs. In some embodiments, the reaction is agitated for about 25 minutes to about 6 hrs. In some embodiments, the reaction is agitated for about 25 minutes to about 3 hrs. In some embodiments, the reaction is agitated for at least 15 minutes. In some embodiments, the reaction is agitated for at least 25 minutes. In some embodiments, the reaction is agitated for at least 45 minutes. In some embodiments, the reaction is agitated for at least 60 minutes. In some embodiments, the reaction is agitated for at least 120 minutes.

In some embodiments, reaction conditions comprise a catalyst. In some embodiments, the catalyst is or comprises tert-butyl dimethylsilyl triflate, triethylsilyl triflate, or trimethylsilyl triflate. In some embodiments, the catalyst is or comprises tert-butyl dimethylsilyl triflate. In some embodiments, the catalyst is or comprises triethylsilyl triflate. In some embodiments, the catalyst is or comprises trimethylsilyl triflate.

In some embodiments, the catalyst is present in a catalytic amount. In some embodiments, the catalyst is present in an amount between about 0.05 and about 0.90 equivalents relative to compound 2, or a salt thereof. In some embodiments, the catalyst is present in an amount between about 0.05 and about 0.80 equivalents relative to compound 2, or a salt thereof. In some embodiments, the catalyst is present in an amount between about 0.05 and about 0.70 equivalents relative to compound 2, or a salt thereof. In some embodiments, the catalyst is present in an amount between about 0.05 and about 0.60 equivalents relative to compound 2, or a salt thereof. In some embodiments, the catalyst is present in an amount between about 0.05 and about 0.50 equivalents relative to compound 2, or a salt thereof. In some embodiments, the catalyst is present in an amount between about 0.05 and about 0.40 equivalents relative to compound 2, or a salt thereof. In some embodiments, the catalyst is present in an amount between about 0.10 and about 0.60 equivalents relative to compound 2, or a salt thereof. In some embodiments, the catalyst is present in an amount between about 0.20 and about 0.60 equivalents relative to compound 2, or a salt thereof. In some embodiments, the catalyst is present in an amount between about 0.30 and about 0.60 equivalents relative to compound 2, or a salt thereof. In some embodiments, the catalyst is present in an amount between about 0.25 and about 0.40 equivalents relative to compound 2, or a salt thereof. In some embodiments, the catalyst is present in an amount between about 0.30 and about 0.38 equivalents relative to compound 2, or a salt thereof. In some embodiments, the catalyst is present in an amount between about 0.32 and about 0.366 equivalents relative to compound 2, or a salt thereof. In some embodiments, the catalyst is present in an amount between about 0.34 and about 0.35 equivalents relative to compound 2, or a salt thereof. In some embodiments, the catalyst is present in an amount of about 0.32, 0.33, 0.34, 0.35, 0.36, 0.37, or 0.38 equivalents relative to compound 2, or a salt thereof. In some embodiments, the catalyst is present in an amount of about 0.32 equivalents relative to compound 2, or a salt thereof. In some embodiments, the catalyst is present in an amount of about 0.33 equivalents relative to compound 2, or a salt thereof. In some embodiments, the catalyst is present in an amount of about 0.34 equivalents relative to compound 2, or a salt thereof. In some embodiments, the catalyst is present in an amount of about 0.349 equivalents relative to compound 2, or a salt thereof. In some embodiments, the catalyst is present in an amount of about 0.35 equivalents relative to compound 2, or a salt thereof. In some embodiments, the catalyst is present in an amount of about 0.36 equivalents relative to compound 2, or a salt thereof. In some embodiments, the catalyst is present in an amount of about 0.37 equivalents relative to compound 2, or a salt thereof. In some embodiments, the catalyst is present in an amount of about 0.38 equivalents relative to compound 2, or a salt thereof.

In some embodiments, suitable reaction conditions comprise providing compounds 2 and 8 at a temperature $T_a$. In some embodiments, temperature $T_a$ is between about 0° C. and about 50° C. In some embodiments, temperature $T_a$ is between about 0° C. and about 35° C. In some embodiments, temperature $T_a$ is between about 0° C. and about 25° C. In some embodiments, temperature $T_a$ is between about 10° C. and about 50° C. In some embodiments, temperature $T_a$ is between about 15° C. and about 50° C. In some embodiments, temperature $T_a$ is between about 5° C. and about 35° C. In some embodiments, temperature $T_a$ is between about 10° C. and about 30° C. In some embodiments, temperature $T_a$ is between about 19° C. and about 25° C. In some embodiments, temperature $T_a$ is between about 21° C. and about 23° C. In some embodiments, temperature $T_a$ is about 19° C., 20° C., 21° C., 22° C., 23° C., 24° C., or 25° C. In some embodiments, temperature $T_a$ is about 20° C. In some embodiments, temperature $T_a$ is about 21° C. In some embodiments, temperature $T_a$ is about 22° C. In some embodiments, temperature $T_a$ is about 23° C. In some embodiments, temperature $T_a$ is about 24° C. In some embodiments, temperature $T_a$ is about 25° C.

In some embodiments, Step 2 further comprises a step of (b) heating to a temperature Tb. In some embodiments, the reaction conditions comprising heating to temperature $T_b$. In some embodiments, temperature $T_b$ is between about 20° C. and about 150° C. In some embodiments, temperature $T_b$ is between about 20° C. and about 120° C. In some embodiments, temperature $T_b$ is between about 20° C. and about 100° C. In some embodiments, temperature $T_b$ is between about 20° C. and about 80° C. In some embodiments, temperature $T_b$ is between about 40° C. and about 150° C. In some embodiments, temperature $T_b$ is between about 60° C. and about 150° C. In some embodiments, temperature $T_b$ is between about 40° C. and about 120° C. In some embodiments, temperature $T_b$ is between about 60° C. and about 90° C. In some embodiments, temperature $T_b$ is between about 65° C. and about 80° C. In some embodiments, temperature $T_b$ is between about 72° C. and about 79° C. In some embodiments, temperature $T_b$ is about 73° C., 74° C., 75° C., 76° C., 77° C., 78° C., 79° C., or 80° C. In some embodiments, temperature $T_b$ is about 74° C. In some embodiments, temperature Tb is about 75° C. In some embodiments, temperature $T_b$ is about 76° C. In some embodiments, temperature $T_b$ is about 77° C. In some embodiments, temperature $T_b$ is about 78° C. In some embodiments, temperature $T_b$ is about 79° C. In some embodiments, temperature $T_b$ is about 80° C.

In some embodiments, reaction conditions comprising aging and/or stirring the reaction mixture at temperature $T_b$ for a period of time. In some embodiments, the period of time between about 1 hrs and about 48 hrs. In some embodiments, the period of time between about 2 hrs and about 36 hrs. In some embodiments, the period of time between about 3 hrs and about 24 hrs. In some embodiments, the period of time between about 4 hrs and about 12 hrs. In some embodiments, the period of time of about 5 hours. In some embodiments, the period of time of at least 2 hours. In some embodiments, the period of time of at least 4 hours. In some embodiments, the period of time of at least 6 hours. In some embodiments, the period of time of at least 8 hours. In some embodiments, the period of time of at least 12 hours. In some embodiments, the period of time of at least 24 hours.

In some embodiments, e.g., after allowing the reaction to proceed at temperature $T_b$ for the period of time, Step 2 further comprises a step of (c) cooling the reaction mixture to a temperature $T_c$. In some embodiments, temperature $T_c$ is between about 0° C. and about 70° C. In some embodiments, temperature $T_c$ is between about 0° C. and about 60° C. In some embodiments, temperature $T_c$ is between about 0° C. and about 50° C. In some embodiments, temperature $T_c$ is between about 0° C. and about 40° C. In some embodiments, temperature Tc is between about 0° C. and about 30° C. In some embodiments, temperature $T_c$ is between about 10° C. and about 60° C. In some embodiments, temperature $T_c$ is between about 20° C. and about 60° C. In some embodiments, temperature $T_c$ is between about 10° C. and about 50° C. In some embodiments, temperature $T_c$ is between about 19° C. and about 55° C. In some embodiments, temperature $T_c$ is between about 15° C. and about 40° C. In some embodiments, temperature $T_c$ is between about 16° C. and about 30° C. In some embodiments, temperature Tc is between about 20° C. and about 25° C. In some embodiments, temperature $T_c$ is about 19° C., 20° C., 21° C., 22° C., 23° C., or 24° C. In some embodiments, temperature $T_c$ is about 19° C. In some embodiments, temperature $T_c$ is about 20° C. In some embodiments, temperature $T_c$ is about 21° C. In some embodiments, temperature $T_c$ is about 22° C. In some embodiments, temperature $T_c$ is about 23° C. In some embodiments, temperature $T_c$ is about 24° C.

In some embodiments, the reaction (e.g., presence of compound 3 or compound 2) is monitored for completion by HPLC. In some embodiments, the reaction is monitored for the presence of compound 3. In some embodiments, the reaction is monitored for the presence of compound 2 in an amount less than or equal to about 50.0% (a/a) (e.g., as measured by HPLC). In some embodiments, the reaction is monitored for the presence of compound 2 in an amount less than or equal to about 25.0% (a/a) (e.g., as measured by HPLC). In some embodiments, the reaction is monitored for the presence of compound 2 in an amount less than or equal to about 15.0% (a/a) (e.g., as measured by HPLC). In some embodiments, the reaction is monitored for the presence of compound 2 in an amount less than or equal to about 10.0% (a/a) (e.g., as measured by HPLC). In some embodiments, the reaction is monitored for the presence of compound 2 in an amount less than or equal to about 5.0% (a/a) (e.g., as measured by HPLC). In some embodiments, the reaction is monitored for the presence of compound 2 in an amount less than or equal to about 4.0% (a/a) (e.g., as measured by HPLC). In some embodiments, the reaction is monitored for the presence of compound 2 in an amount less than or equal to about 3.0% (a/a) (e.g., as measured by HPLC). In some embodiments, the reaction is monitored for the presence of compound 2 in an amount less than or equal to about 2.0% (a/a) (e.g., as measured by HPLC). In some embodiments, the reaction is monitored for the presence of compound 2 in an amount less than or equal to about 1.0% (a/a) (e.g., as measured by HPLC).

In some embodiments, Step 2 further comprises a step of (d) washing and/or quenching the reaction mixture, e.g., to provide a first resulting mixture. In some embodiments, Step 2 further comprises a step of washing the reaction mixture. In some embodiments, Step 2 further comprises a step of quenching the reaction mixture.

In some embodiments, washing and/or quenching comprises a base wash 1. In some embodiments, the base wash 1 is or comprises washing the reaction mixture with an aqueous base. In some embodiments, the aqueous base is or comprises LiOH, NaOH, KOH, $Li_2CO_3$, $Na_2CO_3$, $K_2CO_3$, $LiHCO_3$, $NaHCO_3$, or $KHCO_3$. In some embodiments, the aqueous base is or comprises $KHCO_3$.

In some embodiments, the aqueous base concentration is between about 5% and about 30% wt base. In some embodiments, the aqueous base concentration is between about 10% and 25% wt base. In some embodiments, the aqueous base concentration is between about 15% and about 25% base. In some embodiments, the aqueous base concentration is about 10%, 15%, 20%, 25%, 30% or 35% wt base. In some embodiments, the aqueous base concentration is about 10% wt base. In some embodiments, the aqueous base concentration is about 15% wt base. In some embodiments, the aqueous base concentration is about 20% wt base. In some embodiments, the aqueous base concentration is about 25% wt base. In some embodiments, the aqueous base concentration is about 30% wt base. In some embodiments, the aqueous base concentration is about 35% wt base. In some embodiments the aqueous base comprises potassium hydrogen carbonate (e.g., between about 0.811 kg/kg and 1.02 kg/kg, such as 1.02 kg/kg) and water (e.g., between about 3.672 kg/kg and about 4.488 kg/kg, such as 4.08 kg/kg). In some such embodiments, these amounts are split between two separate washes with the aqueous base.

In some embodiments, the base wash 1 is performed at temperature $T_d$. In some embodiments, temperature $T_d$ is between about 0° C. and about 50° C. In some embodiments, temperature $T_d$ is between about 0° C. and about 40° C. In some embodiments, temperature $T_d$ is between about 10° C. and about 40° C. In some embodiments, temperature $T_d$ is between about 10° C. and about 30° C. In some embodiments, temperature $T_d$ is between about 15° C. and about 25° C. In some embodiments, temperature $T_d$ is about 17° C., 18° C., 19° C., 20° C., 21° C., 22° C., or 23° C. In some embodiments, temperature $T_d$ is about 18° C. In some embodiments, temperature $T_d$ is about 20° C. In some embodiments, temperature $T_d$ is about 22° C.

In some embodiments, base wash 1 further comprises addition of water to the reaction mixture. In some embodiments, additional water is provided in an amount of between about 2 kg/kg and about 6 kg/kg. In some embodiments, additional water is provided in an amount of between about 3.672 kg/kg and about 4.488 kg/kg. In some embodiments, additional water is provided in an amount of about 3, 3.5, 4, 4.5, 5, 5.5, or 6 kg/kg. In some embodiments, additional water is provided in an amount of about 4.488 kg/kg.

In some embodiments, washing and/or quenching comprises a brine wash 2. In some embodiments, brine wash 2 comprises washing the reaction mixture with brine (i.e., an aqueous NaCl solution). In some embodiments, the aqueous NaCl solution is between about 1% and 100% NaCl by weight. In some embodiments, the aqueous NaCl solution is between about 1% and 50% NaCl by weight. In some embodiments, the aqueous NaCl solution is between about 1% and 10% NaCl by weight. In some embodiments, the aqueous NaCl solution is about 0.1%, 0.5%, 1%, 5%, 10%, 15%, 20%, or 25% NaCl by weight. In some embodiments the aqueous NaCl solution is prepared from NaCl (e.g., between about 0.41 kg/kg and 0.69 kg/kg, such as 0.628 kg/kg) and water (e.g., between about 1.835 kg/kg and about 2.243 kg/kg, such as 2.039 kg/kg).

In some embodiments, brine wash 2 proceeds at temperature $T_d$ as described above and herein.

In some embodiments, each of base wash 1 and brine wash 2 independently comprises agitation for a period of time. In some embodiments, the period of time is for between about 5 minutes to about 5 days. In some embodiments, the period of time is for between about 5 minutes to about 1 day. In some embodiments, the period of time is for between about 5 minutes to about 12 hrs. In some embodiments, the period of time is for between about 5 minutes to about 6 hrs. In some embodiments, the period of time is for between about 5 minutes to about 3 hrs. In some embodiments, the period of time is for at least 5 minutes. In some embodiments, the period of time is for at least 15 minutes. In some embodiments, the period of time is for at least 45 minutes. In some embodiments, the period of time is for at least 60 minutes. In some embodiments, the period of time is for at least 120 minutes.

In some embodiments, brine wash 2 comprises allowing the reaction mixture or the first resulting mixture to settle for a period of time. In some embodiments, the period of time is between about 1 minute and 60 minute. In some embodiments, the period of time is between about 10 minute and 30 minute. In some embodiments, the period of time is greater than 20 minutes.

In some embodiments, Step 2 further comprises a step of (e) distillation and/or solvent exchange of the reaction mixture or first resulting mixture to provide a second resulting mixture comprising compound 3, or a pharmaceutically acceptable salt thereof, and a solvent.

In some embodiments, distillation and/or solvent exchange comprises (i) removing a solvent (e.g., the reaction solvent as described above and herein) from the reaction mixture and/or the first resulting mixture. In some embodiments, removing the solvent (e.g., the reaction solvent as described above and herein) comprises heating the reaction mixture and/or the first resulting mixture to a temperature $T_e$. In some embodiments, the temperature $T_e$ is between about 0° C. and about 100° C. In some embodiments, the temperature $T_e$ is between about 0° C. and about 60° C. In some embodiments, the temperature $T_e$ is between about 0° C. and about 40° C. In some embodiments, the temperature $T_e$ is between about 10° C. and about 60° C. In some embodiments, the temperature $T_e$ is between about 20° C. and about 60° C. In some embodiments, the temperature $T_e$ is between about 30° C. and about 60° C. In some embodiments, the temperature $T_e$ is between about 20° C. and about 50° C. In some embodiments, the temperature $T_e$ is between about 30° C. and about 40° C. In some embodiments, the temperature $T_e$ is between about 40° C. and about 50° C. In some embodiments, the temperature $T_e$ is at an amount less than or equal to about 60° C. In some embodiments, the temperature $T_e$ is at an amount less than or equal to about 45° C. In some embodiments, the temperature $T_e$ is at an amount less than or equal to about 40° C.

In some embodiments, the reaction mixture and/or the first resulting mixture is maintained at temperature $T_e$ for a period of time. In some embodiments, the period of time is until a certain volume of solvent is collected from the reaction mixture or first resulting mixture. For example, in some embodiments, the collected volume of solvent is between about 388 L and about 430 L, such as about 409 L.

In some embodiments, distillation and/or solvent exchange comprises (ii) adding a distillation solvent to the reaction mixture or first resulting mixture. In some embodiments, the distillation solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the distillation solvent is or comprises chloroform. In some embodiments, the distillation solvent is or comprises diethyl ether. In some embodiments, the distillation solvent is or comprises ethyl acetate. In some embodiments, the distillation solvent is or comprises isopropyl acetate. In some embodiments, the distillation solvent is or comprises cyclopentyl methyl ether. In some embodiments, the distillation solvent is or comprises toluene. In some embodiments, the distillation solvent is or comprises benzene. In some embodiments, the distillation solvent is or comprises α,α,α-trifluorotoluene. In some embodiments, the distillation solvent is or comprises chlorobenzene. In some embodiments, the distillation solvent is or comprises xylene. In some embodiments, the distillation solvent is or comprises dichloromethane. In some embodiments, the distillation solvent is or comprises tert-butyl methyl ether.

In some embodiments, the solution containing compound 3, or salt thereof is charged with an amount of distillation solvent. In some embodiments, the amount of distillation solvent is between about 100 kg and about 1000 kg. In some embodiments, the amount of distillation solvent is between about 100 kg and about 800 kg. In some embodiments, the amount of distillation solvent is between about 100 kg and about 600 kg. In some embodiments, the amount of distillation solvent is between about 100 kg and about 400 kg. In some embodiments, the amount of distillation solvent is between about 200 kg and about 1000 kg. In some embodiments, the amount of distillation solvent is between about 300 kg and about 1000 kg. In some embodiments, the amount of distillation solvent is between about 400 kg and about 1000 kg. In some embodiments, the amount of distillation solvent is between about 200 kg and about 600 kg. In some embodiments, the amount of distillation solvent is between about 300 kg and about 500 kg. In some embodiments, the amount of distillation solvent is between about 350 kg and about 450 kg. In some embodiments, the amount of distillation solvent is between about 367 kg and 407 kg. In some embodiments, the amount of distillation solvent is between about 375 kg and about 400 kg. In some embodiments, the amount of distillation solvent is about 375 kg, 382 kg, 387 kg, 392 kg or 400 kg. In some embodiments, the amount of distillation solvent is about 375 kg. In some embodiments, the amount of distillation solvent is about 387 kg. In some embodiments, the amount of distillation solvent is about 400 kg.

In some embodiments, the distillation solvent is added at temperature $T_f$. In some embodiments, the temperature $T_f$ is between about 0° C. and about 50° C. In some embodiments, the temperature $T_f$ is between about 0° C. and about 40° C. In some embodiments, the temperature $T_f$ is between about 0° C. and about 30° C. In some embodiments, the temperature $T_f$ is between about 0° C. and about 20° C. In some embodiments, the temperature $T_f$ is between about 10° C. and about 40° C. In some embodiments, the temperature $T_f$ is between about 15° C. and about 40° C. In some embodiments, the temperature $T_f$ is between about 20° C. and about 40° C. In some embodiments, the temperature $T_f$ is between about 10° C. and about 35° C. In some embodiments, the temperature $T_f$ is between about 15° C. and about 30° C. In some embodiments, the temperature $T_f$ is between about 18° C. and about 23° C. In some embodiments, the temperature $T_f$ is about 18° C., 19° C., 20° C., 21° C., 22° C., or 23° C. In some embodiments, the temperature $T_f$ is about 18° C. In some embodiments, the temperature $T_f$ is about 20° C. In some embodiments, the temperature $T_f$ is about 21° C. In some embodiments, the temperature $T_f$ is about 22° C.

In some embodiments, the second resulting mixture is agitated at temperature $T_f$ (as described above and herein).

In some embodiments, Step 2 further comprises a step of (f) crystallization of compound 3, or a pharmaceutically acceptable salt thereof (e.g., from the reaction mixture, first resulting mixture, or second resulting mixture). In some embodiments, crystallization comprises formation of a salt of compound 3 (e.g. a salt as described above and herein).

In some embodiments, crystallization comprises providing a crystallization mixture comprising compound 3, or a pharmaceutically acceptable salt thereof, and a crystallization solvent. In some embodiments, the crystallization solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the crystallization solvent is or comprises chloroform. In some embodiments, the crystallization solvent is or comprises diethyl ether. In some embodiments, the crystallization solvent is or comprises ethyl acetate. In some embodiments, the crystallization solvent is or comprises cyclopentyl methyl ether. In some embodiments, the crystallization solvent is or comprises toluene. In some embodiments, the crystallization solvent is or comprises benzene. In some embodiments, the crystallization solvent is or comprises α,α,α-trifluorotoluene. In some embodiments, the crystallization solvent is or comprises chlorobenzene. In some embodiments, the crystallization solvent is or comprises xylene. In some embodiments, the crystallization solvent is or comprises dichloromethane. In some embodiments, the crystallization solvent is or comprises isopropyl acetate.

In some embodiments, the crystallization mixture further comprises an acid. In some embodiments, the acid is camphorsulfonic acid (CSA), benzenesulfonic acid ($PhSO_3H$), methanesulfonic acid (MsOH), toluenesulfonic acid (TsOH), 1,5-naphthalenedisulfonic acid (napsic acid), 1,2-ethanedisulfonic acid (edisic acid), ethanesulfonic acid (esic acid), 4-chlorobenzenesulfonic acid (closic acid), 6,7-dihydroxycoumarin-4-methanesulfonic acid (cromesic acid), or trifluoromethanesulfonic acid (HOTf). In some embodiments, the acid is hydrochloric acid ("HCl").

In some embodiments, the crystallization mixture comprises compound 3 as a salt of the acid described above and herein. In some embodiments, the crystallization mixture comprises compound 3 as a hydrohalide salt. In some embodiments, the crystallization mixture comprises compound 3 as an HCl salt. In some embodiments, the crystallization mixture comprises compound 3 as an HBr salt.

In some embodiments, the acid is provided in an amount between about 0.5 and 1.5 equivalents relative to compound 3, or a salt thereof. In some embodiments, the acid is provided in an amount between about 0.75 and 1.5 equivalents relative to compound 3, or a salt thereof. In some embodiments, the acid is provided in an amount between about 0.95 and 1.5 equivalents relative to compound 3, or a salt thereof. In some embodiments, the acid is provided in an amount between about 1.05 and 1.5 equivalents relative to compound 3, or a salt thereof. In some embodiments, the acid is provided in an amount between about 0.5 and 1.25 equivalents relative to compound 3, or a salt thereof. In some embodiments, the acid is provided in an amount between about 0.5 and 1.15 equivalents relative to compound 3, or a salt thereof. In some embodiments, the acid is provided in an amount between about 0.5 and 1.05 equivalents relative to compound 3, or a salt thereof. In some embodiments, the acid is provided in an amount between about 0.6 and 1.4 equivalents relative to compound 3, or a salt thereof. In some embodiments, the acid is provided in an amount between about 0.8 and 1.2 equivalents relative to compound 3, or a salt thereof. In some embodiments, the acid is provided in an amount between about 0.95 and 1.05 equivalents relative to compound 3, or a salt thereof. In some embodiments, the acid is present in an amount of about 0.95, 0.98, 1.01, 1.03, 1.04, 1.05, 1.06, or 1.07 equivalents relative to compound 3, or a salt thereof. In some embodiments, the acid is present in an amount of about 1.01 equivalents relative to compound 3, or a salt thereof. In some embodiments, the acid is present in an amount of about 1.037 equivalents relative to compound 3, or a salt thereof. In some embodiments, the acid is present in an amount of about 1.05 equivalents relative to compound 3, or a salt thereof.

In some embodiments, the acid provided is a hydrochloric acid solution. In some embodiments, the acid is provided as an ethyl acetate solution of hydrochloric acid. In some embodiments, the acid is provided as an aqueous solution of hydrochloric acid. In some embodiments, the acid is provided as a methanolic solution of hydrochloric acid. In some embodiments, the acid is provided as a dioxane solution of hydrochloric acid. In some embodiments, the acid is provided as a diethyl ether solution of hydrochloric acid.

In some embodiments, the crystallization mixture is provided at a temperature $T_g$. In some embodiments, temperature $T_g$ is between about 0° C. and about 50° C. In some embodiments, temperature $T_g$ is between about 10° C. and about 50° C. In some embodiments, temperature $T_g$ is between about 20° C. and about 50° C. In some embodiments, temperature $T_g$ is between about 0° C. and about 30° C. In some embodiments, temperature $T_g$ is between about 5° C. and about 40° C. In some embodiments, temperature $T_g$ is between about 10° C. and about 30° C. In some embodiments, temperature $T_g$ is between about 15° C. and about 25° C. In some embodiments, temperature $T_g$ is about 18° C., 20° C., 22° C., or 24° C. In some embodiments, temperature $T_g$ is about 20° C. In some embodiments, temperature $T_g$ is about 22° C. In some embodiments, temperature $T_g$ is about 24° C.

In some embodiments, crystallization comprises adding the acid to the crystallization mixture over a period of time. In some embodiments, the period of time is between about 5 and about 120 minutes. In some embodiments, the period of time between about 5 and about 90 minutes. In some embodiments, the period of time between about 5 and about 60 minutes. In some embodiments, the period of time between about 5 and about 30 minutes. In some embodiments, the period of time between about 15 and about 120 minutes. In some embodiments, the period of time between about 30 and about 120 minutes. In some embodiments, the period of time of at least 15 minutes. In some embodiments, the period of time of at least 30 minutes. In some embodiments, the period of time of at least 60 minutes. In some embodiments, the period of time of at least 120 minutes. In some embodiments, the period of time of about 15 minutes. In some embodiments, the period of time of about 30 minutes. In some embodiments, the period of time of about 60 minutes. In some embodiments, crystallization comprising adding the acid to the crystallization mixture at temperature $T_g$, wherein temperature $T_g$ is as described above and herein.

In some embodiments, a seed crystal is added to the crystallization mixture. In some embodiments, the seed crystal is compound 3, or a salt thereof. In some embodiments, the seed crystal is added in an amount between about 0.01% and about 0.12% w/w relative to compound 2, or a salt thereof. In some embodiments, the seed crystal is added in an amount between about 0.01% and about 0.10% w/w relative to compound 2, or a salt thereof. In some embodiments, the seed crystal is added in an amount between about 0.01% and about 0.08% w/w relative to compound 2, or a salt thereof. In some embodiments, the seed crystal is added in an amount between about 0.01% and about 0.07% w/w relative to compound 2, or a salt thereof. In some embodiments, the seed crystal is added in an amount between about 0.01% and about 0.06% w/w relative to compound 2, or a salt thereof. In some embodiments, the seed crystal is added in an amount between about 0.03% and about 0.10% w/w relative to compound 2, or a salt thereof. In some embodiments, the seed crystal is added in an amount between about 0.04% and about 0.10% w/w relative to compound 2, or a salt thereof. In some embodiments, the seed crystal is added in an amount between about 0.05% and about 0.10% w/w relative to compound 2, or a salt thereof. In some embodiments, the seed crystal is added in an amount between about 0.06% and about 0.10% w/w relative to compound 2, or a salt thereof. In some embodiments, the seed crystal is added in an amount between about 0.03% and about 0.08% w/w relative to compound 2, or a salt thereof. In some embodiments, the seed crystal is added in an amount between about 0.05% and about 0.07% w/w relative to compound 2, or a salt thereof. In some embodiments, the seed crystal is added in an amount of about 0.04%, 0.05%, 0.06%, 0.07%, or 0.08% w/w relative to compound 2, or a salt thereof. In some embodiments, the seed crystal is added in an amount of about 0.04% w/w relative to compound 2, or a salt thereof. In some embodiments, the seed crystal is added in an amount of about 0.05% w/w relative to compound 2, or a salt thereof. In some embodiments, the seed crystal is added in an amount of about 0.06% w/w relative to compound 2, or a salt thereof. In some embodiments, the seed crystal is added in an amount of about 0.07% w/w relative to compound 2, or a salt thereof. In some embodiments, the seed crystal is added in an amount of about 0.08% w/w relative to compound 2, or a salt thereof.

In some embodiments, the seed crystal is provided in a seed crystal solvent (e.g., the crystallization solvent, as described above and herein). In some embodiments, the seed crystal solvent is or comprises an amount between about 0 kg and about 0.41 kg. In some embodiments, the seed crystal solvent suspension is or comprises an amount between about 0 kg and about 0.31 kg. In some embodiments, the seed crystal solvent suspension is or comprises an amount between about 0 kg and about 0.21 kg. In some embodiments, the seed crystal solvent suspension is or comprises an amount between about 0 kg and about 0.16 kg. In some embodiments, the seed crystal solvent suspension is or comprises an amount between about 0 kg and about 0.11 kg. In some embodiments, the seed crystal solvent suspension is or comprises an amount between about 0 kg and about 0.60 kg. In some embodiments, the seed crystal solvent suspension is or comprises an amount between about 0.10 kg and about 0.21 kg. In some embodiments, the seed crystal solvent suspension is or comprises an amount between about 0.16 kg and about 0.21 kg. In some embodiments, the seed crystal solvent suspension is or comprises an amount of about 0.10 kg, 0.15 kg, 0.20 kg, or 0.25 kg. In some embodiments, the seed crystal solvent suspension is or comprises an amount of about 0.10 kg. In some embodiments, the seed crystal solvent suspension is or comprises an amount of about 0.15 kg. In some embodiments, the seed crystal solvent suspension is or comprises an amount of about 0.20 kg. In some embodiments, the seed crystal solvent suspension is or comprises an amount of about 0.25 kg.

In some embodiments, the crystallization mixture is aged for a period of time at temperature $T_g$, wherein temperature $T_g$ is as described above and herein. In some embodiments, the period of time is between about 5 and about 300 minutes. In some embodiments, the period of time is between about 5 and about 240 minutes. In some embodiments, the period of time is between about 10 and about 180 minutes. In some embodiments, the period of time is between about 30 and about 120 minutes. In some embodiments, the period of time is between about 60 and about 100 minutes. In some embodiments, the period of time is about 30, 60, 90, or 120 minutes. In some embodiments, the period of time is about 90 minutes. In some embodiments, the period of time is at least 10 minutes. In some embodiments, the period of time is at least 30 minutes. In some embodiments, the period of time is at least 60 minutes. In some embodiments, the period of time is at least 90 minutes. In some embodiments, the crystallization mixture is aged for a period of time of at least 120 minutes.

In some embodiments, the crystallization mixture is cooled to temperature $T_i$ over a period of time. In some embodiments, the period of time is between about 15 minutes and about 240 minutes. In some embodiments, the period of time is between about 15 minutes and about 200 minutes. In some embodiments, the period of time is between about 15 minutes and about 180 minutes. In some embodiments, the period of time is between about 15 minutes and about 150 minutes. In some embodiments, the period of time is between about 15 minutes and about 120 minutes. In some embodiments, the period of time is between about 15 minutes and about 90 minutes. In some embodiments, the period of time is between about 30 minutes and about 180 minutes. In some embodiments, the period of time is between about 60 minutes and about 180 minutes. In some embodiments, the period of time is between about 90 minutes and about 180 minutes. In some embodiments, the period of time is between about 30 minutes and about 150 minutes. In some embodiments, the period of time is between about 60 minutes and about 120 minutes. In some embodiments, the period of time is between about 80 minutes and about 100 minutes. In some embodiments, the period of time is about 90 minutes. In some embodiments, the period of time is about 100 minutes. In some embodiments, the period of time is about 120 minutes. In some embodiments, the period of time is about 150 minutes. In some embodiments, the period of time is at least 30 minutes. In some embodiments, the period of time is at least 60 minutes. In some embodiments, the period of time is at least 90 minutes. In some embodiments, the period of time is at least 120 minutes.

In some embodiments, the temperature $T_i$ is between about −40° C. and about 40° C. In some embodiments, the temperature $T_i$ is between about −40° C. and about 30° C. In some embodiments, the temperature $T_i$ is between about −40° C. and about 20° C. In some embodiments, the temperature $T_i$ is between about −40° C. and about 10° C. In some embodiments, the temperature $T_i$ is between about −20° C. and about 40° C. In some embodiments, the temperature $T_i$ is between about −10° C. and about 40° C. In some embodiments, the temperature $T_i$ is between about 0° C. and about 40° C. In some embodiments, the temperature $T_i$ is between about −30° C. and about 30° C. In some embodiments, the temperature $T_i$ is between about −20° C. and about 20° C. In some embodiments, the temperature $T_i$ is between about −10° C. and about 10° C. In some embodiments, the temperature $T_i$ is between about −5° C. and about 5° C. In some embodiments, the temperature $T_i$ is about −2° C., 0° C., 2° C., 4° C., or 6° C. In some embodiments, the temperature $T_i$ is about −2° C. In some embodiments, the temperature $T_i$ is about 0° C. In some embodiments, the temperature $T_i$ is about 2° C. In some embodiments, the temperature $T_i$ is about 4° C.

In some embodiments, the crystallization mixture is aged at temperature $T_i$ for a period of time. In some embodiments, the period of time is between about 30 minutes and 7 days. In some embodiments, the period of time is between about 30 minutes and 1 days. In some embodiments, the period of time is between about 30 minutes and 12 hrs. In some embodiments, the period of time is between about 30 minutes and 6 hrs. In some embodiments, the period of time is between about 30 minutes and 3 hrs. In some embodiments, the period of time is between about 30 minutes and 2 hrs. In some embodiments, the period of time is about 30 minutes. In some embodiments, the period time is about 60 minutes. In some embodiments, the crystallization mixture is aged for a period time is about 90 minutes. In some embodiments, the crystallization mixture is aged for a period time is about 120 minutes. In some embodiments, the period of time is at least 30 minutes. In some embodiments, the period of time is at least 60 minutes. In some embodiments, the period of time is at least 90 minutes. In some embodiments, the period of time is at least 120 minutes. In some embodiments, the period of time is at least 5 minutes. In some embodiments, the period of time is less than 7 days.

In some embodiments, Step 2 further comprises a step of (g) optionally filtering or washing the crystallization mixture to provide a filtered mixture. In some embodiments, Step 2 further comprises filtering the crystallization mixture to provide the filtered mixture. In some embodiments, Step 2 further comprises washing the crystallization mixture to provide the filtered mixture.

In some embodiments, filtering is performed at temperature Ti, wherein temperature $T_i$ is as described above and herein.

In some embodiments, filtrating is performed over a period of time. In some embodiments, the period of time is between about 10 minutes and about 4 days. In some embodiments, the period of time is between about 10 minutes and about 1 day. In some embodiments, the period of time is between about 10 minutes and about 12 hrs. In some embodiments, the period of time is between about 10 minutes and about 6 hrs. In some embodiments, the period of time is between about 10 minutes and about 1 hr. In some embodiments, the period of time is between about 10 minutes and about 30 minutes. In some embodiments, the period of time is at least 10 minutes. In some embodiments, the period of time is at least 20 minutes. In some embodiments, the period of time is at least 30 minutes. In some embodiments, the period of time is at least 60 minutes.

In some embodiments, washing comprises Wash A. In some embodiments, Wash A comprises washing with wash solvent A. In some embodiments, wash solvent A is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, wash solvent A is or comprises chloroform. In some embodiments, the wash solvent A is or comprises diethyl ether. In some embodiments, wash solvent A is or comprises ethyl acetate. In some embodiments, wash solvent A is or comprises cyclopentyl methyl ether. In some embodiments, wash solvent A is or comprises toluene. In some embodiments, wash solvent A is or comprises benzene. In some embodiments, wash solvent A is or comprises α,α,α-trifluorotoluene. In some embodiments, wash solvent A is or comprises chlorobenzene. In some embodiments, wash solvent A is or comprises xylene. In some embodiments, wash solvent A is or comprises dichloromethane. In some embodiments, wash solvent A is or comprises isopropyl acetate.

In some embodiments, wash solvent A is present in an amount between about 0.30 kg/kg and about 5.0 kg/kg. In some embodiments, wash solvent A is present in an amount between about 0.30 kg/kg and about 4.0 kg/kg. In some embodiments, wash solvent A is present in an amount between about 0.30 kg/kg and about 3.0 kg/kg. In some embodiments, wash solvent A is present in an amount between about 0.30 kg/kg and about 2.0 kg/kg. In some embodiments, wash solvent A is present in an amount between about 0.50 kg/kg and about 5.0 kg/kg. In some embodiments, wash solvent A is present in an amount between about 1.00 kg/kg and about 5.0 kg/kg. In some embodiments, wash solvent A is present in an amount between about 1.25 kg/kg and about 5.0 kg/kg. In some embodiments, wash solvent A is present in an amount between about 0.25 kg/kg and about 4.0 kg/kg. In some embodiments, wash solvent A is present in an amount between about 0.50 kg/kg and about 3.0 kg/kg. In some embodiments, wash solvent A is present in an amount between about 0.69 kg/kg and about 2.5 kg/kg. In some embodiments, wash solvent A is present in an amount between about 0.95 kg/kg and about 1.75 kg/kg. In some embodiments, wash solvent A is present in an amount between about 1.25 kg/kg and about 1.5 kg/kg. In some embodiments, wash solvent A is present in an amount of about 1.15 kg/kg, 1.25 kg/kg, 1.35 kg/kg, 1.55 kg/kg, or 1.75 kg/kg. In some embodiments, wash solvent A is present in an amount of about 1.15 kg/kg. In some embodiments, wash solvent A is present in an amount of about 1.35 kg/kg. In some embodiments, wash solvent A is present in an amount of about 1.55 kg/kg.

In some embodiments, wash solvent A is present at a temperature Ti, wherein Ti is as described above and herein.

In some embodiments, after the addition of wash solvent A, the filtered mixture is agitated for a period of time. In some embodiments, the period of time between about 5 minutes and about 60 minutes. In some embodiments, the period of time between about 5 minutes and about 45 minutes. In some embodiments, the period of time between about 5 minutes and about 30 minutes. In some embodiments, the period of time between about 5 minutes and about 15 minutes. In some embodiments, the period of time of about 5 minutes or more. In some embodiments, the period of time of about 10 minutes or more. In some embodiments, the period of time of about 15 minutes or more. In some embodiments, the period of time of about 20 minutes or more. In some embodiments, the period of time of about 30 minutes or more. In some embodiments, the period of time of about 60 minutes or more.

In some embodiments, washing comprises Wash B. In some embodiments, Wash B comprises washing with wash solvent B. In some embodiments, wash solvent B is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, wash solvent B is or comprises chloroform. In some embodiments, the wash solvent B is or comprises diethyl ether. In some embodiments, wash solvent B is or comprises ethyl acetate. In some embodiments, wash solvent B is or comprises cyclopentyl methyl ether. In some embodiments, wash solvent B is or comprises toluene. In some embodiments, wash solvent B is or comprises benzene. In some embodiments, wash solvent B is or comprises α,α,α-trifluorotoluene In some embodiments, wash solvent B is or comprises chlorobenzene. In some embodiments, wash solvent B is or comprises xylene. In some embodiments, wash solvent B is or comprises dichloromethane. In some embodiments, wash solvent B is or comprises isopropyl acetate. In some embodiments, wash solvent B is or comprises tert-butyl methyl ether.

In some embodiments, wash solvent B is present in an amount between about 0.50 kg/kg and 4.0 kg/kg. In some embodiments, wash solvent B is present in an amount between about 0.50 kg/kg and 3.0 kg/kg. In some embodiments, wash solvent B is present in an amount between about 0.50 kg/kg and 2.0 kg/kg. In some embodiments, wash solvent B is present in an amount between about 1.0 kg/kg and 4.0 kg/kg. In some embodiments, wash solvent B is present in an amount between about 1.50 kg/kg and 4.0 kg/kg. In some embodiments, wash solvent B is present in an amount between about 1.75 kg/kg and 4.0 kg/kg. In some embodiments, wash solvent B is present in an amount between about 1.0 kg/kg and 3.0 kg/kg. In some embodiments, wash solvent B is present in an amount between about 1.25 kg/kg and 2.55 kg/kg. In some embodiments, wash solvent B is present in an amount between about 1.50 kg/kg and 2.05 kg/kg. In some embodiments, wash solvent B is present in an amount between about 1.75 kg/kg and 1.85 kg/kg. In some embodiments, wash solvent B is present in an amount of about 1.65 kg/kg, 1.70 kg/kg, 1.75 kg/kg, 1.80 kg/kg, or 1.85 kg/kg. In some embodiments, wash solvent B is present in an amount of about 1.65 kg/kg. In some embodiments, wash solvent B is present in an amount of about 1.70 kg/kg. In some embodiments, wash solvent B is present in an amount of about 1.75 kg/kg. In some embodiments, wash solvent B is present in an amount of about 1.80 kg/kg. In some embodiments, wash solvent B is present in an amount of about 1.85 kg/kg.

In some embodiments, wash solvent B is present at a temperature Ti, wherein Ti is as described above and herein.

In some embodiments, after the addition of wash solvent B, the filtered mixture is agitated for a period of time, e.g., as described above and herein with respect to wash A.

In some embodiments, washing comprises Wash C. In some embodiments, Wash C is the same as Wash B, as described above and herein.

In some embodiments, Step 2 further comprises a step of (h) drying the filtered mixture.

In some embodiments, drying comprises heating the filtered mixture to temperature $T_m$ for a period of time. In some embodiments, temperature $T_m$ is between about 0° C. and about 60° C. In some embodiments, temperature $T_m$ is between about 0° C. and about 50° C. In some embodiments, temperature $T_m$ is between about 0° C. and about 40° C. In some embodiments, temperature $T_m$ is between about 0° C. and about 30° C. In some embodiments, temperature $T_m$ is between about 10° C. and about 40° C. In some embodiments, temperature $T_m$ is between about 20° C. and about 40° C. In some embodiments, temperature $T_m$ is between about 30° C. and about 40° C. In some embodiments, temperature $T_m$ is less than or about 10° C. In some embodiments, temperature $T_m$ is less than or about 20° C. In some embodiments, temperature $T_m$ is less than or about 25° C. In some embodiments, temperature $T_m$ is less than or about 30° C. In some embodiments, temperature $T_m$ is less than or about 35° C. In some embodiments, temperature $T_m$ is less than or about 40° C. In some embodiments, temperature $T_m$ is less than or about 100° C. In some embodiments, the filtered mixture is agitated for the period of time.

In some embodiments, the filtered mixture is held at temperature $T_m$ for a period of time. In some embodiments, the period of time is until minimal condensate is visible in the filter drier.

In some embodiments, the filtered mixture is agitated at temperature $T_m$ (as described above and herein).

In some embodiments, the filtered mixture is dried at a temperature Tn between about 0° C. and about 80° C. In some embodiments, the filtered mixture is dried at a temperature $T_n$ between about 20° C. and about 80° C. In some embodiments, the filtered mixture is dried at a temperature $T_n$ between about 40° C. and about 80° C. In some embodiments, the filtered mixture is dried at a temperature $T_n$ between about 60° C. and about 80° C. In some embodiments, the filtered mixture is dried at a temperature $T_n$ between about 10° C. and about 60° C. In some embodiments, the filtered mixture is dried at a temperature $T_n$ between about 20° C. and about 50° C. In some embodiments, the filtered mixture is dried at a temperature $T_n$ between about 40° C. and about 50° C. In some embodiments, the filtered mixture is dried at a temperature $T_n$ between about 25° C. and about 60° C. In some embodiments, the filtered mixture is dried at a temperature $T_n$ less than or about 45° C. In some embodiments, the filtered mixture is dried at a temperature $T_n$ less than or about 50° C. In some embodiments, the filtered mixture is dried at a temperature $T_n$ less than or about 55° C. In some embodiments, the filtered mixture is dried at a temperature $T_n$ less than or about 60° C. In some embodiments, the filtered mixture is dried at a temperature $T_n$ less than or about 65° C. In some embodiments, the filtered mixture is dried at a temperature $T_n$ less than or about 70° C.

In some embodiments, the filtered mixture is held at temperature $T_n$ for a period of time. In some embodiments, the period of time is until total solvent content is below 1.5% w/w (e.g., as measured by GCHS). In some embodiments, the period of time is until total solvent content is below 1.3% w/w (e.g., as measured by GCHS). In some embodiments, the period of time is until total solvent content is below 1.1% w/w (e.g., as measured by GCHS). In some embodiments, the period of time is until total solvent content is below 0.8% w/w (e.g., as measured by GCHS). In some embodiments, the period of time is until total solvent content is below 0.5% w/w (e.g., as measured by GCHS). In some embodiments, the period of time is until total solvent content is below 0.2% w/w (e.g., as measured by GCHS). In some embodiments, the period of time is until total solvent content is below 0.1% w/w (e.g., as measured by GCHS).

In some embodiments, the filtered mixture is held at temperature $T_n$ for a period of time. In some embodiments, the period of time is until water content is below 1.5% w/w (e.g., as measured by Karl Fischer). In some embodiments, the period of time is until water content is below 1.3% w/w (e.g., as measured by Karl Fischer). In some embodiments, the period of time is until water content is below 1.1% w/w (e.g., as measured by Karl Fischer). In some embodiments, the period of time is until water content is below 0.8% w/w (e.g., as measured by Karl Fischer). In some embodiments, the period of time is until water content is below 0.5% w/w (e.g., as measured by Karl Fischer). In some embodiments, the period of time is until water content is below 0.2% w/w (e.g., as measured by Karl Fischer). In some embodiments, the period of time is until water content is below 0.1% w/w (e.g., as measured by Karl Fischer).

Step 3

In some embodiments, the present disclosure provides an improved synthesis of compound 1:

1

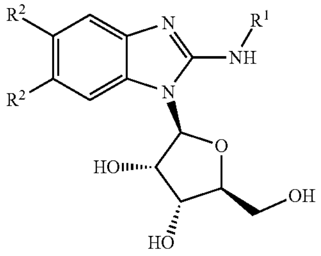

or a pharmaceutically salt thereof, wherein each $R^1$ and $R^2$ is as defined above and described herein.

In some embodiments, the present disclosure provides an improved synthesis of maribavir:

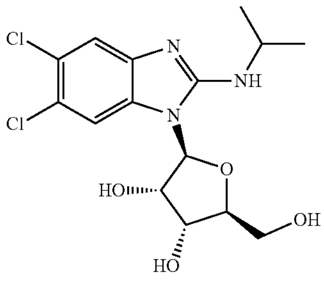 [SMILES: CC(C)Nc1nc2cc(Cl)c(Cl)cc2n1[C@H]1O[C@@H](CO)[C@H](O)[C@@H]1O]

or a pharmaceutically salt thereof.

As shown in Scheme 4, Step 3 is the last of three steps for preparing maribavir as disclosed herein. Any byproducts formed within Steps 1, 2, or 3 (or derivatives thereof) may be present in a provided composition comprising maribavir and/or may lower the overall yield or quality of maribavir. In some embodiments, the present disclosure provides methods of preparing maribavir, or a pharmaceutically acceptable salt thereof with reduced and/or low levels of impurities (e.g., as described herein).

In some embodiments, the present disclosure provides a composition comprising maribavir, or a pharmaceutically acceptable salt thereof, and one or more of the following compounds:

2

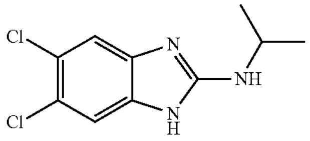

3

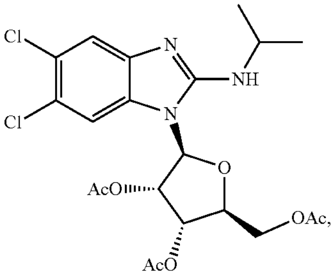

or

4

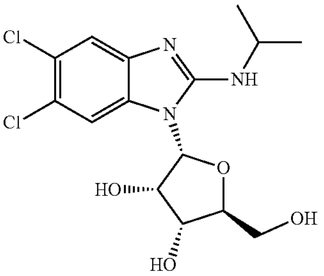

or salts thereof.

In some embodiments, provided compositions comprising maribavir are as described herein.

In some embodiments, the present disclosure also provides the recognition that certain reagents (and amounts thereof) and/or reaction conditions may provide improved quality maribavir, or a pharmaceutically salt thereof (e.g., with higher purity and/or minimal byproducts), and/or improve the yield of maribavir, or a pharmaceutically salt thereof. Without wishing to be bound by a particular theory, the present disclosure provides the recognition that incorporation of a crystallization into Step 3 may improve the yield and/or reduce the formation of byproducts (e.g., compounds 2, 3, or 4, or salts thereof). In some embodiments, the present disclosure provides the recognition that the amount of maribavir, or a salt thereof, and/or water in the crystallization mixture may affect the yield and/or quality of maribavir (e.g., particle size distribution). Additionally or alternatively, the present disclosure provides the recognition that incorporation of a phase separation and/or extraction into Step 3 at particular pH's may improve the yield and/or reduce the formation of byproducts (e.g., compounds 2, 3, or 4, or salts thereof).

In some embodiments, compound 1, or a pharmaceutically salt thereof, is prepared as shown in Step 3 of Scheme 4. In some embodiments, at Step 3, compound 1, or a pharmaceutically salt thereof, is prepared by a method comprising a step of:

(a) reacting compound 3a:

3a

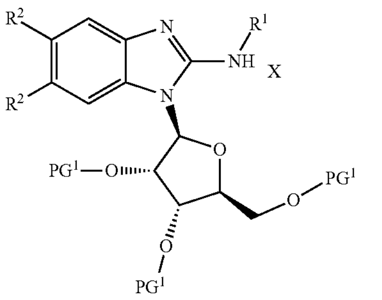

or a salt thereof, wherein each $R^1$, $R^2$, X, and $PG^1$ is as defined above and described herein;

under suitable reaction conditions to provide maribavir, or a pharmaceutically acceptable salt thereof.

In some embodiments, maribavir, or a pharmaceutically salt thereof, is prepared as shown in Step 3 of Scheme 5. In some embodiments, at Step 3, maribavir, or a pharmaceutically salt thereof, is prepared by a method comprising a step of:

(a) reacting compound 3:

3

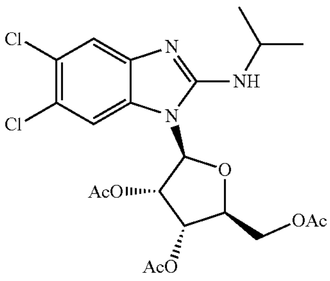

or a salt thereof, under suitable reaction conditions to provide maribavir, or a pharmaceutically acceptable salt thereof.

In some embodiments, Step 3 further provides one or more of the following compounds:

2

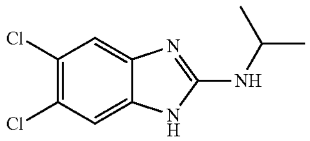

3

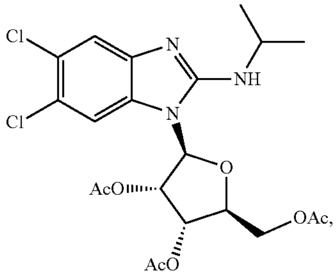

, or

4

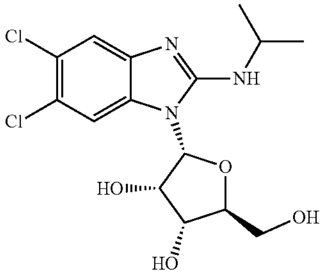

or salts thereof.

In some embodiments, Step 2 provides a composition comprising 0.01-0.10% (w/w HPLC) of compound 2, relative to maribavir. In some embodiments, Step 2 provides a composition comprising 0.01-0.05% (w/w HPLC) of compound 2, relative to maribavir. In some embodiments, Step 2 provides a composition comprising 0.02-0.05% (w/w HPLC) of compound 2, relative to maribavir. In some embodiments, Step 2 provides a composition comprising less than 1%, 0.5%, 0.1%, 0.05%, 0.02%, or 0.01% (w/w HPLC) of compound 2, relative to maribavir. In some embodiments, Step 2 provides a composition comprising 0.01-0.10% (a/a HPLC) of compound 2, relative to maribavir. In some embodiments, Step 2 provides a composition comprising 0.01-0.05% (a/a HPLC) of compound 2, relative to maribavir. In some embodiments, Step 2 provides a composition comprising 0.02-0.05% (a/a HPLC) of compound 2, relative to maribavir. In some embodiments, Step 2 provides a composition comprising less than 1%, 0.5%, 0.1%, 0.05%, 0.02%, or 0.01% (a/a HPLC) of compound 2, relative to maribavir. In some embodiments, Step 2 provides a composition comprising about 1%, about 0.5%, about 0.1%, about 0.05%, about 0.02%, or about 0.01% (a/a HPLC) of compound 2, relative to maribavir. In some embodiments, Step 2 provides a composition comprising about 1%, about 0.5%, about 0.1%, about 0.05%, about 0.02%, or about 0.01% (w/w HPLC) of compound 2, relative to maribavir. In some embodiments, Step 3 provides a composition, wherein compound 2, or a salt thereof, is not detectable (e.g., by HPLC or $^1$H NMR).

In some embodiments, Step 2 provides a composition comprising 0.01-0.10% (w/w HPLC) of compound 3, relative to maribavir. In some embodiments, Step 2 provides a composition comprising 0.01-0.05% (w/w HPLC) of compound 3, relative to maribavir. In some embodiments, Step 2 provides a composition comprising 0.02-0.05% (w/w HPLC) of compound 3, relative to maribavir. In some embodiments, Step 2 provides a composition comprising less than 1%, 0.5%, 0.1%, 0.05%, 0.02%, or 0.01% (w/w HPLC) of compound 3, relative to maribavir. In some embodiments, Step 2 provides a composition comprising 0.01-0.10% (a/a HPLC) of compound 3, relative to maribavir. In some embodiments, Step 2 provides a composition comprising 0.01-0.05% (a/a HPLC) of compound 3, relative to maribavir. In some embodiments, Step 2 provides a composition comprising 0.02-0.05% (a/a HPLC) of compound 3, relative to maribavir. In some embodiments, Step 2 provides a composition comprising less than 1%, 0.5%, 0.1%, 0.05%, 0.02%, or 0.01% (a/a HPLC) of compound 3, relative to maribavir. In some embodiments, Step 2 provides a composition comprising about 1%, about 0.5%, about 0.1%, about 0.05%, about 0.02%, or about 0.01% (a/a HPLC) of compound 3, relative to maribavir. In some embodiments, Step 2 provides a composition comprising about 1%, about 0.5%, about 0.1%, about 0.05%, about 0.02%, or about 0.01% (w/w HPLC) of compound 3, relative to maribavir. In some embodiments, Step 3 provides a composition, wherein compound 3, or a salt thereof, is not detectable (e.g., by HPLC or $^1$H NMR).

In some embodiments, Step 2 provides a composition comprising 0.01-0.10% (w/w HPLC) of compound 4, relative to maribavir. In some embodiments, Step 2 provides a composition comprising 0.01-0.05% (w/w HPLC) of compound 4, relative to maribavir. In some embodiments, Step 2 provides a composition comprising 0.02-0.05% (w/w HPLC) of compound 4, relative to maribavir. In some embodiments, Step 2 provides a composition comprising less than 1%, 0.5%, 0.1%, 0.05%, 0.02%, or 0.01% (w/w HPLC) of compound 4, relative to maribavir. In some embodiments, Step 2 provides a composition comprising 0.01-0.10% (a/a HPLC) of compound 4, relative to maribavir. In some embodiments, Step 2 provides a composition comprising 0.01-0.05% (a/a HPLC) of compound 4, relative to maribavir. In some embodiments, Step 2 provides a composition comprising 0.02-0.05% (a/a HPLC) of compound 4, relative to maribavir. In some embodiments, Step 2 provides a composition comprising less than 1%, 0.5%, 0.1%, 0.05%, 0.02%, or 0.01% (a/a HPLC) of compound 4, relative to maribavir. In some embodiments, Step 2 provides a composition comprising about 1%, about 0.5%, about 0.1%, about 0.05%, about 0.02%, or about 0.01% (a/a HPLC) of compound 4, relative to maribavir. In some embodiments, Step 2 provides a composition comprising about 1%, about 0.5%, about 0.1%, about 0.05%, about 0.02%, or about 0.01% (w/w HPLC) of compound 4, relative to maribavir. In some embodiments, Step 3 provides a composition, wherein compound 4, or a salt thereof, is not detectable (e.g., by HPLC or $^1$H NMR).

In some embodiments, Step 3 provides a composition comprising 0.01-0.10% (w/w HPLC) of compound 2, relative to maribavir. In some embodiments, Step 3 provides a composition comprising 0.01-0.05% (w/w HPLC) of compound 2, relative to maribavir. In some embodiments, Step 3 provides a composition comprising 0.02-0.05% (w/w HPLC) of compound 2, relative to maribavir. In some embodiments, Step 3 provides a composition comprising less than 1%, 0.5%, 0.1%, 0.05%, 0.02%, or 0.01% (w/w HPLC) of compound 2, relative to maribavir. In some embodiments, Step 3 provides a composition comprising 0.01-0.10% (a/a HPLC) of compound 2, relative to maribavir. In some embodiments, Step 3 provides a composition comprising 0.01-0.05% (a/a HPLC) of compound 2, relative to maribavir. In some embodiments, Step 3 provides a composition comprising 0.02-0.05% (a/a HPLC) of compound 2, relative to maribavir. In some embodiments, Step 3 provides a composition comprising less than 1%, 0.5%, 0.1%, 0.05%, 0.02%, or 0.01% (a/a HPLC) of compound 2, relative to maribavir. In some embodiments, Step 3 provides a composition comprising about 1%, about 0.5%, about 0.1%, about 0.05%, about 0.02%, or about 0.01% (a/a HPLC) of compound 2, relative to maribavir. In some embodiments, Step 3 provides a composition comprising about 1%, about 0.5%, about 0.1%, about 0.05%, about 0.02%, or about 0.01% (w/w HPLC) of compound 2, relative to maribavir. In some embodiments, Step 3 provides a composition, wherein compound 2, or a salt thereof, is not detectable (e.g., by HPLC or $^1$H NMR).

In some embodiments, Step 3 provides a composition comprising 0.01-0.10% (w/w HPLC) of compound 3, relative to maribavir. In some embodiments, Step 3 provides a composition comprising 0.01-0.05% (w/w HPLC) of compound 3, relative to maribavir. In some embodiments, Step 3 provides a composition comprising 0.02-0.05% (w/w HPLC) of compound 3, relative to maribavir. In some embodiments, Step 3 provides a composition comprising less than 1%, 0.5%, 0.1%, 0.05%, 0.02%, or 0.01% (w/w HPLC) of compound 3, relative to maribavir. In some embodiments, Step 3 provides a composition comprising 0.01-0.10% (a/a HPLC) of compound 3, relative to maribavir. In some embodiments, Step 3 provides a composition comprising 0.01-0.05% (a/a HPLC) of compound 3, relative to maribavir. In some embodiments, Step 3 provides a composition comprising 0.02-0.05% (a/a HPLC) of compound 3, relative to maribavir. In some embodiments, Step 3 provides a composition comprising less than 1%, 0.5%, 0.1%, 0.05%, 0.02%, or 0.01% (a/a HPLC) of compound 3, relative to maribavir. In some embodiments, Step 3 provides a composition comprising about 1%, about 0.5%, about 0.1%, about 0.05%, about 0.02%, or about 0.01% (a/a HPLC) of compound 3, relative to maribavir. In some embodiments, Ste 3 provides a composition comprising about 1%, about 0.5%, about 0.1%, about 0.05%, about 0.02%, or about 0.01% (w/w HPLC) of compound 3, relative to maribavir. In some embodiments, Step 3 provides a composition, wherein compound 3, or a salt thereof, is not detectable (e.g., by HPLC or $^1$H NMR).

In some embodiments, Step 3 provides a composition comprising 0.01-0.10% (w/w HPLC) of compound 4, relative to maribavir. In some embodiments, Step 3 provides a composition comprising 0.01-0.05% (w/w HPLC) of compound 4, relative to maribavir. In some embodiments, Step 3 provides a composition comprising 0.02-0.05% (w/w HPLC) of compound 4, relative to maribavir. In some embodiments, Step 3 provides a composition comprising less than 1%, 0.5%, 0.1%, 0.05%, 0.02%, or 0.01% (w/w HPLC) of compound 4, relative to maribavir. In some embodiments, Step 3 provides a composition comprising 0.01-0.10% (a/a HPLC) of compound 4, relative to maribavir. In some embodiments, Step 3 provides a composition comprising 0.01-0.05% (a/a HPLC) of compound 4, relative to maribavir. In some embodiments, Step 3 provides a composition comprising 0.02-0.05% (a/a HPLC) of compound 4, relative to maribavir. In some embodiments, Step 3 provides a composition comprising less than 1%, 0.5%, 0.1%, 0.05%, 0.02%, or 0.01% (a/a HPLC) of compound 4, relative to maribavir. In some embodiments, Step 3 provides a composition comprising about 1%, about 0.5%, about 0.1%, about 0.05%, about 0.02%, or about 0.01% (a/a HPLC) of compound 4, relative to maribavir. In some embodiments, Step 3 provides a composition comprising about 1%, about 0.5%, about 0.1%, about 0.05%, about 0.02%, or about 0.01% (w/w HPLC) of compound 4, relative to maribavir. In some embodiments, Step 3 provides a composition, wherein compound 4, or a salt thereof, is not detectable (e.g., by HPLC or $^1H$ NMR).

In some embodiments, Step 3 provides a composition as provided in any of Tables 4-12 to 4-21 in Example 4.

In some embodiments, reaction conditions comprise a solvent. In some embodiments the solvent is or comprises methanol, ethanol, isopropranol, tert-butanol, tert-butyl methyl ether, dimethyl sulfoxide, dimethylformamide, tetrahydrofuran, cyclopentyl methyl ether, 2-methyl tetrahydrofuran, or water. In some embodiments, the solvent is or comprises methanol. In some embodiments, the solvent is or comprises ethanol. In some embodiments, the solvent is or comprises isopropanol. In some embodiments, the solvent is or comprises tert-butanol. In some embodiments, the solvent is or comprises dimethyl sulfoxide. In some embodiments, the solvent is or comprises dimethylformamide. In some embodiments, the solvent is or comprises tetrahydrofuran. In some embodiments, the solvent is or comprises cyclopentyl methyl ether. In some embodiments, the solvent is or comprises 2-methyl tetrahydrofuran. In some embodiments, the solvent is or comprises water. In some embodiments, the solvent is or comprises tert-butyl methyl ether. In some embodiments, the solvent comprises methanol and tert-butyl methyl ether.

In some embodiments, the solvent is provided in an amount between about 1 L/kg and about 12 L/kg. In some embodiments, the solvent is provided in an amount between about 2 L/kg and about 12 L/kg. In some embodiments, the solvent is provided in an amount between about 4 L/kg and about 12 L/kg. In some embodiments, the solvent is provided in an amount between about 1 L/kg and about 8 L/kg. In some embodiments, the solvent is provided in an amount between about 1 L/kg and about 6 L/kg. In some embodiments, the solvent is provided in an amount between about 1 L/kg and about 4 L/kg. In some embodiments, the solvent is provided in an amount between about 3 L/kg and about 9 L/kg. In some embodiments, the solvent is provided in an amount between about 4 L/kg and about 8 L/kg. In some embodiments, the solvent is provided in an amount between about 5 L/kg and about 7 L/kg. In some embodiments, the solvent is provided in an amount of about 1 L/kg, 2 L/kg, 3 L/kg, 4 L/kg, 5 L/kg, 6 L/kg, 7 L/kg, 8 L/kg, 9 L/kg, 10 L/kg, 11 L/kg, or 12 L/kg. In some embodiments, the solvent is provided in an amount of about 3 L/kg. In some embodiments, the solvent is provided in an amount of about 4 L/kg. In some embodiments, the solvent is provided in an amount of about 5 L/kg. In some embodiments, the solvent is provided in an amount of about 6 L/kg. In some embodiments, the solvent is provided in an amount of about 7 L/kg.

In some embodiments, methanol is provided in an amount of between about 0.10 L/kg and about 2.0 L/kg. In some embodiments, methanol is provided in an amount of between about 0.25 L/kg and about 2.0 L/kg. In some embodiments, methanol is provided in an amount of between about 0.50 L/kg and about 2.0 L/kg. In some embodiments, methanol is provided in an amount of between about 0.10 L/kg and about 1.5 L/kg. In some embodiments, methanol is provided in an amount of between about 0.10 L/kg and about 1.0 L/kg. In some embodiments, methanol is provided in an amount of between about 0.10 L/kg and about 0.5 L/kg. In some embodiments, methanol is provided in an amount of between about 0.20 L/kg and about 1.0 L/kg. In some embodiments, methanol is provided in an amount of between about 0.3 L/kg and about 0.7 L/kg. In some embodiments, methanol is provided in an amount of between about 0.4 L/kg and about 0.6 L/kg. In some embodiments, methanol is provided in an amount of about 0.2 L/kg, 0.3 L/kg, 0.4 L/kg, 0.5 L/kg, 0.6 L/kg, 0.7 L/kg, or about 0.8 L/kg. In some embodiments, methanol is provided in an amount of about 0.3 L/kg. In some embodiments, methanol is provided in an amount of about 0.4 L/kg. In some embodiments, methanol is provided in an amount of about 0.5 L/kg. In some embodiments, methanol is provided in an amount of about 0.6 L/kg. In some embodiments, methanol is provided in an amount of about 0.7 L/kg.

In some embodiments, tert-butyl methyl ether is provided in an amount of between about 2 L/kg and about 12 L/kg. In some embodiments, tert-butyl methyl ether is provided in an amount of between about 4 L/kg and about 12 L/kg. In some embodiments, tert-butyl methyl ether is provided in an amount of between about 6 L/kg and about 12 L/kg. In some embodiments, tert-butyl methyl ether is provided in an amount of between about 2 L/kg and about 8 L/kg. In some embodiments, tert-butyl methyl ether is provided in an amount of between about 2 L/kg and about 6 L/kg. In some embodiments, tert-butyl methyl ether is provided in an amount of between about 3 L/kg and about 7 L/kg. In some embodiments, tert-butyl methyl ether is provided in an amount of between about 4 L/kg and about 6 L/kg. In some embodiments, tert-butyl methyl ether is provided in an amount of about 3 L/kg, 4 L/kg, 5 L/kg, 6 L/kg, or about 7 L/kg. In some embodiments, tert-butyl methyl ether is provided in an amount of about 3 L/kg. In some embodiments, tert-butyl methyl ether is provided in an amount of about 4 L/kg. In some embodiments, tert-butyl methyl ether is provided in an amount of about 5 L/kg. In some embodiments, tert-butyl methyl ether is provided in an amount of about 6 L/kg. In some embodiments, tert-butyl methyl ether is provided in an amount of about 7 L/kg.

In some embodiments, methanol is provided in an amount of between about 0.10 L/kg and about 2.0 L/kg, and tert-butyl methyl ether is provided in an amount of between about 2 L/kg and about 12 L/kg. In some embodiments, methanol is provided in an amount of between about 0.4 L/kg and about 0.6 L/kg, and tert-butyl methyl ether is provided in an amount of between about 4 L/kg and about 6 L/kg. In some embodiments, methanol is provided in an amount of between about 0.34 L/kg and about 0.56 L/kg, and tert-butyl methyl ether is provided in an amount of between about 3.65 L/kg and about 6.35 L/kg. In some embodiments, methanol is provided in an amount of about 0.48 L/kg, and tert-butyl methyl ether is provided in an amount of about 5.3 L/kg.

In some embodiments, reaction conditions comprise a base. In some embodiments, the base is or comprises LiOH, NaOH, or KOH. In some embodiments, the base is LiOH. In some embodiments, the base is NaOH. In some embodiments, the base is KOH. In some embodiments, the base is aqueous LiOH. In some embodiments, the base is aqueous NaOH. In some embodiments, the base is aqueous KOH. In some embodiments, the aqueous base is between about 5% and about 50%. In some embodiments, the aqueous base is between about 10% and about 50%. In some embodiments, the aqueous base is between about 15% and about 50%. In some embodiments, the aqueous base is between about 20% and about 50%. In some embodiments, the aqueous base is between about 25% and about 50%. In some embodiments, the aqueous base is between about 30% and about 50%. In some embodiments, the aqueous base is between about 5% and about 45%. In some embodiments, the aqueous base is between about 5% and about 40%. In some embodiments, the aqueous base is between about 5% and about 35%. In some embodiments, the aqueous base is between about 5% and about 30%. In some embodiments, the aqueous base is between about 20% and about 45%. In some embodiments, the aqueous base is between about 25% and about 40%. In some embodiments, the aqueous base is between about 28% and about 34%. In some embodiments, the aqueous base is about 5%, 10%, 15%, 20%, 25%, 30%, 35%, or 40% w/w. In some embodiments, the aqueous base is about 5% w/w. In some embodiments, the aqueous base is about 10% w/w. In some embodiments, the aqueous base is about 10% w/w. In some embodiments, the aqueous base is about 15% w/w. In some embodiments, the aqueous base is about 25% w/w. In some embodiments, the aqueous base is about 30% w/w. In some embodiments, the aqueous base is about 35% w/w. In some embodiments, the aqueous base is about 40% w/w. In some embodiments, the base is LiOR, NaOR, or KOR, wherein R is optionally substituted $C_{1-6}$ aliphatic or aryl. In some embodiments, the base is an alkoxide such as LiOR, NaOR, or KOR, wherein R is optionally substituted $C_{1-6}$ aliphatic. In some embodiments, the base is an alkoxide such as LiOR, NaOR, or KOR, wherein R is methyl. In some embodiments, the base is an alkoxide such as LiOR, NaOR, or KOR, wherein R is ethyl. In some embodiments, the base is an alkoxide such as LiOR, NaOR, or KOR, wherein R is propyl. In some embodiments, the base is an alkoxide such as LiOR, NaOR, or KOR, wherein R is butyl. In some embodiments, the base is an alkoxide such as LiOR, NaOR, or KOR, wherein R is pentyl. In some embodiments, the base is an alkoxide such as LiOR, NaOR, or KOR, wherein R is hexyl. In some embodiments, the base is LiOMe. In some embodiments, the base is NaOMe. In some embodiments, the base is KOMe. In some embodiments, the base is LiOEt. In some embodiments, the base is NaOEt. In some embodiments, the base is KOEt. In some embodiments, the base is LiOtBu. In some embodiments, the base is NaOtBu. In some embodiments, the base is KOtBu.

In some embodiments, the reaction conditions comprise performing the reaction at a temperature $T_1$ (e.g., heating to a temperature Ti). In some embodiments, temperature $T_1$ is between about 0° C. and 60° C. In some embodiments, temperature $T_1$ is between about 20° C. and 60° C. In some embodiments, temperature $T_1$ is between about 24° C. and 45° C. In some embodiments, temperature $T_1$ is between about 24° C. and 40° C. In some embodiments, temperature $T_1$ is between about 24° C. and 35° C. In some embodiments, temperature $T_1$ is between about 24° C. and 30° C. In some embodiments, temperature $T_1$ is about 25° C., 26° C., 27° C., 28° C., 29° C., 30° C., 31° C., 32° C., 33° C., 34° C., or 35° C. In some embodiments, temperature $T_1$ is about 30° C.

In some embodiments, the reaction is allowed proceed for a period of time. In some embodiments, the reaction is agitated for a period of time. In some embodiments, the period of time is greater than 1 hr. In some embodiments, the period of time is greater than 4 hrs. In some embodiments, the period of time is greater than 8 hrs. In some embodiments, the period of time is between about 2 and about 8 hrs. In some embodiments, the period of time is between about 1 and about 12 hrs. In some embodiments, the period of time is between about 2.5 and about 4 hrs. In some embodiments, the period of time is less than 4 hrs. In some embodiments, the period of time is less than 2 hrs. In some embodiments, the period of time is less than 1 hr.

In some embodiments, the reaction conditions comprising cooling the reaction mixture to a temperature $T_2$. In some embodiments, temperature $T_2$ is between about 0° C. and about 60° C. In some embodiments, temperature $T_2$ is between about 0° C. and about 50° C. In some embodiments, temperature $T_2$ is between about 0° C. and about 40° C. In some embodiments, temperature $T_2$ is between about 0° C. and about 30° C. In some embodiments, temperature $T_2$ is between about 10° C. and about 60° C. In some embodiments, temperature $T_2$ is between about 20° C. and about 60° C. In some embodiments, temperature $T_2$ is between about 20° C. and about 30° C. In some embodiments, temperature $T_2$ is between about 15° C. and about 25° C. In some embodiments, temperature $T_2$ is between about 20° C. and about 25° C. In some embodiments, temperature $T_2$ is about 18° C., 19° C., 20° C., 21° C., 22° C., 23° C., 24° C., or 25° C. In some embodiments, temperature $T_2$ is about 21° C. In some embodiments, temperature $T_2$ is about 22° C. In some embodiments, temperature $T_2$ is about 23° C.

In some embodiments, the reaction is monitored for completion (e.g., presence of maribavir or compound 3). In some embodiments, the reaction is monitored for presence of maribavir or compound 3 (e.g., by HPLC). In some embodiments, the reaction is monitored for the presence of maribavir in an amount greater than 95.0% a/a (e.g., by HPLC). In some embodiments, the reaction is monitored for the presence of maribavir in an amount greater than 96.0% a/a (e.g., by HPLC). In some embodiments, the reaction is monitored for the presence of maribavir in an amount greater than 97.0% a/a (e.g., by HPLC). In some embodiments, the reaction is monitored for the presence of maribavir in an amount greater than 97.5% a/a (e.g., by HPLC). In some embodiments, the reaction is monitored for the presence of maribavir in an amount greater than 98.0% a/a (e.g., by HPLC). In some embodiments, the reaction is monitored for the presence of maribavir in an amount greater than 98.1% a/a (e.g., by HPLC). In some embodiments, the reaction is monitored for the presence of maribavir in an amount greater than 98.2% a/a (e.g., by HPLC). In some embodiments, the reaction is monitored for the presence of maribavir in an amount greater than 98.3% a/a (e.g., by HPLC). In some embodiments, the reaction is monitored for the presence of maribavir in an amount greater than 98.4% a/a (e.g., by HPLC). In some embodiments, the reaction is monitored for the presence of maribavir in an amount greater than 98.5% a/a (e.g., by HPLC). In some embodiments, the reaction is monitored for the presence of maribavir in an amount greater than 99.0% a/a (e.g., by HPLC).

In some embodiments, Step 3 further comprises a step of (b) phase separation and/or extraction of maribavir, or a pharmaceutically acceptable salt thereof, from the reaction mixture to provide a first resulting mixture.

In some embodiments, phase separation and/or extraction of maribavir, or a pharmaceutically acceptable salt thereof, comprises adding a first phase separation solvent. In some embodiments, the first phase separation solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the first phase separation solvent is or comprises chloroform. In some embodiments, the first phase separation solvent is or comprises diethyl ether. In some embodiments, the first phase separation solvent is or comprises ethyl acetate. In some embodiments, the first phase separation solvent is or comprises isopropyl acetate. In some embodiments, the first phase separation solvent is or comprises cyclopentyl methyl ether. In some embodiments, the first phase separation solvent is or comprises toluene. In some embodiments, the first phase separation solvent is or comprises benzene. In some embodiments, the first phase separation solvent is or comprises α,α,α-trifluorotoluene. In some embodiments, the first phase separation solvent is or comprises chlorobenzene. In some embodiments, the first phase separation solvent is or comprises xylene. In some embodiments, the first phase separation solvent is or comprises dichloromethane. In some embodiments, the first phase separation solvent is or comprises tert-butyl methyl ether.

In some embodiments, phase separation and/or extraction of maribavir, or a pharmaceutically acceptable salt thereof, comprises adding a second phase separation solvent. In some embodiments, the second phase separation solvent is aqueous sodium chloride, aqueous lithium chloride, aqueous calcium chloride, or aqueous potassium chloride. In some embodiments, the second phase separation solvent is aqueous sodium chloride. In some embodiments, the second phase separation solvent is aqueous lithium chloride. In some embodiments, the second phase separation solvent is aqueous calcium chloride. In some embodiments, the second phase separation solvent is aqueous potassium chloride.

In some embodiments, phase separation and/or extraction of maribavir, or a pharmaceutically acceptable salt thereof, comprises adjusting the pH of the reaction mixture to between about 4.0 to about 14.0. In some embodiments, phase separation and/or extraction of maribavir, or a pharmaceutically acceptable salt thereof, comprises adjusting the pH of the reaction mixture to between about 6.0 to about 10.0. In some embodiments, phase separation and/or extraction of maribavir, or a pharmaceutically acceptable salt thereof, comprises adjusting the pH of the reaction mixture to between about 6.0 to about 9.0. In some embodiments, phase separation and/or extraction of maribavir, or a pharmaceutically acceptable salt thereof, comprises adjusting the pH of the reaction mixture to between about 6.0 to about 8.0. In some embodiments, phase separation and/or extraction of maribavir, or a pharmaceutically acceptable salt thereof, comprises adjusting the pH of the reaction mixture to between about 6.0 to about 7.5. In some embodiments, phase separation and/or extraction of maribavir, or a pharmaceutically acceptable salt thereof, comprises adjusting the pH of the reaction mixture to between about 6.0 to about 7.0. In some embodiments, phase separation and/or extraction of maribavir, or a pharmaceutically acceptable salt thereof, comprises adjusting the pH of the reaction mixture to between about 6.5 to about 10.0. In some embodiments, phase separation and/or extraction of maribavir, or a pharmaceutically acceptable salt thereof, comprises adjusting the pH of the reaction mixture to between about 7.5 to about 10.0. In some embodiments, phase separation and/or extraction of maribavir, or a pharmaceutically acceptable salt thereof, comprises adjusting the pH of the reaction mixture to between about 6.8 to about 7.5. In some embodiments, phase separation and/or extraction of maribavir, or a pharmaceutically acceptable salt thereof, comprises adjusting the pH of the reaction mixture to about 6.0, 6.2, 6.4, 6.6, 6.8, 7.0, 7.2, 7.4, 7.6, 7.8, or 8.0. In some embodiments, phase separation and/or extraction of maribavir, or a pharmaceutically acceptable salt thereof, comprises adjusting the pH of the reaction mixture to about 6.8. In some embodiments, phase separation and/or extraction of maribavir, or a pharmaceutically acceptable salt thereof, comprises adjusting the pH of the reaction mixture to about 7.0. In some embodiments, phase separation and/or extraction of maribavir, or a pharmaceutically acceptable salt thereof, comprises adjusting the pH of the reaction mixture to about 7.2. In some embodiments, phase separation and/or extraction of maribavir, or a pharmaceutically acceptable salt thereof, comprises adjusting the pH of the reaction mixture to about 7.4. In some embodiments, phase separation and/or extraction of maribavir, or a pharmaceutically acceptable salt thereof, comprises adjusting the pH of the reaction mixture to about 7.6.

In some embodiments, Step 3 further comprises a step of (c) distillation and/or solvent exchange of the reaction mixture or first resulting mixture to provide a second resulting mixture comprising maribavir, or a pharmaceutically acceptable salt thereof, and a solvent.

In some embodiments, the reaction mixture or first resulting mixture comprises a first solvent. In some embodiments, the first solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the first solvent is or comprises chloroform. In some embodiments, the first solvent is or comprises diethyl ether. In some embodiments, the first solvent is or comprises ethyl acetate. In some embodiments, the first solvent is or comprises isopropyl acetate. In some embodiments, the first solvent is or comprises cyclopentyl methyl ether. In some embodiments, the first solvent is or comprises toluene. In some embodiments, the first solvent is or comprises benzene. In some embodiments, the first solvent is or comprises α,α,α-trifluorotoluene. In some embodiments, the first solvent is or comprises chlorobenzene. In some embodiments, the first solvent is or comprises xylene. In some embodiments, the first solvent is or comprises dichloromethane. In some embodiments, the first solvent is tert-butyl methyl ether. In some embodiments, the first solvent is removed from the reaction mixture or first resulting mixture. In some embodiments, the first solvent is removed by distillation.

In some embodiments, a second solvent is added to the reaction mixture or first resulting mixture. In some embodiments, the second solvent is or comprises isopropyl alcohol, methanol, ethanol, n-propanol, n-butanol, sec-butanol, tert-butanol, chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the second solvent is or comprises methanol. In some embodiments, the second solvent is or comprises ethanol. In some embodiments, the second solvent is or comprises n-propanol. In some embodiments, the second solvent is or comprises n-butanol. In some embodiments, the second solvent is or comprises sec-butanol. In some embodiments, the second solvent is or comprises tert-butanol. In some embodiments, the second solvent is or comprises chloroform. In some embodiments, the second solvent is or comprises diethyl ether. In some embodiments, the second solvent is or comprises ethyl acetate. In some embodiments, the second solvent is or comprises isopropanol. In some embodiments, the second solvent is or comprises cyclopentyl methyl ether. In some embodiments, the second solvent is or comprises toluene. In some embodiments, the second solvent is or comprises benzene. In some embodiments, the second solvent is or comprises α,α,α-trifluorotoluene. In some embodiments, the second solvent is or comprises chlorobenzene. In some embodiments, the second solvent is or comprises xylene. In some embodiments, the second solvent is or comprises dichloromethane. In some embodiments, the second solvent is tert-butyl methyl ether. In some embodiments, the second solvent is or comprises isopropyl acetate.

In some embodiments, the second resulting mixture comprises less than 1.0% w/w of water (e.g., as measured by $^1$H NMR or Karl Fischer). In some embodiments, the second resulting mixture comprises less than 0.75% w/w of water (e.g., as measured by $^1$H NMR or Karl Fischer). In some embodiments, the second resulting mixture comprises less than 0.50% w/w of water (e.g., as measured by $^1$H NMR or Karl Fischer). In some embodiments, the second resulting mixture comprises less than 0.25% w/w of water (e.g., as measured by $^1$H NMR or Karl Fischer). In some embodiments, the second resulting mixture comprises less than 1.0% w/w of water (e.g., as measured by $^1$H NMR or Karl Fischer). In some embodiments, the second resulting mixture comprises less than 0.2% w/w of water (e.g., as measured by $^1$H NMR or Karl Fischer). In some embodiments, the second resulting mixture comprises less than 0.09% w/w of water (e.g., as measured by $^1$H NMR or Karl Fischer). In some embodiments, the second resulting mixture comprises less than 0.05% w/w of water (e.g., as measured by $^1$H NMR or Karl Fischer). In some embodiments, the second resulting mixture comprises an undetectable amount of water (e.g., as measured by $^1$H NMR or Karl Fischer). In some embodiments, the amount of water within the second resulting mixture is measured by $^1$H NMR. In some embodiments, the amount of water within the second resulting mixture is measured by Karl Fischer.

In some embodiments, the second resulting mixture comprises between about 10-30% w/w of maribavir, or a pharmaceutically acceptable salt thereof (e.g., as measured by $^1$H NMR). In some embodiments, the second resulting mixture comprises between about 13-25% w/w of maribavir, or a pharmaceutically acceptable salt thereof (e.g., as measured by $^1$H NMR). In some embodiments, the second resulting mixture comprises between about 15-22% w/w of maribavir, or a pharmaceutically acceptable salt thereof (e.g., as measured by $^1$H NMR). In some embodiments, the second resulting mixture comprises between about 16-20% w/w of maribavir, or a pharmaceutically acceptable salt thereof (e.g., as measured by $^1$H NMR). In some embodiments, the second resulting mixture comprises between about 17-20% w/w of maribavir, or a pharmaceutically acceptable salt thereof (e.g., as measured by $^1$H NMR). In some embodiments, the second resulting mixture comprises between about 17-19% w/w of maribavir, or a pharmaceutically acceptable salt thereof (e.g., as measured by $^1$H NMR). In some embodiments, the second resulting mixture comprises about 15%, 16%, 17%, 18%, 19%, 20%, 21%, or 22% w/w of maribavir, or a pharmaceutically acceptable salt thereof (e.g., as measured by $^1$H NMR). In some embodiments, the second resulting mixture comprises about 15% w/w of maribavir, or a pharmaceutically acceptable salt thereof (e.g., as measured by $^1$H NMR). In some embodiments, the second resulting mixture comprises about 16% w/w of maribavir, or a pharmaceutically acceptable salt thereof (e.g., as measured by $^1$H NMR). In some embodiments, the second resulting mixture comprises about 17% w/w of maribavir, or a pharmaceutically acceptable salt thereof (e.g., as measured by $^1$H NMR). In some embodiments, the second resulting mixture comprises about 18% w/w of maribavir, or a pharmaceutically acceptable salt thereof (e.g., as measured by $^1$H NMR). In some embodiments, the second resulting mixture comprises about 19% w/w of maribavir, or a pharmaceutically acceptable salt thereof (e.g., as measured by $^1$H NMR). In some embodiments, the second resulting mixture comprises about 20% w/w of maribavir, or a pharmaceutically acceptable salt thereof (e.g., as measured by $^1$H NMR). In some embodiments, the second resulting mixture comprises about 21% w/w of maribavir, or a pharmaceutically acceptable salt thereof (e.g., as measured by $^1$H NMR). In some embodiments, the second resulting mixture comprises about 22% w/w of maribavir, or a pharmaceutically acceptable salt thereof (e.g., as measured by $^1$H NMR).

In some embodiments, Step 3 further comprises a step of (d) crystallization of maribavir, or a pharmaceutically acceptable salt thereof (e.g., from the reaction mixture, first resulting mixture, or second resulting mixture).

In some embodiments, crystallization comprises providing a crystallization mixture comprising maribavir, or a pharmaceutically acceptable salt thereof, and a primary solvent. In some embodiments, the primary solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the primary solvent is or comprises chloroform. In some embodiments, the primary solvent is or comprises diethyl ether. In some embodiments, the primary solvent is or comprises ethyl acetate. In some embodiments, the primary solvent is or comprises cyclopentyl methyl ether. In some embodiments, the primary solvent is or comprises toluene. In some embodiments, the primary solvent is or comprises benzene. In some embodiments, the primary solvent is or comprises α,α,α-trifluorotoluene. In some embodiments, the primary solvent is or comprises chlorobenzene. In some embodiments, the primary solvent is or comprises xylene. In some embodiments, the primary solvent is or comprises dichloromethane. In some embodiments, the primary solvent is or comprises isopropyl acetate.

In some embodiments, the crystallization mixture comprises less than 0.2% w/w of water (e.g., as measured by $^1$H NMR). In some embodiments, the crystallization mixture comprises less than 0.09% w/w of water (e.g., as measured by $^1$H NMR). In some embodiments, the crystallization mixture comprises less than 1.0% w/w of water (e.g., as measured by $^1$H NMR or Karl Fischer). In some embodiments, the crystallization mixture comprises less than 0.75% w/w of water (e.g., as measured by $^1$H NMR or Karl Fischer). In some embodiments, the crystallization mixture comprises less than 0.50% w/w of water (e.g., as measured by $^1$H NMR or Karl Fischer). In some embodiments, the crystallization mixture comprises less than 0.25% w/w of water (e.g., as measured by $^1$H NMR or Karl Fischer). In some embodiments, the crystallization mixture comprises less than 1.0% w/w of water (e.g., as measured by $^1$H NMR or Karl Fischer). In some embodiments, the crystallization mixture comprises less than 0.2% w/w of water (e.g., as measured by $^1$H NMR or Karl Fischer). In some embodiments, the crystallization mixture comprises less than 0.09% w/w of water (e.g., as measured by $^1$H NMR or Karl Fischer). In some embodiments, the crystallization mixture comprises less than 0.05% w/w of water (e.g., as measured by $^1$H NMR or Karl Fischer). In some embodiments, the second resulting mixture comprises an undetectable amount of water (e.g., as measured by $^1$H NMR or Karl Fischer). In some embodiments, the amount of water within the crystallization mixture is measured by $^1$H NMR. In some embodiments, the amount of water within the crystallization mixture is measured by Karl Fischer.

Without wishing to be bound by a particular theory, it was thought that too low concentrations of maribavir, or a pharmaceutically acceptable salt thereof, may result in possible dissolution of the seed crystals and potentially impact yield and/or particle size of maribavir. It was also thought that too high concentrations of maribavir, or a pharmaceutically acceptable salt thereof, may result in spontaneous crystallization and/or may affect particle size of maribavir. In some embodiments, the crystallization mixture comprises between about 10-30% w/w of maribavir, or a pharmaceutically acceptable salt thereof (e.g., as measured by $^1H$ NMR). In some embodiments, the crystallization mixture comprises between about 13-25% w/w of maribavir, or a pharmaceutically acceptable salt thereof (e.g., as measured by $^1H$ NMR). In some embodiments, the crystallization mixture comprises between about 15-22% w/w of maribavir, or a pharmaceutically acceptable salt thereof (e.g., as measured by $^1H$ NMR). In some embodiments, the crystallization mixture comprises between about 16-20% w/w of maribavir, or a pharmaceutically acceptable salt thereof (e.g., as measured by $^1H$ NMR). In some embodiments, the crystallization mixture comprises between about 17-20% w/w of maribavir, or a pharmaceutically acceptable salt thereof (e.g., as measured by $^1H$ NMR). In some embodiments, the crystallization mixture comprises between about 17-19% w/w of maribavir, or a pharmaceutically acceptable salt thereof (e.g., as measured by $^1H$ NMR). In some embodiments, the crystallization mixture comprises about 15%, 16%, 17%, 18%, 19%, 20%, 21%, or 22% w/w of maribavir, or a pharmaceutically acceptable salt thereof (e.g., as measured by $^1H$ NMR). In some embodiments, the crystallization mixture comprises about 15% w/w of maribavir, or a pharmaceutically acceptable salt thereof (e.g., as measured by $^1H$ NMR). In some embodiments, the crystallization mixture comprises about 16% w/w of maribavir, or a pharmaceutically acceptable salt thereof (e.g., as measured by $^1H$ NMR). In some embodiments, the crystallization mixture comprises about 17% w/w of maribavir, or a pharmaceutically acceptable salt thereof (e.g., as measured by $^1H$ NMR). In some embodiments, the crystallization mixture comprises about 18% w/w of maribavir, or a pharmaceutically acceptable salt thereof (e.g., as measured by $^1H$ NMR). In some embodiments, the crystallization mixture comprises about 19% w/w of maribavir, or a pharmaceutically acceptable salt thereof (e.g., as measured by $^1H$ NMR). In some embodiments, the crystallization mixture comprises about 20% w/w of maribavir, or a pharmaceutically acceptable salt thereof (e.g., as measured by $^1H$ NMR). In some embodiments, the crystallization mixture comprises about 21% w/w of maribavir, or a pharmaceutically acceptable salt thereof (e.g., as measured by $^1H$ NMR). In some embodiments, the crystallization mixture comprises about 22% w/w of maribavir, or a pharmaceutically acceptable salt thereof (e.g., as measured by $^1H$ NMR).

In some embodiments, crystallization further comprising heating the crystallization mixture to a temperature $T_3$. In some embodiments, temperature $T_3$ is greater than about 60° C. In some embodiments, temperature $T_3$ is greater than about 25° C. In some embodiments, temperature $T_3$ is less than about 100° C. In some embodiments, temperature $T_3$ is between about 50° C. and about 150° C. In some embodiments, temperature $T_3$ is between about 50° C. and about 100° C. In some embodiments, temperature $T_3$ is between about 50° C. and about 90° C. In some embodiments, temperature $T_3$ is between about 50° C. and about 85° C. In some embodiments, temperature $T_3$ is between about 60° C. and about 110° C. In some embodiments, temperature $T_3$ is between about 70° C. and about 110° C. In some embodiments, temperature $T_3$ is between about 80° C. and about 110° C. In some embodiments, temperature $T_3$ is between about 60° C. and about 100° C. In some embodiments, temperature $T_3$ is between about 70° C. and about 90° C. In some embodiments, temperature $T_3$ is between about 74° C. and about 90° C. In some embodiments, temperature $T_3$ is between about 77° C. and about 88° C. In some embodiments, temperature $T_3$ is between about 82° C. and about 86° C. In some embodiments, temperature $T_3$ is between about 83° C. and about 85° C. In some embodiments, temperature $T_3$ is about 77° C., 78° C., 79° C., 80° C., 81° C., 82° C., 83° C., 84° C., 85° C., 86° C., 87° C., 88° C. In some embodiments, temperature $T_3$ is about 81° C. In some embodiments, temperature $T_3$ is about 82° C. In some embodiments, temperature $T_3$ is about 83° C. In some embodiments, temperature $T_3$ is about 84° C. In some embodiments, temperature $T_3$ is about 85° C. In some embodiments, temperature $T_3$ is about 86° C.

In some embodiments, a secondary solvent is added to the crystallization mixture. In some embodiments, the secondary solvent is or comprises chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the secondary solvent is or comprises chloroform. In some embodiments, the secondary solvent is or comprises diethyl ether. In some embodiments, the secondary solvent is or comprises ethyl acetate. In some embodiments, the secondary solvent is or comprises isopropyl acetate. In some embodiments, the secondary solvent is or comprises cyclopentyl methyl ether. In some embodiments, the secondary solvent is or comprises benzene. In some embodiments, the secondary solvent is or comprises α,α,α-trifluorotoluene. In some embodiments, the secondary solvent is or comprises chlorobenzene. In some embodiments, the secondary solvent is or comprises xylene. In some embodiments, the secondary solvent is or comprises dichloromethane. In some embodiments, the secondary solvent is or comprises toluene.

In some embodiments, after the addition of the secondary solvent, the crystallization mixture is aged for an amount of time between 10 minutes and 2 hrs. In some embodiments, after the addition of the secondary solvent, the crystallization mixture is aged for an amount of time between 10 minutes and 1.5 hrs. In some embodiments, after the addition of the secondary solvent, the crystallization mixture is aged for an amount of time between 10 minutes and 1 hr. In some embodiments, after the addition of the secondary solvent, the crystallization mixture is aged for an amount of time between 10 minutes and 45 minutes. In some embodiments, after the addition of the secondary solvent, the crystallization mixture is aged for an amount of time between 10 minutes and 30 minutes. In some embodiments, after the addition of the secondary solvent, the crystallization mixture is aged for less than about two hrs. In some embodiments, after the addition of the secondary solvent, the crystallization mixture is aged for less than about 60 minutes. In some embodiments, after the addition of the secondary solvent, the crystallization mixture is aged for less than about 30 minutes. In some embodiments, after the addition of the secondary solvent, the crystallization mixture is aged for less than about 10 minutes. In some embodiments, after the addition of the secondary solvent, the crystallization mixture is aged for less than about 5 minutes.

In some embodiments, after the addition of the secondary solvent, the crystallization mixture is aged for at least about 30 minutes.

In some embodiments, a seed crystal is added to the crystallization mixture. Without wishing to be bound by a particular theory, it was thought that too low amounts of seed crystal may permit spontaneous/uncontrolled crystallization, which may impact particle size. In addition, it was thought that higher amounts of seed crystals may adversely affect particle size.

In some embodiments, the seed crystal is maribavir, or a pharmaceutically acceptable salt thereof. In some embodiments, the seed crystal is added in an amount of between about 0.01% and 0.50% w/w relative to compound 3, or a salt thereof. In some embodiments, the seed crystal is added in an amount of between about 0.01% and 0.15% w/w relative to compound 3, or a salt thereof. In some embodiments, the seed crystal is added in an amount of between about 0.15% and 0.30% w/w relative to compound 3, or a salt thereof. In some embodiments, the seed crystal is added in an amount of between about 0.05% and 0.30% w/w relative to compound 3, or a salt thereof. In some embodiments, the seed crystal is added in an amount of between about 0.10% and 0.20% w/w relative to compound 3, or a salt thereof. In some embodiments, the seed crystal is added in an amount of between about 0.12% and 0.18% w/w relative to compound 3, or a salt thereof. In some embodiments, the seed crystal is added in an amount of between about 0.14% and 0.16% w/w relative to compound 3, or a salt thereof. In some embodiments, the seed crystal is added in an amount of about 0.13% w/w relative to compound 3, or a salt thereof. In some embodiments, the seed crystal is added in an amount of about 0.14% w/w relative to compound 3, or a salt thereof. In some embodiments, the seed crystal is added in an amount of about 0.15% w/w relative to compound 3, or a salt thereof. In some embodiments, the seed crystal is added in an amount of about 0.16% w/w relative to compound 3, or a salt thereof. In some embodiments, the seed crystal is added in an amount of about 0.17% w/w relative to compound 3, or a salt thereof.

Without wishing to be bound by a particular theory, it was thought that the size of the seed crystals may affect particle size of maribavir (e.g., too small seed crystals may result in smaller particle size of maribavir, and too large seed crystals may result in larger particle size of maribavir). In some embodiments, the size of a seed crystal may be characterized by its d(50) value or Specific Surface Area ("SSA") value. In some embodiments, the size of a seed crystal may be characterized by its d(50) value. It will be understood that "d(50) value" refers to the median particle size of a sample (e.g., 50% of the particles are smaller than the d(50) value and 50% of the particles are larger than the d(50) value). In some embodiments, seed crystals comprise a d(50) value between about 1.00 μm and about 10.00 μm. In some embodiments, seed crystals comprise a d(50) value between about 1.00 μm and about 9.00 μm. In some embodiments, seed crystals comprise a d(50) value between about 1.00 μm and about 8.00 μm. In some embodiments, seed crystals comprise a d(50) value between about 1.00 μm and about 7.00 μm. In some embodiments, seed crystals comprise a d(50) value between about 1.00 μm and about 6.00 μm. In some embodiments, seed crystals comprise a d(50) value between about 1.00 μm and about 5.00 μm. In some embodiments, seed crystals comprise a d(50) value between about 1.00 μm and about 4.00 μm. In some embodiments, seed crystals comprise a d(50) value between about 1.00 μm and about 3.00 μm. In some embodiments, seed crystals comprise a d(50) value between about 2.00 μm and about 10.00 μm. In some embodiments, seed crystals comprise a d(50) value between about 3.00 μm and about 10.00 μm. In some embodiments, seed crystals comprise a d(50) value between about 4.00 μm and about 10.00 μm. In some embodiments, seed crystals comprise a d(50) value between about 5.00 μm and about 10.00 μm. In some embodiments, seed crystals comprise a d(50) value between about 6.00 μm and about 10.00 μm. In some embodiments, seed crystals comprise a d(50) value between about 7.00 μm and about 10.00 μm. In some embodiments, seed crystals comprise a d(50) value between about 1.25 μm and 9.00 μm. In some embodiments, seed crystals comprise a d(50) value between about 1.75 μm and about 8.00 μm. In some embodiments, seed crystals comprise a d(50) value between about 2.25 μm and about 7.00 μm. In some embodiments, seed crystals comprise a d(50) value between about 2.75 μm and about 6.25 μm. In some embodiments, seed crystals comprise a d(50) value between about 3.00 μm and 6.00 μm. In some embodiments, seed crystals comprise a d(50) value of about 1.25 μm, about 1.75 μm, about 2.25 μm, about 2.75 μm, about 3.00 μm, about 4.00 μm, about 5.00 μm, about 6.00 μm, about 6.25 μm, about 7.00 μm, about 8.00 μm, about 9.00 μm, or about 10.00 μm. In some embodiments, seed crystals comprise a d(50) value of about 1.25 μm. In some embodiments, seed crystals comprise a d(50) value of about 1.75 μm. In some embodiments, seed crystals comprise a d(50) value of about 2.25 μm. In some embodiments, seed crystals comprise a d(50) value of about 2.75 μm. In some embodiments, seed crystals comprise a d(50) value of about 3.00 μm. In some embodiments, seed crystals comprise a d(50) value of about 4.00 μm. In some embodiments, seed crystals comprise a d(50) value of about 5.00 μm. In some embodiments, seed crystals comprise a d(50) value of about 6.00 μm. In some embodiments, seed crystals comprise a d(50) value of about 6.25 μm. In some embodiments, seed crystals comprise a d(50) value of about 7.00 μm. In some embodiments, seed crystals comprise a d(50) value of about 8.00 μm. In some embodiments, seed crystals comprise a d(50) value of about 9.00 μm. In some embodiments, seed crystals comprise a d(50) value of about 10.00 μm.

In some embodiments, after the seed crystal is added, the crystallization mixture is aged between about 15 minutes and about 120 minutes. In some embodiments, after the seed crystal is added, the crystallization mixture is aged between about 30 minutes and about 90 minutes. In some embodiments, after the seed crystal is added, the crystallization mixture is aged between about 30 minutes and about 60 minutes. In some embodiments, after the seed crystal is added, the crystallization mixture is aged between about 60 minutes and about 90 minutes. In some embodiments, after the seed crystal is added, the crystallization mixture is aged between about 90 minutes and about 120 minutes. In some embodiments, after the seed crystal is added, the crystallization mixture is aged for at least about 5 minutes. In some embodiments, after the seed crystal is added, the crystallization mixture is aged for at least about 15 minutes. In some embodiments, after the seed crystal is added, the crystallization mixture is aged for at least about 30 minutes. In some embodiments, after the seed crystal is added, the crystallization mixture is aged for at least about 60 minutes. In some embodiments, after the seed crystal is added, the crystallization mixture is aged for at least about 90 minutes. In some embodiments, after the seed crystal is added, the crystallization mixture is aged for at least about 120 minutes. In some embodiments, after the seed crystal is added, the crystallization mixture is aged for about 30 minutes. In some embodiments, after the seed crystal is added, the crystallization mixture is aged for about 60 minutes. In some embodiments, after the seed crystal is added, the crystallization mixture is aged for about 90 minutes. In some embodiments, after the seed crystal is added, the crystallization mixture is aged for about 120 minutes.

In some embodiments, additional secondary solvent is added to the crystallization mixture. In some embodiments, the additional secondary solvent is added in an amount of between about 5/1 and about ⅕ of total primary solvent (kg/kg). In some embodiments, the additional secondary solvent is added in an amount of between about 2/1 and about ½ of total primary solvent (kg/kg). In some embodiments, the additional secondary solvent is added in an amount of between about 24/7 and about 2/7 of total primary solvent (kg/kg). In some embodiments, the additional secondary solvent is added in an amount of between about 16/7 and about 4/7 of total primary solvent (kg/kg). In some embodiments, the additional secondary solvent is added in an amount of about 8/7 of total primary solvent (kg/kg). In some embodiments, the additional secondary solvent is added in an amount of about 9/7 of total primary solvent (kg/kg). In some embodiments, the additional secondary solvent is added in an amount of about 10/7 of total primary solvent (kg/kg). In some embodiments, the additional secondary solvent is added in an amount of about 11/7 of total primary solvent (kg/kg). In some embodiments, the additional secondary solvent is added in an amount of about 12/7 of total primary solvent (kg/kg). In some embodiments, the additional secondary solvent is added in an amount of about 13/7 of total primary solvent (kg/kg). In some embodiments, the additional secondary solvent is added in an amount of about 15/7 of total primary solvent (kg/kg).

In some embodiments, after the additional secondary solvent is added, the crystallization mixture is agitated for a period of time. In some embodiments, the period of time is at least 30 minutes. In some embodiments, the period of time is at least 60 mins. In some embodiments, the period of time is between about 15 minutes and 120 minutes. In some embodiments, the period of time is between about 15 minutes and 90 minutes. In some embodiments, the period of time is between about 15 minutes and 60 minutes. In some embodiments, the period of time is between about 30 minutes and 90 minutes. In some embodiments, the period of time is between about 45 minutes and 90 minutes. In some embodiments, the period of time is between about 60 minutes and 90 minutes. In some embodiments, the period of time is about 15 minutes. In some embodiments, the period of time is about 30 minutes. In some embodiments, the period of time is about 45 minutes. In some embodiments, the period of time is about 60 minutes. In some embodiments, the period of time is about 90 minutes.

In some embodiments, after the additional secondary solvent is added, the crystallization mixture is agitated at temperature $T_3$. In some embodiments, temperature $T_3$ is between about 50° C. and about 150° C. In some embodiments, temperature $T_3$ is between about 50° C. and about 100° C. In some embodiments, temperature $T_3$ is between about 50° C. and about 90° C. In some embodiments, temperature $T_3$ is between about 50° C. and about 80° C. In some embodiments, temperature $T_3$ is between about 70° C. and about 115° C. In some embodiments, temperature $T_3$ is between about 80° C. and about 115° C. In some embodiments, temperature $T_3$ is between about 60° C. and about 105° C. In some embodiments, temperature $T_3$ is between about 70° C. and about 95° C. In some embodiments, temperature $T_3$ is between about 75° C. and about 90° C. In some embodiments, temperature $T_3$ is between about 77° C. and about 88° C. In some embodiments, temperature $T_3$ is between about 81° C. and about 87° C. In some embodiments, temperature $T_3$ is between about 81° C. and about 86° C. In some embodiments, temperature $T_3$ is about 80° C., 81° C., 82° C., 84° C., 85° C., 86° C., 87° C., 88° C., 89° C., or 90° C. In some embodiments, temperature $T_3$ is about 83° C. In some embodiments, temperature $T_3$ is about 84° C. In some embodiments, temperature $T_3$ is about 85° C.

In some embodiments, the crystallization mixture is cooled to temperature $T_4$. In some embodiments, temperature $T_4$ is between about −20° C. and about 25° C. In some embodiments, temperature $T_4$ is between about −15° C. and about 20° C. In some embodiments, temperature $T_4$ is between about −15° C. and about 15° C. In some embodiments, temperature $T_4$ is between about −15° C. and about 10° C. In some embodiments, temperature $T_4$ is between about −15° C. and about 5° C. In some embodiments, temperature $T_4$ is between about −15° C. and about 0° C. In some embodiments, temperature $T_4$ is between about −5° C. and about 25° C. In some embodiments, temperature $T_4$ is between about 0° C. and about 25° C. In some embodiments, temperature $T_4$ is between about 5° C. and about 25° C. In some embodiments, temperature $T_4$ is between about 10° C. and about 25° C. In some embodiments, temperature $T_4$ is between about −10° C. and about 20° C. In some embodiments, temperature $T_4$ is between about −5° C. and about 15° C. In some embodiments, temperature $T_4$ is between about 0° C. and about 10° C. In some embodiments, temperature $T_4$ is between about 3° C. and about 7° C. In some embodiments, temperature $T_4$ is about 0° C., 1° C., 2° C., 3° C., 4° C., 5° C., 6° C., 7° C., 8° C., 9° C., or 10° C. In some embodiments, temperature $T_4$ is about 4° C. In some embodiments, temperature $T_4$ is about 5° C. In some embodiments, temperature $T_4$ is about 6° C.

In some embodiments, the crystallization mixture is cooled to temperature $T_4$ over between about 0.5 hrs and about 8 hrs. In some embodiments, the crystallization mixture is cooled to temperature $T_4$ over between about 1 hr and about 5 hrs. In some embodiments, the crystallization mixture is cooled to temperature $T_4$ over between about 2 hrs and about 4 hrs. In some embodiments, the crystallization mixture is cooled to temperature $T_4$ over at least 1 hr. In some embodiments, the crystallization mixture is cooled to temperature $T_4$ over at least 3 hrs. In some embodiments, the crystallization mixture is cooled to temperature $T_4$ over about 0.5, 1, 2, 3, 4, 5, 6, 7, or 8 hrs. In some embodiments, the crystallization mixture is cooled to temperature $T_4$ over about 2 hrs. In some embodiments, the crystallization mixture is cooled to temperature $T_4$ over about 3 hrs. In some embodiments, the crystallization mixture is cooled to temperature $T_4$ over about 4 hrs. In some embodiments, the crystallization mixture is cooled to temperature $T_4$ over about 6 hrs. In some embodiments, the crystallization mixture is cooled to temperature $T_4$ over about 8 hrs.

In some embodiments, the crystallization mixture is agitated at temperature $T_4$ for a period of time. In some embodiments, the period of time is between about 3 hrs and about 30 hrs. In some embodiments, the period of time is between about 3 hrs and about 18 hrs. In some embodiments, the period of time is between about 3 hrs and about 15 hrs. In some embodiments, the period of time is between about 3 hrs and about 12 hrs. In some embodiments, the period of time is between about 3 hrs and about 8 hrs. In some embodiments, the period of time is between about 3 hrs and about 5 hrs. In some embodiments, the period of time is less than about 18 hrs. In some embodiments, the period of time is less than about than 12 hrs. In some embodiments, the period of time is less than about 6 hrs. In some embodiments, the period of time is less than about 3 hrs.

In some embodiments, Step 3 further comprises a step of (e) optionally filtering or washing the crystallization mixture to provide a filtered mixture. In some embodiments, Step 3 further comprises filtering the crystallization mixture to provide the filtered mixture. In some embodiments, Step 3 further comprises washing the crystallization mixture to provide the filtered mixture. In some embodiments, the crystallization mixture is washed with chloroform, diethyl ether, ethyl acetate, isopropyl acetate, tert-butyl methyl ether, cyclopentyl methyl ether, toluene, benzene, α,α,α-trifluorotoluene, chlorobenzene, xylene, or dichloromethane. In some embodiments, the crystallization mixture is washed with chloroform. In some embodiments, the crystallization mixture is washed with diethyl ether. In some embodiments, the crystallization mixture is washed with ethyl acetate. In some embodiments, the crystallization mixture is washed with isopropyl acetate. In some embodiments, the crystallization mixture is washed with cyclopentyl methyl ether. In some embodiments, the crystallization mixture is washed with benzene. In some embodiments, the crystallization mixture is washed with α,α,α-trifluorotoluene. In some embodiments, the crystallization mixture is washed with chlorobenzene. In some embodiments, the crystallization mixture is washed with xylene. In some embodiments, the crystallization mixture is washed with dichloromethane. In some embodiments, the crystallization mixture is washed with toluene.

In some embodiments, the crystallization wash solvent is provided in an amount between about 0.30 L/kg and about 2.00 L/kg. In some embodiments, the crystallization wash solvent is provided in an amount between about 0.30 L/kg and about 1.50 L/kg. In some embodiments, the crystallization wash solvent is provided in an amount between about 0.30 L/kg and about 1.25 g/g. In some embodiments, the crystallization wash solvent is provided in an amount between about 0.30 L/kg and about 1.00 L/kg. In some embodiments, the crystallization wash solvent is provided in an amount between about 0.30 L/kg and about 0.9 L/kg. In some embodiments, the crystallization wash solvent is provided in an amount between about 0.50 L/kg and about 2.00 L/kg. In some embodiments, the crystallization wash solvent is provided in an amount between about 0.75 L/kg and about 2.00 L/kg. In some embodiments, the crystallization wash solvent is provided in an amount between about 0.85 L/kg and about 2.00 L/kg. In some embodiments, the crystallization wash solvent is provided in an amount between about 0.30 L/kg and about 2.00 L/kg. In some embodiments, the crystallization wash solvent is provided in an amount between about 0.40 L/kg and about 1.75 L/kg. In some embodiments, the crystallization wash solvent is provided in an amount between about 0.50 L/kg and about 1.50 L/kg. In some embodiments, the crystallization wash solvent is provided in an amount between about 0.60 L/kg and about 1.25 L/kg. In some embodiments, the crystallization wash solvent is provided in an amount between about 0.67 L/kg and about 1.00 L/kg. In some embodiments, the crystallization wash solvent is provided in an amount between about 0.75 L/kg and about 0.90 L/kg. In some embodiments, the crystallization wash solvent is provided in an amount between about 0.80 L/kg and about 0.85 L/kg. In some embodiments, the crystallization wash solvent is provided in an amount of about 0.60 L/kg, 0.65 L/kg, 0.70 L/kg, 0.75 L/kg, 0.80 L/kg, 0.84 L/kg, 0.90 L/kg, or 0.95 L/kg. In some embodiments, the crystallization wash solvent is provided in an amount of about 0.75 L/kg. In some embodiments, the crystallization wash solvent is provided in an amount of about 0.80 L/kg. In some embodiments, the crystallization wash solvent is provided in an amount of about 0.84 L/kg. In some embodiments, the crystallization wash solvent is provided in an amount of about 0.90 L/kg. In some embodiments, the crystallization wash solvent is provided in an amount of about 0.95 L/kg.

In some embodiments, the crystallization wash solvent is provided at a temperature between about −20° C. and about 60° C. In some embodiments, the crystallization wash solvent is provided at a temperature between about −10° C. and about 30° C. In some embodiments, the crystallization wash solvent is provided at a temperature between about −10° C. and about 20° C. In some embodiments, the crystallization wash solvent is provided at a temperature between about −10° C. and about 10° C. In some embodiments, the crystallization wash solvent is provided at a temperature between about −5° C. and about 40° C. In some embodiments, the crystallization wash solvent is provided at a temperature between about 0° C. and about 40° C. In some embodiments, the crystallization wash solvent is provided at a temperature between about 5° C. and about 40° C. In some embodiments, the crystallization wash solvent is provided at a temperature between about −5° C. and about 30° C. In some embodiments, the crystallization wash solvent is provided at a temperature between about −5° C. and about 20° C. In some embodiments, the crystallization wash solvent is provided at a temperature between about 0° C. and about 20° C. In some embodiments, the crystallization wash solvent is provided at a temperature between about 0° C. and about 15° C. In some embodiments, the crystallization wash solvent is provided at a temperature between about 0° C. and about 10° C. In some embodiments, the crystallization wash solvent is provided at a temperature between about 2° C. and about 8° C. In some embodiments, the crystallization wash solvent is provided at a temperature between about 4° C. and about 6° C. In some embodiments, the crystallization wash solvent is provided at a temperature of about 1° C., 2° C., 3° C., 4° C., 5° C., 6° C., 7° C., 8° C., or 9° C. In some embodiments, the crystallization wash solvent is provided at a temperature of about 4° C. In some embodiments, the crystallization wash solvent is provided at a temperature of about 5° C. In some embodiments, the crystallization wash solvent is provided at a temperature of about 6° C.

In some embodiments, the crystallization wash solvent is provided for a period of time, that period of time is less than 5 days. In some embodiments, the crystallization wash solvent is provided for a period of time, that period of time is between about 1 minute and about 5 days. In some embodiments, the crystallization wash solvent is provided for a period of time, that period of time is between about 1 minute and about 24 hrs. In some embodiments, the crystallization wash solvent is provided for a period of time, that period of time is between about 1 minute and about 12 hrs. In some embodiments, the crystallization wash solvent is provided for a period of time, that period of time is between about 1 minute and about 8 hrs. In some embodiments, the crystallization wash solvent is provided for a period of time, that period of time is between about 1 minute and about 6 hrs. In some embodiments, the crystallization wash solvent is provided for a period of time, that period of time is between about 1 minute and about 4 hrs. In some embodiments, the crystallization wash solvent is provided for a period of time, that period of time is between about 1 minute and about 2 hrs. In some embodiments, the crystallization wash solvent is provided for a period of time, that period of time is between about 1 minute and about 1 hr. In some embodiments, the crystallization wash solvent is provided for a period of time, that period of time is between about 1 minute and about 45 minutes. In some embodiments, the crystallization wash solvent is provided for a period of time, that period of time is between about 1 minute and about 30 minutes. In some embodiments, the crystallization wash solvent is provided for a period of time, that period of time is between about 1 minute and about 30 minutes. In some embodiments, the crystallization wash solvent is provided for a period of time, that period of time is about 15 minutes. In some embodiments, the crystallization wash solvent is provided for a period of time, that period of time is at least 15 minutes. In some embodiments, the crystallization wash solvent is provided for a period of time, that period of time is at least 30 minutes. In some embodiments, the crystallization wash solvent is provided for a period of time, that period of time is at least 60 minutes. In some embodiments, the crystallization wash solvent is provided for a period of time, that period of time is at least 90 minutes. In some embodiments, the crystallization wash solvent is provided for a period of time, that period of time is at least 1 day.

In some embodiments, Step 3 further comprises a step of (f) drying the filtered mixture.

In some embodiments, drying comprises heating the filtered mixture to temperature $T_5$ without agitation for a period of time. In some embodiments, temperature $T_5$ is between about 20° C. and about 100° C. In some embodiments, temperature $T_5$ is between about 20° C. and about 70° C. In some embodiments, temperature $T_5$ is between about 20° C. and about 50° C. In some embodiments, temperature $T_5$ is between about 30° C. and about 80° C. In some embodiments, temperature $T_5$ is between about 40° C. and about 80° C. In some embodiments, temperature $T_5$ is between about 50° C. and about 80° C. In some embodiments, temperature $T_5$ is between about 35° C. and about 60° C. In some embodiments, temperature $T_5$ is between about 40° C. and about 50° C. In some embodiments, temperature $T_5$ is less than or equal to 20° C. In some embodiments, temperature $T_5$ is less than or equal to about 20° C., 30° C., 40° C., 50° C., 60° C., 70° C., 80° C., 90° C., or 100° C. In some embodiments, temperature $T_5$ is less than or equal to 40° C. In some embodiments, temperature $T_5$ is less than or equal to 50° C. In some embodiments, temperature $T_5$ is less than or equal to 60° C.

In some embodiments, the filtered mixture is held at temperature $T_5$ for a period of time. In some embodiments, the period of time is at least 1 hr. In some embodiments, the period of time is at least 2 hrs. In some embodiments, the period of time is at least 3 hrs. In some embodiments, the period of time is at least 4 hrs. In some embodiments, the period of time is at least 5 hrs. In some embodiments, the period of time is at least 6 hrs. In some embodiments, the period of time is at least 7 hrs. In some embodiments, the period of time is at least 8 hrs. In some embodiments, the period of time is at least 9 hrs. In some embodiments, the period of time is at least 10 hrs.

In some embodiments, drying further comprises heating the filtered mixture to temperature $T_6$ without agitation for a period of time. In some embodiments, temperature $T_6$ is between about 20° C. and about 100° C. In some embodiments, temperature $T_6$ is between about 40° C. and about 100° C. In some embodiments, temperature $T_6$ is between about 20° C. and about 80° C. In some embodiments, temperature $T_6$ is between about 20° C. and about 70° C. In some embodiments, temperature $T_6$ is between about 20° C. and about 60° C. In some embodiments, temperature $T_6$ is between about 30° C. and about 60° C. In some embodiments, temperature $T_6$ is between about 40° C. and about 60° C. In some embodiments, temperature $T_6$ is between about 45° C. and about 55° C. In some embodiments, temperature $T_6$ is between about 45° C. and about 50° C. In some embodiments, temperature $T_6$ is less than or equal to 25° C., 30° C., 40° C., 45° C., 50° C., 55° C., 60° C. In some embodiments, temperature $T_6$ is less than or equal to 90° C. In some embodiments, temperature $T_6$ is less than or equal to 70° C. In some embodiments, temperature $T_6$ is less than or equal to 60° C. In some embodiments, temperature $T_6$ is less than or equal to 55° C. In some embodiments, temperature $T_6$ is less than or equal to 50° C. In some embodiments, temperature $T_6$ is less than or equal to 45° C. In some embodiments, temperature $T_6$ is less than or equal to 40° C.

In some embodiments, the filtered mixture is held at temperature $T_6$ for a period of time. In some embodiments, the period of time is between about 1 hr and 5 days. In some embodiments, the period of time is between about 1 hr and 2 days. In some embodiments, the period of time is between about 1 hr and 1 day. In some embodiments, the period of time is between about 1 hr and 12 hrs. In some embodiments, the period of time is between about 1 hr and 6 hrs. In some embodiments, the period of time is at least 1 hr. In some embodiments, the period of time is at least 2 hrs. In some embodiments, the period of time is at least 3 hrs. In some embodiments, the period of time is at least 4 hrs. In some embodiments, the period of time is at least 5 hrs. In some embodiments, the period of time is at least 6 hrs. In some embodiments, the period of time is until the filtered mixture appears dry.

In some embodiments, the period of time is until between about 100 ppm and about 1600 ppm of toluene is present (e.g., as measured by GCHS). In some embodiments, the period of time is until between about 100 ppm and about 1400 ppm of toluene is present (e.g., as measured by GCHS). In some embodiments, the period of time is until between about 100 ppm and about 1200 ppm of toluene is present (e.g., as measured by GCHS). In some embodiments, the period of time is until between about 100 ppm and about 1000 ppm of toluene is present (e.g., as measured by GCHS). In some embodiments, the period of time is until between about 100 ppm and about 800 ppm of toluene is present (e.g., as measured by GCHS). In some embodiments, the period of time is until between about 100 ppm and about 700 ppm of toluene is present (e.g., as measured by GCHS). In some embodiments, the period of time is until between about 300 ppm and about 1400 ppm of toluene is present (e.g., as measured by GCHS). In some embodiments, the period of time is until between about 500 ppm and about 1400 ppm of toluene is present (e.g., as measured by GCHS). In some embodiments, the period of time is until between about 700 ppm and about 1400 ppm of toluene is present (e.g., as measured by GCHS). In some embodiments, the period of time is until between about 300 ppm and about 1200 ppm of toluene is present (e.g., as measured by GCHS). In some embodiments, the period of time is until between about 500 ppm and about 1000 ppm of toluene is present (e.g., as measured by GCHS). In some embodiments, the period of time is until between about 600 ppm and about 800 ppm of toluene is present (e.g., as measured by GCHS). In some embodiments, the period of time is until between about 650 ppm and about 750 ppm of toluene is present (e.g., as measured by GCHS). In some embodiments, the period of time is until less than 1500 ppm of toluene is present (e.g., as measured by GCHS). In some embodiments, the period of time is until less than 1200 ppm of toluene is present (e.g., as measured by GCHS). In some embodiments, the period of time is until less than 1000 ppm of toluene is present (e.g., as measured by GCHS). In some embodiments, the period of time is until less than 800 ppm of toluene is present (e.g., as measured by GCHS). In some embodiments, the period of time is until less than 700 ppm of toluene is present (e.g., as measured by GCHS). In some embodiments, the period of time is until less than 600 ppm of toluene is present (e.g., as measured by GCHS). In some embodiments, the period of time is until less than 500 ppm of toluene is present (e.g., as measured by GCHS). In some embodiments, the period of time is until less than 400 ppm of toluene is present (e.g., as measured by GCHS). In some embodiments, the period of time is until less than 300 ppm of toluene is present (e.g., as measured by GCHS).

In some embodiments, the period of time is until between about 1,000 ppm and about 10,000 ppm of isopropyl acetate is present (e.g., as measured by GCHS). In some embodiments, the period of time is until between about 1,000 ppm and about 8,000 ppm of isopropyl acetate is present (e.g., as measured by GCHS). In some embodiments, the period of time is until between about 1,000 ppm and about 6,000 ppm of isopropyl acetate is present (e.g., as measured by GCHS). In some embodiments, the period of time is until between about 1,000 ppm and about 5,000 ppm of isopropyl acetate is present (e.g., as measured by GCHS). In some embodiments, the period of time is until between about 1,000 ppm and about 4,000 ppm of isopropyl acetate is present (e.g., as measured by GCHS). In some embodiments, the period of time is until between about 1,000 ppm and about 3,000 ppm of isopropyl acetate is present (e.g., as measured by GCHS). In some embodiments, the period of time is until between about 3,000 ppm and about 10,000 ppm of isopropyl acetate is present (e.g., as measured by GCHS). In some embodiments, the period of time is until between about 4,000 ppm and about 10,000 ppm of isopropyl acetate is present (e.g., as measured by GCHS). In some embodiments, the period of time is until between about 5,000 ppm and about 10,000 ppm of isopropyl acetate is present (e.g., as measured by GCHS). In some embodiments, the period of time is until between about 2,000 ppm and about 8,000 ppm of isopropyl acetate is present (e.g., as measured by GCHS). In some embodiments, the period of time is until between about 3,000 ppm and about 6,000 ppm of isopropyl acetate is present (e.g., as measured by GCHS). In some embodiments, the period of time is until between about 4,000 ppm and about 5,000 ppm of isopropyl acetate is present (e.g., as measured by GCHS). In some embodiments, the period of time is until less than 10,000 ppm of isopropyl acetate is present (e.g., as measured by GCHS). In some embodiments, the period of time is until less than 8,000 ppm of isopropyl acetate is present (e.g., as measured by GCHS). In some embodiments, the period of time is until less than 6,000 ppm of isopropyl acetate is present (e.g., as measured by GCHS). In some embodiments, the period of time is until less than 5,000 ppm of isopropyl acetate is present (e.g., as measured by GCHS). In some embodiments, the period of time is until less than 4,000 ppm of isopropyl acetate is present (e.g., as measured by GCHS). In some embodiments, the period of time is until less than 3,000 ppm of isopropyl acetate is present (e.g., as measured by GCHS). In some embodiments, the period of time is until less than 2,000 ppm of isopropyl acetate is present (e.g., as measured by GCHS). In some embodiments, the period of time is until less than 1,000 ppm of isopropyl acetate is present (e.g., as measured by GCHS).

In some embodiments, Step 3 provides unmilled maribavir, or a pharmaceutically acceptable salt thereof. In some embodiments, Step 3 further comprises a step of (g) milling the unmilled maribavir, or a pharmaceutically acceptable salt thereof, to provide milled maribavir, or a pharmaceutically acceptable salt thereof. In some embodiments, milling comprises formulating into a tablet (e.g., a 200 mg tablet).

Formulations & Compositions

In some embodiments, provided compositions comprise at least 90% by weight of maribavir. In some embodiments, provided compositions comprise at least 95% by weight of maribavir. In some embodiments, provided compositions comprise at least 99% by weight of maribavir. In some embodiments, provided compositions comprise at least 99.5% by weight of maribavir. In some embodiments, provided compositions comprise at least 99.6% by weight of maribavir. In some embodiments, provided compositions comprise at least 99.7% by weight of maribavir. In some embodiments, provided compositions comprise at least 99.8% by weight of maribavir. In some embodiments, provided compositions comprise at least 99.9% by weight of maribavir.

In some embodiments, provided composition comprise maribavir substantially free of impurities. As used herein, the term "substantially free of impurities" means that the composition or compound contains no significant amount of extraneous matter. Such extraneous matter may include starting materials, residual solvents, or other impurities that may result from the preparation of, and/or isolation of maribavir.

In some embodiments, the present disclosure provides a composition comprising maribavir and one or more compound selected from compound 2, compound 3, and compound 4. In some embodiments, such compositions comprise 0.01-0.05% (w/w) of compound 2, 0.01-0.05% (w/w) compound 3, and/or 0.01-0.05% (w/w) compound 4. In some embodiments, such compositions comprise 0.01-0.05% (a/a) of compound 2, 0.01-0.05% (a/a) compound 3, and/or 0.01-0.05% (a/a) compound 4, as measured by HPLC. In some embodiments, the present disclosure provides a composition comprising maribavir and 0.01-0.5% ent-maribavir (i.e., D-maribavir):

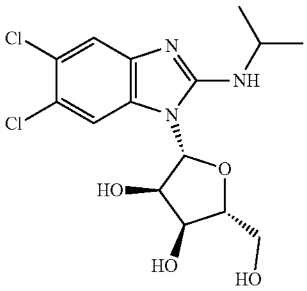

D-maribavir

In some embodiments, the present disclosure provides a composition as set forth in any of Tables 4-12 to 4-20 in Example 4.

In some embodiments, Steps 1-3 provide a particular polymorphic form of maribavir. In some embodiments, Steps 1-3 provide Form VI of maribavir (e.g., at least 90%, 95%, or 99% by weight of Form VI of maribavir), as described in U.S. Pat. No. 6,482,939. In some embodiments, Steps 1-3 provide Form VI of maribavir substantially free of other polymorphic forms of maribavir. As used herein, the term "polymorphic forms" includes solvates and hydrates.

In some embodiments, provided compositions comprises Form VI of maribavir, as described in described in U.S. Pat. No. 6,482,939 (e.g., at least 90%, 95%, or 99% by weight of Form VI of maribavir). In some embodiments, provided compositions comprises Form VI of maribavir (e.g., at least 90%, 95%, or 99% by weight of Form VI of maribavir), as described in described in U.S. Pat. No. 6,482,939, and another polymorphic form of maribavir, e.g., as described in U.S. Pat. Nos. 6,482,939, 8,546,344, or U.S. Pat. No. 11,130,777. In some embodiments, provided compositions comprises Form VI of maribavir, as described in described in U.S. Pat. No. 6,482,939, and an isopropyl acetate solvate of maribavir (e.g., as described in U.S. Pat. Nos. 6,482,939, 8,546,344, or U.S. Pat. No. 11,130,777). In some embodiments, provided composition comprise Form VI of maribavir, and less than 10%, 5%, 1%, or 0.5% by weight of another polymorphic form of maribavir, e.g., as described in U.S. Pat. Nos. 6,482,939, 8,546,344, or U.S. Pat. No. 11,130,777. In some embodiments, provided composition comprise Form VI of maribavir, and less than 10%, 5%, 1%, or 0.5% by weight of another polymorphic form of maribavir, e.g., as described in U.S. Pat. Nos. 6,482,939, 8,546,344, or U.S. Pat. No. 11,130,777. In some embodiments, provided composition comprise Form VI of maribavir substantially free of other polymorphic forms, e.g., as described in U.S. Pat. Nos. 6,482,939, 8,546,344, or U.S. Pat. No. 11,130,777.

In some embodiments, maribavir (e.g., Form VI) is milled (e.g., hammer milled) and formulated into a tablet (e.g., a 200 mg tablet).

Particle size distribution ("PSD") is a measurement that defines the number of particles present according to their size. It will be appreciated that PSD is a valuable indicator of quality and performance and is necessary to ensure consistent drug product manufacturability. For example, PSD may impact ease of handling of a compound and excipients when formulating (e.g., into a tablet). Consistent formulations are important to ensure that the active drug is delivered to the correct location within the body, in the right concentration, and at the correct rate. In some embodiments, the present disclosure provides compositions of maribavir, and methods of making maribavir and compositions comprising maribavir, with PSDs that result in consistent formulation into tables. In some embodiments, Steps 1, 2, 3, and/or milling (e.g., hammer milling) provide maribavir with a PSD that permits manufacture of tablets with uniformity. In some embodiments, Steps 3 provides maribavir Form VI particle with a desirable PSD. In some embodiments, the present disclosure provides compositions comprising maribavir Form VI particle with a PSD of d(50) as between about 100 and about 400 μm. In some embodiments, the present disclosure provides compositions comprising maribavir Form VI particle with a PSD of d(50) as between about 100 and about 400 μm wherein such maribavir Form VI is manufactured by using maribavir seed with a PSD of d(50) between about between about 1 and about 10 μm. In some embodiments, the present disclosure provides methods of manufacturing maribavir Form VI particle by using maribavir Form VI seed with a PSD of d(50) between about between about 1 and about 10 μm.

In some embodiments, maribavir, or a pharmaceutically acceptable salt thereof, has a PSD of d(50) as between about 50 and about 500 μm. In some embodiments, maribavir, or a pharmaceutically acceptable salt thereof, has a PSD of d(50) as between about 100 and about 400 μm. In some embodiments, maribavir, or a pharmaceutically acceptable salt thereof, has a PSD of d(50) as between about 170 and about 350 μm. In some embodiments, maribavir, or a pharmaceutically acceptable salt thereof, has a PSD of d(50) as between about 170 and about 226 μm. In some embodiments, maribavir, or a pharmaceutically acceptable salt thereof, has a PSD of d(50) as between about 227 and about 280 μm. In some embodiments, maribavir, or a pharmaceutically acceptable salt thereof, has a PSD of d(50) as between about 281 and about 336 μm.

In some aspects, the present disclosure provides compositions comprising maribavir or a pharmaceutically acceptable salt thereof. In some embodiments, the present disclosure provides compositions made by a method disclosed here (e.g., Steps 1-3). In some embodiments, the present disclosure provides compositions comprising maribavir, or a pharmaceutically acceptable salt thereof, and one or more compounds selected from:

2

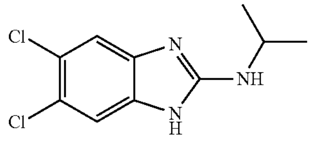

3

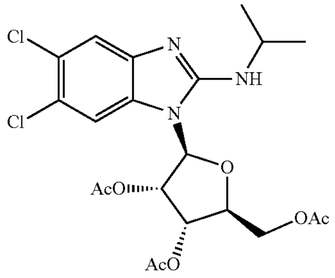

or

4

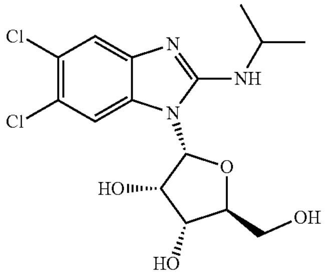

or pharmaceutically acceptable salts thereof.

In some embodiments, the present disclosure provides compositions comprising 0.01-0.10% (w/w HPLC) of compound 2, relative to maribavir. In some embodiments, the present disclosure provides compositions comprising 0.01-0.05% w/w (e.g., as measured by HPLC) of compound 2, relative to maribavir. In some embodiments, the present disclosure provides compositions comprising 0.02-0.05% w/w (e.g., as measured by HPLC) of compound 2, relative to maribavir. In some embodiments, the present disclosure provides compositions comprising less than 1%, 0.5%, 0.1%, 0.05%, 0.02%, or 0.01% w/w (e.g., as measured by HPLC) of compound 2, relative to maribavir. In some embodiments, the present disclosure provides compositions comprising 0.01-0.10% a/a (e.g., as measured by HPLC) of compound 2, relative to maribavir. In some embodiments, the present disclosure provides compositions comprising 0.01-0.05% a/a (e.g., as measured by HPLC) of compound 2, relative to maribavir. In some embodiments, the present disclosure provides compositions comprising 0.02-0.05% a/a (e.g., as measured by HPLC) of compound 2, relative to maribavir. In some embodiments, the present disclosure provides compositions comprising less than 1%, 0.5%, 0.1%, 0.05%, 0.02%, or 0.01% a/a (e.g., as measured by HPLC) of compound 2, relative to maribavir. In some embodiments, the present disclosure provides compositions, wherein compound 2, or a salt thereof, is not detectable (e.g., by HPLC or $^{1}$H NMR).

In some embodiments, the present disclosure provides compositions comprising 0.01-0.10% (w/w HPLC) of compound 3, relative to maribavir. In some embodiments, the present disclosure provides compositions comprising 0.01-0.05% w/w (e.g., as measured by HPLC) of compound 3, relative to maribavir. In some embodiments, the present disclosure provides compositions comprising 0.02-0.05% w/w (e.g., as measured by HPLC) of compound 3, relative to maribavir. In some embodiments, the present disclosure provides compositions composition comprising less than 1%, 0.5%, 0.1%, 0.05%, 0.02%, or 0.01% w/w (e.g., as measured by HPLC) of compound 3, relative to maribavir. In some embodiments, the present disclosure provides compositions comprising 0.01-0.10% a/a (e.g., as measured by HPLC) of compound 3, relative to maribavir. In some embodiments, the present disclosure provides compositions comprising 0.01-0.05% a/a (e.g., as measured by HPLC) of compound 3, relative to maribavir. In some embodiments, the present disclosure provides compositions comprising 0.02-0.05% a/a (e.g., as measured by HPLC) of compound 3, relative to maribavir. In some embodiments, the present disclosure provides compositions comprising less than 1%, 0.5%, 0.1%, 0.05%, 0.02%, or 0.01% a/a (e.g., as measured by HPLC) of compound 3, relative to maribavir. In some embodiments, the present disclosure provides compositions, wherein compound 3, or a salt thereof, is not detectable (e.g., by HPLC or $^{1}$H NMR).

In some embodiments, the present disclosure provides compositions comprising 0.01-0.10% (w/w HPLC) of compound 4, relative to maribavir. In some embodiments, the present disclosure provides compositions comprising 0.01-0.05% w/w (e.g., as measured by HPLC) of compound 4, relative to maribavir. In some embodiments, the present disclosure provides compositions comprising 0.02-0.05% w/w (e.g., as measured by HPLC) of compound 4, relative to maribavir. In some embodiments, the present disclosure provides compositions composition comprising less than 1%, 0.5%, 0.1%, 0.05%, 0.02%, or 0.01% w/w (e.g., as measured by HPLC) of compound 4, relative to maribavir. In some embodiments, the present disclosure provides compositions comprising 0.01-0.10% a/a (e.g., as measured by HPLC) of compound 4, relative to maribavir. In some embodiments, the present disclosure provides compositions comprising 0.01-0.05% a/a (e.g., as measured by HPLC) of compound 4, relative to maribavir. In some embodiments, the present disclosure provides compositions comprising 0.02-0.05% a/a (e.g., as measured by HPLC) of compound 4, relative to maribavir. In some embodiments, the present disclosure provides compositions comprising less than 1%, 0.5%, 0.1%, 0.05%, 0.02%, or 0.01% a/a (e.g., as measured by HPLC) of compound 4, relative to maribavir. In some embodiments, the present disclosure provides compositions, wherein compound 4, or a salt thereof, is not detectable (e.g., by HPLC or $^{1}$H NMR).

Dosing Regimens

Provided herein are methods of treating a patient suffering from CMV, comprising administering maribavir (e.g., by administering a composition that comprises and/or delivers maribavir as described herein) to the patient. In some embodiments, provided methods comprise administering about 400 mg of maribavir orally to the patient twice daily. In some embodiments, provided methods comprise administering about 200 mg of maribavir orally to the patient twice daily.

Maribavir can administered with or without food. In some embodiments, maribavir is administered as 200 mg tablets. In some embodiments, maribavir is administered as 400 mg tablets. In some embodiments, maribavir is administered as 200 mg oral solid composition. In some embodiments, maribavir is administered as 400 mg oral solid composition.

In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients. In some embodiments, the present disclosure provides methods of treating patients with post-transplant CMV infection or disease that is intolerant to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, (v) less than 0.05% of D-maribavir or a salt thereof, and (v) pharmaceutically acceptable excipients. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients are administered immunosuppressant drugs that are CYP3A4 and/or P-gp substrates including tacrolimus, cyclosporine, sirolimus and everolimus. In some embodiments, the present disclosure provides methods of controlling drug concentrations of maribavir and immunosuppressant in patients with post-transplant CMV infection or disease comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients are administered immunosuppressant drugs. In some embodiments, the present disclosure provides methods of controlling drug concentrations of maribavir and immunosuppressant in patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients are administered immunosuppressant drugs that are CYP3A4 and/or P-gp substrates including tacrolimus, cyclosporine, sirolimus and everolimus. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients are administered immunosuppressant drugs that are CYP3A4 and/or P-gp substrates including tacrolimus, cyclosporine, sirolimus and everolimus, wherein immunosuppressant drug levels in said patients are monitored after administration of maribavir. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 800 mg twice a day, wherein maribavir is administered as an oral solid composition, wherein such composition comprises (i) maribavir Form VI particle having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients have received carbamazepine before the administration of maribavir. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 1200 mg twice a day, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients, wherein said patients have received phenytoin or phenobarbital before the administration of maribavir. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day for more than 6 months, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day for more than 12 months, wherein maribavir is administered as an oral solid composition, wherein such composition comprises (i) maribavir Form VI having a PSD of d(50) less than about 400 μm, (ii) less than 0.05% of Compound 2 or a salt thereof, (iii) less than 0.05% of Compound 3 or a salt thereof, (iv) less than 0.05% of Compound 4 or a salt thereof, and (v) pharmaceutically acceptable excipients. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) between about 50 and about 400 μm, (ii) less than 0.1% of Compound 2 or a salt thereof, (iii) less than 0.15% of Compound 3 or a salt thereof, (iv) less than 0.1% of Compound 4 or a salt thereof, and (v) pharmaceutically acceptable excipients. In some embodiments, the present disclosure provides methods of treating patients with post-transplant CMV infection or disease that is refractory to treatment with ganciclovir, valganciclovir, cidofovir or foscarnet comprising orally administering maribavir or a salt thereof to said patients in an amount of 400 mg twice a day, wherein maribavir is administered as an oral solid composition, wherein such composition comprises (i) maribavir Form VI having a PSD of d(50) between about 50 and about 400 μm, (ii) less than 0.1% of intermediate impurities, (iii) less than 0.1% of enantiomeric impurities, (iv) less than 0.1% of unspecified impurities, and (v) pharmaceutically acceptable excipients.

Enumerated Embodiments

1. A composition comprising (i) maribavir:

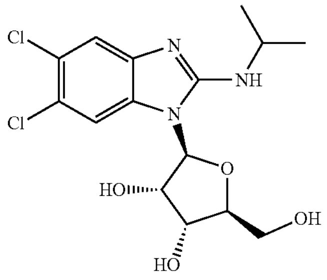 [SMILES: CC(C)Nc1nc2cc(Cl)c(Cl)cc2n1[C@H]1O[C@@H](CO)[C@H](O)[C@@H]1O]

or a pharmaceutically acceptable salt thereof, and (ii) and one or more of the following:

Compound 2,

2

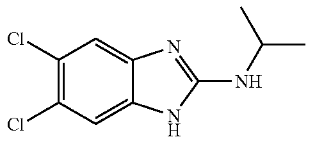

or a pharmaceutically acceptable salt thereof,

Compound 3,

3

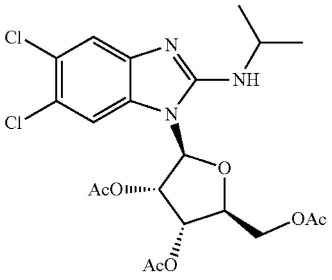

or a pharmaceutically acceptable salt thereof; or

Compound 4:

4

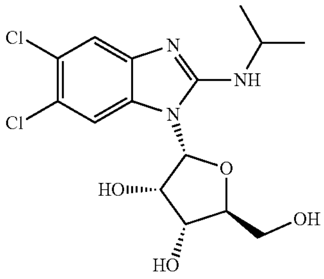

or a pharmaceutically accept salt thereof

2. The composition of embodiment 1, comprising Compound 2:

2

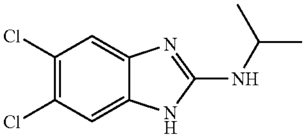

or a pharmaceutically acceptable salt thereof.

3. The composition of embodiment 2, comprising 0.01-0.10% w/w of Compound 2, relative to maribavir (e.g., as measured by HPLC).

4. The composition of embodiment 2 or 3, comprising 0.01-0.05% w/w of Compound 2, relative to maribavir (e.g., as measured by HPLC).

5. The composition of any one of embodiments 2-4, comprising 0.02-0.05% w/w of Compound 2, relative to maribavir (e.g., as measured by HPLC).

6. The composition of embodiment 2, comprising less than 1%, 0.5%, 0.1%, 0.05%, 0.02%, or 0.01% w/w of Compound 2, relative to maribavir (e.g., as measured by HPLC).

7. The composition of embodiment 2, comprising 0.01-0.10% a/a of Compound 2, relative to maribavir (e.g., as measured by HPLC).

8. The composition of embodiment 2 or 7, comprising 0.01-0.5% a/a of Compound 2, relative to maribavir (e.g., as measured by HPLC).

9. The composition of any one of embodiments 2 or 7-8, comprising 0.02-0.05% a/a of Compound 2, relative to maribavir (e.g., as measured by HPLC).

10. The composition of embodiment 2, comprising less than 1%, 0.5%, 0.1%, 0.05%, 0.02%, or 0.01% a/a of Compound 2, relative to maribavir (e.g., as measured by HPLC).

11. The composition of any one of embodiments 1-10, comprising Compound 3:

3

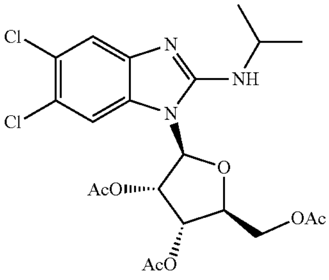

or a pharmaceutically acceptable salt thereof.

12. The composition of embodiment 11, comprising 0.01-0.10% w/w of Compound 3, relative to maribavir (e.g., as measured by HPLC).

13. The composition of embodiment 11 or 12, comprising 0.01-0.5% w/w of Compound 3, relative to maribavir (e.g., as measured by HPLC).

14. The composition of any one of embodiments 11-13, comprising 0.02-0.05% w/w of Compound 3, relative to maribavir (e.g., as measured by HPLC).

14. The composition of embodiment 11, comprising less than 1%, 0.5%, 0.1%, 0.05%, 0.02%, or 0.01% w/w of Compound 3, relative to maribavir (e.g., as measured by HPLC).

15. The composition of embodiment 11, comprising 0.01-0.10% a/a of Compound 3, relative to maribavir (e.g., as measured by HPLC).

16. The composition of embodiment 11 or 15, comprising 0.01-0.5% a/a of Compound 3, relative to maribavir (e.g., as measured by HPLC).

17. The composition of any one of embodiments 11 or 15-16, comprising 0.02-0.05% a/a of Compound 3, relative to maribavir (e.g., as measured by HPLC).

18. The composition of embodiment 11, comprising less than 1%, 0.5%, 0.1%, 0.05%, 0.02%, or 0.01% a/a of Compound 3, relative to maribavir (e.g., as measured by HPLC).

19. The composition of any one of embodiments 1-18, comprising Compound 4:

4

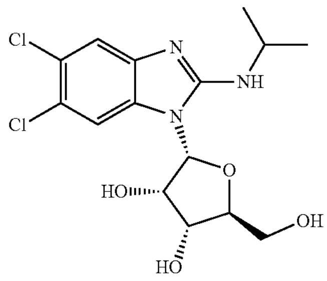

or a pharmaceutically acceptable salt thereof.

20. The composition of embodiment 19, comprising 0.01-0.10% w/w of Compound 4, relative to maribavir (e.g., as measured by HPLC).

21. The composition of embodiment 19 or 20, comprising 0.01-0.5% w/w of Compound 4, relative to maribavir (e.g., as measured by HPLC).

22. The composition of any one of embodiments 19-21, comprising 0.02-0.05% w/w of Compound 4, relative to maribavir (e.g., as measured by HPLC).

23. The composition of embodiment 19, comprising less than 1%, 0.5%, 0.1%, 0.05%, 0.02%, or 0.01% w/w of Compound 4, relative to maribavir (e.g., as measured by HPLC).

24. The composition of embodiment 19, comprising 0.01-0.10% a/a of Compound 4, relative to maribavir (e.g., as measured by HPLC).

25. The composition of embodiment 19 or 24, comprising 0.01-0.5% a/a of Compound 4, relative to maribavir (e.g., as measured by HPLC).

26. The composition of any one of embodiments 19 or 24-25, comprising 0.02-0.05% a/a of Compound 4, relative to maribavir (e.g., as measured by HPLC).

27. The composition of embodiment 19, comprising less than 1%, 0.5%, 0.1%, 0.05%, 0.02%, or 0.01% a/a of Compound 3, relative to maribavir (e.g., as measured by HPLC).

28. The composition of any one of embodiments 1-27, comprising maribavir having a particle size distribution (PSD) of between of d(50) of about 170 and about 350 μm (e.g., about 170 and about 226 μm, about 227 and about 280 μm, or about 281 and about 336 μm).

29. The composition of any one of embodiments 1-28, further comprising a pharmaceutically acceptable excipient.

30. An oral solid formulation of maribavir comprising the composition of any of embodiments 1-29.

31. The oral solid formulation of embodiment 31, wherein the formulation is a tablet.

32. The oral solid formulation of embodiment 30 or 31, comprising about 200 mg of maribavir.

33. The composition of any one of embodiments 1-29 or the oral solid formulation of any one of embodiments 30-32, wherein maribavir is prepared by a process of any one of embodiments 37-186.

34. A method of treating a patient suffering from cytomegalovirus (CMV) infection comprising administering to the patient the pharmaceutical composition of any one of embodiments 1-29, or the oral solid formulation of any one of embodiments 30-33.

35. The method of embodiment 34, wherein the patient is a transplant recipient.

36. The method of embodiment 34 or 35, wherein the patient is refractory to treatment with ganciclovir, valganciclovir, cidofovir, or foscarnet.

37. A method of preparing maribavir:

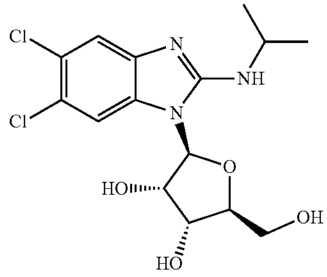 [SMILES: CC(C)Nc1nc2cc(Cl)c(Cl)cc2n1[C@H]1O[C@@H](CO)[C@H](O)[C@@H]1O]

or a pharmaceutically acceptable salt thereof, comprising a step of:

(a) reacting compound 3:

3

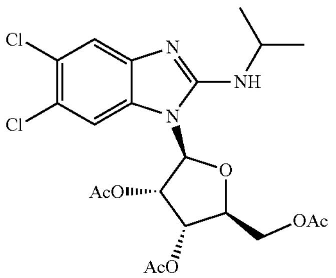

or a salt thereof, under suitable reaction conditions to provide maribavir, or a pharmaceutically acceptable salt thereof.

38. A method of preparing a composition according to any one of embodiments 1-32, comprising a step of:
(a) reacting compound 3:

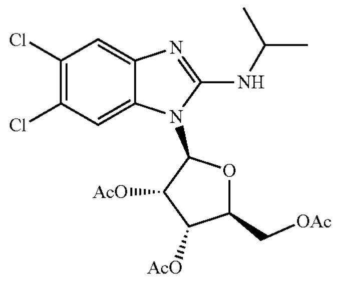

3 or a salt thereof,
under suitable reaction conditions to provide maribavir, or a pharmaceutically acceptable salt thereof.
39. The method of embodiment 37 or 38, wherein the reaction conditions comprise a solvent.
40. The method of embodiment 39, wherein the solvent is or comprises methanol.
41. The method of embodiment 39, wherein the solvent is or comprises MTBE.
42. The method of any one of embodiments 39-41, wherein the solvent comprises methanol and MTBE.
43. The method of embodiment 42, wherein methanol is provided in an amount of between about 0.34 L/kg and about 0.56 L/kg, and MTBE is provided in an amount of between about 3.65 L/kg and about 6.35 L/kg.
44. The method of embodiment 42 or 43, wherein methanol is provided in an amount of about 0.48 L/kg, and MTBE is provided in an amount of about 5.3 L/kg.
45. The method of any one of embodiments 37-43, wherein the reaction conditions comprise a base.
46. The method of embodiment 45, wherein the base is NaOH.
47. The method of embodiment 45 or 46, wherein the base is aqueous NaOH.
48. The method of any one of embodiments 37-47, wherein the reaction conditions comprise heating to temperature Ti.
49. The method of embodiment 48, wherein temperature $T_1$ is between about 24° C. and 45° C.
50. The method of embodiment 48 or 49, wherein temperature $T_1$ is about 30° C.
51. The method of any one of embodiments 37-50, wherein the reaction is allowed proceed for a period of time.
52. The method of embodiment 51, wherein the reaction is agitated for a period of time.
53. The method of embodiment 51 or 52, wherein the period of time is between about 2.5 and about 4 hrs.
54. The method of any one of embodiments 37-53, wherein the reaction conditions comprise cooling the reaction mixture to a temperature $T_2$.
55. The method of embodiment 54, wherein temperature $T_2$ is about 22° C.
56. The method of any one of embodiments 37-55, wherein the reaction is monitored for the presence of maribavir in an amount greater than 98.3% a/a by HPLC.
57. The method of any one of embodiments 37-56, further comprising a step of (b) phase separation and/or extraction of maribavir, or a pharmaceutically acceptable salt thereof, from the reaction mixture to provide a first resulting mixture.
58. The method of embodiment 57, wherein phase separation and/or extraction of maribavir, or a pharmaceutically acceptable salt thereof, comprises adding a first phase separation solvent.
59. The method of embodiment 58, wherein the first phase separation solvent is MBTE.
60. The method of any one of embodiments 57-59, wherein phase separation and/or extraction comprises adding a second phase separation solvent.
61. The method of embodiment 60, wherein the second phase separation solvent is aqueous sodium chloride.
62. The method of any one of embodiments 57-61, wherein phase separation and/or extraction comprises adjusting the pH of the reaction mixture to between about 6.0 to about 10.0.
63. The method of any one of embodiments 57-62, wherein phase separation and/or extraction comprises adjusting the pH of the reaction mixture to between about 6.8 to about 7.5.
64. The method of any one of embodiments 37-63, further comprising a step of (c) distillation and/or solvent exchange of the reaction mixture or first resulting mixture to provide a second resulting mixture comprising maribavir, or a pharmaceutically acceptable salt thereof.
65. The method of embodiment 64, wherein the reaction mixture or first resulting mixture comprises a first solvent.
66. The method of embodiment 65, wherein the first solvent is TBME.
67. The method of any one of embodiments 65-67, wherein the first solvent is removed from the reaction mixture or first resulting mixture.
68. The method of embodiment 67, wherein the first solvent is removed by distillation.
69. The method of any one of embodiments 63-68, wherein a second solvent is added to the reaction mixture or first resulting mixture.
70. The method of embodiment 69, wherein the second solvent is isopropyl acetate.
71. The method of any one of embodiments 64-70, wherein the second resulting mixture comprises isopropyl acetate.
72. The method of any one of embodiments 64-71, wherein the second resulting mixture comprises less than 0.2% w/w of water (e.g., as measured by $^1$H NMR or Karl Fischer).
73. The method of any one of embodiments 64-72, wherein the second resulting mixture comprises less than 0.09% w/w of water (e.g., as measured by $^1$H NMR or Karl Fischer).
74. The method of any one of embodiments 64-73, wherein the second resulting mixture comprises between about 17-20% w/w of maribavir, or a pharmaceutically acceptable salt thereof (e.g., as measured by $^1$H NMR).
75. The method of any one of embodiments 64-74, wherein the second resulting mixture comprises between about 17-19% w/w of maribavir, or a pharmaceutically acceptable salt thereof (e.g., as measured by $^1$H NMR).
76. The method of any one of embodiments 37-75, further comprising a step of (d) crystallization of maribavir, or a pharmaceutically acceptable salt thereof (e.g., from the reaction mixture, first resulting mixture, or second resulting mixture).

77. The method of embodiment 76, crystallization comprises providing a crystallization mixture comprising maribavir, or a pharmaceutically acceptable salt thereof, and a primary solvent.

78. The method of embodiment 77, wherein the primary solvent is isopropyl acetate.

79. The method of any one of embodiments 76-78, wherein the crystallization resulting mixture comprises less than 0.2% w/w of water (e.g., as measured by $^1$H NMR or Karl Fischer).

80. The method of any one of embodiments 76-79, wherein the crystallization mixture comprises less than 0.09% w/w of water (e.g., as measured by $^1$H NMR or Karl Fischer).

81. The method of any one of embodiments 76-80, wherein the crystallization mixture comprises between about 17-20% w/w of maribavir, or a pharmaceutically acceptable salt thereof (e.g., as measured by $^1$H NMR).

82. The method of any one of embodiments 76-81, wherein the crystallization resulting mixture comprises between about 17-19% w/w of maribavir, or a pharmaceutically acceptable salt thereof (e.g., as measured by $^1$H NMR).

83. The method of any one of embodiments 76-82, wherein crystallization further comprising heating the crystallization mixture to a temperature $T_3$.

84. The method of embodiment 83, wherein temperature $T_3$ is between about 77 and about 88° C.

85. The method of embodiment 83 or 84, wherein temperature $T_3$ is about 84° C.

86. The method of any one of embodiments 76-85, wherein a secondary solvent is added to the crystallization mixture.

87. The method of embodiment 86, wherein the secondary solvent is toluene.

88. The method of any one of embodiments 86-87, wherein, after the addition of the secondary solvent, the crystallization mixture is aged for less than about 30 minutes.

89. The method of any one of embodiments 76-88, wherein a seed crystal is added to the crystallization mixture.

90. The method of embodiment 89, the seed crystal is maribavir, or a pharmaceutically acceptable salt thereof.

91. The method of embodiment 89 or 90, wherein the seed crystal is added in an amount of between about 0.05% and 0.30 w/w relative to compound 3, or a salt thereof.

92. The method of any one of embodiments 89-91, wherein the seed crystal is added in an amount of about 0.15% w/w relative to compound 3, or a salt thereof.

93. The method of any one of embodiments 89-92, wherein the size of the seed crystals (d(50)) is between about 2.25-7.00 μm.

94. The method of any one of embodiments 89-93, wherein the size of the seed crystals (d(50)) is between about 2.75-6.25 μm.

95. The method of any one of embodiments 89-94, wherein after the seed crystal is added, the crystallization mixtures is aged for about 30 minutes.

96. The method of any one of embodiments 76-95, wherein additional secondary solvent is added to the crystallization mixture.

97. The method of embodiment 96, wherein the additional secondary solvent is added in an about of about 11/7 of total primary solvent (kg/kg).

98. The method of embodiment 96 or 97, wherein, after the additional secondary solvent is added, the crystallization mixture is agitated for a period of time.

99. The method of embodiment 98, wherein the period of time is about 1 hr.

100. The method of embodiments 98 or 99, wherein, after the additional secondary solvent is added, the crystallization mixture is agitated at temperature $T_3$.

101. The method of embodiment 100, wherein temperature $T_3$ is between about 77 and about 88° C.

102. The method of embodiment 100 or 101, wherein temperature $T_3$ is about 84° C.

103. The method of any one of embodiments 76-102, wherein the crystallization mixture is cooled to temperature $T_4$.

104. The method of embodiment 103, wherein temperature $T_4$ is between about 3° C. and about 7° C.

105. The method of embodiment 103 or 104, wherein temperature $T_4$ is about 5° C.

106. The method of any one of embodiments 103-105, wherein the crystallization mixture is cooled to temperature $T_4$ over about 3 hrs.

107. The method of any one of embodiments 103-106, wherein the crystallization mixture is agitated at temperature $T_4$ for a period of time.

108. The method of embodiment 107, wherein the period of time is between about 3 and about 18 hrs.

109. The method of any one of embodiments 76-108, further comprising a step of (e) optionally filtering or washing the crystallization mixture to provide a filtered mixture.

110. The method of embodiment 109, comprising a step of filtering the crystallization mixture to provide the filtered mixture.

111. The method of embodiment 109 or 110, comprising a step of washing the crystallization mixture to provide the filtered mixture.

112. The method of embodiment 111, wherein the crystallization mixture is washed with toluene.

113. The method of any one of embodiments 76-112, further comprising a step of (f) drying the filtered mixture.

114. The method of embodiment 113, wherein drying comprises heating the filtered mixture to temperature $T_5$ without agitation for a period of time.

115. The method of embodiment 114, wherein temperature $T_5$ is less than or equal to 40° C.

116. The method of embodiment 114 or 115, wherein the period of time is at least 5 hrs.

117. The method of any one of embodiments 113-116, wherein drying further comprises heating the filtered mixture to temperature $T_6$ without agitation for a period of time.

119. The method of embodiment 117, wherein temperature $T_6$ is less than or equal to 50° C.

120. The method of embodiment 117 or 118, wherein the period of time is at least 3 hrs.

121. The method of any one of embodiments 34-120, wherein compound 3, or a salt thereof, is prepared by a method comprising:

(a) providing compound

2

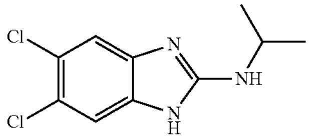

or a salt thereof, and compound 8:

8

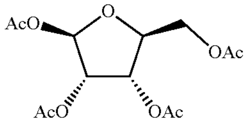

or a salt thereof, under suitable reaction conditions to afford compound 3, or a salt thereof.

122. The method of embodiment 121, wherein compound 3 is prepared as an HCl salt.

123. The method of embodiment 121 or 122, wherein compound 2, or a salt thereof, is prepared by a method comprising:

(a) reacting compound 5:

5

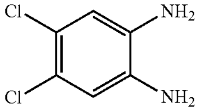

or a salt thereof, with compounds 6 and 7:

6

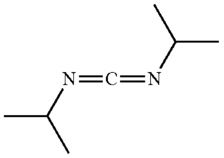

7

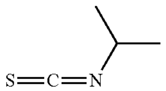

under suitable reaction conditions to provide compound 2, or a salt thereof.

124. A method of preparing compound 2:

2

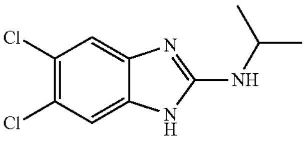

or a salt thereof, comprising the step of:

(a) reacting compound 5:

5

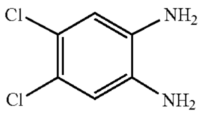

or a salt thereof, with compounds 6 and 7:

6

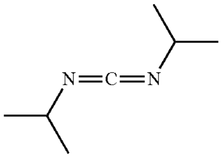

7

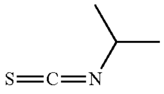

or salts thereof, under suitable reaction conditions to provide compound 2, or a salt thereof.

125. The method of embodiment 123 or 124, further providing one or more of the following compounds:

9

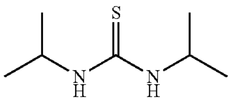

10

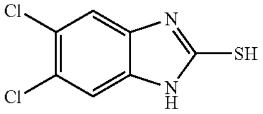

11

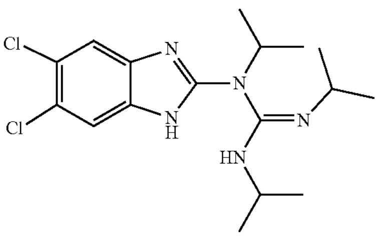

-continued

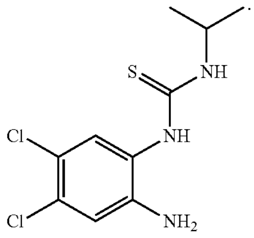

12 or salts thereof.

126. The method of embodiment 125, wherein compound 9 is provided in an amount less than 1.00%, 0.5%, 0.1%, 0.05%, or 0.02% w/w, relative to compound 2 (e.g., as measured by HPLC or $^1$H NMR).

127. The method of embodiment 125, wherein compound 10 is provided in an amount less than 1.00%, 0.5%, 0.1%, 0.05%, or 0.02% w/w, relative to compound 2 (e.g., as measured by HPLC or $^1$H NMR).

128. The method of embodiment 125, wherein compound 11 is provided in an amount less than 1.00%, 0.5%, 0.1%, 0.05%, or 0.02% w/w, relative to compound 2 (e.g., as measured by HPLC or $^1$H NMR).

129. The method of embodiment 125, wherein compound 12 is provided in an amount less than 1.00%, 0.5%, 0.1%, 0.05%, or 0.02% w/w, relative to compound 2 (e.g., as measured by HPLC or $^1$H NMR).

130. The method of any one of embodiments 123-129, wherein compound 6, or a salt thereof, is present at an amount of about 0.90 to about 1.09 equivalents relative to compound 5, or a salt thereof.

131. The method of embodiment 130, wherein compound 6, or a salt thereof, is present at an amount of about 1.00 equivalents relative to compound 5, or a salt thereof.

132. The method of embodiment 130, wherein compound 6, or a salt thereof, is present at an amount of about 1.04 equivalents relative to compound 5, or a salt thereof.

133. The method of any one of embodiments 123-132, wherein compound 7, or a salt thereof, is present at an amount of about 1.03 to about 1.13 equivalents relative to compound 5, or a salt thereof.

134. The method of embodiment 133, wherein compound 7, or a salt thereof, is present at an amount of about 1.08 equivalents relative to compound 5, or a salt thereof.

135. The method of any one of embodiments 123-134, wherein the reaction conditions comprise a solvent.

136. The method of embodiment 135, wherein the solvent is 1,4-dioxane.

137. The method of embodiment 136, wherein 1,4-dioxane is present in an amount of about 5.0 L/kg.

138. The method of any one of embodiments 123-137, wherein the reaction conditions comprise heating to a temperature $T_7$.

139. The method of embodiment 138, wherein the temperature $T_7$ is about 100° C.

140. The method of embodiment 138 or 139, wherein the reaction conditions comprise maintaining the reaction at temperature $T_7$ for a period of time.

141. The method of embodiment 140, wherein the period of time is between about 2 hrs and about 20 hrs.

142. The method of embodiment 140 or 141, wherein the period of time is between about 14 and about 15 hours.

143. The method of any one of embodiments 139-142, wherein, after heating to a temperature $T_7$, the reaction conditions further comprise (b) cooling the reaction mixture to a temperature $T_8$.

144. The method of embodiment 143, wherein the temperature $T_8$ is between about 60° C. and about 90° C.

145. The method of embodiment 143 or 144, wherein the temperature $T_8$ is about 80° C.

146. The method of any one of embodiments 138-145, wherein the reaction mixture is cooled to temperature $T_8$ at a rate of between about 5° C./hr and about 10° C./hr.

147. The method of any one of embodiments 138-145, wherein the reaction mixture is cooled to the second temperature at a rate of about 6.5° C./hr.

148. The method of any one of embodiments 123-147, wherein the reaction is monitored for completion by HPLC.

149. The method of embodiment 148, wherein the reaction is determined to be complete when less than 1.0% a/a of compound 5, or a salt thereof, is detected (e.g., by HPLC).

150. The method of any one of embodiments 123-149, further comprising a step of (c) crystallization of compound 2, or a salt thereof (e.g., from the reaction mixture).

151. The method of embodiment 150, wherein crystallization of compound 2, or a salt thereof, comprises providing a primary mixture, wherein the primary mixture comprises compound 2, or a salt thereof, and a primary solvent.

152. The method of embodiment 150 or 151, wherein the primary solvent is 1,4-dioxane.

153. The method of any one of embodiments 150-152, wherein the primary solvent is present at an amount of about 4.9 L/kg of solute.

154. The method of any one of embodiments 151-153, wherein the primary mixture is provided at temperature $T_8$.

155. The method of embodiment 154, wherein the temperature $T_8$ is between about 60° C. and about 90° C.

156. The method of embodiment 154 or 155, wherein the temperature $T_8$ is about 80° C.

157. The method of any one of embodiments 150-156, wherein crystallization of compound 2, or a salt thereof, comprises adding a seed crystal to the primary mixture.

158. The method of embodiment 157, wherein the seed crystal is added in an amount between about 0.1 wt % and about 1 wt % of compound 5, or a salt thereof.

159. The compound of embodiment 157 or 158, wherein the seed crystal is added in an amount of about 0.25 wt % of compound 5, or a salt thereof.

160. The compound of any one of embodiments 157-159, wherein the seed crystal is compound 2, or a salt thereof.

161. The method of any one of embodiments 150-160, wherein crystallization of compound 2, or a salt thereof, comprises cooling the primary mixture to a temperature $T_9$.

162. The method of embodiment 161, wherein temperature $T_9$ is between about 18 and about 32° C.

163. The method of embodiment 161 or 162, wherein the temperature $T_9$ is about 27° C.

164. The method of any one of embodiments 161-163, wherein the primary mixture is cooled at a rate of between about 5° C./hr and about 10° C./hr.

165. The method of any one of embodiments 161-164, wherein the primary mixture is cooled at a rate of about 6.5° C./hr.
166. The method of any one of embodiments 123-165, further comprising a step of (d) recrystallization of compound 2, or a salt thereof (e.g., from the reaction mixture or the primary mixture).
167. The method of embodiment 166, wherein recrystallization of compound 2, or a salt thereof, comprises (i) providing a primary mixture, wherein the primary mixture comprises compound 2, or a salt thereof, and a primary solvent.
168. The method of embodiment 167, wherein the primary mixture is provided at the temperature $T_9$.
169. The method of embodiment 168, wherein temperature $T_9$ is between about 18 and about 32° C.
170. The method of embodiment 168 or 169, wherein the temperature $T_9$ is about 27° C.
171. The method of any one of embodiments 167-170, wherein the primary solvent is 1,4-dioxane.
172. The method of any one of embodiments 167-171, wherein the primary solvent is present at an amount of about 4.9 L/kg of solute.
173. The method of any one of embodiments 166-172, wherein recrystallization of compound 2, or a salt thereof, further comprises (ii) adding a secondary solvent to the primary mixture to form a secondary mixture.
174. The method of embodiment 173, wherein the secondary solvent is dichloromethane.
175. The method of embodiment 173 or 174, wherein the secondary solvent is present at an amount between about 8 and about 12 L/kg of solute.
176. The method of any one of embodiments 173-175, wherein the secondary solvent is present at an amount of about 10 L/kg of solute.
177. The method of any one of embodiments 166-176, wherein recrystallization of compound 2, or a salt thereof, further comprises (iii) holding and optionally agitating the secondary mixture at temperature $T_9$ for a period of time.
178. The method of embodiment 177 wherein the secondary mixture is agitated at temperature $T_9$ for the period of time.
179. The method of embodiment 177 or 178, wherein the period of time is between about 2 and bout 6 hrs.
180. The method of any one of embodiments 159-161, wherein the period of time is about 3 hrs.
181. The method of any one of embodiments 123-180, further comprising a step of (e) filtering (e.g., the reaction mixture, primary mixture, or secondary mixture) to provide a filtered mixture.
182. The method of embodiment 181, wherein the secondary mixture is filtered at a temperature $T_{10}$.
183. The method of embodiment 182, wherein temperature $T_{10}$ is between about 24° C. and about 32° C.
184. The method of embodiment 182 or 183, wherein temperature $T_{10}$ is about 27° C.
185. The method of any one of embodiments 123-184, further comprising a step of (f) washing, e.g. the filtered mixture or secondary mixture, to provide a final mixture.
186. The method of any one of embodiments 123-185, further comprising a step of (g) deliquoring, drying, and/or isolating compound 2, or a salt thereof.

187. A method of preparing maribavir:

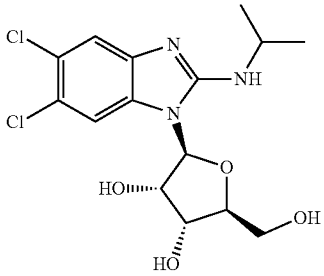 [SMILES: CC(C)Nc1nc2cc(Cl)c(Cl)cc2n1[C@H]1O[C@@H](CO)[C@H](O)[C@@H]1O]

or a pharmaceutically acceptable salt thereof, comprising a step of:

(a) reacting compound 3:

3

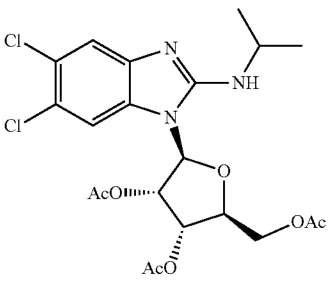

or a salt thereof, under suitable reaction conditions to provide maribavir, or a pharmaceutically acceptable salt thereof;

wherein compound 3, or a salt thereof, is prepared by a method comprising a step of:

(a) reacting compound 2:

2

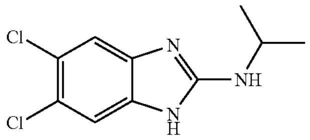

or a salt thereof, under suitable reaction conditions to provide compound 3, or a pharmaceutically acceptable salt thereof.

188. The composition of any one of embodiments 1-29 or the oral solid formulation of any one of embodiments 30-32, wherein maribavir is polymorphic Form VI which is crystalized by using isopropyl acetate/toluene as a crystallization solvent.
189. The composition of any one of embodiments 1-29 or the oral solid formulation of any one of embodiments 30-32, wherein maribavir is polymorphic Form VI which is crystalized by using isopropyl acetate/toluene as a crystallization solvent and maribavir seed crystals having a PSD of d(50) between about 1.00 μm and about 10.00 μm.
190. A method of treating a patient with post-transplant cytomegalovirus (CMV) infection and/or disease comprising orally administering maribavir or a pharmaceutically acceptable salt thereof to the patient in an amount of 400 mg twice a day, wherein maribavir is administered as the composition of any one of embodiments 1-29, 188 or 189 or the oral solid formulation of any one of embodiments 30-32, 188 or 189.

1A. A composition comprising a unit dose of maribavir, wherein the composition comprises (i) 200 mg or 400 mg of maribavir:

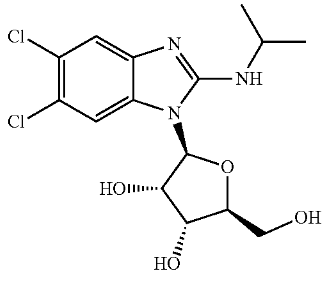 [SMILES: CC(C)Nc1nc2cc(Cl)c(Cl)cc2n1[C@H]1O[C@@H](CO)[C@H](O)[C@@H]1O]

or a pharmaceutically acceptable salt thereof, and (ii) one or more of the following:

Compound 2,

2

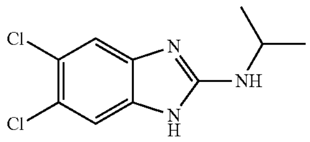

or a pharmaceutically acceptable salt thereof,

Compound 3,

3

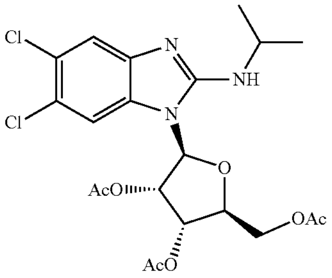

or a pharmaceutically acceptable salt thereof, or

Compound 4:

4

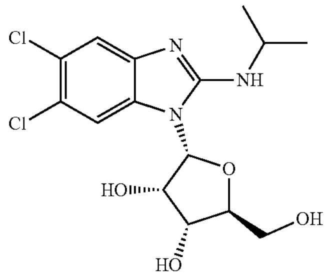

or a pharmaceutically accept salt thereof

2A. The composition of embodiment 1A, wherein the composition comprises Compound 2:

2

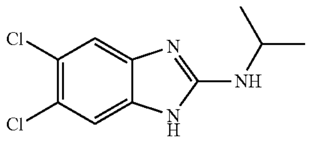

or a pharmaceutically acceptable salt thereof.

3A. The composition of embodiment 2A, wherein the composition comprises 0.01-0.10% w/w of Compound 2, relative to maribavir (e.g., as measured by HPLC).

4A. The composition of embodiment 2A or 3A, wherein the composition comprises 0.01-0.05% w/w of Compound 2, relative to maribavir (e.g., as measured by HPLC).

5A. The composition of any one of embodiments 2A-4A, wherein the composition comprises 0.02-0.05% w/w of Compound 2, relative to maribavir (e.g., as measured by HPLC).

6A. The composition of embodiment 2A, wherein the composition comprises less than 1%, 0.5%, 0.1%, 0.05%, 0.02%, or 0.01% w/w of Compound 2, relative to maribavir (e.g., as measured by HPLC).

7A. The composition of embodiment 2A, wherein the composition comprises 0.01-0.10% a/a of Compound 2, relative to maribavir (e.g., as measured by HPLC).

8A. The composition of embodiment 2A or 7A, wherein the composition comprises 0.01-0.5% a/a of Compound 2, relative to maribavir (e.g., as measured by HPLC).

9A. The composition of any one of embodiments 2A or 7A-8A, wherein the composition comprises 0.02-0.05% a/a of Compound 2, relative to maribavir (e.g., as measured by HPLC).

10A. The composition of embodiment 2A, wherein the composition comprises less than 1%, 0.5%, 0.1%, 0.05%, 0.02%, or 0.01% a/a of Compound 2, relative to maribavir (e.g., as measured by HPLC).

11A. The composition of any one of embodiments 1A-10A, wherein the composition comprises Compound 3:

3

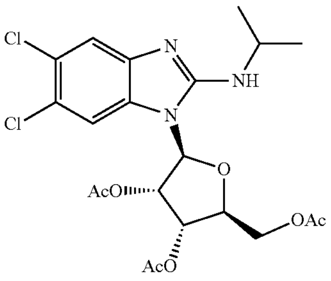

or a pharmaceutically acceptable salt thereof.

12A. The composition of embodiment 11A, wherein the composition comprises 0.01-0.10% w/w of Compound 3, relative to maribavir (e.g., as measured by HPLC).

13A. The composition of embodiment 11A or 12A, wherein the composition comprises 0.01-0.5% w/w of Compound 3, relative to maribavir (e.g., as measured by HPLC).

14A. The composition of any one of embodiments 11A-13A, wherein the composition comprises 0.02-0.05% w/w of Compound 3, relative to maribavir (e.g., as measured by HPLC).

15A. The composition of embodiment 11A, wherein the composition comprises less than 1%, 0.5%, 0.1%, 0.05%, 0.02%, or 0.01% w/w of Compound 3, relative to maribavir (e.g., as measured by HPLC).

16A. The composition of embodiment 11A, wherein the composition comprises 0.01-0.10% a/a of Compound 3, relative to maribavir (e.g., as measured by HPLC).

17A. The composition of embodiment 11A or 16A, wherein the composition comprises 0.01-0.5% a/a of Compound 3, relative to maribavir (e.g., as measured by HPLC).

18A. The composition of any one of embodiments 11A or 16A-17A, wherein the composition comprises 0.02-0.05% a/a of Compound 3, relative to maribavir (e.g., as measured by HPLC).

19A. The composition of embodiment 11A, wherein the composition comprises less than 1%, 0.5%, 0.1%, 0.05%, 0.02%, or 0.01% a/a of Compound 3, relative to maribavir (e.g., as measured by HPLC).

20A. The composition of any one of embodiments 1A-19A, wherein the composition comprises Compound 4:

4

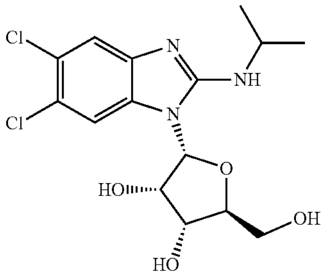

or a pharmaceutically acceptable salt thereof.

21A. The composition of embodiment 20A, wherein the composition comprises 0.01-0.10% w/w of Compound 4, relative to maribavir (e.g., as measured by HPLC).

22A. The composition of embodiment 20A or 21A, wherein the composition comprises 0.01-0.5% w/w of Compound 4, relative to maribavir (e.g., as measured by HPLC).

23A. The composition of any one of embodiments 20A-22A, wherein the composition comprises 0.02-0.05% w/w of Compound 4, relative to maribavir (e.g., as measured by HPLC).

24A. The composition of embodiment 20A, wherein the composition comprises less than 1%, 0.5%, 0.1%, 0.05%, 0.02%, or 0.01% w/w of Compound 4, relative to maribavir (e.g., as measured by HPLC).

25A. The composition of embodiment 20A, wherein the composition comprises 0.01-0.10% a/a of Compound 4, relative to maribavir (e.g., as measured by HPLC).

26A. The composition of embodiment 20A or 25A, wherein the composition comprises 0.01-0.5% a/a of Compound 4, relative to maribavir (e.g., as measured by HPLC).

27A. The composition of any one of embodiments 20A or 25A-26A, wherein the composition comprises 0.02-0.05% a/a of Compound 4, relative to maribavir (e.g., as measured by HPLC).

28A. The composition of embodiment 20A, wherein the composition comprises less than 1%, 0.5%, 0.1%, 0.05%, 0.02%, or 0.01% a/a of Compound 3, relative to maribavir (e.g., as measured by HPLC).

29A. The composition of any one of embodiments 1A-28A, wherein the composition comprises maribavir having a particle size distribution (PSD) of between of d(50) of about 170 and about 350 μm (e.g., about 170 and about 226 μm, about 227 and about 280 μm, or about 281 and about 336 μm).

30A. The composition of any one of embodiments 1A-29A, further comprising a pharmaceutically acceptable excipient.

31A. An oral solid formulation of maribavir comprising the composition of any of embodiments 1A-30A.

32A. The oral solid formulation of embodiment 31A, wherein the formulation is a tablet.

33A. The oral solid formulation of embodiment 31A or 32A, comprising about 200 mg of maribavir.

34A. The composition of any one of embodiments 1A-30A or the oral solid formulation of any one of embodiments 31A-33A.

35A. The composition of any one of embodiments 1A-34A or the oral solid formulation of any one of embodiments 31A-33A, wherein the composition comprises less than 0.05% of D-maribavir.

36A. The composition of any one of embodiments 1A-35A, wherein maribavir has a particle size distribution (d(50)) of between about 50 and about 400 μm.

EXAMPLES

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of 5,6-dichloro-N-isopropyl-1H-benzo[d]imidazol-2-amine (Compound 2)

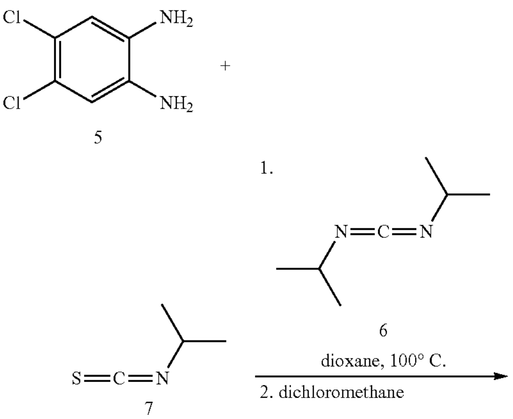

5

6

7

-continued

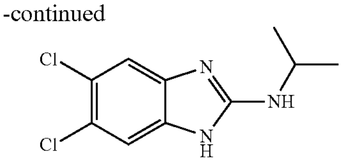

2

Exemplary Synthesis of 5,6-dichloro-N-isopropyl-1H-benzo[d]imidazol-2-amine (Compound 2)

Batch size in Qualified Equipment. 100 kg±20 kg of Compound 2; the process description below outlines an example production using ~100 kg of Compound 5. Operating ranges have been established for all process parameters as described herein, and the description provides the target for each of the parameters as described herein.

Chemical Reaction. Compound 5 (100.07 kg, limiting reagent), 1,4-dioxane (488.9 L), Compound 7 (61.70 kg, 1.08 molar equivalents), and Compound 6 (74.10 kg, 1.04 molar equivalents) were charged to the reactor at ambient temperature. The resultant mixture was heated to 104.8° C. for at least 2 hours with agitation. The mixture was then kept at 104.8° C. for about 14 to 15 hours and was then cooled to 80.0° C. over 3 hours, 40 mins (cooling rate=6.8° C./hour). If the following criteria are not met: ≤1.0% a/a by HPLC of Compound 5, and Loss on Drying ("LOD") of ≤0.5%, the batch is reheated to about 103° C., held at that temperature a minimum of 2 hours, and then re-cooled to about 80° C. using about the same cooling rate as above and resampled. The process is repeated until criteria are met. These criteria were met.

Crystallization. Upon meeting the criteria, the batch was examined to ascertain if crystallization had started. If crystallization had not started, a Compound 2 seed slurry (Compound 2, 0.25 kg and 1,4-dioxane, 2 kg) would be charged to the batch. In this exemplary synthesis, Compound 2 seed slurry was not added as crystallization started spontaneously. After crystallization had started, the batch was cooled from 79.5° C. to a temperature of 27.0° C. over 8 hours, 31 mins (cooling rate 6.2° C./hour).

Recrystallization. DCM (1002.7 L) was charged into the reactor while maintaining a batch temperature of about 27.0° C., and the batch was agitated for a minimum of 3 hours. The resultant slurry was filtered with the filter dryer jacket set at 27.0° C.

Filtration and Wetcake Washing. DCM (164.5 L) and 1,4-dioxane (85.8 L) were charged to the reactor, and the resultant mixture was agitated while the reactor batch temperature was adjusted to 27.2-27.3° C. The jacket temperature of the filter/dryer was adjusted to about 27.0° C., and the resultant solvent mixture was transferred onto the Compound 2 wetcake in the filter/drier. Solvent was then pushed through the cake with inert gas pressure.

1,4-dioxane (249.8 L) was charged to the reactor. (If significant amounts of solids are observed on the vessel wall, the batch temperature is adjusted to about 50° C. and agitated for at least 1 hour). The reactor batch temperature and temperature of the filter/dryer were adjusted to about 27.2-27.3° C. and the resultant solvent was transferred onto the Compound 2 wetcake in the filter/drier in one portion. The slurry was agitated on the filter/drier for about 20 minutes, allowed to settle, the solvent was then pushed through the cake with inert gas pressure. This 1,4-dioxane wash was repeated two more times with 499.0 L total of 1,4-dioxane between the two additional washes.

Methyl-t-butyl ether (184.9 kg) was charged to the reactor. Batch temperature and the jacket temperature of the filter/dryer were adjusted to 27.0° C. and resultant solvent was transferred onto the Compound 2 wetcake in the filter/drier in one portion. The slurry was agitated on the filter/drier for about 20 minutes, allowed to settle, and the solvent was then pushed through the cake with inert gas pressure.

n-Heptane (250.0 L) was charged to the reactor. Batch temperature and the jacket temperature of the filter/dryer were adjusted to about 27.0° C. and resultant solvent was transferred onto the Compound 2 wetcake in the filter/drier in one portion. The solvent was then pushed through the cake with inert gas pressure.

Drying and Isolation. After deliquoring, the cake was dried with a partial vacuum and the filter/drier jacket temperature was set to ≤60° C. with intermittent agitation until condensate was no longer visible. The filter/drier jacket temperature was adjusted to ≤100° C., with intermittent agitation, and vacuum applied until the material met the LOD criteria. The yield was 72.6%, and the product had a purity of 100.0%, with 99.7% w/w by HPLC.

Process Characterization.

Process characterization studies were performed in order to ensure consistent production of Compound 2 with a defined impurity profile. A defined impurity profile of Compound 2 allows for more consistent impurity profiles in downstream reactions involved in the formation of maribavir.

In particular, multiple process characterization studies were conducted to assess certain parameters involved in the synthesis of Compound 2. The following exemplary studies were designed to examine impurity formation and retention of Compound 2 product for the following: (i) reaction conditions so as to maximize yield and minimize impurity formation, (ii) identify optimal conditions for the crystallization of Compound 2, (iii) identify optimal conditions for the recrystallization for Compound 2, (iv) identify optimal conditions for filtration and washing of the wetcake product Compound 2, and (v) identify optimal conditions for drying of the product Compound 2. The process characterization studies performed on a laboratory scale are summarized below in Table 1-2, and further details are provided herein in Examples 1-1 through 1-3.

At the completion of studies outlined in Table 1-2, further studies were conducted on larger laboratory scale to confirm findings from the laboratory studies, and process robustness studies were also performed on the recrystallization, in particular, focusing upon the slurry temperature for the recrystallization (see Examples 1-1 through 1-4). Based upon all of these studies, the tested ranges for the reaction provide control over the formation of impurities in Compound 2. Further, the tested ranges for the crystallization and recrystallization, and filtration and washing of Compound 2 product purge the impurities formed in the reaction process. In addition, the tested conditions for drying of the final Compound 2 do not produce new impurities nor are the levels of impurities increased. Hence, this example leads to the experimentally verified process parameter ranges presented in Table 1-1.

TABLE 1-1

Exemplary Process Parameters.

| Unit of Operation | Step/Parameter | Lower value | Standard Value | Upper value |
|---|---|---|---|---|
| Charge chemicals/ Prepare for chemical reaction | Charge Compound 5 | 0.99 molar equivalent | 1.0 molar equivalent | 1.01 molar equivalent |
| | 1,4-dioxane | 2.7 L/kg[1] | 4.9 L/kg | 5.5 L/kg |
| | Charge isopropyl isothiocyanate (Compound 7) | 1.04 molar equivalent[2] | 1.08 molar equivalent | 1.13 molar equivalent |
| | Charge 1,4-dioxane (transfer line rinse after Compound 7 charge) | 5 L | 5 L | 13 L |
| | Charge N,N'-diisopropyl carbodiimide (Compound 6) | 0.99 molar equivalent | 1.04 molar equivalent[2] | 1.10 molar equivalent |
| | Temperature before heating the batch | 15° C. | 20° C. | 30° C. |
| | Hold time for unreacted reaction mixture | 0 | N/A | 256 hrs |
| | Charge 1,4-dioxane (transfer line rise after Compound 6 charge) | 5 L | 5 L | 13 L |
| Heat to effect chemical reaction | Heat to temperature | 95° C. | 103° C. | 110° C. |
| | Ramp heating time | 0.77 hrs | ≥2 hrs | N/A |
| | Reaction time prior to taking first sample and test criteria | 10 hrs | 14.5 hrs | 48 hrs |
| | Temperature during reaction | 92° C. | 103° C. | 110° C. |
| Cool and sample for reaction criteria | Cool for criteria. Maintain temperature until criteria results available | 75° C. | 80° C. | 85° C. |
| | Hold time at 80° C. | 0 hr | Until criteria results are available | 132 hrs |
| | Rate of cooling | 4° C./hr | 6.5° C./hr | 10° C./hr |
| Crystallization | Hold time at 80° C. prior to optional seeding | 0 hr | ≥1.5 hrs | 4 hrs |
| | Seeding (optional) | 0 kg | 0.25 kg | 0.263 kg |
| | 1,4-dioxane (for seed slurry) | 0 kg | 2 kg | 4 kg |
| | Jacket temperature | 18° C. | 27° C. | 35° C. |
| | Hold time. 1,4-dioxane slurry at ~27° C. | 0 hrs | N/A | 168 hrs |
| | Rate of cooling | 4° C./hr | 6.5° C./hr | 10° C./hr |
| Recrystallization | Charge DCM | 8.0 L/kg | 10 L/kg | 12 L/kg |
| | Agitation time for DCM/1,4-dioxane | 2 hrs | 3.5 hrs | 72 hrs |
| | slurry temperature | 18° C. | 27° C. | 32° C. |
| Filtration Washing | Jacket temperature | 18° C. | 27° C. | 32° C. |
| Wash 1 | DCM for wash | 0 | 1.64 L/kg | 1.95 L/kg |
| | 1,4-dioxane for wash | 0 | 0.86 L/kg | 1.05 L/kg |
| | Temperature of DCM/1,4-dioxane wash | 18° C. | 25° C. | 32° C. |
| | DCM/1,4-dioxane wash contact time | N/A | N/A | N/A |
| Wash 2 | 1,4-dioxane for wash | 2 L/kg | 2.5 L/kg | 3 L/kg |
| | Optional heat 1,4 dioxane | 25° C. | 50° C. | 65° C. |
| | Optional agitation time | 30 mins | ≥60 mins | ≥60 mins |
| | Optional cool prior to filtration | 18° C. | 25° C. | 32° C. |
| | Wash 2 agitation time | 10 mins | 20 mins | 79 mins |

TABLE 1-1-continued

| Exemplary Process Parameters. | | | | |
|---|---|---|---|---|
| Unit of Operation | Step/Parameter | Lower value | Standard Value | Upper value |
| | Settlement time prior to filtration | ≥10 mins | ≥10 mins | ≥10 mins |
| | Wash 2 temperature | 18° C. | 25° C. | 32° C. |
| Wash 3 | 1,4-dioxane for wash 3 | 2 L/kg | 2.5 L/kg | 3 L/kg |
| | Wash 3 agitation time | 10 mins | 20 mins | 63 mins |
| | Settlement time | ≥10 mins | ≥10 mins | ≥10 mins |
| | Wash 3 temperature | 18° C. | 25° C. | 32° C. |
| Wash 4 | 1,4-dioxane for wash 4 | 2 L/kg | 2.5 L/kg | 3 L/kg |
| | Wash 4 agitation time | 10 mins | 20 mins | 59 mins |
| | Settlement time | ≥10 mins | ≤10 mins | ≥10 mins |
| | Wash 4 temperature | 18° C. | 25° C. | 32° C. |
| | MBTE for wash 5 | 1.5 L/kg | 2.5 L/kg | 3 L/kg |
| Wash 5 | Wash 5 agitation time | 10 mins | 20 mins | 77 mins |
| | Settlement time | ≥10 mins | ≥10 mins | ≥10 mins |
| | Wash 5 temperature | 18° C. | 25° C. | 32° C. |
| Wash 6 | n-heptane for wash 6 | 1.66 L/kg | 2.5 L/kg | 3 L/kg |
| | Wash 6 agitation time | 0 mins | 0 mins | 30 mins |
| | Wash 6 temperature | 18° C. | 25° C. | 32° C. |
| Drying | Deliquoring | 1 hr | 2 hrs | 6 hrs |
| | Preliminary drying under vacuum, temperature ≤ 60° C. | 20° C. | ≤60° C. | 60° C. |
| | Preliminary drying time | N/A | Until no condensate visible in filter drier | N/A |
| | Temperature during drying | 85° C. | 100° C. | 120° C. |
| | Drying time | 8 hrs | Until IPC met LOD ≤0.5% | 168 hrs at 100° C. or 72 hrs at 120° C. |

[1]Expressed in L/kg of Compound 5 charged.
[2]Expressed in molar equivalents relative to the amount of Compound 5 charged.

TABLE 1-2

| Process Characterization Studies. | | | | |
|---|---|---|---|---|
| Example | Operation | Process Parameter | Lower Limit tested | Upper Limit tested |
| 1-1 | Reaction | Compound 6 molar equivalents | 1.00 | 1.12 |
| | | Compound 7 molar equivalents | 1.04 | 1.12 |
| | | Reaction Time (hours) | 10 | 18 |
| 1-2 | Crystal-lization | 1,4-dioxane volumes (L/kg) | 3.5 | 5.5 |
| | | Crystallization Temperature (° C.) | 65 | 85 |
| | | Hold Time at Crystallization Temperature (hours) | 0 | 4 |
| | | Cooling Rate (° C./hour) | 5 | 10 |
| | Recrystal-lization | Dichloromethane volumes (L/kg) | 8 | 12 |
| | | Recrystallization Temperature (° C.) | 18 | 32 |
| | | Agitation time (hours) | 2 | 6 |
| 1-3 | Filtration, washing, drying | Input quality (see Table 1-3) | Marginal | Good |
| | | Filtration Temperature (° C.) | 24 | 32 |
| | | Solvent Wash Volumes (L/kg) | 2 | 3 |

TABLE 1-2-continued

| Process Characterization Studies. | | | | |
|---|---|---|---|---|
| Example | Operation | Process Parameter | Lower Limit tested | Upper Limit tested |
| | | Wash Time (minutes) | 10 | 30 |
| | | Wash Temperature (° C.) | 18 | 32 |
| | | Deliquor Time (hours) | 2 | 6 |
| | | Drying Temperature (° C.) | 85 | 105 |

Example 1-1: Optimization of Compound 6 and Compound 7 Stoichiometries and Reaction Time This example focused on the following three factors: (i) stoichiometry of Compound 6, (ii) stoichiometry of Compound 7, and (iii) reaction time (in hours). The reaction temperature was kept constant at about 100° C., since lower reaction temperatures resulted in considerably slower reaction kinetics and substantially increased reaction time.

The first samples examined equivalents of Compound 6 (1.04, 1.08, and 1.12); equivalents of Compound 7 (1.04, 1.08, and 1.12) and reaction time (10, 14, and 18 hrs). Analysis indicated that lower levels of reagents (i.e., Compounds 6 and 7 less than 1.12 equivalents) were superior to higher levels of reagents, and in particular the lower levels of Compound 6 resulted in lower levels of the impurity Compound 11, and that a reaction time of 14 hrs ensured complete conversion and lower levels of impurities.

Additional samples examined lower levels of Compound 6 (1.04, 1.06, and 1.08 equiv) and combined with higher levels of Compound 7 (1.1, 1.11, and 1.12 equiv), while keeping the reaction time constant (14 hrs). Reduced input stoichiometries of Compound 6 resulted in lower levels of the impurity Compound 11.

Additional samples examined further reduced levels of Compound 6 (1.00, 1.03, and 1.06 equiv) and lower levels of Compound 7 (1.05, 1.08, and 1.11 equiv), while keeping the reaction time constant at 14 hrs. These samples produced the lowest total levels of impurities of Compounds 10 and 11. These findings suggest employing: (i) 1.00 equiv of Compound 6, (ii) 1.08 equiv of Compound 7, and (iii) a reaction time of no longer than 14 hrs.

A pair of laboratory scale-up studies were performed on 21 g input (using 4 volumes of dioxane), which appear to confirm prior findings described here. However, without wishing to be bound to a particular theory, substoichiometric amounts of Compound 6 indicated that the level of Compound 10 would be substantially higher at the end of the reaction, and its level in isolated Compound 2 would be problematic. Alternatively or additionally, given this risk and the fact the Compound 7 is readily decomposed by moisture (offering challenges when a container of it is used for multiple batches of Compound 2), it was decided to set the stoichiometry of Compound 6 at 1.04 equivalents as product quality had a lower risk of failure and yields of isolated material were comparable.

Example 1-2: Optimization of Dioxane Volume, Crystallization Temperature, Crystallization Hold Time, Temperature Ramp Rate, DCM Volume, Recrystallization Temperature, and Agitation Time Table 1-2 outlines the parameters examined in this example. After final recrystallized materials were filtered, they were washed with: (i) dioxane 1.5 volumes, (ii) dioxane 1.0 volumes, and (iii) MTBE 1.5 volumes, and the solid material was then analyzed. Samples were prepared according to Table 1-2.

It was desired to identify conditions that result in minimal production of Compound 9, e.g., of ≤1.0%. In particular, samples associated with a Recrystallization Temperature of 18° C. and a DCM volume of 8 L/kg generally resulted in Compound 9 values of greater than 10.00%, which indicates that these parameters are not acceptable for producing quality Compound 2 product. Such samples were omitted from any further analysis.

Furthermore, of the samples that utilized 12 volumes of DCM and a recrystallization temperature of 18° C., some produced acceptable quality Compound 2 and others produced unacceptable quality Compound 2. Closer examination of this subset revealed that if a temperature ramp rate of 5° C./hr is utilized, three of the four samples produced acceptable quality Compound 2, and one sample produced unacceptable quality Compound 2. In addition, closer examination of this subset revealed that if a temperature ramp rate of 10° C./hr was utilized, only one of the four samples produced acceptable quality Compound 2, wherein three of the four samples produced unacceptable quality Compound 2. This may indicate that when using marginal conditions (e.g., 12 volumes of DCM and a recrystallization temperature of 18° C.), a more controlled cooling temperature ramp rate of 5° C./hr can help improve Compound 2 quality. Notably, twelve of sixteen samples that utilized a recrystallization temperature of 18° C. produced unacceptable quality Compound 2, and therefore it was found that a recrystallization temperature of 18° C. should be avoided. When using higher recrystallization temperatures (i.e., 32° C.), there were only two samples which produced unacceptable quality Compound 2, indicating that higher recrystallization temperatures are preferred.

Two other transformations were incorporated to determine when determining acceptable conditions. First, given that there was a significant number of samples associated with 0% Compound 9, an adjustment factor was incorporated as a means of improving the model fit. The adjustment factor was defined as half the magnitude of the smallest non-zero response represented as a proportion. Specifically, an adjustment factor of 0.00052/2=0.0026 was added to samples associated with 0% Compound 9. Second, the logit transformation was applied to the adjusted Compound 9 values represented as a proportion. Specifically, the adjusted Compound 9 values were transformed via:

$$Logit(p) = \ln\left(p/1 - p\right)$$

The corresponding predicted responses were then back-transformed via:

$$\text{Predicted Compound 9} = \exp(\text{predicted } logit)/1 + \exp(\text{predicted } logit)$$

Example 1-3. Optimization of Washing and Drying Operation

Table 1-2 outlines the parameters examined in this Example. Parameters for “Marginal” and “Good” input are provided in Table 1-11. For the wetcake washes, the following wash sequence was performed: (i) wash 1: dioxane, (ii) wash 2: dioxane, (iii) wash 3: dioxane, (iv) wash 3: MBTE, and (v) wash 5: heptane. The solvent washes were kept constant for all samples. The solvent wash volumes were kept consistent and constant for all washes of a given sample (e.g., a solvent volume of two means that all five washes used two solvent volumes).

TABLE 1-3

Definition of Marginal and Good Quality Input Conditions

| Operation | Marginal Quality Input Settings | Good Quality Input Settings |
|---|---|---|
| Reaction Stoichiometry | Compound 6-1.04 equiv; Compound 7-1.08 equiv | Compound 6-1.04 equiv; Compound 7-1.08 equiv |
| Reaction Dioxane Volume | 4.0 | 5.5 |
| Ramp Cooling Rate | 10° C./hour | 10° C./hour |
| Final crystallization, recrystallization, and first filtration temperatures | 24° C. | 32° C. |
| DCM Volumes added | 8.5 | 12.0 |
| Recrystallization agitation time | 2.0 hrs | 3.0 hrs |

Notably, using “Good” input conditions (i.e., reaction, crystallization, and recrystallization conditions) afforded a wetcake with acceptable quality Compound 2 (e.g., greater than 99% HPLC area). However, using “Marginal” input conditions afforded wetcake with significantly lower in-process Compound 2 product quality (e.g., less than 99% HPLC area) with only one of the eight samples being capable of producing acceptable quality Compound 2.

However, even using “Marginal” input quality conditions with the full five wash sequence afforded acceptable quality product for all but one set of conditions examined. Notably, this failed sample used the minimal wash solvent volumes (2 volumes), the minimal wetcake washing temperature (18° C.), and the minimal wetcake washing hold times (10 minutes), which represented the lower limit settings for the wetcake washing operations.

FIG. 1 displays a plot of Compound 2 purity as a function of input quality, after filtration of the recrystallized Compound 2 (i.e., before the wash steps). “Good” quality input afforded high purity material in a fairly narrow range of Compound 2 purity between 80.89% and 90.84%, indicating that “Good” quality input conditions were robust. “Marginal” quality input afforded much lower quality material at this stage with a wide distribution of Compound 2 purity ranging from 18.13% to 72.19%, indicating that “Marginal” quality input was less robust.

Example 1-4. Process Robustness Studies: Recrystallization Temperatures

A sequence of robustness studies were performed to determine a lower temperature bound for the dioxane/DCM recrystallization, and temperatures between 18-30° C. were tested. For the reactions tested, 4.25 volumes of dioxane were used, and the mixtures (after meeting criteria) were cooled to the desired temperature (either 18, 22, 26, or 30° C.) with a ramp rate of 10° C./hour. DCM (10 volumes) was then added, and the mixtures were agitated at the requisite temperature for 3 hours, filtered, and subjected to an identical wetcake wash sequence (i.e., all washes performed with the wash solvent at 25° C.: wash 1 (dioxane 2 volumes), wash 2 (dioxane 2 volumes), wash 3 (dioxane 2 volumes), wash 4 (MTBE 2 volumes), wash 5 heptane (2 volumes)) and dry sequence (100° C. vacuum oven ~36 hours). A significant Compound 2 failure rate (i.e., Compound 2<99.0% by HPLC) was observed at the lower recrystallization temperatures of 18° C. and 22° C., whereas no product failure was observed when the recrystallization temperature was either 26° C. or 30° C.

Figure 2:
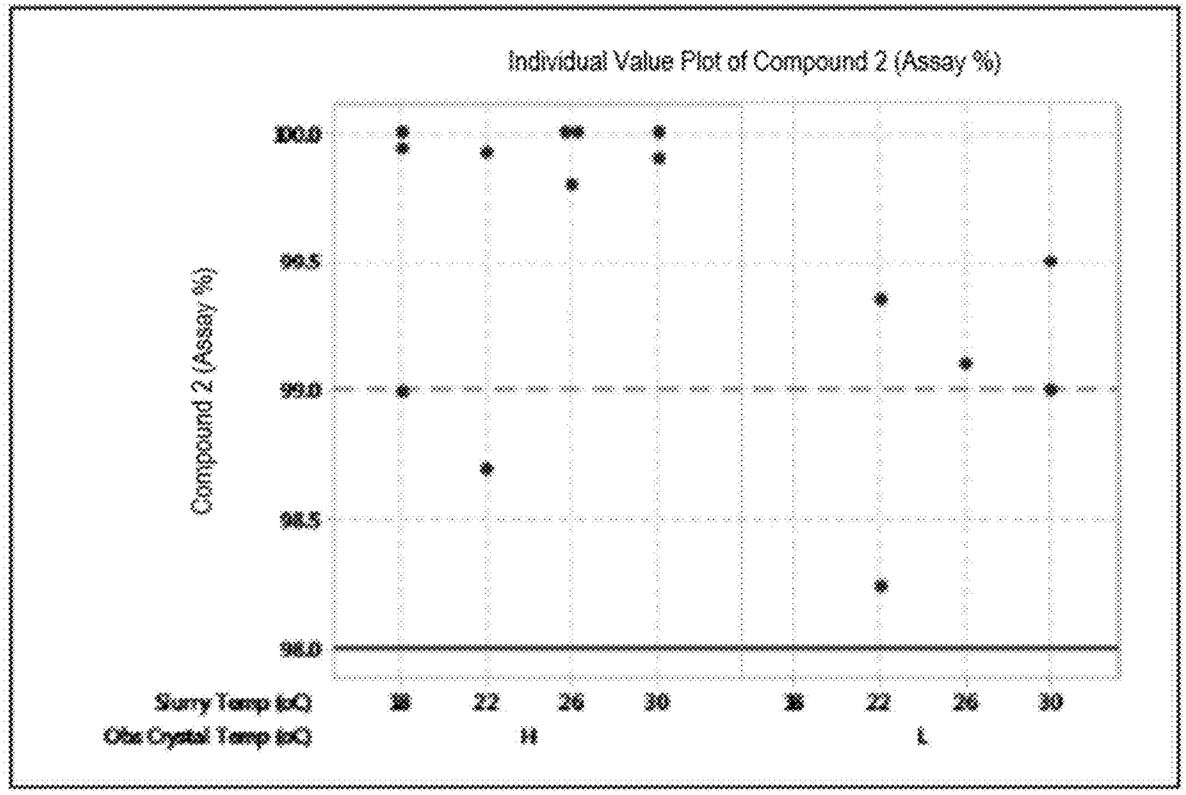
FIG. 2 depicts a plot of Compound 2 (HPLC purity) versus Recrystallization Temperature and Observed Crystallization Temperature (H=high temperature wherein T>90° C. & L=low temperature wherein T<40° C.).
Figure 3:
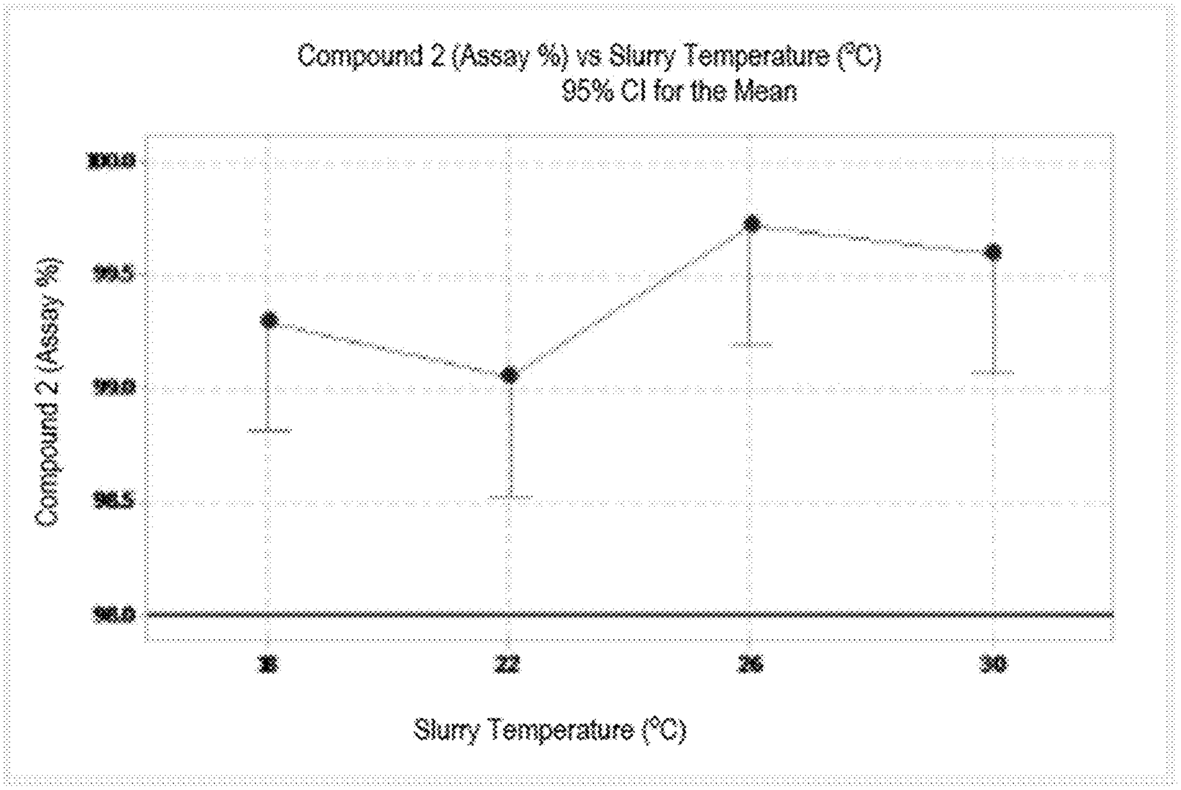
FIG. 3 depicts an Interval Plot of Compound 2 versus Recrystallization Temp. The pooled standard deviation is used to calculate the intervals.

Product quality as a function of observed crystallization temperature was analyzed as shown in FIG. 2. Product quality was lower when Compound 2 spontaneously crystalized at lower temperatures (see FIG. 2). In addition, an interval plot of Compound 2 versus the recrystallization temperature shows higher recrystallization temperatures (i.e., preferably above 24° C.) are preferred (see FIG. 3).

Figure 4:
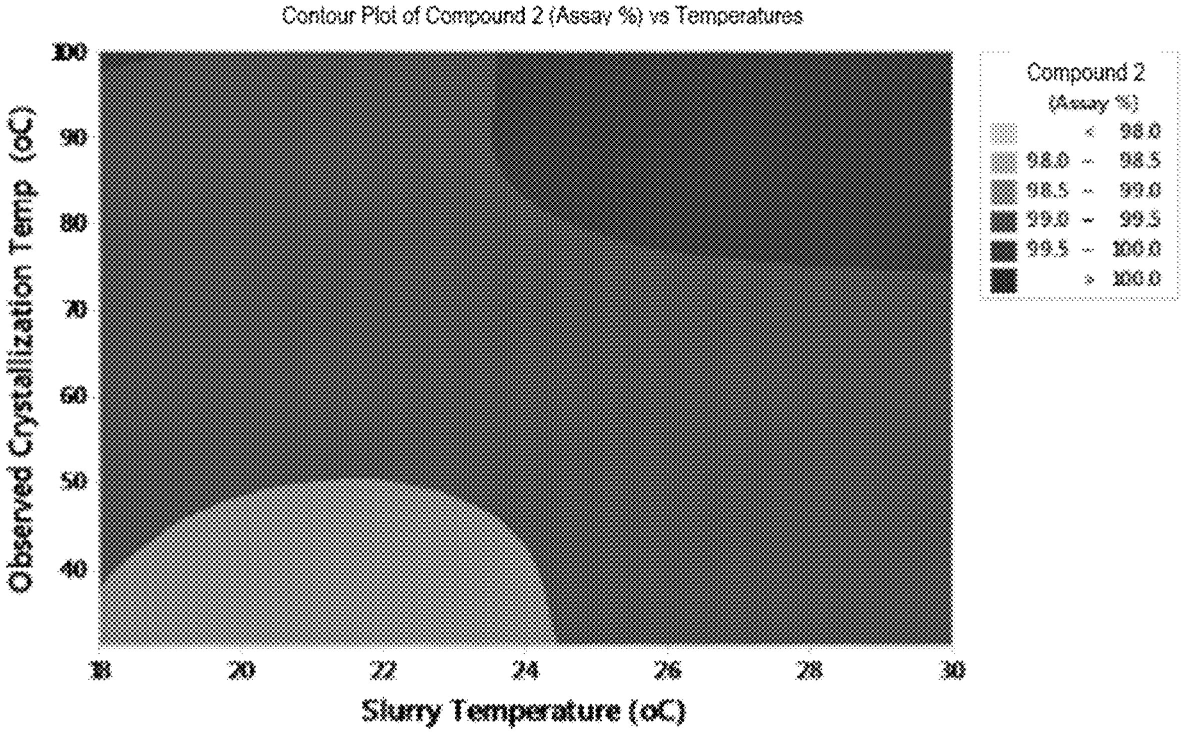
FIG. 4 depicts a Contour Plot of Compound 2 purity examining the effects of Recrystallization Temperature and Observed Crystallization Temperature

Furthermore, a contour plot of Compound 2 purity looking at the Effects of Recrystallization Temperature and Observed Crystallization Temperature was generated in FIG. 4, which indicates a lower bound for the Recrystallization Temperature should be about 23° C., and the Observed Crystallization Temperature should be at a temperature ≥75° C. For these studies the material crystallized spontaneously and was not controlled. In order to ensure the crystallization occur at 75° C. or higher, the batch could be seeded at 75° C. if spontaneous crystallization does not occur.

Furthermore, two studies were performed to examine seeding at relatively high temperatures (e.g., 70° C. and 85° C.) to assess if seeding would be viable. Both examples afforded material that would be of acceptable quality.

Example 2. Synthesis of (2S,3S,4S,5S)-2-(acetoxymethyl)-5-(5,6-dichloro-2-(isopropylamino)-1H-benzo[d]imidazol-1-yl)tetrahydrofuran-3,4-diyl diacetate hydrochloride (Compound 3 HCl)

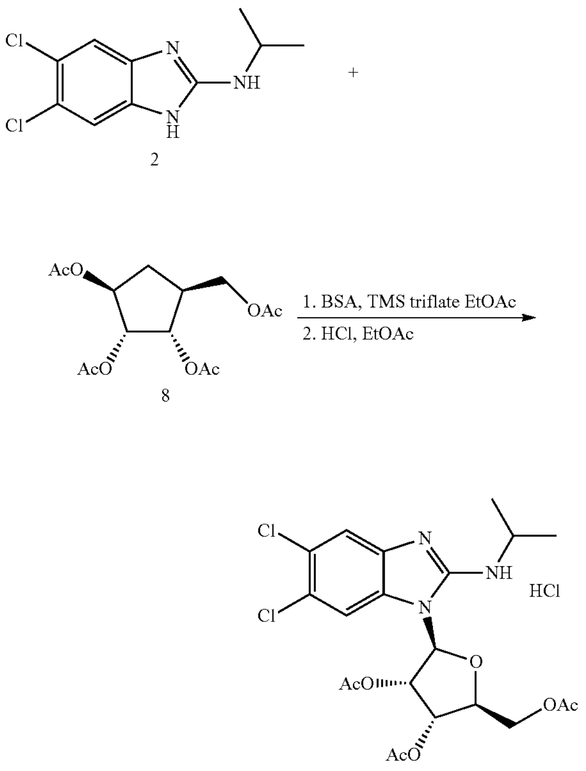

2

+

8

3-HCl

Exemplary Synthesis of(2S,3S,4S,5S)-2-(acetoxymethyl)-5-(5,6-dichloro-2-(isopropylamino)-1H-benzo[d]imidazol-1-yl)tetrahydrofuran-3,4-diyl diacetate hydrochloride (Compound 3 HCl)

Batch size in Qualified Equipment. 62 kg±12.4 kg of input Compound 2; the process description below outlines an example production using 62.0 kg of Compound 2. Operating ranges have been established for all process parameters as described herein, and the description provides the target for each of the parameters as described herein.

Chemical Reaction. Compound 2 (62.00 kg, limiting reagent), ethyl acetate (347.0 kg), Compound 8 (105.00 kg, 1.3 molar equivalents), N,O-Bis(TMS)-acetamide (30.60 kg, 0.593 molar equivalents) with a rinse of the transfer line using ethyl acetate (~20 kg), trimethylsilyl triflate (19.70 kg, 0.349 molar equivalents) with a rinse of the transfer line using ethyl acetate (~20 kg) were charged to the reactor at ambient temperature, and the mixture was stirred for at least 25 minutes at ambient temperature. The resultant mixture was heated to 78.8-80.1° C. (reflux) with agitation and kept for 5 hours, 1 min. The mixture was then cooled to 22° C.; when the mixture reached a temperature of <50° C. a sample was taken for reaction criteria. If the criteria are not met (Compound 2≤5% a/a by HPLC; Total solvent content ≤0.5% (w/w) or 5000 ppm by GC HS, and water content ≤0.5% w/w) by Karl Fischer), the batch is reheated to about 77° C., is held at that temperature for about 3 hours, and then is re-cooled to 22° C. and is sampled again for reaction criteria. These criteria were met.

Aqueous Quench and Workups. Upon meeting the reaction criteria, an aqueous solution of potassium hydrogen carbonate (31.60 kg) dissolved in water (126.4 kg) was added slowly to the reaction mixture while maintaining the temperature at about 20° C. The resultant mixture was agitated for at least 15 minutes and allowed to settle without agitation and the resultant denser aqueous phase was removed. This wash with aqueous potassium hydrogen carbonate was repeated one more time.

To the resultant Compound 3 rich organic phase, an aqueous solution of sodium chloride was added and agitated at about 20° C. for at least 15 minutes. The mixture was allowed to settle without agitation for at least 20 minutes and the resultant, denser aqueous, phase was removed.

Distillation. Solvent was removed via vacuum distillation at a jacket temperature of <45° C. (while maintaining a batch temperature of <40° C.). The distillation was stopped when about 408 L distillate had been collected. Ethyl acetate (386.8 kg) was charged, and the mixture was agitated while maintaining the internal temperature at about 20° C.

Hydrochloric Acid Salt Formation and Crystallization. To the mixture was added HCl in water (32% w/w, 30.0 kg) with agitation while maintaining an internal temperature of about 22° C. After about 10% of the HCl solution had been added, the batch was examined and crystallization had commenced. If crystallization has not commenced, the batch can be seeded by the addition of a slurry of Compound 3 HCl suspended in ethyl acetate (about 0.2 kg). Once crystals were evident in the batch, the remainder of the HCl was added commensurate with a total addition time of about 30 minutes. The mixture was agitated at about 25° C. for about 1.5 hours and then cooled to about 2° C. over a period of about 1.5 hours and was held for about 1.5 hours.

Filtration and Wetcake Washing. The resultant slurry was transferred to an agitated filter drier with the jacket set to a temperature of about 2° C.

Wash 1. After filtration, ethyl acetate (49.9 kg) at a temperature of about 2° C. was transferred onto the wetcake and the mixture was agitated for at least ten minutes and then was filtered.

Wash 2. Methyl-t-butyl ether (108.9 kg) at a temperature of about 2° C. was transferred onto the wetcake and the mixture was agitated for at least ten minutes and then was filtered.

Wash 3. Methyl-t-butyl ether (108.9 kg) at a temperature of about 2° C. was transferred onto the wetcake and the mixture was agitated for at least ten minutes and then was filtered.

Drying and Isolation. The wet cake was dried under vacuum at a jacket temperature ≤40° C. until a minimal amount of condensate was visible. The cake was dried with agitation under vacuum and a jacket temperature 40° C. until IPC criteria are met (Compound 2≤5% a/a by HPLC; Total solvent content ≤0.5% (w/w) or 5000 ppm by GC HS, and water content ≤0.5% w/w) by Karl Fischer). The batch was cooled and then is discharged and was packaged. The yield was 74.2%, with a purity of 97.7% by HPLC.

Example 3. Synthesis and Characterization of Maribavir

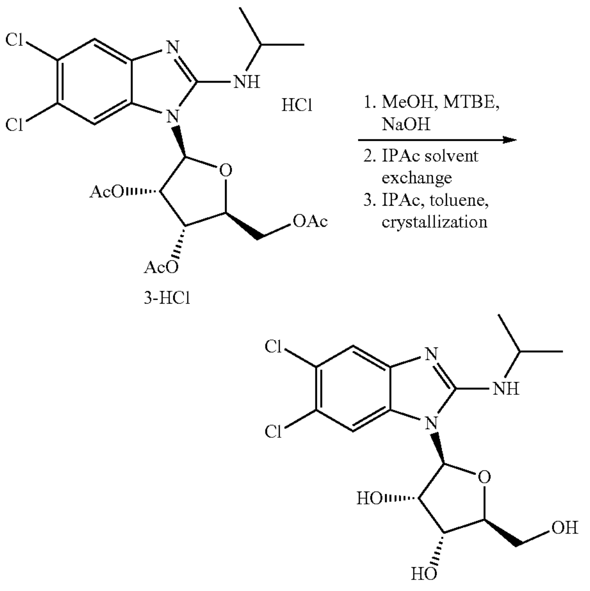

3-HCl

1

Exemplary Synthesis of Maribavir (Maribavir).

Batch Size and Qualified Equipment. 64.0-96.0 kg Compound 3 HCl; the process description below outlines an example production using 80.0 kg of Compound 3 HCl. Operating ranges have been established for all process parameters as described herein and the description provides the target for each of the parameters as described herein.

Chemical Reaction. Compound 3 HCl (80.0 kg, limiting reagent), MeOH (38.6 L), and MTBE (419.9 L) were charged to the reactor, and 30% NaOH (103.3 kg) was added such that the temperature is maintained at ≤35° C. The resultant mixture was agitated at about 30° C. between 2.5-4 h. After cooling the contents to a temperature of about 22° C., a sample was taken to monitor reaction completion. If the reaction criteria are not met (≥99% (a/a) by RP-HPLC of maribavir), the batch is reheated to about 30° C., and stirred at that temperature for a minimum of 0.5-2 h, and then re-cooled to 22° C. and resampled for reaction criteria. These criteria were met.

Phase separation/Extraction. Upon meeting the reaction criteria, agitation was stopped, and the phases were allowed to separate. After transferring the aqueous layer into a separate reactor, MTBE (96 L) was added, and the mixture was stirred for at least 20 minutes. Agitation was stopped, the phases were allowed to separate, and the lower aqueous layer was discarded. A solution of sodium chloride was added to the combined organic phases and stirred. 1% w/w aqueous HCl (24.6 kg) was added while stirring to adjust the pH of the solution to 6.8-7.5. If needed, the pH was adjusted with 1% aqueous NaOH. The organic phase was washed two additional times with a solution of sodium chloride with adjustment of the pH after each wash. Aqueous phase was discarded, and the organic phase was transferred to a distillation reactor.

Distillation and solvent exchange. About 254 L of distillate was distilled under vacuum at a jacket temperature of ≤55° C. After distillation, the reactor was cooled and the vacuum was released with nitrogen. IPAc (374.7 L) was charged to the reactor with stirring, and vacuum distillation was resumed at a jacket temperature of 65° C. until additional about 268 L of distillate was distilled. The reactor was cooled again to about 30° C., and the vacuum is released with nitrogen. A second charge of IPAc (~1.32 L/kg) was added to the reactor with stirring in two portions (~0.83 L/kg and ~0.49 L/kg) to ensure homogeneous solution, and vacuum distillation was resumed at a jacket temperature of 65° C. and batch temperature of ≤60° C. to distill about 93 L of distillate. The reactor was cooled, and a sample to determine the water content is drawn. The process of charging IPAc (~1.32 L/kg) and azeotropic vacuum distillation and testing criteria is repeated until the water content is <0.09% w/w by Karl-Fischer, after which, the same sample is tested for concentration of crude maribavir in IPAc by $^1H$ NMR (17-20% w/w).

Crystallization. The concentration of crude maribavir in IPAc was adjusted to the required target of about 18% (w/w) [17-19% (w/w)] either by dilution with additional IPAc or by distillation to an amount of about 243.6 kg. The resulting solution was heated to a batch temperature of about 84° C., and toluene in the amount of about 3/7 of total IPAc (kg/kg) (104.4 kg) was charged to the reactor in about 30 minutes. A slurry of micronized maribavir seed crystals (about 121 g, 0.15% (w/w) of Compound 3) in about 185 g of toluene (seed slurry) was prepared. The seed slurry was added via a sampler to the reactor at batch temperature of about 84° C. The bottle was rinsed with about 185 g of toluene, and the rinsate was added to the reactor. Seeding was completed in not more than 30 minutes after addition of toluene. In about 30 minutes after seeding, a second charge of toluene in the amount of about 11/7 of total IPAc (kg/kg) (382.7 kg) was charged to the reactor. The contents of the reactor were stirred at medium speed for about 1 hour at a batch temperature of about 84° C. The contents were then cooled to a batch temperature of about 5° C. over a period of about 3 hours and were stirred at medium speed for 3-18 hours at about 5° C.

Filtration and Wetcake Washing. The jacket temperature of the filter/dryer was adjusted to about 5° C. and the contents of the crystallization reactor were transferred to the filter/dryer in one or more portions allowing the wetcake to settle, pushing the solvent through the cake with inert gas pressure, if necessary. Toluene (66.8 L) at a batch temperature of about 5° C. was charged to the reactor and agitated. The slurry was transferred to the filter/dryer, and the wet cake was deliquored until the filtrate stops running.

Drying and Isolation. The cake was pre-dried for at least 5 hours without stirring at a filter/drier jacket temperature of ≤40° C. and a partial vacuum such that no condensation was visible in the agitated pressure filter. For the main drying, jacket temperature of the filter/drier was set to ≤50° C. with best possible vacuum. The cake was dried without stirring for at least 3 hours or until the material meets the reaction criteria for Loss on Drying (≤0.4% by gravimetric). Afterwards, the filter cake was agitated for one minute at medium speed for homogenization and a sample for residual solvent by GCHS was taken. Intermittent agitation of the filter cake with a stirring time of 1 minute and pause time of 60 minutes was continued for at least 2.5 hours or until the material meets the reaction criteria for residual toluene and IPAc (≤700 ppm toluene and ≤4000 ppm IPAc by GC). The filter/drier was cooled to a jacket temperature of 10° C., and the filter cake was subjected to intermittent agitation with a stirring time of 1 minute and pause time of 20 minutes for at least 1 hour before discharging. The yield was 84.7%.

Process Characterization.

Process characterization studies were performed in order to ensure maribavir's consisting production with a defined impurity profile.

In particular, multiple studies, one variable at a time (OVAT) laboratory scale studies and full-scale production runs were conducted to optimize process control and assess the current operating space for operations within synthesis of maribavir from Compound 3 within the drug substance manufacturing process. The studies focused on assessing variability on the process parameters in 1) the saponification reaction; 2) extraction and work-up; 3) distillation; 4) crystallization; 5) filtration/washing and 6) drying steps. Table 3-2 outlines the parameters investigated either through studies and/or full scale production runs, and further details are provided herein in Examples 3-1 through 3-22. Based on these studies, the current operating range for each operation of the process provides adequate control over the quality of unmilled maribavir, as shown in Table 3-1. For each parameter, statistical evaluation was carried out using the program Modde®. The model was calculated using a negative logarithmic transformation and showed good robustness/predictability/validity/reproducibility. For determination of preferred ranges (i.e., lower and upper limits) for each parameter, design space plots were calculated. The preferred lower and upper limits were defined from the design space plots having three parameters fixed at the set-point while two parameters are flexible, and were defined using ~5% failure probability.

TABLE 3-1

Process Parameters.

| Unit of Operation | Step/Parameter | Lower Value | Standard Value | Upper Value |
|---|---|---|---|---|
| Charge chemicals/prepare for chemical reaction | Charge of Compound 3 | 0.87 molar equivalents | 1.00 molar equivalents | 1.04 molar equivalents |
| | MeOH[1] | 0.34 L/kg | 0.48 L/kg | 0.56 L/kg |
| | MTBE[1] | 3.65 L/kg | 5.26 L/kg | 6.35 L/kg |
| | Deionized water[1] | 2.70 L/kg | 4.4 L/kg | 5.10 L/kg |
| | 30% w/w aqueous NaOH | 5.00 molar equivalents | 5.21 molar equivalents | 5.90 molar equivalents |
| Chemical reaction | Reaction temperature | 24° C. | 30° C. | 45° C. |
| | Reaction time | 1.5 hrs | 2.5-4 hrs | 7 days |

TABLE 3-1-continued

| Process Parameters. | | | | |
|---|---|---|---|---|
| Unit of Operation | Step/Parameter | Lower Value | Standard Value | Upper Value |
| Cool and sample for reaction criteria | Cooling temperature of reaction mixture for IPC sampling | N/A | 22° C. | N/A |
| | Reaction criteria (HPLC) | ≥98.34% (a/a) of maribavir | ≥99.0% (a/a) of maribavir | N/A |
| Phase separation/ extraction | Temperature of phase separation | 10° C. | 25° C. | 40° C. |
| | Time for phase separation after reaction | 2 mins | At least 20 mins | 7 days |
| | Time for phase separation for extraction/ washing | 2 mins | At least 5 mins to at least 20 mins | 7 days |
| | MBTE for wash | 0.96 L/kg | 1.2 L/kg | 1.44 L/kg |
| | Sodium Chloride | 14.3 kg | 17.8 kg | 21.5 kg |
| | Deionized water | 1.97 L/kg | 2.46 L/kg | 2.95 L/kg |
| | pH of reaction mixture during/after washing | 6.0 | 6.8-7.5 | 10.0 |
| Distillation/ Solvent change | Volume of distillate-first vacuum distillation | 216 L | ~254 L | 292 L |
| | First IPAc charge[1] | 3.98 L/kg | 4.69 L/kg | 5.39 L/kg |
| | Volume of distillate-second vacuum distillation | 228 L | ~268 L | 322 L |
| | Second IPAc charge[1] | 1.1 L/kg | 1.32 L/kg | 1.51 L/kg |
| | Volume of distillate-third vacuum distillation | 79 L | ~93 L | 107 L |
| | Reaction criteria (KF) for water content | N/A | ≤0.09% (w/w) | <0.2% (w/w) |
| | Reaction criteria for concentration of maribavir in IPAc (NMR) | 17% (w/w) | 17-19% (w/w) target: 18% w/w | 20% w/w |
| | IPAc charge to adjust concentration[2] | 0.93 L/kg | ~1.10 L/kg | 1.26 L/kg |
| Crystallization | Stirring rate during crystallization | 56-87 rpm | 56-87 rpm | 88-120 rpm |
| | Temperature during dosage of toluene/seeding | 77° C. | 84° C. | 88° C. |
| | First toluene charge[3] | 2.55/7 of IPAc (kg/kg) | 3/7 of IPAc (kg/kg) | 3.45/7 of IPAc (kg/kg) |
| | Dosage time of toluene before seeding | 5 mins | 15-45 mins | 90 mins |
| | Time between toluene addition and seeding | N/A | Not more than 30 mins | N/A |
| | Amount of maribavir seed[4] | 0.05% (w/w) | 0.14-0.16% (w/w) target: 0.15% (w/w) | 0.30% (w/w) |
| | maribavir seed size: d(50) in μm | 2.25 | 2.75-6.25 | 7.00 |
| | Stirring time after seeding | 10 mins | 30 mins | 60 mins |
| | Second toluene charge[5] | 9.35/7 of IPAc (kg/kg) | 11/7 of IPAc (kg/kg) | 12.65/7 of IPAc (kg/kg) |
| | Dosage time of second toluene charge | 60 mins | ~120 mins | 240 mins |

TABLE 3-1-continued

| Process Parameters. | | | | |
|---|---|---|---|---|
| Unit of Operation | Step/Parameter | Lower Value | Standard Value | Upper Value |
| | Stirring time after second toluene addition | 15 mins | 60 mins | 120 mins |
| | Final temperature of crystallization mixture | −5° C. | 3-7° C. | 20° C. |
| | Cooling time | 1.5 hrs | 2.5-3.5 hrs | 4.5 hrs |
| | Stirring time of crystallization mixture at final temperature | 0 mins | 3.0-18.0 mins | 7 mins |
| Filtration and washing | Temperature during dosage filtration/ washing | −5° C. | 5° C. | 20° C. |
| | Toluene for wash[1] | 0.67 L/kg | 0.84 L/kg | 1.00 L/kg |
| | Duration of slurry wash | 0 mins | ≥15 mins | 5 mins |
| Drying | Temperature for pre-drying | N/A | ≤40° C. | 70° C. |
| | Time for pre-drying | N/A | ≥5 hrs | N/A |
| | Temperature for main drying | N/A | ≤50° C. | 70° C. |
| | Reaction criteria for LOD | N/A | ≤0.4% (w/w) | N/A |
| | Reaction criteria for residual solvent by HC-HS | N/A | ≤700 ppm toluene ≤4000 ppm IPAc | N/A |

[1]Expressed as L/kg of Compound 3 HCl

[2]Actual amount to be charged is calculated based on the result from the concentration reaction criteria.

[3]Amount of toluene is calculated based on mass and assay of reaction mixture. Upper and lower values are determined in combination with amount of 2nd toluene charge.

[4]Expressed as (w/w) of Compound 3 HCl charged.

[5]Amount of toluene is calculated based on mass and assay of reaction mixture. Upper and lower values are determined in combination with amount of 1st toluene charge.

TABLE 3-2

| Process Characterization studies. | | | | |
|---|---|---|---|---|
| Example | Operation | Process Parameter | Lower Limit studied | Upper Limit studied |
| 3-1 | Reaction | Amount of MeOH | 0.27 g/g | 0.44 g/g |
| | | Amount of MTBE | 2.70 g/g | 5.10 g/g |
| | | Amount of water | 2.70 g/g | 5.10 g/g |
| | | Amount of NaOH | 5 eq. | 5.90 eq. |
| | | Reaction Temperature | 15° C. | 45° C. |
| | | Reaction Time | 1.5 h | 7 days |
| 3-2 | | Conversion | 98.4% a/a | 100% a/a |
| 3-3 | Workup | Temperature during extractions, washes, and phase separations | 10° C. | 40° C. |
| 3-4 | | Amount of MBTE for extraction | 0.713 g/g | 1.069 g/g |
| 3-5 | | Extraction/washing time | 2 minutes | 7 days |
| 3-6 | | Amount of NaCl solution for washing | NaCl: 2.44 eq Water: 1.97 g/g | NaCl: 3.66 eq Water: 2.954 g/g |
| 3-7 | | pH after work-up | 6.0 | 10.0 |
| 3-8 | Distillation | Amount of distillates during first, second, and third distillations | 216 mL 228 mL 79 mL | 292 mL 322 mL 107 mL |
| | | Amount of IPAc during first, second, and third feed | 3.465 g/g 0.974 g/g 0.811 g/g | 4.689 g/g 1.318 g/g 1.097 g/g |

TABLE 3-2-continued

| Process Characterization studies. | | | | |
|---|---|---|---|---|
| Example | Operation | Process Parameter | Lower Limit studied | Upper Limit studied |
| 3-9 | Crystallization | Concentration of maribavir in IPAc before crystallization | 15% w/w | 20% w/w |
| 3-10 | | Water content before crystallization | 0% (w/w) | 0.5% (w/w) |
| 3-11 | | Hold time after $1^{st}$ toluene addition and pre-seeding | 0 minutes | 1 hours |
| 3-12 | | Temperature during toluene addition and seeding | 60° C. | 88° C. |
| 3-13 | | Amounts of toluene during crystallization | 32.5% (w/w) | 67.5% (w/w) |
| 3-14 | | Dosing times of toluene before and after seeding | First: 5 mins Second: 60 mins | First: 90 mins Second: 240 mins |
| 3-15 | | Seed loading of maribavir seeds for crystallization | 0.05% (w/w) | 1.40% (w/w) |
| 3-16 | | Time post-seeding before addition of $2^{nd}$ toluene charge | 10 mins | 2 hours |
| 3-17 | | Time after $2^{nd}$ toluene addition before cooling | 15 mins | 120 mins |
| 3-18 | | Cooling duration | 1.5 h | 5 h |
| 3-19 | | Cooling Temperature | 5° C. | 20° C. |

TABLE 3-2-continued

| Process Characterization studies. | | | | |
|---|---|---|---|---|
| Example | Operation | Process Parameter | Lower Limit studied | Upper Limit studied |
| 3-20 | Filtration and | Temperature during filtration and washing | −5° C. | 20° C. |
| 3-21 | washing | Amount of toluene for washing | 0.58 g/g | 0.87 g/g |
| 3-22 | | Stirring time during toluene wash | 0 mins | 5 days |

Example 3-1. Optimization of Amount of MeOH, MTBE, Water, NaOH, and Reaction Temperature Time This example focuses on the following six factors: (i) amount of MeOH, (ii) amount of MBTE, (iii) amount of water, (iv), amount of NaOH, (v) reaction time, and (vi) reaction temperature. The amounts of Compound 3 HCl were adapted accordingly. The reactions were carried until reaction criteria were met and not worked up. Samples were tested in accordance with the solvent and temperature ranges shown in Table 3-2. The six factors focused on within this example were determined to have no impact on the quality or yield of maribavir.

Example 3-2. Impact of Lower Conversion

Prior studies indicated that before extraction, maribavir was measured with a purity of 95.51% a/a by HPLC, but after extraction of the aqueous phase with TBME and stirring the organic layer (at pH ~11.7) at room temperature for about 10.25 hrs, the amount of maribavir rose to 99.71% a/a by HPLC. To justify obtaining ≥99.0% maribavir, an example with lower content of maribavir was conducted to track the fate and purge of residual Compound 3 and/or partially de-acetylated intermediates. The reaction times were set to 45 min and 2.5 h, and a sample was pulled from the reaction mixture, directly cooled down to 20° C., and worked-up without waiting for reaction criteria result. Stability of the reaction mixtures was also assessed at 40° C. over 7 days (see Example 3-23).

The amount of maribavir in the organic layer was checked by HPLC after every phase separation operation. The amount of 99.23% a/a was reached after re-extraction of the alkaline aqueous layer and did not change any further during NaCl washes where the pH was adjusted to 6.8-7.5. The remaining 0.50% a/a of partially de-acetylated intermediate was identified as the 3-mono acetate of maribavir. Accordingly, this example demonstrates that >99.0% a/a of maribavir ensures delivery of maribavir in the desired yield and quality. This example also demonstrates that a failed reaction criteria can be corrected by a prolonged hold time of the biphasic alkaline reaction mixture at 20° C.

Example 3-3. Influence of Temperature During Extractions, Washes, and Phase Separations The phase separations are generally performed at 25° C. for at least 20 minutes. Without wishing to be bound to a particular theory, it was thought that a lower temperature could possibly result in a lower yield or longer times for phase separations. To evaluate, a study with aqueous work-ups at 10 and 25° C. was conducted. In addition, to assess the influence of a higher temperature, the stability of the biphasic mixtures at 40° C. was tested (see Example 3-23).

Notably, the phase separation at 10° C. did not have an impact on purity of maribavir in solution. After aqueous work-up the water content and assay of the organic layer were comparable. The biphasic mixture before and after NaCl washes showed good stability over 7 days (see Example 3-23). Accordingly, it was determined that the temperature during phase separation has no impact on the quality or yield of maribavir.

Example 3-4. Influence of the Amount of Tert-Butylmethyl Ether for Extraction

With wishing to be bound to a particular theory, it was thought that a lower amount of TBME for the extraction of the first aqueous layer could lead to a diminished yield. Additionally, an altered solvent composition could impact the crystallization properties. Therefore, higher or lower amounts of TBME for extraction were evaluated, as shown in Table 3-2.

A lower or higher amount of TBME for extraction did not have an impact on the purity of maribavir in solution or the solvent composition after distillation. The water content after distillation was slightly higher, but still lower than the desired <0.1% w/w, and the altered amounts of TBME only had a minor impact on crude yield in solution after distillation, which is within the error range. A lower amount of TBME led to a higher concentration of crude maribavir in iPrOAc after distillation (e.g., 24.58% by NMR; typical concentrations in range of 19-23% w/w), but even with this higher concentration, the filtration was feasible without precipitation of maribavir. Accordingly, it was found that these amounts of TMBE for extraction did not impact the yield or quality of maribavir.

Example 3-5. Influence of Time for Extraction and Washing

Without wishing to be bound to a particular theory, it was thought that a shorter extraction time could impact the yield and purging of impurities. In addition, shorter NaCl-washings could potentially impact water content after washing steps. To evaluate this, a study with short extraction/washing times for all of these steps was performed (max. 5 mins each). Since the first NaCl washing will take ≥5 mins in the standard process, this washing was tested for ≤2 min. A longer contact with aqueous media could lead to formation of impurities. To assess the influence of a higher temperature, the stability of the biphasic mixtures at 40° C. was tested (see Example 3-23). It was determined that shorter washing times do not impact product quality. The product content in the organic layers was slightly lower at shorter washing times but still within standard error. In addition, the yield for crude maribavir after distillation was 93.1%, which is at the upper end of the expected range. The biphasic mixture before and after NaCl-washes showed good stability over 7 d (see Example 3-23). Accordingly, it was determined that the time for washing has no impact on the quality or yield of maribavir.

Example 3-6. Influence of the Amounts of NaCl-Solutions for Washings

Without wishing to be bound to a particular theory, it was thought that a lower or higher amount of 10% NaCl-solutions could lead to undesired effects during washings (e.g., dissolution of maribavir into aqueous layer). Additionally, an organic layer with different residual water content could be obtained, which could possibly impact the crystallization. Another possible impact could be dissolution of inorganics into the organic layer.

Various amounts of 10% NaCl-solution for washing were tested in accordance with Table 3-2. It was determined that the amount of NaCl-solutions for washing did not impact the purity or the concentration of maribavir in solution. The time for phase separation remained quick regardless of the amount of NaCl solution. Accordingly, it was determined that the amount of NaCl for washing has no impact on quality or yield of maribavir.

Example 3-7. Influence of Lower or Higher pH after Aqueous Work-Up

Within the work-up to afford maribavir, the pH is adjusted with either 1% HCl or NaOH solutions to 6.8-7.5. The impact of a pH outside of this range was unknown. Workups with lower or higher pH were performed. For this purpose, the reaction mixture was split up into two aliquots before NaCl washes. pH's were tested in accordance with Table 3-2.

A preliminary test was done to determine the lower pH to be tested: Three samples of the biphasic mixture during 1st NaCl-wash was taken and adjusted separately to pH 4, 5, and 6. These samples were refluxed overnight and sampled for HPLC purity at different time points. All three samples showed perfect stability. It was observed that at lower pH values, some white precipitate occurred. This precipitate dissolved upon raising the pH with NaOH. It was assumed that this was the hydrochloride salt of maribavir. Upon further review, at pH<5.5, the precipitate occurred. Therefore, the lowest pH tested was 6. The distilled reaction mixtures were subjected to crystallization on a 400 ml Easymax scale. Samples and results are shown in Table 3-3.

TABLE 3-3

Reaction Samples and Results.

| Sample | (adjusted) pH after work-up | PSD | XRPD |
|---|---|---|---|
| 3-7-1 | ~7.0 | d(0.1) = 163 μm<br>d(0.5) = 240 μm<br>d(0.9) = 351 μm | Complies |
| 3-7-2 | 6.04 | d(0.1) = 195 μm<br>d(0.5) = 327 μm<br>d(0.9) = 482 μm | Complies |
| 3-7-3 | 10.01 | d(0.1) = 44.6 μm<br>d(0.5) = 305 μm<br>d(0.9) = 441 μm | Complies |

[1] Approximate amount of product in organic layer after extraction.

The yield of both samples with altered pH after work-up gave slightly lower yields, but still within the expected range. There was no impact on purity or concentration of maribavir. The desired polymorph was obtained in all cases. The altered pH values impacted PSD: both PSD curves showed a small shoulder peak in the small particle size area. For the lower pH, overall particles became larger. For the higher pH d(0.1) became significantly smaller while d(0.5) and d(0.9) became larger. Since both samples matched the desired d(0.5)>176 μm, the results are generally acceptable. Accordingly, it was determined that the pH after aqueous work-up has no impact on yield but a minor impact on quality of maribavir.

Example 3-8. Influence of Lower or Higher Amounts of Feed/Distill During Solvent-Swap Without wishing to be bound to a particular theory, the solvent composition and water content after the distillation steps were expected to be crucial for successful crystallization, For example, undesired solvent composition and water content could lead to a lower yield, lower purity, or undesired particle size distribution.

Here, ranges were tested in accordance with Table 3-2. For example, a sample was performed simulating a worst-case solvent-swap: using a lower amount of iPrOAc as feed and a lower amount of distillate. After the distillation, the concentration was adjusted as described in the exemplary synthesis provided above. This reaction mixture was subjected to a 400 mL scale crystallization. Concomitantly, another part of the reaction mixture was spiked with TBME and water to simulate a worst-case distillation outcome with 95:5 w:w ratio iPrOAc:TBME and 0.20% w/w water in total and crystallized accordingly. A distillation with a higher amount of feed and distillate will most likely lead to a solution of crude maribavir in iPrOAc with a low water content. The only effect would be a prolonged distillation time. This was evaluated in a stability test (see Example 3-23).

Reducing the feed and distill amounts led to higher contents of TBME. Additionally, the amount of water exceeds the internal process control of <0.10% w/w. While higher TBME and water led to a unimodal PSD curves with a bit higher values, no negative impact on PSD and XRPD was detected. Therefore, it was assessed that the amount of feed and distill has no impact on the quality or yield of maribavir.

Example 3-9. Influence of Lower or Higher Concentration of Maribavir in iPrOAc Before Crystallization Samples were performed using lower or higher concentration of maribavir crude before crystallization. Without wishing to be bound to a particular theory, it was thought that a concentrated solution of the crude maribavir in iPrOAc might spontaneously crystallize during filtration/transfer operations, or sampling for NMR assay. This risk was evaluated with solubility data (see Example 3-24). Samples and results are shown in Table 3-4.

TABLE 3-4

Reaction Samples and Results.

| Sample | maribavir (% w/w) | PSD | XRPD |
|---|---|---|---|
| 3-9-1 | 17 | d(0.1) = 163 μm<br>d(0.5) = 240 μm<br>d(0.9) = 351 μm | Complies |
| 3-9-2 | 15 | d(0.1) = 198 μm<br>d(0.5) = 287 μm<br>d(0.9) = 409 μm | Complies |
| 3-9-3 | 20 | d(0.1) = 178 μm<br>d(0.5) = 284 μm<br>d(0.9) = 452 μm | Complies |

[1] Approximate amount of product in organic layer after extraction.

The variation of maribavir concentrations did not affect product purity and assay. The higher concentration of 20% w/w before toluene addition did not lead to spontaneous crystallization after addition of $1^{st}$ amount of toluene before seeding. The resulting PSD and polymorph for both 3-9-2 and 3-9-3 show slightly larger PSD. The values tested did not show an impact on quality or yield of maribavir. However, deviating from a range of 15-20% w/w may lead to an undesired PSD and/or a lower yield.

Example 3-10. Influence of Higher Water-Content Before Crystallization

Without wishing to be bound to particular theory, it was thought that the presence of water leads to higher solubility of maribavir, which may impact the yield and PSD. Therefore, higher water-content before crystallization was studied in accordance with Table 3-2.

In one sample, the higher amount of water led to a yield below 70%, although it was not determined whether this yield was representative.

Regardless, a higher water content (without a higher TBME content) is highly unrealistic for the following reasons, for example: a) an unsuccessful solvent exchange could lead to an elevated water content, and would also likely result in an elevated level of TBME; b) water up-take by the added solvents (e.g. iPrOAc for feed or dilution) is unlikely since water contents are controlled by raw material specifications (<0.05% water specified); and c) the water content is controlled and can be corrected by another distillation step. The higher water content by spiking had no impact on product purity, PSD, or XRPD. Therefore, it was assessed that the amount of water did not impact quality of maribavir, but could impact yield.

Example 3-11. Influence of Hold Time after $1^{st}$ Toluene Addition and Pre-Seeding The stability of the supersaturated solution of maribavir with respect to self-nucleation was investigated by allowing the iPrOAc/toluene solution at 77° C. to stir for a period of time without seeding. When the solution was stirred before seeding for 1 hour, a very low trace amount of solid particles was spotted in the reaction mixture before the seeds were added. Nevertheless, the resulting PSD still matched the specifications. When the solution was stirred before seeding for 30 minutes, no solid particles were spotted in the reaction mixture before the seeds were added. Since seeding was assessed to be effective in this case, the reaction mixture was then used to test the impact of 0.5% wt seeds (see Example 3-15). The resulting PSD still matched the specifications.

The supersaturated solution of crude maribavir in iPrOAc: toluene 7:3 v:v was susceptible to self-seeding at Ti=77±3° C., since after 1 h of stirring pre-seeding led to the formation of small amounts of seeds. The self-seeding of the solution after 1 h didn't appear to impact the PSD negatively. After 30 min, no self-seeding occurred. Therefore, it is recommend to limit time between finished $1^{st}$ toluene dosage and seeding.

Example 3-12. Influence of Lower or Higher Temperature During Toluene Additions and Seeding Samples were performed evaluating a lower and higher temperature during toluene addition and seeding (temperature was maintained during seeding, $2^{nd}$ addition of toluene and stirring time prior to cooling to 5° C.). Samples were prepared in according to Table 3-2.

The temperature had no impact on the yield or purity of maribavir. Seeding temperatures of 67 and 87° C. gave a similar PSD as the standard reaction. The desired polymorph was obtained in all cases. Therefore, it was assessed that the temperature during seeding had no impact on the quality or yield of maribavir.

Example 3-13. Influence of Lower or Higher Amounts of Toluene for Crystallization The ideal volume ratios for iPrOAc:toluene prior to seeding was thought to be 7:3, and 7:11 for the final crystallization solution. Without wishing to be bound to a particular theory, it was thought that deviation from these ratios may lead to different PSD and may impact yield. Studies were performed using less or more toluene for crystallization, in accordance with Table 3-2.

The amount of toluene for crystallization had no impact on product yield and purity for the range examined. The PSD was not impacted significantly when the toluene amounts were altered and the correct polymorph was obtained. Therefore, it was assessed that the amount of toluene had no impact on the yield and quality for maribavir.

Example 3-14. Influence of Shorter or Longer Dosing Times of Toluene Before and After Seeding Without wishing to be bound by a particular theory, it was thought that the dosing times of toluene might have an impact on crystallization properties, e.g., the resultant PSD. A quick dosage might even lead to spontaneous crystallization. Therefore, studies were performed for assessment of shorter and longer dosing times. The standard dosing times for toluene before seeding as 15-45 minutes, and after seeding was 120-140 mins. Samples were tested in accordance with Table 3-2.

The variation of the dosing times of toluene had no impact on product purity, yield, and PSD. Therefore, it was assessed that the dosing time for both toluene amounts had no impact on yield or quality of maribavir.

Example 3-15. Influence of Lower or Higher Amount of Seeds for Crystallization Without wishing to be bound to a particular theory, it was thought that the amount of micronized seeds may have an impact on the crystallization. Typically, between 0.5-1.0% w/w of seed loading was used. Therefore, studies were performed for assessment of amount of seeds for crystallization in accordance with Table 3-2.

Lower or higher seed amounts had no impact on product purity and assay. The XRPD results matched the desired polymorph in all cases. The particles obtained with 0.3% seeds were larger than usual. All other PSDs were in good accordance to the standard procedure. Therefore, it was assessed that the amount of seeds has no impact on the quality or yield of maribavir. However, without wishing to be bound by a particular theory, there could be a risk that higher amounts of seed crystals can result in a product with decreased quality.

Example 3-16. Influence of Shorter or Longer Stirring Time Post-Seeding Before Addition of $2^{nd}$ Amount of Toluene Without wishing to be bound to a particular theory, it was thought that maintaining the seeded crystallization mixture at a fixed temperature and solvent composition may impact crystal growth and PSD. Studies were performed to assess the impact of a shorter or longer stirring time post-seeding before the addition of the $2^{nd}$ amount of toluene (standard 25-35 mins). Samples and were prepared in accordance with Table 3-2.

Changing the stirring time post-seeding had no significant impact on product and crystal quality. Therefore, it was assessed that stirring time post-seeding had no impact on the quality or yield of maribavir.

Example 3-17. Influence of Shorter or Longer Stirring Time after Addition of $2^{nd}$ Amount of Toluene Typically, after addition of the $2^{nd}$ amount of toluene to the seeded mixture, the batch was stirred over 45-75 min maintaining 77±3° C. before cooling down. Without wishing to be bound to a particular theory, it was thought that a shorter or longer hold time might impact the crystal quality. Therefore, assess the impact of a shorter or longer stirring time after addition of the 2nd amount of toluene were assessed. Sample were prepared in accordance with Table 3-2

Changing the stirring time after adding the second amount of toluene had no significant impact on product and crystal quality. Therefore, it was assessed that the stirring time after the second amount of toluene had no impact on the quality or yield of maribavir.

Example 3-18. Influence of Shorter or Longer Cooling Time During Crystallization Studies were performed to assess if the cooling ramp affects the PSD. Samples and were prepared in accordance with Table 3-2.

The duration of the cooling time had no impact on product purity and yield. A shorter cooling led to a very similar PSD than the standard example. Therefore, it was assessed that the time for cooling had no impact on purity and yield of maribavir.

Example 3-19. Influence of Lower or Higher Final Temperature of Crystallization The crystallization mixture is typically cooled to 3-7° C. Without wishing to be bound to a particular theory, it was thought that the temperature might impact the crystal quality or maribavir purity and yield: a lower temperature may lead to precipitation of impurities while a higher temperature could lead to dissolution of product and a lower yield. Therefore, examples were performed to assess the impact of a lower or higher final temperature in accordance with Table 3-2.

The final temperature after crystallization has no impact on product purity and yield. A lower final temperature leads to larger particles with a wider shape of the PSD. A microscope image showed the presence of agglomerates. A higher temperature leads to a slightly larger, but similar PSD than in the standard reaction. Therefore, it was assessed that the final temperature had no impact on quality or yield.

Example 3-20. Influence of Temperature During Filtration and Washing

The filtration/slurry wash is typically performed at 5° C. Without wishing to be bound to a particular theory, it was thought that a lower temperature could lead to precipitation of impurities while a higher temperature could lead to a lower yield. Therefore, samples with filtration/washing at a lower temperature or higher temperature where examined in accordance with Table 3-2.

A lower or higher temperature during washing the filter cake had no significant impact on product purity and yield. The results of this section are supported by the results of Example 3-19. Therefore, it was assessed that the temperature during washing has no impact on the quality or yield of maribavir.

Example 3-21. Influence of the Amount of Toluene for Washing

Without wishing to be bound to a particular theory, it was thought that the amount of toluene for washing the filter cake may possibly impact the yield and purity of the product. For example, a higher amount of toluene may reduce the yield of maribavir. This was evaluated based on the solubility of maribavir in toluene (see Example 3-24). A lower amount could have an influence on product quality. Therefore, washing with less toluene was performed in accordance with Table 3-2.

The lower amount of toluene for washing did not have an impact on product yield and quality. The solubility of maribavir in toluene at 20-25° C. is 0.2% w/w (see Example 3-24), and washing with higher amounts is not expected to lead to high product losses. Therefore, it was assessed that the amount of toluene for washing had no impact on the quality or yield of maribavir.

Example 3-22. Influence of Stirring Time During Toluene Wash

Without wishing to be bound by a particular theory, shorter stirring time during the wash could was that to result in suboptimal washing. Nevertheless, no additional studies are performed to test this, because the wash was done as displacement wash during this PAR study. The upper limit of the PAR was defined based on stability tests (see Example 3-23). The results were also supported by solubility data (see Example 3-24).

Example 3-23. Stability Data

The following stability data was generated and referenced in one or more of the prior examples. Stability of the following systems were studied and found to be stable for at least 7 days: Stability of Compound 3 HCl in MeOH/TBME at 40° C.; Stability of reaction mixture at 40° C. (amount of maribavir); Stability of biphasic mixture at 40° C. (before extraction); Stability of biphasic mixture at 40° C. (during last NaCl washing); Stability of reaction mixture after final distillation step at Stability of biphasic mixture at 75° C.; Stability of reaction mixture after final distillation step at 90° C.; Stability of crystallization mixture after dosage of $2^{nd}$ portion of toluene at reflux; Stability of crystallization at 20° C.; Stability of mixture during slurry wash at 20-25° C.; Stability of maribavir in the mother liquor at 20-25° C.; Stability of wet cake at 70° C.; and Stability of dry cake at 70° C.

Example 3-24. Solubility Data

The following solubility data was generated and referenced in one or more of the prior examples. A mixture of approx. 2 g of maribavir and 5 mL solvent was stirred overnight in sealed vials at different temperatures. The clear supernatant solutions were sampled for NMR assay. All examples were done in triplicates. The samples and results are shown in Table 3-5.

TABLE 3-5

Maribavir solubilities in iPrOAc and toluene.

| Solvent | Temperature (° C.) | Solubility (% w/w) |
|---|---|---|
| Toluene | 20-25 | 0.2% w/w |
| iPrOAc | 5 | 37.85 |
| | 10 | 39.71 |
| | 20 | 23.42 |
| | 25 | 19.66 |
| | 30 | 17.82 |
| | 35 | 15.89 |
| | 40 | 15.10 |
| | 60 | 3.05 |
| | 85 | 0.59 |

Maribavir showed a good solubility in iPrOAc below 30° C. leading to a low risk of spontaneous crystallization in solution.

Example 3-267 Scale-Up Studies

Scaled-up reactions were performed as outlined in Table 3-2. Additional lab-scale runs were also performed and confirmed to be successful since the PSD followed the same trends at the scaled-up runs. The scaled-up samples are shown in Table 3-6.

TABLE 3-6

Scaled-Up Samples and Results.

| Sample: | 1 | 2 | 3 | 4 | 5 | 6 | 7 | 8 |
|---|---|---|---|---|---|---|---|---|
| Crystallization Temperature (° C.) | 77 | 77 | 77 | 88 | 88 | 85 | 88 | 85 |
| Concentration maribavir in IPAC (wt %) | 17.5 | 17.5 | 17.5 | 17.5 | 17.5 | 17.5 | 19.5 | 17.5 |
| Seed loading rel. to Compound 3 (wt %) | 0.70 | 0.35 | 0.35 | 0.15 | 0.35 | 0.35 | 0.15 | 0.10 |
| Seeds d(50) (μm) | 2.72 | 2.72 | 4.47 | 4.47 | 4.47 | 2.25 | 2.25 | 2.25 |
| Agitation after seeding (rpm) | 100 | 65 | 60 | 65 | 65 | 65 | 65 | 65 |
| Agitation cool down (rpm) | 80 | 75 | 60 | 65 | 65 | 65 | 65 | 65 |
| Agitation aging at 5° C. | 80 | 75 | 60 | 65 | 65 | 65 | 65 | 65 |
| PSD d(50) after crystallization (μm) | n/a | 177 | 210 | 278 | 235 | 174 | 215 | 219 |
| Acceptable | No | No | Yes | Yes | Yes | No | Yes | Yes |

Among the tested parameters, seed loading and seed characteristics were demonstrated as having the greater impact on the resulting PSD. The crystallization temperature and concentration showed a lower significant as a single variant. The combined data between the laboratory and scaled-up runs was analyzed and preferred parameters shown in Table 3-1.

Example 4. Summary of Batch History

The batch histories are summarized below in Tables 4-1 to 4-20.

Step I: Synthesis of Compound 2

TABLE 4-1

Batch Analysis

| | | Batch No. 1 | Batch No. 2 | Batch No. 3 |
|---|---|---|---|---|
| | | Batch Size (kg) | | |
| Test | | 81.48 | 89.02 | 89.02 |
| | | Results | | |
| Color Appearance | | Off-white Solid | Off-white Solid | Off-white Solid |
| HPLC (Purity) (a/a) | Compound 5[a] | ND | ND | ND |
| | Compound 10[b] | <0.1% | <0.1% | <0.1% |
| | Compound 9[c] | 0.1% | 0.1% | 0.1% |
| | Unknown Impurities Each individual impurity | 0.1% | 0.1% | 0.1% |
| | Sum of impurities | 0.4% | 0.4% | 0.3% |
| HPLC Content (w/w) | | 99.1% | 99.8% | 99.4% |

ND = not detected

[a]Limit of detection for Compound 5 = 0.01%

[b]Limit of detection for Compound 10 = 0.02%

[c]Limit of detection for Compound 9 = 0.02%

TABLE 4-2

Batch Analysis

| | Batch No. | 4 | 5 | 6 | 7 | 8 |
|---|---|---|---|---|---|---|
| | Batch Size (kg) | 110.73 | 119.2 | 118.05 | 117.62 | 120.46 |
| | Test | | | Result | | |
| | Color | Off-white | Off-white | Off-white | Off-white | Off-white |
| | Appearance | Solid | Solid | Solid | Solid | Solid |
| HPLC (Purity) | Compound 5 (w/w) | ND | ND | ND | ND | ND |
| | Compound 10 (w/w) | 0.1% | 0.1% | 0.1% | 0.1% | 0.1% |
| | Compound 9 (w/w) | 0.5% | 0.5% | 0.6% | 1.1% | 0.6% |
| | Compound 12 (w/w)[a] | ND | ND | ND | ND | ND |
| | Impurity m/z | ND | ND | ND | ND | ND |
| | Each unspecified (a/a) | 0.1% | ND | 0.1% | 0.1% | 0.1% |
| | Total unknown impurities (a/a) | 0.1% | ND | 0.1% | 0.1% | 0.1% |
| | Total known impurities (w/w) | 0.5% | 0.6% | 0.7% | 1.2% | 0.6% |
| | HPLC Content (w/w) | 99.4% | 99.5% | 99.6% | 99.4% | 99.5% |

ND = not detected

[a]Limit of detection for Compound 12 = 0.01%

TABLE 4-3

Batch Analysis

| | Batch No. | 9 | 10 | 11 | 12 | 13 |
|---|---|---|---|---|---|---|
| | Batch Size (kg) | 118.77 | 117.69 | 118.86 | 121.7 | 123.7 |
| | Test | | | Result | | |
| | Color | Off-white | Off-white | Off-white | Off-white | Off-white |
| | Appearance | Solid | Solid | Solid | Solid | Solid |
| HPLC (Purity) | Compound 5 (w/w) | ND | ND | ND | ND | ND |
| | Compound 10 (w/w) | 0.1% | 0.1% | 0.1% | ND | ND |
| | Compound 9 (w/w) | 0.7% | 0.6% | 0.6% | 0.1% | 0.4% |
| | Compound 12 (w/w)[a] | ND | ND | ND | ND | ND |
| | Impurity m/z[b] | ND | ND | ND | 0.1% (a/a) (RRT = 0.81) | ND |
| | Each unspecified (a/a) | 0.1% | 0.1% | 0.1% | 0.1% | ND |
| | Total unknown impurities (a/a) | 0.1% | 0.1% | 0.1% | 0.1% | ND |
| | Total known impurities (w/w) | 0.8% | 0.7% | 0.7% | 0.1% | 0.4% |
| | HPLC Content (w/w) | 99.4% | 99.5% | 99.6% | 99.9% | 99.6% |

ND = Not detected

[a]Limit of detection for Compound 12 = 0.01%

TABLE 4-4

Batch Analysis

| | | Batch No. | | | |
|---|---|---|---|---|---|
| | | 14 | 15 | 16 | 17 |
| | | Batch Size (kg) | | | |
| | | 116.64 | 113.44 | 107.78 | 104.69 |
| Test | Acceptance Criteria | Results | Results | Results | Results |
| Color Appearance | White to off-white solid | white solid | white solid | white solid | white solid |
| HPLC (Purity) | Compound 5 (w/w)[a] | <0.05% | <0.05% | <0.05% | <0.05% |
| | Compound 10 (w/w)[c] | 0.08% | 0.05% | 0.11% | 0.10% |
| | Compound 9 (w/w)[d] | <0.05% | <0.05% | <0.05% | <0.05% |
| | Compound 12 (w/w)[e] | <0.05% | <0.05% | <0.05% | <0.05% |
| | Compound 11 (w/w)[f] | <0.05% | <0.05% | <0.05% | <0.05% |
| | Sum unspecified impurities[b] (w/w) | 0.14%[g] | 0.15%[g] | 0.13%[g] | 0.16%[g] |
| | Sum specified impurities (w/w) | 0.08% | 0.05% | 0.11% | 0.1% |

TABLE 4-4-continued

| Batch Analysis | | | | | |
|---|---|---|---|---|---|
| | | Batch No. | | | |
| | | 14 | 15 | 16 | 17 |
| | | Batch Size (kg) | | | |
| | | 116.64 | 113.44 | 107.78 | 104.69 |
| Test | Acceptance Criteria | Results | Results | Results | Results |
| | Largest unspecified impurity[g] (w/w) | 0.14%[g] | 0.15%[g] | 0.13%[g] | 0.16%[g] |
| Assay HPLC (w/w) | | 98.6% | 99.8% | 98.3% | 98.8% |

[a]Limit of detection for Compound 5 = 0.01%

[b]% (a/a) Relative Response Factor Corrected.

[c]Limit of detection for Compound 10 = 0.02%

[d]Limit of detection for Compound 9 = 0.02%

[e]Limit of detection for Compound 12 = 0.01%

[f]Limit of detection for Compound 11 = 0.01% (a/a), Not Relative Response Factor Corrected

[g]The unknown was identified as being 5,6-dichloro-N-ethyl-1H-benzo[d]imidazol-2-amine

TABLE 4-5

| Batch Analysis | | | | | | |
|---|---|---|---|---|---|---|
| | Batch No. | 18 | 19 | 20 | 21 | 22 |
| Batch Size (kg) | | 18.82 | 15.05 | 16 | 17.75 | 30.34 |
| | Test | | | Result | | |
| | Color | White | White | White | White | White |
| | Appearance | Solid | Solid | Solid | Solid | Solid |
| HPLC | Compound 5[a] | ND | ND | ND | ND | ND |
| (Purity) | Compound 10 (a/a)[c] | 0.63% | 0.1% | <0.05% | 0.05% | <0.1% |
| | Compound 9 (a/a)[d] | ND | 0.09% | <0.05% | ND | <0.1% |
| | Compound 12[e] | ND | ND | ND | ND | ND |
| | Compound 11[f] | ND | ND | ND | ND | ND |
| | Sum unspecified impurities (a/a)[b] | ND | ND | ND | <0.05% | 0.1% |
| | Sum specified impurities (a/a) | 0.63% | 0.19% | <0.05% | 0.05% | <0.10% |
| | Largest unspecified impurity[g] (a/a) | ND | ND | ND | <0.05% | 0.10% |
| Assay HPLC (w/w) | | 99.0% | 99.4% | 98.6% | 99.3% | 99.5% |

ND = not detected

[a]Limit of detection for Compound 5 = 0.01%

[b]% (a/a) Relative Response Factor Corrected

[c]Limit of detection for Compound 10 = 0.02%

[d]Limit of detection for Compound 9 = 0.02%

[e]Limit of detection for Compound 12 = 0.01%

[f]Limit of detection for Compound 11 = 0.01% (a/a), Not Relative Response Factor Corrected

[g]The unknown was identified as being 5,6-dichloro-N-ethyl-1H-benzo[d]imidazol-2-amine

TABLE 4-6

| Batch Analysis | | | | | | |
|---|---|---|---|---|---|---|
| | Batch No. | 23 | 24 | 25 | 26 | 27 |
| Batch Size (kg) | | 32.58 | 32.13 | 31.58 | 33.13 | 32.13 |
| | Test | | | Result | | |
| | Color | White | White | White | White | White |
| | Appearance | Solid | Solid | Solid | Solid | Solid |
| HPLC | Compound 5[a] | ND | ND | ND | ND | ND |
| (Purity) | Compound 10 (a/a)[c] | <0.1% | 0.1% | 0.1% | <0.1% | <0.1% |
| | Compound 9 (a/a)[d] | <0.1% | <0.1% | 0.1% | <0.1% | <0.1% |
| | Compound 12[e] | ND | ND | ND | ND | ND |
| | Compound 11[f] | ND | ND | ND | ND | ND |
| | Sum unspecified impurities[b] (a/a) | 0.1% | 0.1% | 0.1% | 0.1% | 0.1% |
| | Total specified impurities (a/a) | <0.10% | 0.10% | 0.10% | <0.10% | <0.10% |

TABLE 4-6-continued

| Batch Analysis | | | | | |
|---|---|---|---|---|---|
| Batch No. | 23 | 24 | 25 | 26 | 27 |
| Largest unspecified impurity[g] (a/a) | 0.10% | 0.10% | 0.10% | 0.10% | 0.10% |
| Assay HPLC (w/w) | 99.6% | 99.5% | 99.4% | 99.6% | 99.5% |

ND = not detected
[a]Limit of detection for Compound 5 = 0.01%
[b]% (a/a) Relative Response Factor Corrected
[c]Limit of detection for Compound 10 = 0.02%
[d]Limit of detection for Compound 9 = 0.02%
[e]Limit of detection for Compound 12 = 0.01%
[f]Limit of detection for Compound 11 = 0.01% (a/a), Not Relative Response Factor Corrected
[g]The unknown was identified as being 5,6-dichloro-N-ethyl-1H-benzo[d]imidazol-2-amine Step II: Synthesis of Compound 3

TABLE 4-7

| Batch Analysis | | | | |
|---|---|---|---|---|
| | | Batch No. | | |
| | | 1 | 2 | 3 |
| | | Batch Size (kg) | | |
| Test | | 175.6 Results | 173.8 Results | 180.5 Results |
| | Color | White | White | White |
| | Appearance | Solid | Solid | Solid |
| HPLC | Compound 3 (a/a) | 100.0% | 100.0% | 100.0% |
| (Purity) | Compound 2 (a/a) | ND[a] | ND | ND |
| | Maribavir | ND | ND | ND |
| | Compound 12 | ND | ND | ND |

TABLE 4-7-continued

| Batch Analysis | | | |
|---|---|---|---|
| | Batch No. | | |
| | 1 | 2 | 3 |
| | Batch Size (kg) | | |
| Test | 175.6 Results | 173.8 Results | 180.5 Results |
| Sum unknown impurities | ND | ND | ND |
| Biggest unspecified impurity (a/a) | ND | ND | ND |
| Sum all impurities (a/a) | ND | ND | ND |

ND = not detected
[a]Limit of detection = 0.01%

TABLE 4-8

| Batch Analysis | | | | | |
|---|---|---|---|---|---|
| | | Batch No. | | | |
| | | 4 | 5 | 6 | 7 |
| | | Batch Size (kg) | | | |
| | | 119.62 | 119.1 | 118.19 | 124.39 |
| Test | | Results | | | |
| | Color | White | White | White | White |
| | Appearance | Solid | Solid | Solid | Solid |
| | Appearance Further Observations | Complies | Complies | Complies | Complies |
| HPLC | Compound 3 (a/a) | 98.96% | 99.12% | 99.04% | 98.76% |
| (Purity) | Compound 2 (a/a) | 0.07% | 0.12% | 0.09% | 0.08% |
| | Maribavir (a/a) | 0.07% | ND | ND | ND |
| | Compound 12 | ND | ND | ND | ND |
| | Biggest unspecified impurity (a/a) | RRT = 0.37, 0.12% (a/a) RRT = 0.40, 0.11% (a/a) RRT = 0.57, 0.27%, (a/a) RRT = 0.60, 0.3% (a/a) RRT = 0.70, 0.09% (a/a) 0.3% | RRT = 0.37, 0.09% (a/a) RRT = 0.40, 0.08% (a/a) RRT = 0.57, 0.21%, (a/a) RRT = 0.60, 0.31% (a/a) RRT = 0.70, 0.08% (a/a) 0.31% (a/a) | RRT = 0.37, 0.09% (a/a) RRT = 0.40, 0.07% (a/a) RRT = 0.57, 0.28%, (a/a) RRT = 0.60, 0.34% (a/a) RRT = 0.70, 0.09% (a/a) 0.34% (a/a) | RRT = 0.37, 0.13% (a/a) RRT = 0.40, 0.10% (a/a) RRT = 0.57, 0.31%, (a/a) RRT = 0.60, 0.44% (a/a) RRT = 0.70, 0.11% (a/a) 0.44%, (a/a) |
| | Sum all impurities (a/a) | 1.04% | 0.88% | 0.96% | 1.24% |

ND = not detected

TABLE 4-9

| Batch Analysis | | | |
|---|---|---|---|
| | | Batch No. | |
| | | 8 | 9 |
| | | Batch Size (kg) | |
| | | 99.45 | 99.1 |
| Test | | Result | |
| Color | | White | White |
| Appearance | | Solid | Solid |
| Appearance | Further Observations | Complies | Complies |
| HPLC (Purity) | Compound 3 (a/a) | 99.49% | 99.11% |
| | Compound 2 (a/a) | <0.1% | <0.1% |
| | Biggest unspecified impurity (a/a). | N/A | RRT = 0.36, 0.11% (a/a) |
| | | N/A | RRT = 0.40, 0.10% (a/a) |
| | | RRT = 0.57, 0.21%, (a/a) | RRT = 0.57, 0.26%, (a/a) |
| | | RRT = 0.59, 0.27% (a/a) | RRT = 0.59, 0.34% (a/a) |
| | | 0.27% (a/a) | 0.34% (a/a) |
| Sum all impurities (a/a) | | 0.48% | 0.81% |

N/A = not applicable

TABLE 4-10

| Batch Analysis | | | | | |
|---|---|---|---|---|---|
| | | Batch No. | | | |
| | | 10 | 11 | 12 | 13 |
| | | Batch Size (kg) | | | |
| | | 145.96 | 144 | 78.2 | 300.65 |
| Test | | Results | | | |
| Color | | White solid | White solid | White solid | White solid |
| HPLC (Purity) | Compound 3 (a/a) | 99.7% | 98.5% | 99.33% | 99.50% |
| | Compound 2 (a/a) | <0.05% | <0.05% | <0.05% | <0.05% |
| | Largest unspecified impurity (a/a) | 0.11% | 0.42% | 0.2% | 0.15% |
| | Sum all impurities (a/a) | 0.26% | 1.6% | 0.69% | 0.50% |

TABLE 4-11

| Batch Analysis | | | | | |
|---|---|---|---|---|---|
| | | Batch No. | | | |
| | | 14 | 15 | 16 | 17 |
| | | Batch Size (kg) | | | |
| | | 106.46 | 106.65 | 105.64 | 107.89 |
| Test | | Results | | | |
| | Color | White | White | White | White |
| | Appearance | Solid | Solid | Solid | Solid |
| | Appearance | Complies | Complies | Complies | Complies |
| HPLC (Purity) | Compound 3 (a/a) | 98.5% | 98.5% | 98.0% | 99.5% |
| | Compound 2 (a/a) | <0.1% | <0.1% | <0.1% | <0.1% |
| | Maribavir (a/a) | 0.18% | 0.17% | 0.30% | 0.07% |
| | Biggest unspecified impurity (a/a) | RRT = 0.37, 0.22% (a/a) | RRT = 0.37, 0.21% (a/a) | RRT = 0.37, 0.31% (a/a) | N/A |
| | | RRT = 0.41, 0.17% (a/a) | RRT = 0.41, 0.16% (a/a) | RRT = 0.41, 0.23% (a/a) | N/A |
| | | RRT = 0.57, 0.37%, (a/a) | RRT = 0.57, 0.43%, (a/a) | RRT = 0.57, 0.61%, (a/a) | RRT = 0.57, 0.24%, (a/a) |
| | | RRT = 0.60, 0.46% (a/a) | RRT = 0.60, 0.41% (a/a) | RRT = 0.60, 0.43% (a/a) | RRT = 0.60, 0.30% (a/a) |
| | | RRT = 0.70, 0.12% (a/a) | RRT = 0.70, 0.12% (a/a) | RRT = 0.70, 0.12% (a/a) | N/A |
| | | 0.46% (a/a) | 0.43% (a/a) | 0.61% (a/a) | 0.30% |
| | Sum all impurities (a/a) | 1.5% | 1.5% | 2.0% | 0.54% |

Step III: Synthesis of Maribavir

TABLE 4-12

| Unmilled Maribavir Batch Analysis | | | | | | | |
|---|---|---|---|---|---|---|---|
| Batch No. | | 1 | 2 | 3 | 4 | 5 | 6 |
| Size (kg) | | 22.5 | 22.6 | 25.5 | 26.9 | 44.2 | 49.4 |
| Test | | Results | | | | | |
| Description | | Almost white solid | Almost white solid | White solid | White solid | White solid | White solid |
| Chromatographic Purity[a] | Compound 2 (w/w) | <0.05 | <0.05 | <0.05 | <0.05 | <0.05 | <0.05 |
| | Compound 3 (w/w) | <0.05 | <0.05 | <0.05 | <0.05 | <0.05 | <0.05 |
| | Compound 4 (w/w) | <0.05 | <0.05 | <0.05 | <0.05 | <0.05 | <0.05eb;normal |

TABLE 4-12-continued

| Unmilled Maribavir Batch Analysis | | | | | | | |
|---|---|---|---|---|---|---|---|
| Batch No. | | 1 | 2 | 3 | 4 | 5 | 6 |
| | Unspecified Impurities (w/w) | <0.05 | <0.05 | <0.05 | <0.05 | <0.05 | <0.05 |
| | Total Impurities | <0.05 | <0.05 | <0.05 | <0.05 | <0.05 | <0.05 |
| Assay (w/w), (as is basis) | | 100.2 | 100.2 | 100.1 | 100.4 | 99.8 | 99.8 |
| XRPD | | Conforms | Conforms | Conforms | Conforms | Conforms | Conforms |
| Thermal Analysis | | Onset: 197.2° C. Peak: 199.9° C. | Onset: 197.1° C. Peak: 199.7° C. | Onset: 198.1° C. Peak: 199.3° C. | Onset: 199.5° C. Peak: 201.2° C. | Onset: 196.94° C. Peak: 200.3° C. | Onset: 197.01° C. Peak: 199.72° C. |
| Enantiomeric Purity[b] | D-maribavir | NT | NT | <0.025 | <0.025 | <0.025 | <0.025 |
| Particle Size | d(0.1) (um) | 51 | 50 | 87 | 76 | 128 | 138 |
| | d(0.5) (um) | 214 | 205 | 182 | 174 | 279 | 245 |
| | d(0.9) (um) | 354 | 346 | 233 | 266 | 439 | 244 |

N/A = not applicable,
ND = not detected,
NT = not tested
[a]Reporting Limit (RL) = 0.05%
[b]Reporting Limit (RL) = 0.025%.

TABLE 4-13

| Unmilled Maribavir Batch Analysis | | | | | | | | | | |
|---|---|---|---|---|---|---|---|---|---|---|
| Batch No. | | 7 | 8 | 9 | 10 | 11 | 12 | 13 | 14 | 15 |
| Size (kg) | | 41.1 | 41.4 | 41.4 | 41.4 | 40.9 | 53.7 | 21.24 | 21.3 | 21.5 |
| Test | | | | | | Results | | | | |
| Description | | White Solid | White Solid | White Solid | White Solid | White Solid | White Solid | White Solid | White Solid | White Solid |
| Purity HPLC[a] | Compound 2 (a/a) | ND | ND | ND | ND | ND | ND | ND | ND | ND |
| | Compound 3 (a/a) | ND | ND | ND | ND | ND | ND | ND | ND | ND |
| | Compound 4 (a/a) | ND | ND | ND | ND | ND | ND | ND | ND | ND |
| | Biggest Unknown Impurity (a/a) | ND | ND | ND | ND | ND | ND | ND | ND | ND |
| | Sum all Impurities (a/a) | ND | ND | ND | ND | ND | ND | ND | ND | ND |
| HPLC Identity | | Conforms | Conforms | Conforms | Conforms | Conforms | Conforms | Conforms | Conforms | Conforms |
| Chiral Purity[b] | D-maribavir (a/a) | ND | ND | ND | ND | ND | ND | ND | ND | ND |
| Assay HPLC % (w/w) | | 99.0 | 99.0 | 99.2 | 99.1 | 99.1 | 99.6 | 100.4 | 100.5 | 100.4 |
| Particle Size | d(0.1) (um) | 109.2 | 64.2 | 66.7 | 71.4 | 59.8 | 70.3 | 141.4 | 161.2 | 147.4 |
| | d(0.5) (um) | 267.8 | 125.2 | 145 | 160.2 | 130.5 | 157.2 | 287.6 | 259.6 | 265.6 |
| | d(0.9) (um) | 481.2 | 238.9 | 292 | 346.8 | 283.9 | 368.5 | 503.6 | 405.7 | 451.8 |
| P-XRD Identity | | Conforms | Conforms | Conforms | Conforms | Conforms | Conforms | Conforms | Conforms | Conforms |

ND = not detected
[a]Reporting Limit (RL) = 0.05%
[b]Reporting Limit (RL) = 0.025%

TABLE 4-14

| Unmilled Maribavir Batch Analysis | | | | | | | |
|---|---|---|---|---|---|---|---|
| Batch No. | | 16 | 17 | 18 | 19 | 20 | 21 |
| Size (kg) | | 49.9 | 49.3 | 50.0 | 49.7 | 49.5 | 49.7 |
| Test | | | | Results | | | |
| Description | | Off-white solid | Off-white solid | Off-white solid | Off-white solid | Off-white solid | Off-white solid |
| Purity HPLC[a] | Compound 2 (a/a) | ND | ND | ND | ND | ND | ND |
| | Compound 3 (a/a) | ND | ND | ND | ND | ND | ND |
| | Compound 4 (a/a) | ND | ND | ND | ND | ND | ND |
| | Biggest Unknown Impurity (a/a) | ND | ND | ND | ND | ND | ND |
| | Sum all Impurities (a/a) | ND | ND | ND | ND | ND | ND |

TABLE 4-14-continued

| Unmilled Maribavir Batch Analysis | | | | | | | |
|---|---|---|---|---|---|---|---|
| Batch No. | | 16 | 17 | 18 | 19 | 20 | 21 |
| HPLC Identity | Retention time conforms to reference standard | Conforms | Conforms | Conforms | Conforms | Conforms | Conforms |
| Chiral Purity[b] | D-maribavir (a/a) | NT[g] | ND | NT | NT | NT | NT |
| Assay | HPLC % (w/w) | 100.2 | 100.1 | 99.9 | 100.0 | 99.8 | 99.9 |
| Particle Size | d(0.1) (um) | 164.5 | 147.5 | 140.2 | 170.5 | 165.8 | 166.4 |
| | d(0.5) (um) | 236.8 | 232.9 | 218.0 | 246.2 | 243.1 | 234.6 |
| | d(0.9) (um) | 340.7 | 350.0 | 330.5 | 348.4 | 352.8 | 330.0 |
| P-XRD Identity | Conforms to Reference Standard | Conforms | Conforms | Conforms | Conforms | Conforms | Conforms |

ND = not detected,
NT = not tested
[a]Reporting Limit (RL) = 0.05%
[b]Reporting Limit (RL) = 0.025%.

TABLE 4-15

| Unmilled Maribavir Batch Analysis | | | | | |
|---|---|---|---|---|---|
| | | Batch No. | | | |
| | | 22 | 23 | 24 | 25 |
| | | Size (kg) | | | |
| | | 40.97 | 50.0 | 49.0 | 44.6 |
| Test | | Result | | | |
| Description | | Off-white solid | Off-white solid | Off-white solid | White Solid |
| Purity HPLC[a] | Compound 2 (a/a) | <0.05 | <0.05 | <0.05 | <0.05 |
| | Compound 3 (a/a) | <0.05 | <0.05 | <0.05 | <0.05 |
| | Compound 4 (a/a) | <0.05 | <0.05 | <0.05 | <0.05 |
| | Biggest Unknown Impurity (a/a) | <0.05 | <0.05 | <0.05 | <0.05 |
| | Sum all Impurities (a/a) | <0.05 | <0.05 | <0.05 | <0.05 |

TABLE 4-15-continued

| Unmilled Maribavir Batch Analysis | | | | | |
|---|---|---|---|---|---|
| | | Batch No. | | | |
| | | 22 | 23 | 24 | 25 |
| | | Size (kg) | | | |
| | | 40.97 | 50.0 | 49.0 | 44.6 |
| Test | | Result | | | |
| HPLC Identity | | Conforms | Conforms | Conforms | Conforms |
| Assay | HPLC % (w/w) | 100.2 | 99.9 | 100.1 | 99.9 |
| Particle Size | d(0.1) (um) | 143.0 | 107 | 134 | 129 |
| | d(0.5) (um) | 194.0 | 157 | 201 | 245 |
| | d(0.9) (um) | 265.0 | 223 | 291 | 401 |
| P-XRD Identity | Conforms to Reference Standard | Conforms | Conforms | Conforms | Conforms |

NT = not tested
[a]Reporting Limit (RL) = 0.05%

TABLE 4-16

| Unmilled Maribavir Batch Analysis | | | | |
|---|---|---|---|---|
| | | Batch No. | | |
| | | 26 | 27 | 28 |
| | | Size (kg) | | |
| | | 54.25 | 3.35 | 60.2 |
| Test | | Result | | |
| Description | | White solid | White solid | White solid |
| Melting Point | | 197.1° C. (onset) 198.6° C. (peak) | 197.1° C. (onset) 198.5° C. (peak) | 196.9° C. (onset) 199.6° C. (peak) |
| Water-KF (w/w) | | 0.01 | 0.01 | 0.01 |
| Purity HPLC[a] | Compound 2 (a/a) | ND | ND | ND |
| | Compound 3 (a/a) | ND | ND | ND |
| | Compound 4 (a/a) | ND | ND | ND |
| | Biggest Unknown Impurity (a/a) | ND | ND | ND |
| | Sum all Impurities (a/a) | ND | ND | ND |

TABLE 4-16-continued

Unmilled Maribavir Batch Analysis

| Test | | Batch No. 26 | 27 | 28 |
|---|---|---|---|---|
| | | Size (kg) | | |
| | | 54.25 | 3.35 | 60.2 |
| | | Result | | |
| Assay HPLC % (w/w) | | 100.3 | 100.4 | 100.5 |
| Particle Size | d(0.1) Report Result (um) | 12.9 | 14.2 | 106.4 |
| | d(0.5) Report Result (um) | 62.6 | 69.9 | 251.2 |
| | d(0.9) Report Result (um) | 489.6 | 574.9 | 426.3 |

ND = not detected
[a]Reporting Limit (RL) = 0.05%

TABLE 4-17

Unmilled Maribavir Batch Analysis

| Batch No. | | 29 | 30 | 31 | 32 | 33 |
|---|---|---|---|---|---|---|
| Size (kg) | | 12.3 | 12.9 | 12.7 | 12.7 | 12.9 |
| Test | | | | Results | | |
| Description | | White solid | White solid | White solid | White solid | White solid |
| Purity HPLC[a] | Compound 2 (a/a) | ND | ND | ND | ND | ND |
| | Compound 3 (a/a) | ND | ND | ND | ND | ND |
| | Compound 4 (a/a) | ND | ND | ND | ND | ND |
| | Biggest Unknown Impurity (a/a) | ND | ND | ND | ND | ND |
| | Sum all Impurities (a/a) | ND | ND | ND | ND | ND |
| Assay HPLC % (w/w) | | 100.3 | 100.4 | 100.5 | 100.4 | 100.3 |
| Particle Size | d(0.1) (um) | 200.6 | 83.0 | 183.2 | 169.1 | 96.4 |
| | d(0.5) (um) | 285.9 | 195.4 | 268.6 | 239.3 | 192.7 |
| | d(0.9) (um) | 407.4 | 377.7 | 393.9 | 339.6 | 329.5 |

[a]Reporting Limit (RL) = 0.05%.

TABLE 4-18

Unmilled Maribavir Batch Analysis

| Test | | Batch No. 34 | 35 | 36 | 37 |
|---|---|---|---|---|---|
| | | Size (kg) | | | |
| | | 44.9 | 64.0 | 63.3 | 65.6 |
| | | Result | | | |
| Description | | White solid | White solid | White solid | White solid |
| Purity HPLC[a] | Compound 2 (a/a) | ND | <0.05 | <0.05 | <0.05 |
| | Compound 3 (a/a) | ND | <0.05 | <0.05 | <0.05 |
| | Compound 4 (a/a) | ND | <0.05 | <0.05 | <0.05 |
| | Biggest Unknown Impurity (a/a) | ND | <0.05 | <0.05 | <0.05 |
| | Sum all Impurities (a/a) | ND | <0.05 | <0.05 | <0.05 |

TABLE 4-18-continued

Unmilled Maribavir Batch Analysis

| Test | | Batch No. 34 | 35 | 36 | 37 |
|---|---|---|---|---|---|
| | | Size (kg) | | | |
| | | 44.9 | 64.0 | 63.3 | 65.6 |
| | | Result | | | |
| XRPD | | Conform | Conform | Conform | Conform |
| Assay HPLC (w/w) % | | 99.8 | 99.9 | 100.0 | 99.8 |
| Particle Size | d(0.1) (um) | 252.5 | 219.3 | 174.0 | 227.0 |
| | d(0.5) (um) | 362.5 | 317.9 | 331.3 | 336.2 |
| | d(0.9) (um) | 514.7 | 449.6 | 556.2 | 571.3 |

ND = not detected
[a]Reporting Limit (RL) = 0.05%.

TABLE 4-19

Unmilled Maribavir Batch Analysis

| Batch No. | 38 | 39 | 40 | 41 | 42 | 43 | 44 |
|---|---|---|---|---|---|---|---|
| Size (kg) | 50.1 | 49.5 | 50.36 | 49.6 | 50.39 | 41.6 | 43.6 |
| Test | | | | Result | | | |
| Description | White solid | White solid | White solid | White solid | White solid | White solid | White solid |

TABLE 4-19-continued

| Unmilled Maribavir Batch Analysis | | | | | | | | |
|---|---|---|---|---|---|---|---|---|
| Batch No. | | 38 | 39 | 40 | 41 | 42 | 43 | 44 |
| Purity HPLC[a] (a/a) | Compound 2 | <0.05 | <0.05 | <0.05 | <0.05 | <0.05 | <0.05 | <0.05 |
| | Compound 3 | <0.05 | <0.05 | <0.05 | <0.05 | <0.05 | <0.05 | <0.05 |
| | Compound 4 | <0.05 | <0.05 | <0.05 | <0.05 | <0.05 | <0.05 | <0.05 |
| | Biggest Unknown Impurity | <0.05 | <0.05 | <0.05 | <0.05 | <0.05 | <0.05 | <0.05 |
| | Sum all Impurities | <0.05 | <0.05 | <0.05 | <0.05 | <0.05 | <0.05 | <0.05 |
| HPLC Identity | | Conforms | Conforms | Conforms | Conforms | Conforms | Conforms | Conforms |
| Assay HPLC (w/w)%) | | 99.8 | 99.9 | 99.8 | 99.4 | 99.7 | 100.5 | 101.3 |
| Particle Size (μm) | d(0.1) (um) | 140 | 140 | 124 | 24.6 | 44.1 | 101 | 112 |
| | d(0.5) (um) | 195 | 198 | 182 | 97.5 | 174 | 212 | 180 |
| | d(0.9) (um) | 268 | 275 | 263 | 280 | 346 | 384 | 27 |
| P-XRD Identity | | Conforms | Conforms. | Conforms | Conforms | Conforms | Conforms | Conforms. |

[a]Reporting Limit (RL) = 0.05%

TABLE 4-20

| Unmilled Maribavir Batch Analysis | | | |
|---|---|---|---|
| | | Batch No. | |
| | | 44 | 45 |
| | | Size (kg) | |
| | | 15.083 | 15.837 |
| Test | | Result | |
| | Description | White solid | White solid |
| Purity HPLC[a] | Compound 2 (a/a) | <0.05 | <0.05 |
| | Compound 3 (a/a) | <0.05 | <0.05 |
| | Compound 4 (a/a) | <0.05 | <0.05 |
| | Biggest Unknown Impurity (a/a) | <0.05 | <0.05 |
| | Sum all Impurities (a/a) | <0.05 | <0.05 |
| | HPLC Identity | Conforms | Conforms |
| | Assay HPLC (w/w) %) | 100.1 | 100.2 |
| Particle Size | d(0.1) (um) | 166.0 | 180.4 |
| | d(0.5) (um) | 240.3 | 261.8 |
| | d(0.9) (um) | 346.9 | 380.2 |
| | P-XRD Identity | Conforms | Conforms |

NT = not tested
[a]Reporting Limit (RL) = 0.05%.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of examples.

The invention claimed is:

1. A composition comprising micronized seed crystals of maribavir Form VI, wherein the seed crystals have a particle size distribution (PSD) characterized by a mean particle diameter (d(50)) between about 1.00 μm and about 10.00 μm.

2. The composition of claim 1, wherein the d(50) of the seed crystals is between about 1.00 μm and about 8.00 μm.

3. The composition of claim 1, wherein the d(50) of the seed crystals is between about 1.00 μm and about 6.00 μm.

4. The composition of claim 1, wherein the d(50) of the seed crystals is between about 1.00 μm and about 4.00 μm.

5. The composition of claim 1, wherein the d(50) of the seed crystals is between about 2.00 μm and about 10.00 μm.

6. The composition of claim 1, wherein the d(50) of the seed crystals is between about 4.00 μm and about 10.00 μm.

7. The composition of claim 1, wherein the d(50) of the seed crystals is between about 6.00 μm and about 10.00 μm.

8. The composition of claim 1, wherein the d(50) of the seed crystals is between about 2.25 μm and about 7.00 μm.

9. The composition of claim 1, wherein the d(50) of the seed crystals is between about 2.75 μm and about 6.25 μm.

10. A crystallization mixture comprising a composition according to claim 1 and further comprising Compound 3 or a salt thereof, wherein Compound 3 has the following structure:

3

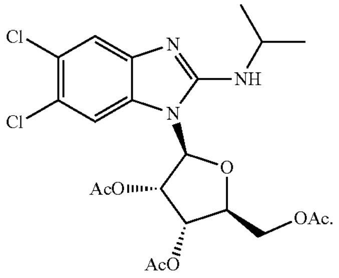

11. The crystallization mixture of claim 10, wherein the seed crystals of maribavir Form VI are present in the mixture in an amount of from about 0.05% to about 0.30% w/w relative to Compound 3 or a salt thereof.

12. The crystallization mixture of claim 11, wherein the seed crystals of maribavir Form VI are present in the mixture in an amount of about 0.15% w/w relative to Compound 3 or a salt thereof.

* * * * *